United States Patent
Cundy et al.

(10) Patent No.: US 11,111,271 B2
(45) Date of Patent: Sep. 7, 2021

(54) THERAPEUTIC PEPTIDES

(71) Applicant: COHBAR, INC., Menlo Park, CA (US)

(72) Inventors: Kenneth C. Cundy, Atherton, CA (US); Kent K. Grindstaff, San Jose, CA (US); Remi Magnan, Sunnyvale, CA (US); Wendy Luo, Sunnyvale, CA (US); Yongjin Yao, Santa Clara, CA (US); Liang Zeng Yan, Carmel, IN (US)

(73) Assignee: COHBAR, INC., Menlo Park, CA (US)

( * ) Notice: Subject to any disclaimer, the term of this patent is extended or adjusted under 35 U.S.C. 154(b) by 0 days.

(21) Appl. No.: 16/336,089

(22) PCT Filed: Sep. 27, 2017

(86) PCT No.: PCT/US2017/053597
§ 371 (c)(1),
(2) Date: Mar. 22, 2019

(87) PCT Pub. No.: WO2018/064098
PCT Pub. Date: Apr. 5, 2018

(65) Prior Publication Data
US 2020/0181197 A1 Jun. 11, 2020

Related U.S. Application Data

(60) Provisional application No. 62/401,123, filed on Sep. 28, 2016.

(51) Int. Cl.
| | |
|---|---|
| *C07K 7/08* | (2006.01) |
| *C07K 14/47* | (2006.01) |
| *A61P 1/16* | (2006.01) |
| *A61P 3/04* | (2006.01) |
| *C07K 7/06* | (2006.01) |
| *A61K 38/00* | (2006.01) |

(52) U.S. Cl.
CPC ........ *C07K 7/08* (2013.01); *A61P 1/16* (2018.01); *A61P 3/04* (2018.01); *C07K 7/06* (2013.01); *C07K 14/47* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 7,998,928 B2 | 8/2011 | Cohen et al. | |
| 8,309,525 B2 | 11/2012 | Barzilai et al. | |
| 8,637,470 B2 | 1/2014 | Cohen et al. | |
| 8,653,027 B2 | 2/2014 | Cohen et al. | |
| 10,064,914 B2 | 9/2018 | Cohen et al. | |
| 10,391,143 B2 | 8/2019 | Cohen et al. | |
| 2010/0254992 A1* | 10/2010 | Das | A61P 25/00 424/139.1 |
| 2012/0121633 A1* | 5/2012 | Paul | A61K 39/12 424/188.1 |
| 2013/0123168 A1 | 5/2013 | Cohen et al. | |
| 2014/0213527 A1 | 7/2014 | Cohen et al. | |
| 2014/0296139 A1* | 10/2014 | Cohen | A61P 35/02 514/4.8 |
| 2017/0049853 A1 | 2/2017 | Cohen et al. | |

FOREIGN PATENT DOCUMENTS

| | | |
|---|---|---|
| WO | 2001/076532 A2 | 10/2001 |
| WO | 2014/144521 A1 | 9/2014 |

OTHER PUBLICATIONS

Wu et al., "Non-alcoholic fatty liver disease incidence, remission and risk factors among a general Chinese population with a 6-year follow-up", Scientific Reports, 7557 (2018) (Year: 2018).*
UniProtKB/Swiss-Prot: A0A0C5B5G6.1; 2015; accessed from https://www.ncbi.nlm.nih.gov/protein/A0A0C5B5G6.1?report=genpept (Year: 2015).*
Fields, "Introduction to Peptide Synthesis", Current Protocols in Protein Science, 2001, p. 18.1.1-18.1.9. (Year: 2001).*
Biosyn, "Why acetylate and amidate a peptide", accessed on Mar. 22, 2021 at https://www.biosyn.com/faq/why-acetylate-and-amidate-a-peptide.aspx., 2008. (Year: 2008).*
Fuku et al., The Mitochondrial-Derived Peptide MOTS-c: A Player in Exceptional Longevity? Aging Cell, 14(6): 921-923 (2015).
International Preliminary Report on Patentability for Corresponding International Application No. PCT/US2017/053597, dated Apr. 11, 2019, 11 pages.
International Search Report and Written Opinion for Corresponding International Application No. PCT/US2017/053597, dated Jan. 22, 2018, 16 pages.
Lee et al., Humanin: A Harbinger of Mitochondrial-Derived Peptides?, Trends Endocrinol. Metab., 24(5):222-228 (2013).
Lee et al., MOTS-c: A Novel Mitochondrial-Derived Peptide Regulating Muscle and Fat Metabolism, Free Radic. Biol. Med., 100:182-187 (2016).
Lee et al., The mitochondrial-derived peptide MOTS-c promotes metabolic homeostasis and reduces obesity and insulin resistance, Cell Metab., 21:443-454 (2015).
Zarse et al., A Mitochondrially Encoded Hormone Ameliorates Obesity and Insulin Resistance, Cell Metab., 21(3):355-356 (2015).

* cited by examiner

*Primary Examiner* — Lianko G Garyu
(74) *Attorney, Agent, or Firm* — Marshall, Gerstein & Borun LLP

(57) ABSTRACT

Provided herein are peptides and peptide analogs and methods of treating a metabolic disease, e.g., obesity, diabetes, methods of treating cancer, methods of treating a liver disease, and methods of modulating fatty acid metabolism.

33 Claims, No Drawings
Specification includes a Sequence Listing.

SEQUENCE LISTING

```
<160> NUMBER OF SEQ ID NOS: 380

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid with a non-polar side
      chain or a polar side chain or is absent
<220> FEATURE:
<221> NAME/KEY: MISC_FEATURE
<222> LOCATION: (2)..(2)
<223> OTHER INFORMATION: Arg may be absent when Xaa at position 1 is
      absent
<220> FEATURE:
<221> NAME/KEY: MISC_FEATURE
<222> LOCATION: (3)..(3)
<223> OTHER INFORMATION: Trp is absent when Xaa at position 2 is absent
<220> FEATURE:
<221> NAME/KEY: MISC_FEATURE
<222> LOCATION: (6)..(6)
<223> OTHER INFORMATION: Xaa is an amino acid with a non-polar side
      chain or a polar side chain
<220> FEATURE:
<221> NAME/KEY: MISC_FEATURE
<222> LOCATION: (7)..(7)
<223> OTHER INFORMATION: Xaa is an amino acid with a non-polar side
      chain or a polar side chain
<220> FEATURE:
<221> NAME/KEY: MISC_FEATURE
<222> LOCATION: (10)..(10)
```

-continued

```
<223> OTHER INFORMATION: Xaa is an amino acid with a non-polar side
      chain
<220> FEATURE:
<221> NAME/KEY: MISC_FEATURE
<222> LOCATION: (12)..(12)
<223> OTHER INFORMATION: Xaa is an amino acid with a non-polar side
      chain
<220> FEATURE:
<221> NAME/KEY: MISC_FEATURE
<222> LOCATION: (14)..(14)
<223> OTHER INFORMATION: Xaa is Lys or an amino acid with a non-polar
      side chain or is absent
<220> FEATURE:
<221> NAME/KEY: MISC_FEATURE
<222> LOCATION: (15)..(15)
<223> OTHER INFORMATION: Leu is absent when Xaa at position 14 is absent
<220> FEATURE:
<221> NAME/KEY: MISC_FEATURE
<222> LOCATION: (16)..(16)
<223> OTHER INFORMATION: Xaa is Arg or an amino acid with a non-polar
      side chain or is absent when Xaa at position 14 is absent

<400> SEQUENCE: 1

Xaa Arg Trp Gln Glu Xaa Xaa Tyr Ile Xaa Tyr Xaa Arg Xaa Leu Xaa
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2

Met Arg Trp Gln Glu Met Gly Tyr Ile Phe Tyr Pro Arg Lys Leu Arg
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 3

Met Arg Trp Gln Glu Met Gly Tyr Ile Phe Tyr Pro Arg Lys Leu Arg
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 4

Met Arg Trp Gln Glu Met Gly Tyr Ile Phe Tyr Pro Arg Lys Leu Arg
1               5                   10                  15
```

```
<210> SEQ ID NO 5
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 5

Met Arg Trp Gln Glu Met Gly Tyr Ile Phe Tyr Pro Arg Lys Leu Arg
1               5                   10                  15

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Ala Arg Trp Gln Glu Met Gly Tyr Ile Phe Tyr Pro Arg Lys Leu Arg
1               5                   10                  15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Met Ala Trp Gln Glu Met Gly Tyr Ile Phe Tyr Pro Arg Lys Leu Arg
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: Synthetic peptide

<400> SEQUENCE: 8

Met Arg Ala Gln Glu Met Gly Tyr Ile Phe Tyr Pro Arg Lys Leu Arg
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

Met Arg Trp Ala Glu Met Gly Tyr Ile Phe Tyr Pro Arg Lys Leu Arg
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: Synthetic peptide

<400> SEQUENCE: 10

Met Arg Trp Gln Ala Met Gly Tyr Ile Phe Tyr Pro Arg Lys Leu Arg
```

<210> SEQ ID NO 11
<211> LENGTH: 16
<212> TYPE: PRT
<213> ORGANISM: Artificial Sequence
<220> FEATURE:
<223> OTHER INFORMATION: Synthetic peptide

<400> SEQUENCE: 11

Met Arg Trp Gln Glu Ala Gly Tyr Ile Phe Tyr Pro Arg Lys Leu Arg
1               5                   10                  15

<210> SEQ ID NO 12
<211> LENGTH: 16
<212> TYPE: PRT
<213> ORGANISM: Artificial Sequence
<220> FEATURE:
<223> OTHER INFORMATION: Synthetic peptide

<400> SEQUENCE: 12

Met Arg Trp Gln Glu Met Ala Tyr Ile Phe Tyr Pro Arg Lys Leu Arg
1               5                   10                  15

<210> SEQ ID NO 13
<211> LENGTH: 16
<212> TYPE: PRT
<213> ORGANISM: Artificial Sequence
<220> FEATURE:
<223> OTHER INFORMATION: Synthetic peptide

<400> SEQUENCE: 13

Met Arg Trp Gln Glu Met Gly Ala Ile Phe Tyr Pro Arg Lys Leu Arg
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide

<400> SEQUENCE: 14

Met Arg Trp Gln Glu Met Gly Tyr Ala Phe Tyr Pro Arg Lys Leu Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide

<400> SEQUENCE: 15

Met Arg Trp Gln Glu Met Gly Tyr Ile Ala Tyr Pro Arg Lys Leu Arg
1               5                   10                  15

<210> SEQ ID NO 16
<211> LENGTH: 16
<212> TYPE: PRT
<213> ORGANISM: Artificial Sequence
<220> FEATURE:
<223> OTHER INFORMATION: Synthetic peptide

<400> SEQUENCE: 16

Met Arg Trp Gln Glu Met Gly Tyr Ile Phe Ala Pro Arg Lys Leu Arg
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic peptide

<400> SEQUENCE: 17

Met Arg Trp Gln Glu Met Gly Tyr Ile Phe Tyr Ala Arg Lys Leu Arg
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic peptide

<400> SEQUENCE: 18

Met Arg Trp Gln Glu Met Gly Tyr Ile Phe Tyr Pro Ala Lys Leu Arg
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: Synthetic peptide

<400> SEQUENCE: 19

Met Arg Trp Gln Glu Met Gly Tyr Ile Phe Tyr Pro Arg Ala Leu Arg
1               5                   10                  15

<210> SEQ ID NO 20
<211> LENGTH: 16
<212> TYPE: PRT
<213> ORGANISM: Artificial Sequence
<220> FEATURE:
<223> OTHER INFORMATION: Synthetic peptide

<400> SEQUENCE: 20

Met Arg Trp Gln Glu Met Gly Tyr Ile Phe Tyr Pro Arg Lys Ala Arg
1               5                   10                  15

<210> SEQ ID NO 21
<211> LENGTH: 16
<212> TYPE: PRT
<213> ORGANISM: Artificial Sequence
<220> FEATURE:
<223> OTHER INFORMATION: Synthetic peptide

<400> SEQUENCE: 21

Met Arg Trp Gln Glu Met Gly Tyr Ile Phe Tyr Pro Arg Lys Leu Ala
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE

```
<222> LOCATION: (16)..(16)
<223> OTHER INFORMATION: C-terminal amidation

<400> SEQUENCE: 22

Ala Arg Trp Gln Glu Met Gly Tyr Ile Phe Tyr Pro Arg Lys Leu Arg
 1               5                  10                  15

<210> SEQ ID NO 23
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 23

Met Ala Trp Gln Glu Met Gly Tyr Ile Phe Tyr Pro Arg Lys Leu Arg
 1               5                  10                  15

<210> SEQ ID NO 24
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 24

Met Arg Ala Gln Glu Met Gly Tyr Ile Phe Tyr Pro Arg Lys Leu Arg
 1               5                  10                  15

<210> SEQ ID NO 25
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 25

Met Arg Trp Ala Glu Met Gly Tyr Ile Phe Tyr Pro Arg Lys Leu Arg
 1               5                  10                  15

<210> SEQ ID NO 26
<211> LENGTH: 16
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 26

Met Arg Trp Gln Ala Met Gly Tyr Ile Phe Tyr Pro Arg Lys Leu Arg
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 27

Met Arg Trp Gln Glu Ala Gly Tyr Ile Phe Tyr Pro Arg Lys Leu Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 28

Met Arg Trp Gln Glu Met Ala Tyr Ile Phe Tyr Pro Arg Lys Leu Arg
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 29

Met Arg Trp Gln Glu Met Gly Ala Ile Phe Tyr Pro Arg Lys Leu Arg
1               5                   10                  15

<210> SEQ ID NO 30
<211> LENGTH: 16
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 30

Met Arg Trp Gln Glu Met Gly Tyr Ala Phe Tyr Pro Arg Lys Leu Arg
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 31

Met Arg Trp Gln Glu Met Gly Tyr Ile Ala Tyr Pro Arg Lys Leu Arg
1               5                   10                  15

<210> SEQ ID NO 32
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 32

Met Arg Trp Gln Glu Met Gly Tyr Ile Phe Ala Pro Arg Lys Leu Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 33

Met Arg Trp Gln Glu Met Gly Tyr Ile Phe Tyr Ala Arg Lys Leu Arg
```

<210> SEQ ID NO 34
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 34

Met Arg Trp Gln Glu Met Gly Tyr Ile Phe Tyr Pro Ala Lys Leu Arg
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 35

Met Arg Trp Gln Glu Met Gly Tyr Ile Phe Tyr Pro Arg Ala Leu Arg
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 36

Met Arg Trp Gln Glu Met Gly Tyr Ile Phe Tyr Pro Arg Lys Ala Arg
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)

```
<223> OTHER INFORMATION: C-terminal amidation

<400> SEQUENCE: 37

Met Arg Trp Gln Glu Met Gly Tyr Ile Phe Tyr Pro Arg Lys Leu Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Synthetic peptide

<400> SEQUENCE: 38

Arg Trp Gln Glu Met Gly Tyr Ile Phe Tyr Pro Arg Lys Leu Arg
1               5                   10                  15

<210> SEQ ID NO 39
<211> LENGTH: 14
<212> TYPE: PRT
<213> ORGANISM: Artificial Sequence
<220> FEATURE:
<223> OTHER INFORMATION: Synthetic peptide

<400> SEQUENCE: 39

Trp Gln Glu Met Gly Tyr Ile Phe Tyr Pro Arg Lys Leu Arg
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Synthetic peptide

<400> SEQUENCE: 40

Gln Glu Met Gly Tyr Ile Phe Tyr Pro Arg Lys Leu Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Synthetic peptide

<400> SEQUENCE: 41

Glu Met Gly Tyr Ile Phe Tyr Pro Arg Lys Leu Arg
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Synthetic peptide

<400> SEQUENCE: 42

Met Gly Tyr Ile Phe Tyr Pro Arg Lys Leu Arg
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 43

Gly Tyr Ile Phe Tyr Pro Arg Lys Leu Arg
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Tyr Ile Phe Tyr Pro Arg Lys Leu Arg
1               5

<210> SEQ ID NO 45
<211> LENGTH: 15
<212> TYPE: PRT
<213> ORGANISM: Artificial Sequence
<220> FEATURE:
<223> OTHER INFORMATION: Synthetic peptide

<400> SEQUENCE: 45

Met Arg Trp Gln Glu Met Gly Tyr Ile Phe Tyr Pro Arg Lys Leu
1               5                   10                  15

<210> SEQ ID NO 46
<211> LENGTH: 14
<212> TYPE: PRT
<213> ORGANISM: Artificial Sequence
<220> FEATURE:
<223> OTHER INFORMATION: Synthetic peptide

<400> SEQUENCE: 46

Met Arg Trp Gln Glu Met Gly Tyr Ile Phe Tyr Pro Arg Lys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic peptide

<400> SEQUENCE: 47

Met Arg Trp Gln Glu Met Gly Tyr Ile Phe Tyr Pro Arg
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic peptide

<400> SEQUENCE: 48

Met Arg Trp Gln Glu Met Gly Tyr Ile Phe Tyr Pro
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 49

Met Arg Trp Gln Glu Met Gly Tyr Ile Phe Tyr
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic peptide

<400> SEQUENCE: 50

Met Arg Trp Gln Glu Met Gly Tyr Ile Phe
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Met Arg Trp Gln Glu Met Gly Tyr Ile
1               5

<210> SEQ ID NO 52
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 52

Arg Trp Gln Glu Met Gly Tyr Ile Phe Tyr Pro Arg Lys Leu Arg
1               5                   10                  15

<210> SEQ ID NO 53
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (14)..(14)
<223> OTHER INFORMATION: C-terminal amidation

<400> SEQUENCE: 53

Trp Gln Glu Met Gly Tyr Ile Phe Tyr Pro Arg Lys Leu Arg
1               5                   10

<210> SEQ ID NO 54
<211> LENGTH: 13
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (13)..(13)
<223> OTHER INFORMATION: C-terminal amidation

<400> SEQUENCE: 54

Gln Glu Met Gly Tyr Ile Phe Tyr Pro Arg Lys Leu Arg
 1               5                  10

<210> SEQ ID NO 55
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (12)..(12)
<223> OTHER INFORMATION: C-terminal amidation

<400> SEQUENCE: 55

Glu Met Gly Tyr Ile Phe Tyr Pro Arg Lys Leu Arg
 1               5                  10

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (11)..(11)
<223> OTHER INFORMATION: C-terminal amidation

<400> SEQUENCE: 56

Met Gly Tyr Ile Phe Tyr Pro Arg Lys Leu Arg
 1               5                  10

<210> SEQ ID NO 57
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: C-terminal amidation

<400> SEQUENCE: 57

Gly Tyr Ile Phe Tyr Pro Arg Lys Leu Arg
 1               5                  10
```

```
<210> SEQ ID NO 58
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(9)
<223> OTHER INFORMATION: C-terminal amidation

<400> SEQUENCE: 58

Tyr Ile Phe Tyr Pro Arg Lys Leu Arg
1               5

<210> SEQ ID NO 59
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 59

Met Arg Trp Gln Glu Met Gly Tyr Ile Phe Tyr Pro Arg Lys Leu
1               5                   10                  15

<210> SEQ ID NO 60
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (14)..(14)
<223> OTHER INFORMATION: C-terminal amidation

<400> SEQUENCE: 60

Met Arg Trp Gln Glu Met Gly Tyr Ile Phe Tyr Pro Arg Lys
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (13)..(13)
<223> OTHER INFORMATION: C-terminal amidation

<400> SEQUENCE: 61
```

```
Met Arg Trp Gln Glu Met Gly Tyr Ile Phe Tyr Pro Arg
1               5                   10
```

<210> SEQ ID NO 62
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (12)..(12)
<223> OTHER INFORMATION: C-terminal amidation

<400> SEQUENCE: 62

```
Met Arg Trp Gln Glu Met Gly Tyr Ile Phe Tyr Pro
1               5                   10
```

<210> SEQ ID NO 63
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (11)..(11)
<223> OTHER INFORMATION: C-terminal amidation

<400> SEQUENCE: 63

```
Met Arg Trp Gln Glu Met Gly Tyr Ile Phe Tyr
1               5                   10
```

<210> SEQ ID NO 64
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: C-terminal amidation

<400> SEQUENCE: 64

```
Met Arg Trp Gln Glu Met Gly Tyr Ile Phe
1               5                   10
```

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:

```
<221> NAME/KEY: MISC_FEATURE
<222> LOCATION: (9)..(9)
<223> OTHER INFORMATION: C-terminal amidation

<400> SEQUENCE: 65

Met Arg Trp Gln Glu Met Gly Tyr Ile
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is norleucine

<400> SEQUENCE: 66

Xaa Arg Trp Gln Glu Met Gly Tyr Ile Phe Tyr Pro Arg Lys Leu Arg
1               5                   10                  15

<210> SEQ ID NO 67
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: Xaa is norleucine

<400> SEQUENCE: 67

Met Arg Trp Gln Glu Xaa Gly Tyr Ile Phe Tyr Pro Arg Lys Leu Arg
1               5                   10                  15

<210> SEQ ID NO 68
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is norleucine
<220> FEATURE:
<221> NAME/KEY: MISC_FEATURE
<222> LOCATION: (6)..(6)
<223> OTHER INFORMATION: Xaa is norleucine

<400> SEQUENCE: 68

Xaa Arg Trp Gln Glu Xaa Gly Tyr Ile Phe Tyr Pro Arg Lys Leu Arg
1               5                   10                  15

<210> SEQ ID NO 69
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Acetylation

<400> SEQUENCE: 69

Met Arg Trp Gln Glu Met Gly Tyr Ile Phe Tyr Pro Arg Lys Leu Arg
```

<210> SEQ ID NO 70
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (14)..(14)
<223> OTHER INFORMATION: Acetylation

<400> SEQUENCE: 70

Met Arg Trp Gln Glu Met Gly Tyr Ile Phe Tyr Pro Arg Lys Leu Arg
1               5                   10                  15

<210> SEQ ID NO 71
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Acetylation
<220> FEATURE:
<221> NAME/KEY: MISC_FEATURE
<222> LOCATION: (16)..(16)
<223> OTHER INFORMATION: C-terminal amidation

<400> SEQUENCE: 71

Met Arg Trp Gln Glu Met Gly Tyr Ile Phe Tyr Pro Arg Lys Leu Arg
1               5                   10                  15

<210> SEQ ID NO 72
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (14)..(14)
<223> OTHER INFORMATION: Acetylation
<220> FEATURE:
<221> NAME/KEY: MISC_FEATURE
<222> LOCATION: (16)..(16)
<223> OTHER INFORMATION: C-terminal amidation

<400> SEQUENCE: 72

Met Arg Trp Gln Glu Met Gly Tyr Ile Phe Tyr Pro Arg Lys Leu Arg
1               5                   10                  15

<210> SEQ ID NO 73
<211> LENGTH: 16
<212> TYPE: PRT
<213> ORGANISM: Artificial Sequence
<220> FEATURE:
<223> OTHER INFORMATION: Synthetic peptide

<400> SEQUENCE: 73

Met Arg Trp Glu Glu Met Gly Tyr Ile Phe Tyr Pro Arg Lys Leu Arg
1               5                   10                  15

<210> SEQ ID NO 74
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 74

Met Arg Trp Glu Glu Met Gly Tyr Ile Phe Tyr Pro Arg Lys Leu Arg
1               5                   10                  15

<210> SEQ ID NO 75
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: C-terminal amidation

<400> SEQUENCE: 75

Met Arg Trp Glu Glu Met Gly Tyr Ile Phe Tyr Pro Arg Lys Leu Arg
1               5                   10                  15

<210> SEQ ID NO 76
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 76

Met Arg Trp Glu Glu Met Gly Tyr Ile Phe Tyr Pro Arg Lys Leu Arg
1               5                   10                  15

<210> SEQ ID NO 77
<211> LENGTH: 16
<212> TYPE: PRT
<213> ORGANISM: Artificial Sequence
<220> FEATURE:
<223> OTHER INFORMATION: Synthetic peptide

<400> SEQUENCE: 77

Met Gly Trp Gln Glu Met Gly Tyr Ile Phe Tyr Pro Arg Lys Leu Arg
1               5                   10                  15

<210> SEQ ID NO 78
<211> LENGTH: 11
<212> TYPE: PRT
<213> ORGANISM: Artificial Sequence
<220> FEATURE:
<223> OTHER INFORMATION: Synthetic peptide

<400> SEQUENCE: 78

Met Gly Tyr Ile Phe Tyr Pro Arg Lys Leu Arg
1               5                   10

<210> SEQ ID NO 79
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 79

Met Asp Trp Gln Glu Met Gly Tyr Ile Phe Tyr Pro Arg Lys Leu Arg
1               5                   10                  15

<210> SEQ ID NO 80
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 80

Met Arg Trp Gln Glu Met Gly Tyr Ile Phe Tyr Pro Asp Lys Leu Arg
1               5                   10                  15

<210> SEQ ID NO 81
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 81

Met Arg Trp Gln Glu Met Gly Tyr Ile Phe Tyr Pro Arg Lys Leu Asp
1               5                   10                  15

<210> SEQ ID NO 82
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

```
<220> FEATURE:
<221> NAME/KEY: MISC_FEATURE
<222> LOCATION: (16)..(16)
<223> OTHER INFORMATION: C-terminal amidation

<400> SEQUENCE: 82

Gly Arg Trp Gln Glu Met Gly Tyr Ile Phe Tyr Pro Arg Lys Leu Arg
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 83

Met Gly Trp Gln Glu Met Gly Tyr Ile Phe Tyr Pro Arg Lys Leu Arg
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 84

Met Arg Gly Gln Glu Met Gly Tyr Ile Phe Tyr Pro Arg Lys Leu Arg
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 85

Met Arg Trp Gly Glu Met Gly Tyr Ile Phe Tyr Pro Arg Lys Leu Arg
1               5                   10                  15

<210> SEQ ID NO 86
<211> LENGTH: 16
<212> TYPE: PRT
<213> ORGANISM: Artificial Sequence
<220> FEATURE:
```

<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 86

Met Arg Trp Gln Gly Met Gly Tyr Ile Phe Tyr Pro Arg Lys Leu Arg
1               5                   10                  15

<210> SEQ ID NO 87
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 87

Met Arg Trp Gln Glu Gly Gly Tyr Ile Phe Tyr Pro Arg Lys Leu Arg
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (7)..(7)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 88

Met Arg Trp Gln Glu Met Ala Tyr Ile Phe Tyr Pro Arg Lys Leu Arg
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 89

```
Met Arg Trp Gln Glu Met Gly Gly Ile Phe Tyr Pro Arg Lys Leu Arg
1               5                   10                  15
```

<210> SEQ ID NO 90
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 90

```
Met Arg Trp Gln Glu Met Gly Tyr Gly Phe Tyr Pro Arg Lys Leu Arg
1               5                   10                  15
```

<210> SEQ ID NO 91
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 91

```
Met Arg Trp Gln Glu Met Gly Tyr Ile Gly Tyr Pro Arg Lys Leu Arg
1               5                   10                  15
```

<210> SEQ ID NO 92
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 92

```
Met Arg Trp Gln Glu Met Gly Tyr Ile Phe Gly Pro Arg Lys Leu Arg
1               5                   10                  15
```

<210> SEQ ID NO 93
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE

```
<222> LOCATION: (16)..(16)
<223> OTHER INFORMATION: C-terminal amidation

<400> SEQUENCE: 93

Met Arg Trp Gln Glu Met Gly Tyr Ile Phe Tyr Gly Arg Lys Leu Arg
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 94

Met Arg Trp Gln Glu Met Gly Tyr Ile Phe Tyr Pro Gly Lys Leu Arg
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 95

Met Arg Trp Gln Glu Met Gly Tyr Ile Phe Tyr Pro Arg Gly Leu Arg
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 96

Met Arg Trp Gln Glu Met Gly Tyr Ile Phe Tyr Pro Arg Lys Gly Arg
1               5                   10                  15

<210> SEQ ID NO 97
<211> LENGTH: 16
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 97

Met Arg Trp Gln Glu Met Gly Tyr Ile Phe Tyr Pro Arg Lys Leu Gly
1               5                   10                  15

<210> SEQ ID NO 98
<211> LENGTH: 33
<212> TYPE: PRT
<213> ORGANISM: Artificial Sequence
<220> FEATURE:
<223> OTHER INFORMATION: Synthetic peptide

<400> SEQUENCE: 98

Met Arg Trp Gln Glu Met Gly Tyr Ile Phe Tyr Pro Arg Lys Leu Arg
1               5                   10                  15

Pro Arg Gly Phe Ser Cys Leu Leu Leu Thr Gly Glu Ile Asp Leu
            20                  25                  30

Pro

<210> SEQ ID NO 99
<211> LENGTH: 33
<212> TYPE: PRT
<213> ORGANISM: Artificial Sequence
<220> FEATURE:
<223> OTHER INFORMATION: Synthetic peptide

<400> SEQUENCE: 99

Pro Arg Gly Phe Ser Cys Leu Leu Leu Thr Gly Glu Ile Asp Leu
1               5                   10                  15

Pro Met Arg Trp Gln Glu Met Gly Tyr Ile Phe Tyr Pro Arg Lys Leu
            20                  25                  30

Arg

<210> SEQ ID NO 100
<211> LENGTH: 28
<212> TYPE: PRT
<213> ORGANISM: Artificial Sequence
<220> FEATURE:
<223> OTHER INFORMATION: Synthetic peptide

<400> SEQUENCE: 100

Met Arg Trp Gln Glu Met Gly Tyr Ile Phe Tyr Pro Arg Gly Phe Ser
1               5                   10                  15

Cys Leu Leu Leu Thr Gly Glu Ile Asp Leu Pro
            20                  25

<210> SEQ ID NO 101
<211> LENGTH: 28
<212> TYPE: PRT
<213> ORGANISM: Artificial Sequence
<220> FEATURE:
<223> OTHER INFORMATION: Synthetic peptide

<400> SEQUENCE: 101

Pro Arg Gly Phe Ser Cys Leu Leu Leu Thr Gly Glu Ile Asp Leu
1               5                   10                  15

Pro Met Arg Trp Gln Glu Met Gly Tyr Ile Phe Tyr
```

```
                        20                  25

<210> SEQ ID NO 102
<211> LENGTH: 35
<212> TYPE: PRT
<213> ORGANISM: Artificial Sequence
<220> FEATURE:
<223> OTHER INFORMATION: Synthetic peptide

<400> SEQUENCE: 102

Met Arg Trp Gln Glu Met Gly Tyr Ile Phe Tyr Met Ala Pro Arg Gly
1               5                   10                  15

Phe Ser Cys Leu Leu Leu Leu Thr Gly Glu Ile Asp Leu Pro Val Lys
            20                  25                  30

Arg Arg Ala
        35

<210> SEQ ID NO 103
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Phospho-Tyr

<400> SEQUENCE: 103

Met Arg Trp Gln Glu Met Gly Tyr Ile Phe Tyr Pro Arg Lys Leu Arg
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: Phospho-Tyr

<400> SEQUENCE: 104

Met Arg Trp Gln Glu Met Gly Tyr Ile Phe Tyr Pro Arg Lys Leu Arg
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal palmitoyl

<400> SEQUENCE: 105

Met Arg Trp Gln Glu Met Gly Tyr Ile Phe Tyr Pro Arg Lys Leu Arg
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (14)..(14)
<223> OTHER INFORMATION: Palmitoylation

<400> SEQUENCE: 106

Met Arg Trp Gln Glu Met Gly Tyr Ile Phe Tyr Pro Arg Lys Leu Arg
1               5                   10                  15

<210> SEQ ID NO 107
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Palmitoylation via Glu linker

<400> SEQUENCE: 107

Met Arg Trp Gln Glu Met Gly Tyr Ile Phe Tyr Pro Arg Lys Leu Arg
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 108

Leu Arg Trp Gln Glu Met Gly Tyr Ile Phe Tyr Pro Arg Lys Leu Arg
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 109

Leu Arg Trp Gln Glu Met Gly Tyr Ile Phe Tyr Pro Leu Arg Lys Arg
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

```
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 110

Leu Arg Trp Gln Glu Met Gly Tyr Ile Phe Tyr Pro Arg Leu Lys Arg
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 111

Leu Arg Trp Gln Glu Met Gly Tyr Ile Phe Tyr Pro Arg Lys Arg Leu
1               5                   10                  15

<210> SEQ ID NO 112
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 112

Leu Lys Trp Gln Glu Met Gly Tyr Ile Phe Tyr Pro Arg Lys Leu Arg
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 113

Leu Lys Trp Gln Glu Met Gly Tyr Ile Phe Tyr Pro Leu Arg Lys Arg
1               5                   10                  15

<210> SEQ ID NO 114
<211> LENGTH: 16
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 114

Leu Lys Trp Gln Glu Met Gly Tyr Ile Phe Tyr Pro Arg Leu Lys Arg
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 115

Leu Lys Trp Gln Glu Met Gly Tyr Ile Phe Tyr Pro Arg Lys Arg Leu
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 116

Leu Arg Trp Gln Glu Met Gly Tyr Ile Phe Tyr Pro Arg Lys Arg
1               5                   10                  15

<210> SEQ ID NO 117
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: C-terminal amidation

<400> SEQUENCE: 117

Leu Lys Trp Gln Glu Met Gly Tyr Ile Phe Tyr Pro Arg Lys Arg
1               5                   10                  15
```

```
<210> SEQ ID NO 118
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Aib

<400> SEQUENCE: 118

Met Xaa Trp Gln Glu Met Gly Tyr Ile Phe Tyr Pro Arg Lys Leu Arg
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (16)..(16)
<223> OTHER INFORMATION: C-terminal amidation

<400> SEQUENCE: 119

Met Xaa Trp Gln Glu Met Gly Tyr Ile Phe Tyr Pro Arg Lys Leu Arg
1               5                   10                  15

<210> SEQ ID NO 120
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: Xaa is Aib

<400> SEQUENCE: 120

Met Xaa Trp Gln Glu Met Gly Tyr Ile Phe Tyr Pro Arg Lys Leu Arg
1               5                   10                  15

<210> SEQ ID NO 121
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (2)..(2)
<223> OTHER INFORMATION: Xaa is Aib
<220> FEATURE:
<221> NAME/KEY: MISC_FEATURE
<222> LOCATION: (16)..(16)
<223> OTHER INFORMATION: C-terminal amidation
```

<400> SEQUENCE: 121

Met Xaa Trp Gln Glu Met Gly Tyr Ile Phe Tyr Pro Arg Lys Leu Arg
1               5                   10                  15

<210> SEQ ID NO 122
<211> LENGTH: 16
<212> TYPE: PRT
<213> ORGANISM: Artificial Sequence
<220> FEATURE:
<223> OTHER INFORMATION: Synthetic peptide

<400> SEQUENCE: 122

Met Lys Trp Gln Glu Met Gly Tyr Ile Phe Tyr Pro Arg Lys Leu Arg
1               5                   10                  15

<210> SEQ ID NO 123
<211> LENGTH: 16
<212> TYPE: PRT
<213> ORGANISM: Artificial Sequence
<220> FEATURE:
<223> OTHER INFORMATION: Synthetic peptide

<400> SEQUENCE: 123

Met Arg Trp Gln Glu Met Gly Tyr Ile Phe Tyr Pro Lys Lys Leu Arg
1               5                   10                  15

<210> SEQ ID NO 124
<211> LENGTH: 16
<212> TYPE: PRT
<213> ORGANISM: Artificial Sequence
<220> FEATURE:
<223> OTHER INFORMATION: Synthetic peptide

<400> SEQUENCE: 124

Met Arg Trp Gln Glu Met Gly Tyr Ile Phe Tyr Pro Arg Lys Leu Lys
1               5                   10                  15

<210> SEQ ID NO 125
<211> LENGTH: 16
<212> TYPE: PRT
<213> ORGANISM: Artificial Sequence
<220> FEATURE:
<223> OTHER INFORMATION: Synthetic peptide

<400> SEQUENCE: 125

Met Arg Trp Gln Glu Met Gly Tyr Ile Phe Tyr Pro Arg Arg Leu Arg
1               5                   10                  15

<210> SEQ ID NO 126
<211> LENGTH: 16
<212> TYPE: PRT
<213> ORGANISM: Artificial Sequence
<220> FEATURE:
<223> OTHER INFORMATION: Synthetic peptide

<400> SEQUENCE: 126

Met Arg Trp Gln Asp Met Gly Tyr Ile Phe Tyr Pro Arg Arg Leu Arg
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Synthetic peptide

<400> SEQUENCE: 127

```
Met Arg Trp Asn Glu Met Gly Tyr Ile Phe Tyr Pro Arg Lys Leu Arg
1               5                   10                  15

<210> SEQ ID NO 128
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 128

Met Lys Trp Gln Glu Met Gly Tyr Ile Phe Tyr Pro Arg Lys Leu Arg
1               5                   10                  15

<210> SEQ ID NO 129
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 129

Met Arg Trp Gln Glu Met Gly Tyr Ile Phe Tyr Pro Lys Lys Leu Arg
1               5                   10                  15

<210> SEQ ID NO 130
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 130

Met Arg Trp Gln Glu Met Gly Tyr Ile Phe Tyr Pro Arg Lys Leu Lys
1               5                   10                  15

<210> SEQ ID NO 131
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
```

```
<221> NAME/KEY: MISC_FEATURE
<222> LOCATION: (16)..(16)
<223> OTHER INFORMATION: C-terminal amidation

<400> SEQUENCE: 131

Met Arg Trp Gln Glu Met Gly Tyr Ile Phe Tyr Pro Arg Arg Leu Arg
1               5                   10                  15

<210> SEQ ID NO 132
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 132

Met Arg Trp Gln Asp Met Gly Tyr Ile Phe Tyr Pro Arg Arg Leu Arg
1               5                   10                  15

<210> SEQ ID NO 133
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 133

Met Arg Trp Asn Glu Met Gly Tyr Ile Phe Tyr Pro Arg Lys Leu Arg
1               5                   10                  15

<210> SEQ ID NO 134
<211> LENGTH: 16
<212> TYPE: PRT
<213> ORGANISM: Artificial Sequence
<220> FEATURE:
<223> OTHER INFORMATION: Synthetic peptide

<400> SEQUENCE: 134

Met Arg Trp Gln Glu Met Gly Glu Ile Phe Glu Pro Arg Lys Leu Arg
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation
```

<400> SEQUENCE: 135

Met Arg Trp Gln Glu Met Gly Glu Ile Phe Glu Pro Arg Lys Leu Arg
1               5                   10                  15

<210> SEQ ID NO 136
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 136

Ala Arg Trp Gln Glu Met Gly Tyr Ile Phe Tyr Pro Arg Lys Leu Arg
1               5                   10                  15

<210> SEQ ID NO 137
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: D-Ala

<400> SEQUENCE: 137

Met Ala Trp Gln Glu Met Gly Tyr Ile Phe Tyr Pro Arg Lys Leu Arg
1               5                   10                  15

<210> SEQ ID NO 138
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: D-Ala

<400> SEQUENCE: 138

Met Arg Ala Gln Glu Met Gly Tyr Ile Phe Tyr Pro Arg Lys Leu Arg
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: D-Ala

<400> SEQUENCE: 139

Met Arg Trp Ala Glu Met Gly Tyr Ile Phe Tyr Pro Arg Lys Leu Arg
1               5                   10                  15

<210> SEQ ID NO 140
<211> LENGTH: 16
<212> TYPE: PRT
<213> ORGANISM: Artificial Sequence

```
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: D-Ala

<400> SEQUENCE: 140

Met Arg Trp Gln Ala Met Gly Tyr Ile Phe Tyr Pro Arg Lys Leu Arg
1               5                   10                  15

<210> SEQ ID NO 141
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (6)..(6)
<223> OTHER INFORMATION: D-Ala

<400> SEQUENCE: 141

Met Arg Trp Gln Glu Ala Gly Tyr Ile Phe Tyr Pro Arg Lys Leu Arg
1               5                   10                  15

<210> SEQ ID NO 142
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: D-Ala

<400> SEQUENCE: 142

Met Arg Trp Gln Glu Met Ala Tyr Ile Phe Tyr Pro Arg Lys Leu Arg
1               5                   10                  15

<210> SEQ ID NO 143
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: D-Ala

<400> SEQUENCE: 143

Met Arg Trp Gln Glu Met Gly Ala Ile Phe Tyr Pro Arg Lys Leu Arg
1               5                   10                  15

<210> SEQ ID NO 144
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: D-Ala

<400> SEQUENCE: 144

Met Arg Trp Gln Glu Met Gly Tyr Ala Phe Tyr Pro Arg Lys Leu Arg
1               5                   10                  15
```

<210> SEQ ID NO 145
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (10)..(10)
<223> OTHER INFORMATION: D-Ala

<400> SEQUENCE: 145

Met Arg Trp Gln Glu Met Gly Tyr Ile Ala Tyr Pro Arg Lys Leu Arg
1               5                   10                  15

<210> SEQ ID NO 146
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: D-Ala

<400> SEQUENCE: 146

Met Arg Trp Gln Glu Met Gly Tyr Ile Phe Ala Pro Arg Lys Leu Arg
1               5                   10                  15

<210> SEQ ID NO 147
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: D-Ala

<400> SEQUENCE: 147

Met Arg Trp Gln Glu Met Gly Tyr Ile Phe Tyr Ala Arg Lys Leu Arg
1               5                   10                  15

<210> SEQ ID NO 148
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: D-Ala

<400> SEQUENCE: 148

Met Arg Trp Gln Glu Met Gly Tyr Ile Phe Tyr Pro Ala Lys Leu Arg
1               5                   10                  15

<210> SEQ ID NO 149
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)

<223> OTHER INFORMATION: D-Ala

<400> SEQUENCE: 149

Met Arg Trp Gln Glu Met Gly Tyr Ile Phe Tyr Pro Arg Ala Leu Arg
1               5                   10                  15

<210> SEQ ID NO 150
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: D-Ala

<400> SEQUENCE: 150

Met Arg Trp Gln Glu Met Gly Tyr Ile Phe Tyr Pro Arg Lys Ala Arg
1               5                   10                  15

<210> SEQ ID NO 151
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Ala

<400> SEQUENCE: 151

Met Arg Trp Gln Glu Met Gly Tyr Ile Phe Tyr Pro Arg Lys Leu Ala
1               5                   10                  15

<210> SEQ ID NO 152
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 152

Ala Arg Trp Gln Glu Met Gly Tyr Ile Phe Tyr Pro Arg Lys Leu Arg
1               5                   10                  15

<210> SEQ ID NO 153
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE

```
<222> LOCATION: (2)..(2)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 153

Met Ala Trp Gln Glu Met Gly Tyr Ile Phe Tyr Pro Arg Lys Leu Arg
1               5                   10                  15

<210> SEQ ID NO 154
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (3)..(3)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 154

Met Arg Ala Gln Glu Met Gly Tyr Ile Phe Tyr Pro Arg Lys Leu Arg
1               5                   10                  15

<210> SEQ ID NO 155
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (4)..(4)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 155

Met Arg Trp Ala Glu Met Gly Tyr Ile Phe Tyr Pro Arg Lys Leu Arg
1               5                   10                  15

<210> SEQ ID NO 156
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(5)
<223> OTHER INFORMATION: D-Ala
<220> FEATURE:
<221> NAME/KEY: MISC_FEATURE
```

```
<222> LOCATION: (16)..(16)
<223> OTHER INFORMATION: C-terminal amidation

<400> SEQUENCE: 156

Met Arg Trp Gln Ala Met Gly Tyr Ile Phe Tyr Pro Arg Lys Leu Arg
1               5                   10                  15

<210> SEQ ID NO 157
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (6)..(6)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 157

Met Arg Trp Gln Glu Ala Gly Tyr Ile Phe Tyr Pro Arg Lys Leu Arg
1               5                   10                  15

<210> SEQ ID NO 158
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (7)..(7)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 158

Met Arg Trp Gln Glu Met Ala Tyr Ile Phe Tyr Pro Arg Lys Leu Arg
1               5                   10                  15

<210> SEQ ID NO 159
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (8)..(8)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 159
```

```
Met Arg Trp Gln Glu Met Gly Ala Ile Phe Tyr Pro Arg Lys Leu Arg
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (9)..(9)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 160

Met Arg Trp Gln Glu Met Gly Tyr Ala Phe Tyr Pro Arg Lys Leu Arg
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (10)..(10)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 161

Met Arg Trp Gln Glu Met Gly Tyr Ile Ala Tyr Pro Arg Lys Leu Arg
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (11)..(11)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 162

Met Arg Trp Gln Glu Met Gly Tyr Ile Phe Ala Pro Arg Lys Leu Arg
1               5                   10                  15
```

```
<210> SEQ ID NO 163
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (12)..(12)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 163

Met Arg Trp Gln Glu Met Gly Tyr Ile Phe Tyr Ala Arg Lys Leu Arg
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (13)..(13)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 164

Met Arg Trp Gln Glu Met Gly Tyr Ile Phe Tyr Pro Ala Lys Leu Arg
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (14)..(14)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 165

Met Arg Trp Gln Glu Met Gly Tyr Ile Phe Tyr Pro Arg Ala Leu Arg
1               5                   10                  15

<210> SEQ ID NO 166
<211> LENGTH: 16
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 166

Met Arg Trp Gln Glu Met Gly Tyr Ile Phe Tyr Pro Arg Lys Ala Arg
1               5                   10                  15

<210> SEQ ID NO 167
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: D-Ala
<220> FEATURE:
<221> NAME/KEY: MISC_FEATURE
<222> LOCATION: (16)..(16)
<223> OTHER INFORMATION: C-terminal amidation

<400> SEQUENCE: 167

Met Arg Trp Gln Glu Met Gly Tyr Ile Phe Tyr Pro Arg Lys Leu Ala
1               5                   10                  15

<210> SEQ ID NO 168
<211> LENGTH: 16
<212> TYPE: PRT
<213> ORGANISM: Artificial Sequence
<220> FEATURE:
<223> OTHER INFORMATION: Synthetic peptide

<400> SEQUENCE: 168

Glu Arg Trp Gln Glu Met Gly Tyr Ile Phe Tyr Pro Arg Lys Leu Arg
1               5                   10                  15

<210> SEQ ID NO 169
<211> LENGTH: 16
<212> TYPE: PRT
<213> ORGANISM: Artificial Sequence
<220> FEATURE:
<223> OTHER INFORMATION: Synthetic peptide

<400> SEQUENCE: 169

Met Glu Trp Gln Glu Met Gly Tyr Ile Phe Tyr Pro Arg Lys Leu Arg
1               5                   10                  15

<210> SEQ ID NO 170
<211> LENGTH: 16
<212> TYPE: PRT
<213> ORGANISM: Artificial Sequence
<220> FEATURE:
<223> OTHER INFORMATION: Synthetic peptide
```

<400> SEQUENCE: 170

Met Arg Glu Gln Glu Met Gly Tyr Ile Phe Tyr Pro Arg Lys Leu Arg
1               5                   10                  15

<210> SEQ ID NO 171
<211> LENGTH: 16
<212> TYPE: PRT
<213> ORGANISM: Artificial Sequence
<220> FEATURE:
<223> OTHER INFORMATION: Synthetic peptide

<400> SEQUENCE: 171

Met Arg Trp Glu Glu Met Gly Tyr Ile Phe Tyr Pro Arg Lys Leu Arg
1               5                   10                  15

<210> SEQ ID NO 172
<211> LENGTH: 16
<212> TYPE: PRT
<213> ORGANISM: Artificial Sequence
<220> FEATURE:
<223> OTHER INFORMATION: Synthetic peptide

<400> SEQUENCE: 172

Met Arg Trp Gln Glu Glu Gly Tyr Ile Phe Tyr Pro Arg Lys Leu Arg
1               5                   10                  15

<210> SEQ ID NO 173
<211> LENGTH: 16
<212> TYPE: PRT
<213> ORGANISM: Artificial Sequence
<220> FEATURE:
<223> OTHER INFORMATION: Synthetic peptide

<400> SEQUENCE: 173

Met Arg Trp Gln Glu Met Glu Tyr Ile Phe Tyr Pro Arg Lys Leu Arg
1               5                   10                  15

<210> SEQ ID NO 174
<211> LENGTH: 16
<212> TYPE: PRT
<213> ORGANISM: Artificial Sequence
<220> FEATURE:
<223> OTHER INFORMATION: Synthetic peptide

<400> SEQUENCE: 174

Met Arg Trp Gln Glu Met Gly Glu Ile Phe Tyr Pro Arg Lys Leu Arg
1               5                   10                  15

<210> SEQ ID NO 175
<211> LENGTH: 16
<212> TYPE: PRT
<213> ORGANISM: Artificial Sequence
<220> FEATURE:
<223> OTHER INFORMATION: Synthetic peptide

<400> SEQUENCE: 175

Met Arg Trp Gln Glu Met Gly Tyr Glu Phe Tyr Pro Arg Lys Leu Arg
1               5                   10                  15

<210> SEQ ID NO 176
<211> LENGTH: 16
<212> TYPE: PRT
<213> ORGANISM: Artificial Sequence
<220> FEATURE:
<223> OTHER INFORMATION: Synthetic peptide

<400> SEQUENCE: 176

Met Arg Trp Gln Glu Met Gly Tyr Ile Glu Tyr Pro Arg Lys Leu Arg
1               5                   10                  15

<210> SEQ ID NO 177
<211> LENGTH: 16
<212> TYPE: PRT
<213> ORGANISM: Artificial Sequence
<220> FEATURE:
<223> OTHER INFORMATION: Synthetic peptide

<400> SEQUENCE: 177

Met Arg Trp Gln Glu Met Gly Tyr Ile Phe Glu Pro Arg Lys Leu Arg
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: Synthetic peptide

<400> SEQUENCE: 178

Met Arg Trp Gln Glu Met Gly Tyr Ile Phe Tyr Glu Arg Lys Leu Arg
1               5                   10                  15

<210> SEQ ID NO 179
<211> LENGTH: 16
<212> TYPE: PRT
<213> ORGANISM: Artificial Sequence
<220> FEATURE:
<223> OTHER INFORMATION: Synthetic peptide

<400> SEQUENCE: 179

Met Arg Trp Gln Glu Met Gly Tyr Ile Phe Tyr Pro Glu Lys Leu Arg
1               5                   10                  15

<210> SEQ ID NO 180
<211> LENGTH: 16
<212> TYPE: PRT
<213> ORGANISM: Artificial Sequence
<220> FEATURE:
<223> OTHER INFORMATION: Synthetic peptide

<400> SEQUENCE: 180

Met Arg Trp Gln Glu Met Gly Tyr Ile Phe Tyr Pro Arg Glu Leu Arg
1               5                   10                  15

<210> SEQ ID NO 181
<211> LENGTH: 16
<212> TYPE: PRT
<213> ORGANISM: Artificial Sequence
<220> FEATURE:
<223> OTHER INFORMATION: Synthetic peptide

<400> SEQUENCE: 181

Met Arg Trp Gln Glu Met Gly Tyr Ile Phe Tyr Pro Arg Lys Glu Arg
1               5                   10                  15

<210> SEQ ID NO 182
<211> LENGTH: 16
<212> TYPE: PRT
<213> ORGANISM: Artificial Sequence
<220> FEATURE:
<223> OTHER INFORMATION: Synthetic peptide

<400> SEQUENCE: 182

```
Met Arg Trp Gln Glu Met Gly Tyr Ile Phe Tyr Pro Arg Lys Leu Glu
1               5                   10                  15

<210> SEQ ID NO 183
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 183

Glu Arg Trp Gln Glu Met Gly Tyr Ile Phe Tyr Pro Arg Lys Leu Arg
1               5                   10                  15

<210> SEQ ID NO 184
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 184

Met Glu Trp Gln Glu Met Gly Tyr Ile Phe Tyr Pro Arg Lys Leu Arg
1               5                   10                  15

<210> SEQ ID NO 185
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 185

Met Arg Glu Gln Glu Met Gly Tyr Ile Phe Tyr Pro Arg Lys Leu Arg
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
```

```
<221> NAME/KEY: MISC_FEATURE
<222> LOCATION: (16)..(16)
<223> OTHER INFORMATION: C-terminal amidation

<400> SEQUENCE: 186

Met Arg Trp Glu Glu Met Gly Tyr Ile Phe Tyr Pro Arg Lys Leu Arg
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 187

Met Arg Trp Gln Glu Glu Gly Tyr Ile Phe Tyr Pro Arg Lys Leu Arg
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 188

Met Arg Trp Gln Glu Met Glu Tyr Ile Phe Tyr Pro Arg Lys Leu Arg
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 189

Met Arg Trp Gln Glu Met Gly Glu Ile Phe Tyr Pro Arg Lys Leu Arg
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Synthetic peptide
```

<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 190

Met Arg Trp Gln Glu Met Gly Tyr Glu Phe Tyr Pro Arg Lys Leu Arg
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 191

Met Arg Trp Gln Glu Met Gly Tyr Ile Glu Tyr Pro Arg Lys Leu Arg
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 192

Met Arg Trp Gln Glu Met Gly Tyr Ile Phe Glu Pro Arg Lys Leu Arg
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 193

Met Arg Trp Gln Glu Met Gly Tyr Ile Phe Tyr Glu Arg Lys Leu Arg
1               5                   10                  15

<210> SEQ ID NO 194

```
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 194

Met Arg Trp Gln Glu Met Gly Tyr Ile Phe Tyr Pro Glu Lys Leu Arg
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 195

Met Arg Trp Gln Glu Met Gly Tyr Ile Phe Tyr Pro Arg Glu Leu Arg
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 196

Met Arg Trp Gln Glu Met Gly Tyr Ile Phe Tyr Pro Arg Lys Glu Arg
1               5                   10                  15

<210> SEQ ID NO 197
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (16)..(16)
<223> OTHER INFORMATION: C-terminal amidation

<400> SEQUENCE: 197
```

```
Met Arg Trp Gln Glu Met Gly Tyr Ile Phe Tyr Pro Arg Lys Leu Glu
1               5                   10                  15

<210> SEQ ID NO 198
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: Xaa is alpha, alpha-diethylglycine

<400> SEQUENCE: 198

Met Arg Trp Gln Glu Met Gly Tyr Ile Phe Tyr Pro Arg Lys Xaa Arg
1               5                   10                  15

<210> SEQ ID NO 199
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: Xaa is alpha, alpha-diethylglycine

<400> SEQUENCE: 199

Met Arg Trp Gln Glu Met Gly Tyr Ile Phe Tyr Pro Arg Lys Xaa Arg
1               5                   10                  15

<210> SEQ ID NO 200
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (15)..(15)
<223> OTHER INFORMATION: Xaa is alpha, alpha-diethylglycine
<220> FEATURE:
<221> NAME/KEY: MISC_FEATURE
<222> LOCATION: (16)..(16)
<223> OTHER INFORMATION: C-terminal amidation

<400> SEQUENCE: 200

Met Arg Trp Gln Glu Met Gly Tyr Ile Phe Tyr Pro Arg Lys Xaa Arg
1               5                   10                  15

<210> SEQ ID NO 201
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (15)..(15)
<223> OTHER INFORMATION: Xaa is alpha, alpha-diethylglycine
<220> FEATURE:
<221> NAME/KEY: MISC_FEATURE
```

```
<222> LOCATION: (16)..(16)
<223> OTHER INFORMATION: C-terminal amidation

<400> SEQUENCE: 201

Met Arg Trp Gln Glu Met Gly Tyr Ile Phe Tyr Pro Arg Lys Xaa Arg
1               5                   10                  15

<210> SEQ ID NO 202
<211> LENGTH: 13
<212> TYPE: PRT
<213> ORGANISM: Artificial Sequence
<220> FEATURE:
<223> OTHER INFORMATION: Synthetic peptide

<400> SEQUENCE: 202

Met Arg Trp Gln Glu Met Gly Tyr Ile Phe Tyr Pro Arg
1               5                   10

<210> SEQ ID NO 203
<211> LENGTH: 14
<212> TYPE: PRT
<213> ORGANISM: Artificial Sequence
<220> FEATURE:
<223> OTHER INFORMATION: Synthetic peptide

<400> SEQUENCE: 203

Met Arg Trp Gln Glu Met Gly Tyr Ile Phe Tyr Pro Arg Asn
1               5                   10

<210> SEQ ID NO 204
<211> LENGTH: 14
<212> TYPE: PRT
<213> ORGANISM: Artificial Sequence
<220> FEATURE:
<223> OTHER INFORMATION: Synthetic peptide

<400> SEQUENCE: 204

Met Arg Trp Gln Glu Met Gly Tyr Ile Phe Tyr Pro Arg Gln
1               5                   10

<210> SEQ ID NO 205
<211> LENGTH: 12
<212> TYPE: PRT
<213> ORGANISM: Artificial Sequence
<220> FEATURE:
<223> OTHER INFORMATION: Synthetic peptide

<400> SEQUENCE: 205

Arg Trp Gln Glu Met Gly Tyr Ile Phe Tyr Pro Arg
1               5                   10

<210> SEQ ID NO 206
<211> LENGTH: 13
<212> TYPE: PRT
<213> ORGANISM: Artificial Sequence
<220> FEATURE:
<223> OTHER INFORMATION: Synthetic peptide

<400> SEQUENCE: 206

Arg Trp Gln Glu Met Gly Tyr Ile Phe Tyr Pro Arg Asn
1               5                   10

<210> SEQ ID NO 207
<211> LENGTH: 13
<212> TYPE: PRT
<213> ORGANISM: Artificial Sequence
<220> FEATURE:
```

<223> OTHER INFORMATION: Synthetic peptide

<400> SEQUENCE: 207

Arg Trp Gln Glu Met Gly Tyr Ile Phe Tyr Pro Arg Gln
1               5                   10

<210> SEQ ID NO 208
<211> LENGTH: 13
<212> TYPE: PRT
<213> ORGANISM: Artificial Sequence
<220> FEATURE:
<223> OTHER INFORMATION: Synthetic peptide

<400> SEQUENCE: 208

Met Arg Trp Gln Glu Met Asn Tyr Ile Phe Tyr Pro Arg
1               5                   10

<210> SEQ ID NO 209
<211> LENGTH: 13
<212> TYPE: PRT
<213> ORGANISM: Artificial Sequence
<220> FEATURE:
<223> OTHER INFORMATION: Synthetic peptide

<400> SEQUENCE: 209

Met Arg Trp Gln Glu Met Gln Tyr Ile Phe Tyr Pro Arg
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Synthetic peptide

<400> SEQUENCE: 210

Arg Trp Gln Glu Met Asn Tyr Ile Phe Tyr Pro Arg
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Synthetic peptide

<400> SEQUENCE: 211

Arg Trp Gln Glu Met Gln Tyr Ile Phe Tyr Pro Arg
1               5                   10

<210> SEQ ID NO 212
<211> LENGTH: 16
<212> TYPE: PRT
<213> ORGANISM: Artificial Sequence
<220> FEATURE:
<223> OTHER INFORMATION: Synthetic peptide

<400> SEQUENCE: 212

Met Arg Trp Gln Glu Met Gly Tyr Ile Phe Tyr Pro Arg Ala Leu Arg
1               5                   10                  15

<210> SEQ ID NO 213
<211> LENGTH: 16
<212> TYPE: PRT
<213> ORGANISM: Artificial Sequence
<220> FEATURE:
<223> OTHER INFORMATION: Synthetic peptide

<400> SEQUENCE: 213

Met Arg Trp Gln Glu Met Gly Tyr Ile Phe Tyr Pro Arg Asn Leu Arg
1               5                   10                  15

<210> SEQ ID NO 214
<211> LENGTH: 16
<212> TYPE: PRT
<213> ORGANISM: Artificial Sequence
<220> FEATURE:
<223> OTHER INFORMATION: Synthetic peptide

<400> SEQUENCE: 214

Met Arg Trp Gln Glu Met Gly Tyr Ile Phe Tyr Pro Arg Gln Leu Arg
1               5                   10                  15

<210> SEQ ID NO 215
<211> LENGTH: 15
<212> TYPE: PRT
<213> ORGANISM: Artificial Sequence
<220> FEATURE:
<223> OTHER INFORMATION: Synthetic peptide

<400> SEQUENCE: 215

Arg Trp Gln Glu Met Gly Tyr Ile Phe Tyr Pro Arg Ala Leu Arg
1               5                   10                  15

<210> SEQ ID NO 216
<211> LENGTH: 15
<212> TYPE: PRT
<213> ORGANISM: Artificial Sequence
<220> FEATURE:
<223> OTHER INFORMATION: Synthetic peptide

<400> SEQUENCE: 216

Arg Trp Gln Glu Met Gly Tyr Ile Phe Tyr Pro Arg Asn Leu Arg
1               5                   10                  15

<210> SEQ ID NO 217
<211> LENGTH: 15
<212> TYPE: PRT
<213> ORGANISM: Artificial Sequence
<220> FEATURE:
<223> OTHER INFORMATION: Synthetic peptide

<400> SEQUENCE: 217

Arg Trp Gln Glu Met Gly Tyr Ile Phe Tyr Pro Arg Gln Leu Arg
1               5                   10                  15

<210> SEQ ID NO 218
<211> LENGTH: 16
<212> TYPE: PRT
<213> ORGANISM: Artificial Sequence
<220> FEATURE:
<223> OTHER INFORMATION: Synthetic peptide

<400> SEQUENCE: 218

Met Arg Trp Gln Glu Met Asn Tyr Ile Phe Tyr Pro Arg Ala Leu Arg
1               5                   10                  15

<210> SEQ ID NO 219
<211> LENGTH: 16
<212> TYPE: PRT
<213> ORGANISM: Artificial Sequence
<220> FEATURE:
<223> OTHER INFORMATION: Synthetic peptide

```
<400> SEQUENCE: 219

Met Arg Trp Gln Glu Met Gln Tyr Ile Phe Tyr Pro Arg Ala Leu Arg
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: DISULFID
<222> LOCATION: (6)..(12)
<223> OTHER INFORMATION: Cyclization

<400> SEQUENCE: 220

Met Arg Trp Gln Glu Cys Gly Tyr Ile Phe Tyr Cys Arg Lys Leu Arg
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (6)..(12)
<223> OTHER INFORMATION: Lactam bridge

<400> SEQUENCE: 221

Met Arg Trp Gln Glu Glu Gly Tyr Ile Phe Tyr Lys Arg Lys Leu Arg
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (5)..(14)
<223> OTHER INFORMATION: Lactam ring

<400> SEQUENCE: 222

Met Arg Trp Gln Glu Met Gly Tyr Ile Phe Tyr Pro Arg Lys Leu Arg
1               5                   10                  15

<210> SEQ ID NO 223
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (4)..(12)
<223> OTHER INFORMATION: Lactam ring
```

-continued

<400> SEQUENCE: 223

Met Arg Trp Glu Glu Met Gly Tyr Ile Phe Tyr Lys Arg Lys Leu Arg
1               5                   10                  15

<210> SEQ ID NO 224
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (5)..(12)
<223> OTHER INFORMATION: Lactam ring

<400> SEQUENCE: 224

Met Arg Trp Gln Glu Met Gly Tyr Ile Phe Tyr Lys Arg Lys Leu Arg
1               5                   10                  15

<210> SEQ ID NO 225
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: DISULFID
<222> LOCATION: (6)..(12)
<223> OTHER INFORMATION: Cyclization
<220> FEATURE:
<221> NAME/KEY: MISC_FEATURE
<222> LOCATION: (16)..(16)
<223> OTHER INFORMATION: C-terminal amidation

<400> SEQUENCE: 225

Met Arg Trp Gln Glu Cys Gly Tyr Ile Phe Tyr Cys Arg Lys Leu Arg
1               5                   10                  15

<210> SEQ ID NO 226
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (6)..(12)
<223> OTHER INFORMATION: Lactam ring
<220> FEATURE:
<221> NAME/KEY: MISC_FEATURE
<222> LOCATION: (16)..(16)
<223> OTHER INFORMATION: C-terminal amidation

<400> SEQUENCE: 226

```
Met Arg Trp Gln Glu Glu Gly Tyr Ile Phe Tyr Lys Arg Lys Leu Arg
1               5                   10                  15

<210> SEQ ID NO 227
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(14)
<223> OTHER INFORMATION: Lactam ring
<220> FEATURE:
<221> NAME/KEY: MISC_FEATURE
<222> LOCATION: (16)..(16)
<223> OTHER INFORMATION: C-terminal amidation

<400> SEQUENCE: 227

Met Arg Trp Gln Glu Met Gly Tyr Ile Phe Tyr Pro Arg Lys Leu Arg
1               5                   10                  15

<210> SEQ ID NO 228
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (4)..(12)
<223> OTHER INFORMATION: Lactam ring
<220> FEATURE:
<221> NAME/KEY: MISC_FEATURE
<222> LOCATION: (16)..(16)
<223> OTHER INFORMATION: C-terminal amidation

<400> SEQUENCE: 228

Met Arg Trp Glu Glu Met Gly Tyr Ile Phe Tyr Lys Arg Lys Leu Arg
1               5                   10                  15

<210> SEQ ID NO 229
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Cyclic peptide
<220> FEATURE:
<221> NAME/KEY: MISC_FEATURE
<222> LOCATION: (1)..(1)
<223> OTHER INFORMATION: N-terminal acetylation
<220> FEATURE:
<221> NAME/KEY: MISC_FEATURE
<222> LOCATION: (5)..(12)
<223> OTHER INFORMATION: Lactam ring
<220> FEATURE:
<221> NAME/KEY: MISC_FEATURE
```

<222> LOCATION: (16)..(16)
<223> OTHER INFORMATION: C-terminal amidation

<400> SEQUENCE: 229

Met Arg Trp Gln Glu Met Gly Tyr Ile Phe Tyr Lys Arg Lys Leu Arg
1               5                   10                  15

<210> SEQ ID NO 230
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 230

Ala Arg Trp Gln Glu Glu Gly Tyr Ile Phe Tyr Pro Arg Lys Leu Ala
1               5                   10                  15

<210> SEQ ID NO 231
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (16)..(16)
<223> OTHER INFORMATION: D-Ala

<400> SEQUENCE: 231

Ala Arg Trp Gln Glu Glu Gly Tyr Ile Phe Tyr Pro Arg Lys Leu Ala
1               5                   10                  15

<210> SEQ ID NO 232
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 232

Ala Arg Trp Gln Glu Glu Gly Tyr Ile Phe Tyr Pro Arg
1               5                   10

<210> SEQ ID NO 233
<211> LENGTH: 16
<212> TYPE: PRT
<213> ORGANISM: Artificial Sequence
<220> FEATURE:
<223> OTHER INFORMATION: Synthetic peptide

<400> SEQUENCE: 233

Glu Arg Trp Gln Glu Ala Gly Tyr Ile Phe Tyr Pro Arg Lys Leu Ala
1               5                   10                  15

<210> SEQ ID NO 234
<211> LENGTH: 16

<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Ala

<400> SEQUENCE: 234

Glu Arg Trp Gln Glu Ala Gly Tyr Ile Phe Tyr Pro Arg Lys Leu Ala
1               5                   10                  15

<210> SEQ ID NO 235
<211> LENGTH: 13
<212> TYPE: PRT
<213> ORGANISM: Artificial Sequence
<220> FEATURE:
<223> OTHER INFORMATION: Synthetic peptide

<400> SEQUENCE: 235

Glu Arg Trp Gln Glu Ala Gly Tyr Ile Phe Tyr Pro Arg
1               5                   10

<210> SEQ ID NO 236
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 236

Ala Arg Trp Gln Glu Glu Gly Tyr Ile Ala Tyr Pro Arg Lys Leu Ala
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (16)..(16)
<223> OTHER INFORMATION: D-Ala

<400> SEQUENCE: 237

Ala Arg Trp Gln Glu Glu Gly Tyr Ile Ala Tyr Pro Arg Lys Leu Ala
1               5                   10                  15

<210> SEQ ID NO 238
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 238

```
Ala Arg Trp Gln Glu Glu Gly Tyr Ile Ala Tyr Pro Arg
1               5                   10
```

<210> SEQ ID NO 239
<211> LENGTH: 16
<212> TYPE: PRT
<213> ORGANISM: Artificial Sequence
<220> FEATURE:
<223> OTHER INFORMATION: Synthetic peptide

<400> SEQUENCE: 239

```
Glu Arg Trp Gln Glu Ala Gly Tyr Ile Ala Tyr Pro Arg Lys Leu Ala
1               5                   10                  15
```

<210> SEQ ID NO 240
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (16)..(16)
<223> OTHER INFORMATION: D-Ala

<400> SEQUENCE: 240

```
Glu Arg Trp Gln Glu Ala Gly Tyr Ile Ala Tyr Pro Arg Lys Leu Ala
1               5                   10                  15
```

<210> SEQ ID NO 241
<211> LENGTH: 13
<212> TYPE: PRT
<213> ORGANISM: Artificial Sequence
<220> FEATURE:
<223> OTHER INFORMATION: Synthetic peptide

<400> SEQUENCE: 241

```
Glu Arg Trp Gln Glu Ala Gly Tyr Ile Ala Tyr Pro Arg
1               5                   10
```

<210> SEQ ID NO 242
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 242

```
Ala Arg Trp Gln Glu Ala Gly Tyr Ile Phe Glu Pro Arg Lys Leu Ala
1               5                   10                  15
```

<210> SEQ ID NO 243
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (16)..(16)
<223> OTHER INFORMATION: D-Ala

```
<400> SEQUENCE: 243

Ala Arg Trp Gln Glu Ala Gly Tyr Ile Phe Glu Pro Arg Lys Leu Ala
1               5                   10                  15

<210> SEQ ID NO 244
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 244

Ala Arg Trp Gln Glu Ala Gly Tyr Ile Phe Glu Pro Arg
1               5                   10

<210> SEQ ID NO 245
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 245

Ala Arg Trp Gln Glu Ala Gly Tyr Ile Ala Glu Pro Arg Lys Leu Ala
1               5                   10                  15

<210> SEQ ID NO 246
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala
<220> FEATURE:
<221> NAME/KEY: MISC_FEATURE
<222> LOCATION: (16)..(16)
<223> OTHER INFORMATION: D-Ala

<400> SEQUENCE: 246

Ala Arg Trp Gln Glu Ala Gly Tyr Ile Ala Glu Pro Arg Lys Leu Ala
1               5                   10                  15

<210> SEQ ID NO 247
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 247

Ala Arg Trp Gln Glu Ala Gly Tyr Ile Ala Glu Pro Arg
1               5                   10

<210> SEQ ID NO 248
```

```
<211> LENGTH: 12
<212> TYPE: PRT
<213> ORGANISM: Artificial Sequence
<220> FEATURE:
<223> OTHER INFORMATION: Synthetic peptide

<400> SEQUENCE: 248

Arg Trp Gln Glu Met Asn Tyr Ile Phe Tyr Pro Arg
1               5                   10

<210> SEQ ID NO 249
<211> LENGTH: 12
<212> TYPE: PRT
<213> ORGANISM: Artificial Sequence
<220> FEATURE:
<223> OTHER INFORMATION: Synthetic peptide

<400> SEQUENCE: 249

Arg Trp Gln Glu Met Asn Tyr Ile Phe Glu Pro Arg
1               5                   10

<210> SEQ ID NO 250
<211> LENGTH: 12
<212> TYPE: PRT
<213> ORGANISM: Artificial Sequence
<220> FEATURE:
<223> OTHER INFORMATION: Synthetic peptide

<400> SEQUENCE: 250

Arg Trp Gln Glu Met Asn Tyr Ile Ala Tyr Pro Arg
1               5                   10

<210> SEQ ID NO 251
<211> LENGTH: 12
<212> TYPE: PRT
<213> ORGANISM: Artificial Sequence
<220> FEATURE:
<223> OTHER INFORMATION: Synthetic peptide

<400> SEQUENCE: 251

Arg Trp Gln Glu Met Asn Tyr Ile Ala Glu Pro Arg
1               5                   10

<210> SEQ ID NO 252
<211> LENGTH: 13
<212> TYPE: PRT
<213> ORGANISM: Artificial Sequence
<220> FEATURE:
<223> OTHER INFORMATION: Synthetic peptide

<400> SEQUENCE: 252

Arg Trp Gln Glu Met Asn Tyr Ile Phe Tyr Pro Ala Arg
1               5                   10

<210> SEQ ID NO 253
<211> LENGTH: 12
<212> TYPE: PRT
<213> ORGANISM: Artificial Sequence
<220> FEATURE:
<223> OTHER INFORMATION: Synthetic peptide

<400> SEQUENCE: 253

Arg Trp Gln Glu Met Gln Tyr Ile Phe Tyr Pro Arg
1               5                   10

<210> SEQ ID NO 254
<211> LENGTH: 12
```

```
<212> TYPE: PRT
<213> ORGANISM: Artificial Sequence
<220> FEATURE:
<223> OTHER INFORMATION: Synthetic peptide

<400> SEQUENCE: 254

Arg Trp Gln Glu Met Gln Tyr Ile Phe Glu Pro Arg
1               5                   10

<210> SEQ ID NO 255
<211> LENGTH: 12
<212> TYPE: PRT
<213> ORGANISM: Artificial Sequence
<220> FEATURE:
<223> OTHER INFORMATION: Synthetic peptide

<400> SEQUENCE: 255

Arg Trp Gln Glu Met Gln Tyr Ile Ala Tyr Pro Arg
1               5                   10

<210> SEQ ID NO 256
<211> LENGTH: 12
<212> TYPE: PRT
<213> ORGANISM: Artificial Sequence
<220> FEATURE:
<223> OTHER INFORMATION: Synthetic peptide

<400> SEQUENCE: 256

Arg Trp Gln Glu Met Gln Tyr Ile Ala Glu Pro Arg
1               5                   10

<210> SEQ ID NO 257
<211> LENGTH: 13
<212> TYPE: PRT
<213> ORGANISM: Artificial Sequence
<220> FEATURE:
<223> OTHER INFORMATION: Synthetic peptide

<400> SEQUENCE: 257

Arg Trp Gln Glu Met Gln Tyr Ile Phe Tyr Pro Ala Arg
1               5                   10

<210> SEQ ID NO 258
<211> LENGTH: 12
<212> TYPE: PRT
<213> ORGANISM: Artificial Sequence
<220> FEATURE:
<223> OTHER INFORMATION: Synthetic peptide

<400> SEQUENCE: 258

Arg Trp Gln Glu Glu Asn Tyr Ile Phe Tyr Pro Arg
1               5                   10

<210> SEQ ID NO 259
<211> LENGTH: 12
<212> TYPE: PRT
<213> ORGANISM: Artificial Sequence
<220> FEATURE:
<223> OTHER INFORMATION: Synthetic peptide

<400> SEQUENCE: 259

Arg Trp Gln Glu Glu Asn Tyr Ile Phe Glu Pro Arg
1               5                   10

<210> SEQ ID NO 260
<211> LENGTH: 12
<212> TYPE: PRT
```

```
<213> ORGANISM: Artificial Sequence
<220> FEATURE:
<223> OTHER INFORMATION: Synthetic peptide

<400> SEQUENCE: 260

Arg Trp Gln Glu Glu Asn Tyr Ile Ala Tyr Pro Arg
1               5                   10

<210> SEQ ID NO 261
<211> LENGTH: 12
<212> TYPE: PRT
<213> ORGANISM: Artificial Sequence
<220> FEATURE:
<223> OTHER INFORMATION: Synthetic peptide

<400> SEQUENCE: 261

Arg Trp Gln Glu Glu Asn Tyr Ile Ala Glu Pro Arg
1               5                   10

<210> SEQ ID NO 262
<211> LENGTH: 13
<212> TYPE: PRT
<213> ORGANISM: Artificial Sequence
<220> FEATURE:
<223> OTHER INFORMATION: Synthetic peptide

<400> SEQUENCE: 262

Arg Trp Gln Glu Glu Asn Tyr Ile Phe Tyr Pro Ala Arg
1               5                   10

<210> SEQ ID NO 263
<211> LENGTH: 12
<212> TYPE: PRT
<213> ORGANISM: Artificial Sequence
<220> FEATURE:
<223> OTHER INFORMATION: Synthetic peptide

<400> SEQUENCE: 263

Arg Trp Gln Glu Glu Gln Tyr Ile Phe Tyr Pro Arg
1               5                   10

<210> SEQ ID NO 264
<211> LENGTH: 12
<212> TYPE: PRT
<213> ORGANISM: Artificial Sequence
<220> FEATURE:
<223> OTHER INFORMATION: Synthetic peptide

<400> SEQUENCE: 264

Arg Trp Gln Glu Glu Gln Tyr Ile Phe Glu Pro Arg
1               5                   10

<210> SEQ ID NO 265
<211> LENGTH: 12
<212> TYPE: PRT
<213> ORGANISM: Artificial Sequence
<220> FEATURE:
<223> OTHER INFORMATION: Synthetic peptide

<400> SEQUENCE: 265

Arg Trp Gln Glu Glu Gln Tyr Ile Ala Tyr Pro Arg
1               5                   10

<210> SEQ ID NO 266
<211> LENGTH: 12
<212> TYPE: PRT
<213> ORGANISM: Artificial Sequence
```

```
<220> FEATURE:
<223> OTHER INFORMATION: Synthetic peptide

<400> SEQUENCE: 266

Arg Trp Gln Glu Glu Gln Tyr Ile Ala Glu Pro Arg
1               5                   10

<210> SEQ ID NO 267
<211> LENGTH: 13
<212> TYPE: PRT
<213> ORGANISM: Artificial Sequence
<220> FEATURE:
<223> OTHER INFORMATION: Synthetic peptide

<400> SEQUENCE: 267

Arg Trp Gln Glu Glu Gln Tyr Ile Phe Tyr Pro Ala Arg
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Synthetic peptide

<400> SEQUENCE: 268

Arg Trp Gln Glu Met Gly Tyr Ile Phe Tyr Pro Arg Lys Leu
1               5                   10

<210> SEQ ID NO 269
<211> LENGTH: 13
<212> TYPE: PRT
<213> ORGANISM: Artificial Sequence
<220> FEATURE:
<223> OTHER INFORMATION: Synthetic peptide

<400> SEQUENCE: 269

Trp Gln Glu Met Gly Tyr Ile Phe Tyr Pro Arg Lys Leu
1               5                   10

<210> SEQ ID NO 270
<211> LENGTH: 12
<212> TYPE: PRT
<213> ORGANISM: Artificial Sequence
<220> FEATURE:
<223> OTHER INFORMATION: Synthetic peptide

<400> SEQUENCE: 270

Gln Glu Met Gly Tyr Ile Phe Tyr Pro Arg Lys Leu
1               5                   10

<210> SEQ ID NO 271
<211> LENGTH: 13
<212> TYPE: PRT
<213> ORGANISM: Artificial Sequence
<220> FEATURE:
<223> OTHER INFORMATION: Synthetic peptide

<400> SEQUENCE: 271

Met Arg Trp Gln Glu Met Asn Tyr Ile Phe Tyr Pro Arg
1               5                   10

<210> SEQ ID NO 272
<211> LENGTH: 12
<212> TYPE: PRT
<213> ORGANISM: Artificial Sequence
<220> FEATURE:
```

<223> OTHER INFORMATION: Synthetic peptide

<400> SEQUENCE: 272

Arg Trp Gln Glu Met Asn Tyr Ile Phe Tyr Pro Arg
1               5                   10

<210> SEQ ID NO 273
<211> LENGTH: 12
<212> TYPE: PRT
<213> ORGANISM: Artificial Sequence
<220> FEATURE:
<223> OTHER INFORMATION: Synthetic peptide

<400> SEQUENCE: 273

Arg Trp Gln Glu Met Asn Tyr Ile Phe Glu Pro Arg
1               5                   10

<210> SEQ ID NO 274
<211> LENGTH: 12
<212> TYPE: PRT
<213> ORGANISM: Artificial Sequence
<220> FEATURE:
<223> OTHER INFORMATION: Synthetic peptide

<400> SEQUENCE: 274

Arg Trp Gln Glu Met Asn Tyr Ile Ala Tyr Pro Arg
1               5                   10

<210> SEQ ID NO 275
<211> LENGTH: 12
<212> TYPE: PRT
<213> ORGANISM: Artificial Sequence
<220> FEATURE:
<223> OTHER INFORMATION: Synthetic peptide

<400> SEQUENCE: 275

Arg Trp Gln Glu Met Asn Tyr Ile Ala Glu Pro Arg
1               5                   10

<210> SEQ ID NO 276
<211> LENGTH: 13
<212> TYPE: PRT
<213> ORGANISM: Artificial Sequence
<220> FEATURE:
<223> OTHER INFORMATION: Synthetic peptide

<400> SEQUENCE: 276

Arg Trp Gln Glu Met Asn Tyr Ile Phe Tyr Pro Ala Arg
1               5                   10

<210> SEQ ID NO 277
<211> LENGTH: 12
<212> TYPE: PRT
<213> ORGANISM: Artificial Sequence
<220> FEATURE:
<223> OTHER INFORMATION: Synthetic peptide

<400> SEQUENCE: 277

Arg Trp Gln Glu Glu Asn Tyr Ile Phe Tyr Pro Arg
1               5                   10

<210> SEQ ID NO 278
<211> LENGTH: 12
<212> TYPE: PRT
<213> ORGANISM: Artificial Sequence
<220> FEATURE:
<223> OTHER INFORMATION: Synthetic peptide

<400> SEQUENCE: 278

Arg Trp Gln Glu Glu Asn Tyr Ile Phe Glu Pro Arg
1               5                   10

<210> SEQ ID NO 279
<211> LENGTH: 12
<212> TYPE: PRT
<213> ORGANISM: Artificial Sequence
<220> FEATURE:
<223> OTHER INFORMATION: Synthetic peptide

<400> SEQUENCE: 279

Arg Trp Gln Glu Glu Asn Tyr Ile Ala Tyr Pro Arg
1               5                   10

<210> SEQ ID NO 280
<211> LENGTH: 12
<212> TYPE: PRT
<213> ORGANISM: Artificial Sequence
<220> FEATURE:
<223> OTHER INFORMATION: Synthetic peptide

<400> SEQUENCE: 280

Arg Trp Gln Glu Glu Asn Tyr Ile Ala Glu Pro Arg
1               5                   10

<210> SEQ ID NO 281
<211> LENGTH: 13
<212> TYPE: PRT
<213> ORGANISM: Artificial Sequence
<220> FEATURE:
<223> OTHER INFORMATION: Synthetic peptide

<400> SEQUENCE: 281

Arg Trp Gln Glu Glu Asn Tyr Ile Phe Tyr Pro Ala Arg
1               5                   10

<210> SEQ ID NO 282
<211> LENGTH: 12
<212> TYPE: PRT
<213> ORGANISM: Artificial Sequence
<220> FEATURE:
<223> OTHER INFORMATION: Synthetic peptide

<400> SEQUENCE: 282

Met Arg Trp Gln Glu Met Asn Tyr Ile Phe Tyr Pro
1               5                   10

<210> SEQ ID NO 283
<211> LENGTH: 11
<212> TYPE: PRT
<213> ORGANISM: Artificial Sequence
<220> FEATURE:
<223> OTHER INFORMATION: Synthetic peptide

<400> SEQUENCE: 283

Arg Trp Gln Glu Met Asn Tyr Ile Phe Tyr Pro
1               5                   10

<210> SEQ ID NO 284
<211> LENGTH: 11
<212> TYPE: PRT
<213> ORGANISM: Artificial Sequence
<220> FEATURE:
<223> OTHER INFORMATION: Synthetic peptide

```
<400> SEQUENCE: 284

Trp Gln Glu Met Asn Tyr Ile Phe Tyr Pro Arg
1               5                   10

<210> SEQ ID NO 285
<211> LENGTH: 10
<212> TYPE: PRT
<213> ORGANISM: Artificial Sequence
<220> FEATURE:
<223> OTHER INFORMATION: Synthetic peptide

<400> SEQUENCE: 285

Trp Gln Glu Met Asn Tyr Ile Phe Tyr Pro
1               5                   10

<210> SEQ ID NO 286
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal acetylation

<400> SEQUENCE: 286

Met Arg Trp Gln Glu Met Asn Tyr Ile Phe Tyr Pro Arg
1               5                   10

<210> SEQ ID NO 287
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: C-terminal amidation

<400> SEQUENCE: 287

Met Arg Trp Gln Glu Met Asn Tyr Ile Phe Tyr Pro
1               5                   10

<210> SEQ ID NO 288
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: D-Ala

<400> SEQUENCE: 288

Ala Arg Trp Gln Glu Met Asn Tyr Ile Phe Tyr Pro Arg
1               5                   10

<210> SEQ ID NO 289
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
```

<223> OTHER INFORMATION: N-terminal palmitoyl

<400> SEQUENCE: 289

Met Arg Trp Gln Glu Met Asn Tyr Ile Phe Tyr Pro Arg
1               5                   10

<210> SEQ ID NO 290
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: C-terminal PEG600

<400> SEQUENCE: 290

Arg Trp Gln Glu Met Asn Tyr Ile Phe Tyr Pro Arg Lys Pro Glu Gly
1               5                   10                  15

<210> SEQ ID NO 291
<211> LENGTH: 11
<212> TYPE: PRT
<213> ORGANISM: Artificial Sequence
<220> FEATURE:
<223> OTHER INFORMATION: Synthetic peptide

<400> SEQUENCE: 291

Trp Gln Glu Met Asn Tyr Ile Phe Tyr Pro Arg
1               5                   10

<210> SEQ ID NO 292
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: C-terminal palmitoyl

<400> SEQUENCE: 292

Trp Gln Glu Met Asn Tyr Ile Phe Tyr Pro Arg Lys
1               5                   10

<210> SEQ ID NO 293
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (11)..(11)
<223> OTHER INFORMATION: C-terminal amidation

<400> SEQUENCE: 293

Trp Gln Glu Met Asn Tyr Ile Phe Tyr Pro Arg
1               5                   10

<210> SEQ ID NO 294
<211> LENGTH: 4
<212> TYPE: PRT
<213> ORGANISM: Artificial Sequence
<220> FEATURE:
<223> OTHER INFORMATION: Synthetic peptide

```
<400> SEQUENCE: 294

Arg Trp Gln Glu
1

<210> SEQ ID NO 295
<211> LENGTH: 4
<212> TYPE: PRT
<213> ORGANISM: Artificial Sequence
<220> FEATURE:
<223> OTHER INFORMATION: Synthetic peptide

<400> SEQUENCE: 295

Tyr Ile Phe Tyr
1

<210> SEQ ID NO 296
<211> LENGTH: 6
<212> TYPE: PRT
<213> ORGANISM: Artificial Sequence
<220> FEATURE:
<223> OTHER INFORMATION: Synthetic peptide

<400> SEQUENCE: 296

Tyr Ile Phe Tyr Pro Arg
1               5

<210> SEQ ID NO 297
<211> LENGTH: 7
<212> TYPE: PRT
<213> ORGANISM: Artificial Sequence
<220> FEATURE:
<223> OTHER INFORMATION: Synthetic peptide

<400> SEQUENCE: 297

Tyr Ile Phe Tyr Pro Arg Lys
1               5

<210> SEQ ID NO 298
<211> LENGTH: 8
<212> TYPE: PRT
<213> ORGANISM: Artificial Sequence
<220> FEATURE:
<223> OTHER INFORMATION: Synthetic peptide

<400> SEQUENCE: 298

Tyr Ile Phe Tyr Pro Arg Lys Leu
1               5

<210> SEQ ID NO 299
<211> LENGTH: 9
<212> TYPE: PRT
<213> ORGANISM: Artificial Sequence
<220> FEATURE:
<223> OTHER INFORMATION: Synthetic peptide

<400> SEQUENCE: 299

Tyr Ile Phe Tyr Pro Arg Lys Leu Arg
1               5

<210> SEQ ID NO 300
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Xaa is any amino acid

<400> SEQUENCE: 300

Xaa Ile Phe Tyr
1

<210> SEQ ID NO 301
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is any amino acid

<400> SEQUENCE: 301

Tyr Xaa Phe Tyr
1

<210> SEQ ID NO 302
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is any amino acid

<400> SEQUENCE: 302

Tyr Ile Xaa Tyr
1

<210> SEQ ID NO 303
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is any amino acid

<400> SEQUENCE: 303

Tyr Ile Phe Xaa
1

<210> SEQ ID NO 304
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an aliphatic or charged amino acid

<400> SEQUENCE: 304

Xaa Trp Gln Glu
1

<210> SEQ ID NO 305
<211> LENGTH: 4
```

```
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is an aliphatic or charged amino acid

<400> SEQUENCE: 305

Arg Xaa Gln Glu
1

<210> SEQ ID NO 306
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is an aliphatic or charged amino acid

<400> SEQUENCE: 306

Arg Trp Xaa Glu
1

<210> SEQ ID NO 307
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa is an aliphatic or charged amino acid

<400> SEQUENCE: 307

Arg Trp Gln Xaa
1

<210> SEQ ID NO 308
<211> LENGTH: 4
<212> TYPE: PRT
<213> ORGANISM: Artificial Sequence
<220> FEATURE:
<223> OTHER INFORMATION: Synthetic peptide

<400> SEQUENCE: 308

Tyr Ile Ala Glu
1

<210> SEQ ID NO 309
<211> LENGTH: 4
<212> TYPE: PRT
<213> ORGANISM: Artificial Sequence
<220> FEATURE:
<223> OTHER INFORMATION: Synthetic peptide

<400> SEQUENCE: 309

Glu Ile Phe Glu
1

<210> SEQ ID NO 310
<211> LENGTH: 16
<212> TYPE: PRT
<213> ORGANISM: Artificial Sequence
```

```
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal linked to C7-C20 lipid moiety

<400> SEQUENCE: 310

Met Arg Trp Gln Glu Met Gly Tyr Ile Phe Tyr Pro Arg Lys Leu Arg
1               5                   10                  15

<210> SEQ ID NO 311
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Linked to C7-C20 lipid moiety

<400> SEQUENCE: 311

Met Arg Trp Gln Glu Met Gly Tyr Ile Phe Tyr Pro Arg Lys Leu Arg
1               5                   10                  15

<210> SEQ ID NO 312
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: Linked to C7-C20 lipid moiety via Glu linker

<400> SEQUENCE: 312

Met Arg Trp Gln Glu Met Gly Tyr Ile Phe Tyr Pro Arg Lys Leu Arg
1               5                   10                  15

<210> SEQ ID NO 313
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal linked to C7-C20 lipid moiety

<400> SEQUENCE: 313

Met Arg Trp Gln Glu Met Asn Tyr Ile Phe Tyr Pro Arg
1               5                   10

<210> SEQ ID NO 314
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: C-terminal linked to C7-C20 lipid moiety

<400> SEQUENCE: 314

Trp Gln Glu Met Asn Tyr Ile Phe Tyr Pro Arg Lys
1               5                   10
```

```
<210> SEQ ID NO 315
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: C-terminal linked to 5-20 kDa polyethylene
      glycol

<400> SEQUENCE: 315

Arg Trp Gln Glu Met Asn Tyr Ile Phe Tyr Pro Arg Lys Pro Glu Gly
1               5                   10                  15

<210> SEQ ID NO 316
<211> LENGTH: 16
<212> TYPE: PRT
<213> ORGANISM: Artificial Sequence
<220> FEATURE:
<223> OTHER INFORMATION: Synthetic peptide

<400> SEQUENCE: 316

Met Arg Trp Gln Glu Met Gly Tyr Ile Phe Tyr Phe Arg Lys Leu Arg
1               5                   10                  15

<210> SEQ ID NO 317
<211> LENGTH: 16
<212> TYPE: PRT
<213> ORGANISM: Artificial Sequence
<220> FEATURE:
<223> OTHER INFORMATION: Synthetic peptide

<400> SEQUENCE: 317

Met Gly Trp Gln Glu Met Gly Tyr Ile Phe Tyr Pro Arg Lys Leu Arg
1               5                   10                  15

<210> SEQ ID NO 318
<211> LENGTH: 11
<212> TYPE: PRT
<213> ORGANISM: Artificial Sequence
<220> FEATURE:
<223> OTHER INFORMATION: Synthetic peptide

<400> SEQUENCE: 318

Met Gly Tyr Ile Phe Tyr Pro Arg Lys Leu Arg
1               5                   10

<210> SEQ ID NO 319
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid

<400> SEQUENCE: 319

Arg Trp Gln Glu Xaa Xaa Tyr Ile Phe Tyr
1               5                   10
```

```
<210> SEQ ID NO 320
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 320

Arg Trp Gln Glu Xaa Xaa Xaa Ile Phe Tyr
1               5                   10

<210> SEQ ID NO 321
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid

<400> SEQUENCE: 321

Arg Trp Gln Glu Xaa Xaa Tyr Xaa Phe Tyr
1               5                   10

<210> SEQ ID NO 322
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is any amino acid

<400> SEQUENCE: 322

Arg Trp Gln Glu Xaa Xaa Tyr Ile Xaa Tyr
1               5                   10

<210> SEQ ID NO 323
<211> LENGTH: 10
<212> TYPE: PRT
```

<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid

<400> SEQUENCE: 323

Arg Trp Gln Glu Xaa Xaa Tyr Ile Phe Xaa
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Synthetic peptide

<400> SEQUENCE: 324

Tyr Ala Arg Ala Ala Ala Arg Gln Ala Arg Ala
1               5                   10

<210> SEQ ID NO 325
<211> LENGTH: 7
<212> TYPE: PRT
<213> ORGANISM: Artificial Sequence
<220> FEATURE:
<223> OTHER INFORMATION: Synthetic peptide

<400> SEQUENCE: 325

Tyr Gly Arg Lys Lys Arg Arg
1               5

<210> SEQ ID NO 326
<211> LENGTH: 11
<212> TYPE: PRT
<213> ORGANISM: Artificial Sequence
<220> FEATURE:
<223> OTHER INFORMATION: Synthetic peptide

<400> SEQUENCE: 326

Tyr Gly Arg Lys Lys Arg Arg Gln Arg Arg
1               5                   10

<210> SEQ ID NO 327
<211> LENGTH: 5
<212> TYPE: PRT
<213> ORGANISM: Artificial Sequence
<220> FEATURE:
<223> OTHER INFORMATION: Synthetic peptide

<400> SEQUENCE: 327

Arg Arg Gln Arg Arg
1               5

<210> SEQ ID NO 328
<211> LENGTH: 17
<212> TYPE: PRT
<213> ORGANISM: Artificial Sequence
<220> FEATURE:

<223> OTHER INFORMATION: Synthetic peptide

<400> SEQUENCE: 328

Met Arg Trp Gln Glu Met Gly Tyr Ile Phe Tyr Pro Arg Lys Phe Tyr
1               5                   10                  15
Asp

<210> SEQ ID NO 329
<211> LENGTH: 17
<212> TYPE: PRT
<213> ORGANISM: Artificial Sequence
<220> FEATURE:
<223> OTHER INFORMATION: Synthetic peptide

<400> SEQUENCE: 329

Met Arg Trp Gln Glu Met Gly Tyr Ile Phe Tyr Pro Arg Lys Phe Tyr
1               5                   10                  15
Asn

<210> SEQ ID NO 330
<211> LENGTH: 16
<212> TYPE: PRT
<213> ORGANISM: Artificial Sequence
<220> FEATURE:
<223> OTHER INFORMATION: Synthetic peptide

<400> SEQUENCE: 330

Met Arg Trp Gln Glu Met Gly Tyr Ile Phe Tyr Phe Arg Lys Leu Arg
1               5                   10                  15

<210> SEQ ID NO 331
<211> LENGTH: 17
<212> TYPE: PRT
<213> ORGANISM: Artificial Sequence
<220> FEATURE:
<223> OTHER INFORMATION: Synthetic peptide

<400> SEQUENCE: 331

Met Arg Trp Gln Glu Met Gly Tyr Ile Phe Tyr Thr Gln Lys Ile Leu
1               5                   10                  15
Leu

<210> SEQ ID NO 332
<211> LENGTH: 17
<212> TYPE: PRT
<213> ORGANISM: Artificial Sequence
<220> FEATURE:
<223> OTHER INFORMATION: Synthetic peptide

<400> SEQUENCE: 332

Met Arg Trp Gln Glu Met Gly Tyr Ile Phe Tyr Ile Arg Gln Ile Ser
1               5                   10                  15
Gln

<210> SEQ ID NO 333
<211> LENGTH: 17
<212> TYPE: PRT
<213> ORGANISM: Artificial Sequence
<220> FEATURE:
<223> OTHER INFORMATION: Synthetic peptide

<400> SEQUENCE: 333

Met Arg Trp Gln Glu Met Gly Tyr Ile Phe Tyr Thr Gln Lys Ile Ser
1               5                   10                  15

```
<210> SEQ ID NO 334
<211> LENGTH: 17
<212> TYPE: PRT
<213> ORGANISM: Artificial Sequence
<220> FEATURE:
<223> OTHER INFORMATION: Synthetic peptide

<400> SEQUENCE: 334

Met Arg Trp Gln Glu Met Gly Tyr Ile Phe Tyr Val Gln Lys Leu Ser
1               5                   10                  15

Arg

<210> SEQ ID NO 335
<211> LENGTH: 55
<212> TYPE: PRT
<213> ORGANISM: Artificial Sequence
<220> FEATURE:
<223> OTHER INFORMATION: Synthetic peptide

<400> SEQUENCE: 335

Met Arg Trp Gln Glu Met Gly Tyr Ile Phe Tyr Thr Gln Lys Ile Ser
1               5                   10                  15

Arg Val Arg Asn Thr Val Asp Ser Arg Val Pro Pro Lys Pro Ser Phe
            20                  25                  30

Gly Ser Arg Leu Thr Asn Gln Leu Ile Pro Val Leu Arg Thr Cys Val
        35                  40                  45

Ala Gly Ser Gly Arg Ser Leu
    50                  55

<210> SEQ ID NO 336
<211> LENGTH: 16
<212> TYPE: PRT
<213> ORGANISM: Homo sapiens

<400> SEQUENCE: 336

Met Arg Trp Gln Glu Met Gly Tyr Ile Phe Tyr Pro Arg Lys Leu Arg
1               5                   10                  15

<210> SEQ ID NO 337
<211> LENGTH: 16
<212> TYPE: PRT
<213> ORGANISM: Pan troglodytes

<400> SEQUENCE: 337

Met Arg Trp Gln Glu Met Gly Tyr Ile Phe Tyr Pro Arg Lys Leu Arg
1               5                   10                  15

<210> SEQ ID NO 338
<211> LENGTH: 16
<212> TYPE: PRT
<213> ORGANISM: Pan paniscus

<400> SEQUENCE: 338

Met Arg Arg Gln Glu Met Gly Tyr Ile Phe Tyr Pro Arg Lys Leu Arg
1               5                   10                  15

<210> SEQ ID NO 339
<211> LENGTH: 16
<212> TYPE: PRT
<213> ORGANISM: Pongo pygmaeus
```

```
<400> SEQUENCE: 339

Met Glu Trp Gln Glu Met Gly Tyr Ile Phe Tyr Phe Arg Lys Leu Arg
1               5                   10                  15

<210> SEQ ID NO 340
<211> LENGTH: 11
<212> TYPE: PRT
<213> ORGANISM: Mus musculus

<400> SEQUENCE: 340

Met Lys Trp Glu Glu Met Gly Tyr Ile Phe Leu
1               5                   10

<210> SEQ ID NO 341
<211> LENGTH: 20
<212> TYPE: PRT
<213> ORGANISM: Rattus norvegicus

<400> SEQUENCE: 341

Met Lys Arg Lys Glu Met Gly Tyr Ile Phe Phe Ser Gln Arg Thr Leu
1               5                   10                  15

Arg Asn Pro Leu
            20

<210> SEQ ID NO 342
<211> LENGTH: 22
<212> TYPE: PRT
<213> ORGANISM: Heterocephalus glaber

<400> SEQUENCE: 342

Met Lys Trp Glu Glu Met Gly Tyr Ile Phe Leu Tyr Lys Asn Ile Asn
1               5                   10                  15

Asp Ser Tyr His Glu Ile
            20

<210> SEQ ID NO 343
<211> LENGTH: 24
<212> TYPE: PRT
<213> ORGANISM: Canis familiaris

<400> SEQUENCE: 343

Met Arg Trp Glu Glu Met Gly Tyr Ile Phe Tyr Pro Arg Thr Phe His
1               5                   10                  15

Glu Cys Phe Tyr Glu Ile Lys Asn
            20

<210> SEQ ID NO 344
<211> LENGTH: 29
<212> TYPE: PRT
<213> ORGANISM: Bos taurus

<400> SEQUENCE: 344

Met Lys Trp Glu Glu Met Gly Tyr Ile Leu Tyr Thr Lys Arg Ile Lys
1               5                   10                  15

His Glu Ser Tyr Tyr Glu Thr Asn Asn Gln Arg Arg Ile
            20                  25

<210> SEQ ID NO 345
<211> LENGTH: 19
<212> TYPE: PRT
<213> ORGANISM: Danio rerio

<400> SEQUENCE: 345
```

```
Met Lys Trp Glu Glu Met Gly Tyr Thr Phe Tyr Pro Arg Ile Tyr Glu
1               5                   10                  15

Asn Val Thr

<210> SEQ ID NO 346
<211> LENGTH: 12
<212> TYPE: PRT
<213> ORGANISM: Panthera leo

<400> SEQUENCE: 346

Met Arg Trp Glu Ala Met Gly Tyr Ile Phe Tyr Asn
1               5                   10

<210> SEQ ID NO 347
<211> LENGTH: 24
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Ursidae

<400> SEQUENCE: 347

Met Gly Trp Glu Glu Met Gly Tyr Ile Phe Tyr Ser Arg Thr Thr Tyr
1               5                   10                  15

Glu Ser Phe Tyr Glu Thr Lys Asn
            20

<210> SEQ ID NO 348
<211> LENGTH: 28
<212> TYPE: PRT
<213> ORGANISM: Equus caballus

<400> SEQUENCE: 348

Met Gly Trp Arg Glu Met Gly Tyr Ile Phe Tyr Pro Lys Asn Lys Asn
1               5                   10                  15

Phe Asn Pro Asp Glu Ser Leu His Glu Thr Gly Asp
            20                  25

<210> SEQ ID NO 349
<211> LENGTH: 16
<212> TYPE: PRT
<213> ORGANISM: Delphinus delphis

<400> SEQUENCE: 349

Met Asp Trp Glu Glu Met Gly Tyr Ile Phe Tyr Asn Lys Asn Thr Pro
1               5                   10                  15

<210> SEQ ID NO 350
<211> LENGTH: 5
<212> TYPE: PRT
<213> ORGANISM: Artificial Sequence
<220> FEATURE:
<223> OTHER INFORMATION: Synthetic peptide

<400> SEQUENCE: 350

Met Arg Trp Gln Glu
1               5

<210> SEQ ID NO 351
<211> LENGTH: 5
<212> TYPE: PRT
<213> ORGANISM: Artificial Sequence
```

```
<220> FEATURE:
<223> OTHER INFORMATION: Synthetic peptide

<400> SEQUENCE: 351

Arg Trp Gln Glu Met
1               5

<210> SEQ ID NO 352
<211> LENGTH: 6
<212> TYPE: PRT
<213> ORGANISM: Artificial Sequence
<220> FEATURE:
<223> OTHER INFORMATION: Synthetic peptide

<400> SEQUENCE: 352

Met Arg Trp Gln Glu Met
1               5

<210> SEQ ID NO 353
<211> LENGTH: 6
<212> TYPE: PRT
<213> ORGANISM: Artificial Sequence
<220> FEATURE:
<223> OTHER INFORMATION: Synthetic peptide

<400> SEQUENCE: 353

Gly Tyr Ile Phe Tyr Pro
1               5

<210> SEQ ID NO 354
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (12)..(12)
<223> OTHER INFORMATION: C-terminal amidation

<400> SEQUENCE: 354

Arg Trp Gln Glu Met Asn Tyr Ile Phe Tyr Pro Arg
1               5                   10

<210> SEQ ID NO 355
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: D-Ala

<400> SEQUENCE: 355

Arg Trp Gln Glu Met Asn Tyr Ile Phe Tyr Pro Arg Ala
1               5                   10

<210> SEQ ID NO 356
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (14)..(14)
<223> OTHER INFORMATION: D-Ala
```

```
<400> SEQUENCE: 356

Arg Trp Gln Glu Met Asn Tyr Ile Phe Tyr Pro Arg Arg Ala
1               5                   10

<210> SEQ ID NO 357
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal PEG600

<400> SEQUENCE: 357

Lys Arg Trp Gln Glu Met Asn Tyr Ile Phe Tyr Pro Arg
1               5                   10

<210> SEQ ID NO 358
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal biotin

<400> SEQUENCE: 358

Arg Trp Gln Glu Met Asn Tyr Ile Phe Tyr Pro Arg
1               5                   10

<210> SEQ ID NO 359
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: C-terminal biotin

<400> SEQUENCE: 359

Arg Trp Gln Glu Met Asn Tyr Ile Phe Tyr Pro Arg Lys
1               5                   10

<210> SEQ ID NO 360
<211> LENGTH: 5
<212> TYPE: PRT
<213> ORGANISM: Artificial Sequence
<220> FEATURE:
<223> OTHER INFORMATION: Synthetic peptide

<400> SEQUENCE: 360

Ile Phe Tyr Pro Arg
1               5

<210> SEQ ID NO 361
<211> LENGTH: 7
<212> TYPE: PRT
<213> ORGANISM: Artificial Sequence
<220> FEATURE:
<223> OTHER INFORMATION: Synthetic peptide

<400> SEQUENCE: 361
```

Asn Tyr Ile Phe Tyr Pro Arg
1               5

<210> SEQ ID NO 362
<211> LENGTH: 8
<212> TYPE: PRT
<213> ORGANISM: Artificial Sequence
<220> FEATURE:
<223> OTHER INFORMATION: Synthetic peptide

<400> SEQUENCE: 362

Glu Met Asn Tyr Ile Phe Tyr Pro
1               5

<210> SEQ ID NO 363
<211> LENGTH: 9
<212> TYPE: PRT
<213> ORGANISM: Artificial Sequence
<220> FEATURE:
<223> OTHER INFORMATION: Synthetic peptide

<400> SEQUENCE: 363

Gln Glu Met Asn Tyr Ile Phe Tyr Pro
1               5

<210> SEQ ID NO 364
<211> LENGTH: 9
<212> TYPE: PRT
<213> ORGANISM: Artificial Sequence
<220> FEATURE:
<223> OTHER INFORMATION: Synthetic peptide

<400> SEQUENCE: 364

Glu Met Asn Tyr Ile Phe Tyr Pro Arg
1               5

<210> SEQ ID NO 365
<211> LENGTH: 9
<212> TYPE: PRT
<213> ORGANISM: Artificial Sequence
<220> FEATURE:
<223> OTHER INFORMATION: Synthetic peptide

<400> SEQUENCE: 365

Trp Gln Glu Met Asn Tyr Ile Phe Tyr
1               5

<210> SEQ ID NO 366
<211> LENGTH: 10
<212> TYPE: PRT
<213> ORGANISM: Artificial Sequence
<220> FEATURE:
<223> OTHER INFORMATION: Synthetic peptide

<400> SEQUENCE: 366

Gln Glu Met Asn Tyr Ile Phe Tyr Pro Arg
1               5                   10

<210> SEQ ID NO 367
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)

<223> OTHER INFORMATION: N-terminal biotin

<400> SEQUENCE: 367

Lys Arg Trp Gln Glu Met Asn Tyr Ile Phe Tyr Pro Arg
1               5                   10

<210> SEQ ID NO 368
<211> LENGTH: 8
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal PEG600

<400> SEQUENCE: 368

Lys Asn Tyr Ile Phe Tyr Pro Arg
1               5

<210> SEQ ID NO 369
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal PEG600

<400> SEQUENCE: 369

Lys Glu Met Asn Tyr Ile Phe Tyr Pro Arg
1               5                   10

<210> SEQ ID NO 370
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal PEG600

<400> SEQUENCE: 370

Lys Trp Gln Glu Met Asn Tyr Ile Phe Tyr Pro Arg
1               5                   10

<210> SEQ ID NO 371
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal PEG600

<400> SEQUENCE: 371

Lys Arg Trp Gln Glu Met Asn Tyr Ile Phe Tyr Pro
1               5                   10

<210> SEQ ID NO 372
<211> LENGTH: 11
<212> TYPE: PRT

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal PEG600

<400> SEQUENCE: 372

Lys Trp Gln Glu Met Asn Tyr Ile Phe Tyr Pro
1               5                   10

<210> SEQ ID NO 373
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is any amino acid

<400> SEQUENCE: 373

Arg Trp Gln Glu Xaa Xaa Xaa Ile Phe Tyr
1               5                   10

<210> SEQ ID NO 374
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid

<400> SEQUENCE: 374

Arg Trp Gln Glu Xaa Xaa Tyr Xaa Phe Tyr
1               5                   10

<210> SEQ ID NO 375
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
```

<221> NAME/KEY: MISC_FEATURE
<222> LOCATION: (9)..(9)
<223> OTHER INFORMATION: Xaa is any amino acid

<400> SEQUENCE: 375

Arg Trp Gln Glu Xaa Xaa Tyr Ile Xaa Tyr
1               5                   10

<210> SEQ ID NO 376
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa is any amino acid
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (10)..(10)
<223> OTHER INFORMATION: Xaa is any amino acid

<400> SEQUENCE: 376

Arg Trp Gln Glu Xaa Xaa Tyr Ile Phe Xaa
1               5                   10

<210> SEQ ID NO 377
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (13)..(13)
<223> OTHER INFORMATION: C-terminal PEG600

<400> SEQUENCE: 377

Arg Trp Gln Glu Met Asn Tyr Ile Phe Tyr Pro Arg Lys
1               5                   10

<210> SEQ ID NO 378
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is an amino acid with a non-polar side
    chain or a polar side chain or is absent when Xaa at position 2 is
    absent
<220> FEATURE:
<221> NAME/KEY: MISC_FEATURE
<222> LOCATION: (2)..(2)
<223> OTHER INFORMATION: Xaa is an amino acid with a non-polar side
    chain or a polar side chain or is absent when Xaa at position 3 is
    absent
<220> FEATURE:
<221> NAME/KEY: MISC_FEATURE
<222> LOCATION: (3)..(3)
<223> OTHER INFORMATION: Xaa is an amino acid with a non-polar side
    chain or a polar side chain or is absent
<220> FEATURE:
<221> NAME/KEY: MISC_FEATURE
<222> LOCATION: (6)..(6)
<223> OTHER INFORMATION: Xaa is an amino acid with a non-polar side

```
      chain or a polar side chain
<220> FEATURE:
<221> NAME/KEY: MISC_FEATURE
<222> LOCATION: (7)..(7)
<223> OTHER INFORMATION: Xaa is an amino acid with a non-polar side
      chain or a polar side chain
<220> FEATURE:
<221> NAME/KEY: MISC_FEATURE
<222> LOCATION: (10)..(10)
<223> OTHER INFORMATION: Xaa is an amino acid with a non-polar side
      chain or a polar side chain
<220> FEATURE:
<221> NAME/KEY: MISC_FEATURE
<222> LOCATION: (12)..(12)
<223> OTHER INFORMATION: Xaa is an amino acid with a non-polar side
      chain or a polar side chain
<220> FEATURE:
<221> NAME/KEY: MISC_FEATURE
<222> LOCATION: (13)..(13)
<223> OTHER INFORMATION: Xaa is an amino acid with a non-polar side
      chain or a polar side chain
<220> FEATURE:
<221> NAME/KEY: MISC_FEATURE
<222> LOCATION: (14)..(14)
<223> OTHER INFORMATION: Xaa is Leu, Lys, Arg or is selected from an
      amino acid with a non-polar side chain or a polar side chain or is
      absent
<220> FEATURE:
<221> NAME/KEY: MISC_FEATURE
<222> LOCATION: (15)..(15)
<223> OTHER INFORMATION: Xaa is Leu, Lys, Arg or is selected from an
      amino acid with a non-polar side chain or a polar side chain or is
      absent when Xaa at position 14 is absent
<220> FEATURE:
<221> NAME/KEY: MISC_FEATURE
<222> LOCATION: (16)..(16)
<223> OTHER INFORMATION: Xaa is Arg or is selected from an amino acid
      with a non-polar side chain or a polar side chain or is absent
      when Xaa at position 15 is absent

<400> SEQUENCE: 378

Xaa Xaa Xaa Gln Glu Xaa Xaa Tyr Ile Xaa Tyr Xaa Xaa Xaa Xaa
1               5                   10                  15

<210> SEQ ID NO 379
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Met, Leu, Gly, Lys, Glu, Ala, D-Ala or
      Nle or is absent when Xaa at position 2 is absent
<220> FEATURE:
<221> NAME/KEY: MISC_FEATURE
<222> LOCATION: (2)..(2)
<223> OTHER INFORMATION: Xaa is Arg, Ala, Gly, Asp, Lys, Aib, D-Ala or
      Glu or is absent when Xaa at position 3 is absent
<220> FEATURE:
<221> NAME/KEY: MISC_FEATURE
<222> LOCATION: (3)..(3)
<223> OTHER INFORMATION: Xaa is Trp, Ala, D-Ala, Gly, or Glu or is
      absent
<220> FEATURE:
<221> NAME/KEY: MISC_FEATURE
<222> LOCATION: (4)..(4)
<223> OTHER INFORMATION: Xaa is Gln, Gly, Ala, D-Ala, Ecyc, Asn or Glu
<220> FEATURE:
<221> NAME/KEY: MISC_FEATURE
<222> LOCATION: (5)..(5)
<223> OTHER INFORMATION: Xaa is Glu, Ecyc, Asp, Gly, D-Ala or Ala
<220> FEATURE:
<221> NAME/KEY: MISC_FEATURE
<222> LOCATION: (6)..(6)
<223> OTHER INFORMATION: Xaa is Nle, Gly, Lys, Ccyc, D-Ala, Met or Ala
```

```
<220> FEATURE:
<221> NAME/KEY: MISC_FEATURE
<222> LOCATION: (7)..(7)
<223> OTHER INFORMATION: Xaa is Gly, Asn, Gln, D-Ala or Ala
<220> FEATURE:
<221> NAME/KEY: MISC_FEATURE
<222> LOCATION: (8)..(8)
<223> OTHER INFORMATION: Xaa is Tyr, Gly, Glu, D-Ala or Ala
<220> FEATURE:
<221> NAME/KEY: MISC_FEATURE
<222> LOCATION: (9)..(9)
<223> OTHER INFORMATION: Xaa is Ile, Gly, Glu, D-Ala or Ala
<220> FEATURE:
<221> NAME/KEY: MISC_FEATURE
<222> LOCATION: (10)..(10)
<223> OTHER INFORMATION: Xaa is Phe, Gly, Glu, D-Ala or Ala
<220> FEATURE:
<221> NAME/KEY: MISC_FEATURE
<222> LOCATION: (11)..(11)
<223> OTHER INFORMATION: Xaa is Tyr, Gly, Glu, D-Ala or Ala
<220> FEATURE:
<221> NAME/KEY: MISC_FEATURE
<222> LOCATION: (12)..(12)
<223> OTHER INFORMATION: Xaa is Pro, Gly, Glu, Phe, Ccyc, Kcyc, D-Ala or
      Ala or is absent
<220> FEATURE:
<221> NAME/KEY: MISC_FEATURE
<222> LOCATION: (13)..(13)
<223> OTHER INFORMATION: Xaa is Arg, Gly, Asp, Leu, Lys, Glu, D-Ala or
      Ala or is absent when Xaa at position 12 is absent
<220> FEATURE:
<221> NAME/KEY: MISC_FEATURE
<222> LOCATION: (14)..(14)
<223> OTHER INFORMATION: Xaa is Lys, K-Ac, Gly, Arg, Leu, Gln, Asn,
      Kcyc, Glu, D-Ala or Ala or is absent when Xaa at position 13 is
      absent
<220> FEATURE:
<221> NAME/KEY: MISC_FEATURE
<222> LOCATION: (15)..(15)
<223> OTHER INFORMATION: Xaa is Leu, Gly, Arg, Lys, Deg, Glu, D-Ala or
      Ala or is absent when Xaa at position 14 is absent
<220> FEATURE:
<221> NAME/KEY: MISC_FEATURE
<222> LOCATION: (16)..(16)
<223> OTHER INFORMATION: Xaa is Arg, Asp, Glu, Leu, Lys, Gly, D-Ala or
      Ala or is absent when Xaa at position 15 is absent
<220> FEATURE:
<221> NAME/KEY: MISC_FEATURE
<222> LOCATION: (17)..(17)
<223> OTHER INFORMATION: Xaa is Glu or is absent when Xaa at position 16
      is absent

<400> SEQUENCE: 379

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 380
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is Arg or an amino acid with a non-polar
      side chain or a polar side chain or is absent
<220> FEATURE:
<221> NAME/KEY: MISC_FEATURE
<222> LOCATION: (2)..(2)
<223> OTHER INFORMATION: Xaa is Trp or an amino acid with a non-polar
      side chain or a polar side chain or is absent
<220> FEATURE:
<221> NAME/KEY: MISC_FEATURE
<222> LOCATION: (5)..(5)
```

```
<223> OTHER INFORMATION: Xaa is an amino acid with a non-polar side
      chain or a polar side chain
<220> FEATURE:
<221> NAME/KEY: MISC_FEATURE
<222> LOCATION: (6)..(6)
<223> OTHER INFORMATION: Xaa is an amino acid with a non-polar side
      chain or a polar side chain
<220> FEATURE:
<221> NAME/KEY: MISC_FEATURE
<222> LOCATION: (9)..(9)
<223> OTHER INFORMATION: Xaa is an amino acid with a non-polar side
      chain
<220> FEATURE:
<221> NAME/KEY: MISC_FEATURE
<222> LOCATION: (11)..(11)
<223> OTHER INFORMATION: Xaa is an amino acid with a non-polar side
      chain
<220> FEATURE:
<221> NAME/KEY: MISC_FEATURE
<222> LOCATION: (13)..(14)
<223> OTHER INFORMATION: Xaa is Lys-Leu, Leu-Arg, amino acids with a
      non-polar side chains or are absent

<400> SEQUENCE: 380

Xaa Xaa Gln Glu Xaa Xaa Tyr Ile Xaa Tyr Xaa Arg Xaa Xaa
1               5                   10
```

THERAPEUTIC PEPTIDES

CROSS-REFERENCE TO RELATED APPLICATIONS

This application is a national phase of International Application No. PCT/US2017/053597, filed Sep. 27, 2017, incorporated herein by reference, which claims priority benefit of U.S. Provisional Application No. 62/401,123, filed on Sep. 28, 2016.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 124,626 byte ACII (Text) file named "51155A_SubSeqListing.txt," created on Jun. 14, 2019.

BACKGROUND

Among adults aged 20 years or more in the United States, more than one third were obese during 2011-2014 (Ogden et al., Prevalence of Obesity Among Adults and Youth: United States, 2011-2014), NCHS Data Brief, No. 219 (November 2015). The prevalence of obesity among children in the U.S. (aged 2-19 years) was 17% during this timeframe. (Ogden, 2015, supra). Obesity is a risk factor for the development of numerous health problems, including metabolic syndrome, insulin resistance, type 2 diabetes, fatty liver disease, cardiovascular disease, obstructive sleep apnoea, stroke, hypertension, osteoarthritis, reproductive problems, and cancer (National Heart, Lung, and Blood Institute article: http://www.nhlbi.nih.gov/health/health-topics/topics/obe/risks).

Diabetes, an obesity-related condition, was the 7$^{th}$ leading cause of death in the U.S. in 2010. In 2012, 9.3% of the American population (or 29.1 million people) had diabetes, and approximately 208,000 children in the U.S. were estimated to have diagnosed diabetes. Every year, 1.4 million people in the U.S. are diagnosed with diabetes. Diabetes is associated with several complications and co-morbid conditions, including hypoglycemia, hypertension, dyslipidemia, cardiovascular disease, stroke, blindness, diabetic retinopathy, kidney disease, and amputations. According to the American Diabetes Association, the estimated total cost of diagnosed diabetes in the U.S. in 2012 was $245 billion (Diabetes Care 36: 1033-1046 (April 2013)). This cost highlights the substantial burden that diabetes imposes on the American society.

Despite the U.S. Food and Drug Administration approval of over 35 drugs during 2000-2015, there still remains a need for better therapeutics for obesity and diabetes.

Non-alcoholic fatty liver disease (NAFLD) is a condition of excessive fat accumulation in the form of triglycerides (steatosis) in the liver. NAFLD is the most common form of chronic liver disease in the United States, affecting as many as 80 million people, particularly those in their 40s and 50s. In addition to liver-related morbidity and mortality, there is growing evidence that NAFLD is a multisystem disease, with increased risk of type-2 diabetess mellitus, cardiovascular and cardiac diseases, cancer, and chronic kidney disease. While the majority of deaths among NAFLD patients are attributable to cardiovascular disease, as many as 15 million people in the US also have liver cell injury and inflammation, a condition called NASH (Non-Alcoholic SteatoHepatitis). NASH most often occurs in persons who are middle-aged and overweight or obese, ranks as one of the major causes of cirrhosis in America, and is predicted to become the most frequent indication for liver transplantation by 2030. There are currently no approved drugs for the treatment of NASH.

SUMMARY

The present disclosure provides peptides and peptide analogs and the use thereof in methods of treating diseases relating to NASH, body weight, blood glucose levels, and fat mass, e.g., metabolic diseases, including obesity, fatty liver disease and diabetes.

In exemplary embodiments, the peptide of the present disclosure comprises an amino acid sequence of Formula I:

(I)
(SEQ ID NO: 1)
$X^1$-Q-E-$X^2$-$X^3$-Y-I-$X^4$-Y-$X^5$-R-$X^6$ or a pharmaceutically acceptable salt thereof;
wherein $X^1$ is absent or if present is $X^7$—RW—, wherein $X^7$ is absent or if present is an amino acid with a non-polar side chain or a polar side chain; $X^2$ and $X^3$ are each independently an amino acid with a non-polar side chain or a polar side chain; $X^4$ and $X^5$ are each independently an amino acid with a non-polar side chain; $X^6$ is absent or if present is —KL-$X^8$ or —$X^9$-LR, wherein $X^8$ is absent or if present is an amino acid with a non-polar side chain and $X^9$ is an amino acid with a non-polar side chain; provided that the peptide is none of: MRWQEMGYIFYPRKLR (SEQ ID NO: 2); MRWQEMGYIFYFRKLR (SEQ ID NO: 316); MGWQEMGYIFYPRKLR (SEQ ID NO: 317); and/or MGYIFYPRKLR (SEQ ID NO: 318).

In some exemplary embodiments, the peptide comprises an amino acid sequence of Formula II or Formula III as set forth in the Detailed Description.

In exemplary embodiments, the peptide of Formula I, Formula II, and/or Formula III is isolated.

In exemplary embodiments, the peptide comprises a modification of a peptide sequence selected from

```
                              (SEQ ID NO: 11)
        MRWQEAGYIFYPRKLR;

(SEQ ID NO: 149)
        MRWQEMGYIFYPR(dA)LR;

(SEQ ID NO: 208)
        MRWQEMNYIFYPR;

(SEQ ID NO: 213)
        MRWQEMGYIFYPRNLR;

(SEQ ID NO: 219)
        MRWQEMQYIFYPRALR;

(SEQ ID NO: 248)
        RWQEMNYIFYPR;

(SEQ ID NO: 19)
        MRWQEMGYIFYPRALR;

(SEQ ID NO: 21)
        MRWQEMGYIFYPRKLA;

(SEQ ID NO: 17)
        MRWQEMGYIFYARKLR;

(SEQ ID NO: 217)
```

-continued

RWQEMGYIFYPRQLR;

MRWQEEGYIFYPRKLR; (SEQ ID NO: 172)

MRWQEMGYIFYPRKL; (SEQ ID NO: 45)

ERWQEAGYIAYPR; (SEQ ID NO: 241)

RWQEMQYIFYPR; (SEQ ID NO: 211)
and

MRWQEMGYIFYPAKLR; (SEQ ID NO: 18)

wherein the modification comprises substituting at least one amino acid in the peptide with another amino acid selected from (i) an amino acid having a D-configuration, and (ii) a non-naturally occurring amino acid residue; or pharmaceutically acceptable salts thereof.

In exemplary embodiments, the peptide is formulated with an excipient to provide a pharmaceutical composition which composition can be used to treat a disease in a patient or another medical condition.

In exemplary embodiments, the peptide comprises an amino acid sequence of Formula I, wherein $X^1$ is absent or if present is $X^7$—RW—, wherein $X^7$ is absent or if present is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); $X^2$ and $X^3$ are each independently selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); $X^4$ and $X^5$ are each independently selected from G, A, (dA), V, (dV), L, (dL), I, (dI), F, (dF), W, (dW), P (dP), M and (dM); $X^6$ is absent or if present is —KL-$X^8$ or —$X^9$-LR, wherein $X^8$ is absent or if present is selected from G, A, (dA), V, (dV), L, (dL), I, (dI), F, (dF), W, (dW), P (dP), M and (dM) and $X^9$ is selected from G, A, (dA), V, (dV), L, (dL), I, (dI), F, (dF), W, (dW), P (dP), M and (dM); or a pharmaceutically acceptable salt thereof.

In exemplary embodiments, the peptide comprises an amino acid sequence of Formula I wherein $X^1$ is absent or if present is $X^7$—RW—, wherein $X^7$ is absent or if present is M or E; $X^2$ is M, A or E; $X^3$ is G, N or Q; $X^4$ is F or A; $X^5$ is P or A; $X^6$ is absent or if present is —KL-$X^8$ or —$X^9$-LR, wherein $X^8$ is absent or if present is R or A and $X^9$ is selected from K, A, (dA), N and Q; or a pharmaceutically acceptable salt thereof.

In exemplary embodiments, the peptide comprises a sequence selected from the group consisting of: MRWQEAGYIFYPRKLR (SEQ ID NO: 11); MRWQEMGYIFYPR(dA)LR (SEQ ID NO: 149); MRWQEMNYIFYPR (SEQ ID NO: 208); MRWQEMGYIFYPRNLR (SEQ ID NO: 213); MRWQEMQYIFYPRALR (SEQ ID NO: 219); RWQEMNYIFYPR (SEQ ID NO: 210); MRWQEMGYIFYPRALR (SEQ ID NO: 19); MRWQEMGYIFYPRKLA (SEQ ID NO: 21); MRWQEMGYIFYARKLR (SEQ ID NO: 17); RWQEMGYIFYPRQLR (SEQ ID NO: 217); MRWQEEGYIFYPRKLR (SEQ ID NO: 172); MRWQEMGYIFYPRKL (SEQ ID NO: 45); ERWQEAGYIAYPR (SEQ ID NO: 241); RWQEMQYIFYPR (SEQ ID NO: 211); MRWQEMGYIFYPAKLR (SEQ ID NO: 18); and a pharmaceutically acceptable salt thereof.

In exemplary embodiments, the peptide or peptide analog of the present disclosure comprises (a) RWQE (SEQ ID NO: 294), (b) YIFY (SEQ ID NO: 295), or (c) both RWQE (SEQ ID NO: 294) and YIFY (SEQ ID NO: 295), wherein the peptide or peptide analog (i) exhibits at least a 10% stability in mouse plasma for 60 minutes at 37 degrees Celsius, (ii) decreases free fatty acid levels in human primary adipocytes, (iii) or both (i) and (ii). In exemplary embodiments, the peptide or peptide analog is 8 to 20 amino acids in length.

In exemplary embodiments, the peptide or peptide analog is a C-terminal acid or amide, or an N-acetyl derivative thereof.

In exemplary embodiments, the peptide or peptide derivative is a PEG, acetyl, biotin or fatty acid derivative thereof. In exemplary embodiments, the peptide derivative includes PEG600, acetyl, biotin or palmityl.

In exemplary embodiments, the peptide or peptide analog of the present disclosure comprises (A) an amino acid sequence of RWQE (SEQ ID NO: 294) and (B) an amino acid sequence of YIFY (SEQ ID NO: 295) with one amino acid substitution. In exemplary embodiments, the amino acid sequence of YIFY (SEQ ID NO: 295) with one amino acid substitution comprises XIFY (SEQ ID NO: 300), YXFY (SEQ ID NO: 301), YIXY (SEQ ID NO: 302), or YIFX (SEQ ID NO: 303), wherein X is any amino acid. In exemplary embodiments, the peptide or peptide analog is 8 to 20 amino acids in length. In exemplary embodiments, the peptide or peptide analog comprises one, two, three or more amino acids between part (A) and part (B). In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises (A) an amino acid sequence of RWQE (SEQ ID NO: 294) and (B) an amino acid sequence of YIFY (SEQ ID NO: 295) with two amino acid modifications. In exemplary embodiments, the peptide or peptide analog of the present disclosure comprises (A) an amino acid sequence of RWQE (SEQ ID NO: 294) and (B) an amino acid sequence of YIFY (SEQ ID NO: 295) with two amino acid substitutions. In exemplary embodiments, the peptide or peptide analog of the present disclosure comprises an amino acid sequence of RWQE (SEQ ID NO: 294) and YIAE (SEQ ID NO: 308) or EIFE (SEQ ID NO: 309). In exemplary embodiments, the peptide or peptide analog of the present disclosure comprises (A) an amino acid sequence of RWQE (SEQ ID NO: 294) and (B) a truncated form of YIFY (SEQ ID NO: 295). In exemplary embodiments, the peptide or peptide analog of the present disclosure comprises (A) an amino acid sequence of RWQE (SEQ ID NO: 294) and (B) YI or YIF. In exemplary embodiments, the peptide or peptide analog is 8 to 20 amino acids in length. In exemplary embodiments, the peptide or peptide analog comprises one, two, three or more amino acids between part (A) and part (B). In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog comprises (A) an amino acid sequence of YIFY (SEQ ID NO: 295) and (B) an amino acid sequence of RWQE (SEQ ID NO: 294) with one amino acid substitution. In exemplary embodiments, the amino acid sequence of RWQE (SEQ ID NO: 294) with one amino acid substitution comprises XWQE (SEQ ID NO: 304), RXQE (SEQ ID NO: 305), RWXE (SEQ ID NO: 306), or RWQX (SEQ ID NO: 307), wherein X is any amino acid. In exemplary embodiments, the peptide or peptide analog is 8 to 20 amino acids in length. In exemplary embodiments, the peptide or peptide analog comprises one, two, three or more amino acids between part (A) and part (B). In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises an amino acid sequence of RWQEX$^1$X$^2$YIFY (SEQ ID NO: 319), wherein each of X$^1$ and X$^2$ is independently any amino acid. In exemplary embodiments, the peptide or peptide analog of the present disclosure comprises an amino acid sequence an amino acid sequence of RWQEX$^1$X$^2$X$^3$IFY (SEQ ID NO: 320), RWQEX$^1$X$^2$YX$^3$FY (SEQ ID NO: 321), RWQEX$^1$X$^2$YIX$^3$Y (SEQ ID NO: 322) or RWQEX$^1$X$^2$YIFX$^3$ (SEQ ID NO: 323), wherein each of X$^1$, X$^2$ and X$^3$ is independently any amino acid. In exemplary embodiments, the peptide or peptide analog of the present disclosure comprises an amino acid sequence of SEQ ID NOs: 1, 3-41, 43-76, and 79-293, 310-315, 319-323 and 354-377. In exemplary embodiments, the peptide or peptide analog of the present disclosure comprises a structure and/or amino acid sequence set forth in Table 1.

In exemplary embodiments, the peptide or peptide analog of the present disclosure is not any of the peptides consisting of the amino acid sequence: MRWQEMGYIFYPRKLR (SEQ ID NO: 2); MRWQEMGYIFYFRKLR (SEQ ID NO: 316); MGWQEMGYIFYPRKLR (SEQ ID NO: 317); or MGYIFYPRKLR (SEQ ID NO: 318).

In some embodiments, peptides disclosed herein comprise a sequence having at least 66% sequence identity to any one of amino acid sequences SEQ ID NO: 11, 17, 18, 19, 21, 45, 149, 172, 208, 210, 211, 213, 217, 219, 217 and 241. In certain embodiments, the % identity is selected from, e.g., at least 70%, at least 75%, at least 80%, at least 85%, at least 90%, or at least 95%, or more sequence identity to a given sequence. In certain embodiments, the % identity is in the range of, e.g., about 65% to about 70%, about 70% to about 80%, about 80% to about 85%, about 85% to about 90%, or about 90% to about 95%; %; between about 70% and about 80%, between about 80% and about 90% and between about 90% and about 99% sequence identity.

In certain embodiments, the peptide comprises a sequence having at least 66% sequence identity to any one of amino acid sequences SEQ ID NO: 11, 17, 18, 19, 21, 45, 149, 172, 208, 210, 211, 213, 217, 219, 217 and 241. In certain embodiments, the % identity is selected from, e.g., at least 70%, at least 75%, at least 80%, at least 85%, at least 90%, or at least 95%, or more sequence identity to a given sequence. In certain embodiments, the % identity is in the range of, e.g., about 65% to about 70%, about 70% to about 80%, about 80% to about 85%, about 85% to about 90%, or about 90% to about 95%; %; between about 70% and about 80%, between about 80% and about 90% and between about 90% and about 99% sequence identity, but does not comprise the sequence set forth in SEQ ID NOs: 2, 42, 77-78, 316-318, or 328-349.

The present disclosure further provides conjugates comprising any one or more of the peptides or peptide analogs of the present disclosures and a heterologous moiety.

The present disclosure furthermore provides a nucleic acid comprising a nucleotide sequence encoding any one or more of the peptides or peptide analogs of the present disclosure. Also, an expression vector comprising the nucleic acid of the present disclosures is provided herein. A host cell comprising the nucleic acid or expression vector is provided by the present disclosure.

Additionally, the present disclosure provides a composition comprising the peptide, peptide analog, conjugate, nucleic acid, expression vector, host cell, or a combination thereof, and a carrier, excipient, or diluent. In exemplary aspects, the composition is a pharmaceutical composition. In exemplary aspects, the pharmaceutical compositions of the present disclosure comprise an amino acid sequence of Formula I, including the amino acid sequences of SEQ ID NOs: 1, 3-41, 43-76, and 79-293, 310-315, 319-323 and 354-377, analogs and derivatives thereof described herein and a pharmaceutically acceptable excipient.

The present disclosure also includes, as an additional embodiment, compositions that comprise mixture of two or more peptides or peptide analogs described herein (or conjugates, nucleic acids, expression vectors, etc.), optionally further including an excipient or carrier.

The present disclosure moreover provides related kits comprising the peptide, peptide analog, conjugate, nucleic acid, expression vector, host cell, or a combination thereof.

A method of producing the peptides or peptide analogs is provided by the present disclosure. In exemplary embodiments, the method comprises (i) reacting a first amino acid with a second amino acid to form a covalent linkage between the first amino acid and the second amino acid, wherein the first amino acid or the second amino acid optionally is attached to another amino acid, and (ii) repeating the reacting step of (i), whereupon the peptide or peptide analog is produced.

Without being bound to a particular theory, the peptides and peptide analogs of the present disclosure are well-suited as a therapeutic agent. Data provided herein support the use of such peptides and peptide analogs in the treatment of diseases, disorders, or medical conditions relating to free fatty acids, body weight, blood glucose levels, lipid distribution, and fat mass.

The present disclosure accordingly provides a method of modulating fatty acid metabolism in a subject in need thereof, comprising administering to the subject a peptide or peptide analog, a conjugate, a nucleic acid, a recombinant expression vector, or a host cell of the present disclosure in an amount effective to modulate fatty acid metabolism.

The present disclosure also provides a method of treating a metabolic disease in a subject in need thereof, comprising administering to the subject a peptide or peptide analog, a conjugate, a nucleic acid, a recombinant expression vector, or a host cell of the present disclosure in an amount effective to treat the metabolic disease.

Also, without being bound to a particular theory, given that some metabolic disease states are related to or associated with the liver, the peptides and peptide analogs of the present disclosure are well-suited to treat liver diseases, including but not limited to NAFLD and NASH. Accordingly, the present disclosure also provides a method of treating a liver disease in a subject in need thereof, comprising administering to the subject a peptide or peptide analog, a conjugate, a nucleic acid, a recombinant expression vector, or a host cell of the present disclosure in an amount effective to treat the liver disease.

The present disclosure also provides a method of treating cancer in a subject in need thereof, comprising administering to the subject a peptide or peptide analog, a conjugate, a nucleic acid, a recombinant expression vector, or a host cell of the present disclosure in an amount effective to treat the cancer.

The present disclosure also provides a method of treating obesity or excessive weight in a subject in need thereof, comprising administering to the subject a peptide or peptide analog, a conjugate, a nucleic acid, a recombinant expression vector, or a host cell of the present disclosure in an amount effective to treat the obesity or excessive weight.

The present disclosure also provides a method of treating stroke in a subject in need thereof, comprising administering to the subject a peptide or peptide analog, a conjugate, a nucleic acid, a recombinant expression vector, or a host cell of the present disclosure in an amount effective to treat the stroke.

The present disclosure also provides a method of treating cardiovascular disease in a subject in need thereof, comprising administering to the subject a peptide or peptide analog, a conjugate, a nucleic acid, a recombinant expression vector, or a host cell of the present disclosure in an amount effective to treat the cardiovascular disease.

The present disclosure also provides a method of treating obstructive sleep apnea in a subject in need thereof, comprising administering to the subject a peptide or peptide analog, a conjugate, a nucleic acid, a recombinant expression vector, or a host cell of the present disclosure in an amount effective to treat the obstructive sleep apnea.

The present disclosure also provides a method of treating hypertension in a subject in need thereof, comprising administering to the subject a peptide or peptide analog, a conjugate, a nucleic acid, a recombinant expression vector, or a host cell of the present disclosure in an amount effective to treat the hypertension.

The present disclosure also provides a method of modulating, including reducing, the level of fatty acids, such as free fatty acids, in an adipocyte or adipocytes, the method comprising contacting the adipocyte(s) with a peptide or peptide analog, a conjugate, a nucleic acid, a recombinant expression vector, or a host cell of the present disclosure, in an amount effective to reduce the level. In some variations, the method is performed in vitro, e.g., in cell culture. In some variations, the method is performed in vivo, e.g., by administering the material to a subject in need.

The present disclosure also provides a method of modulating, including reducing, the level of blood or serum glucose and/or serum triglycerides in a subject, the method comprising administering to a subject a peptide or peptide analog, a conjugate, a nucleic acid, a recombinant expression vector, or a host cell of the present disclosure, in an amount effective to reduce blood/serum glucose.

For embodiments described herein relating to use of nucleic acids and vectors, the method may comprise transforming or transfecting cells in vitro or in vivo.

Aspects of the invention that have been described herein as methods also can be described as "uses," and all such uses are contemplated as aspects of the invention. Likewise, compositions described herein as having a "use" can alternatively be described as processes or methods of using, which are contemplated as aspects of the invention. For example, an embodiment described herein as a method of treatment of a disease or condition should also be understood to include an embodiment directed to the use of the agent or substance to treat the disease or condition, or a use of the substance in the manufacture of a medicament to treat the disease or condition.

Aspects of the invention are described herein as methods of treatment with combinations of two or more agents (or uses of combinations of agents) for a particular purpose. Related aspects of the invention include compositions of matter wherein the two or more agents are in admixture; and kits in which the two or more agents are packaged together, e.g., in unit dose formulations, but not in admixture.

Reference throughout this specification to "one embodiment", "some embodiments" or "an embodiment" means that a particular feature, structure or characteristic described in connection with the embodiment is included in at least one embodiment of the present disclosure. The particular features, structures, or characteristics described herein may be combined in any suitable manner, and all such combinations are contemplated as aspects of the invention.

Unless otherwise specified, the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

The invention includes, as an additional aspect, all embodiments of the invention narrower in scope in any way than the variations defined by specific paragraphs above or by original claims. For example, where certain aspects of the invention that are described as a genus or set, it should be understood that every member of a genus or set is, individually, an aspect of the invention. Likewise, every individual subset is intended as an aspect of the invention. By way of example, if an aspect of the invention is described as a members selected from the group consisting of 1, 2, 3, and 4, then subgroups (e.g., members selected from {1,2,3} or {1,2,4} or {2,3,4} or {1,2} or {1,3} or {1,4} or {2,3} or {2,4} or {3,4}) are contemplated and each individual species {1} or {2} or {3} or {4} is contemplated as an aspect or variation of the invention. Likewise, if an aspect of the invention is characterized as a range, or being practiceable over a range, such as a temperature range, then integer subranges are contemplated as aspects or variations of the invention.

The headings herein are for the convenience of the reader and not intended to be limiting. Additional aspects, embodiments, and variations of the invention will be apparent from the Detailed Description and/or Drawing and/or original claims. The original claims are incorporated here in the summary of invention by reference.

Although the Applicant invented the full scope of the invention described herein, the Applicant does not intend to claim subject matter described in the prior art work of others. Therefore, in the event that statutory prior art within the scope of a claim is brought to the attention of the Applicant by a Patent Office, tribunal, or other entity or individual, the Applicant reserves the right to exercise amendment rights under applicable patent laws to redefine the subject matter of such a claim to specifically exclude such statutory prior art or obvious or noninventive variations of statutory prior art from the scope of such a claim. Variations of the invention defined by such amended claims also are intended as aspects of the invention.

DETAILED DESCRIPTION

Definitions

In describing and claiming the invention, the following terminology will be used in accordance with the definitions set forth below.

The terms "peptide" refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or non-covalently, modified peptides. A peptide may be monomeric or polymeric. In certain embodiments, "peptides" are chains of amino acids whose alpha carbons may be linked through peptide bonds. The terminal amino acid at one end of the chain (amino terminal) therefore has a free amino group, while the terminal amino acid at the other end of the chain (carboxy terminal) has a free carboxyl group. As used herein, the term "amino terminus" (abbreviated N-terminus) refers to the free α-amino group on an amino acid at the amino terminal of a peptide or to the α-amino group (imino group when participating in a peptide bond) of an amino acid at any other location within the peptide. Similarly, the term "carboxy terminus" refers to the free carboxyl group on the carboxy terminus of a peptide or the carboxyl group of an amino acid at any other location within the peptide. Peptides also include essentially any polyamino acid including, but not limited to, peptide mimetics such as amino acids joined by an ether as opposed to an amide bond.

The term "therapeutic peptide" refers to peptides or fragments or variants thereof, having one or more therapeutic and/or biological activities.

The term "analog" or "peptide analog" as used herein describes a peptide comprising one or more amino acid modifications, such as but not limited to substitution and/or one or more deletion(s) and/or one or more addition(s) of any one of the amino acid residues with any natural or unnatural amino acid, synthetic amino acids or peptidomimetics and/or the attachment of a substituent to any one of the natural or unnatural amino acids, synthetic amino acids or peptidomimetics at any available position. The addition or deletion of amino acid residues can take place at the N-terminal of the peptide and/or at the C-terminal of the peptide.

In some embodiments, the analog has 1, 2, 3, 4, or 5 such modifications. In some embodiments, the analog retains biological activity of the original peptide. In some embodiments, the analog is a competitive or non-competitive inhibitor of the original peptide.

Peptide sequences are indicated using standard one- or three-letter abbreviations. Unless otherwise indicated, peptide sequences have their amino termini at the left and their carboxy termini at the right, A particular section of a peptide can be designated by amino acid residue number such as amino acids 3 to 6, or by the actual residue at that site such as Met3 to Gly6. A particular peptide sequence also can be described by explaining how it differs from a reference sequence.

When used herein the term "natural amino acid" is an amino acid (with the usual three letter codes & one letter codes in parenthesis) selected from the group consisting of: Glycine (Gly & G), proline (Pro & P), alanine (Ala & A), valine (Val & V), leucine (Leu & L), isoleucine (Ile & I), methionine (Met & M), cysteine (Cys & C), phenylalanine (Phe & F), tyrosine (Tyr & Y), tryptophan (Trp & W), histidine (His & H), lysine (Lys & K), arginine (Arg & R), glutamine (Gin & Q), asparagine (Asn & N), glutamic acid (Glu & E), aspartic acid (Asp & D), serine (Ser & S) and threonine (Thr & T). If anywhere herein, reference is made to a peptide, analog or derivative or peptides comprising or not comprising G, P, A, V, L, I, M, C, F, Y, H, K, R, Q, N, E, D, S or T, without specifying further, amino acids are meant. If not otherwise indicated, amino acids indicated with a single letter code in CAPITAL letters indicate the L-isoform. If however, the amino acid designated in single letter code in CAPITAL letters is preceded by a lower case "d" and in parentheses, such as "(dD)" and "(dE)", this amino acid is used/applied as its D-isoform. For example, "(dD)" refers to the D-isomer of D or aspartic acid, "(dA)" refers to the D-isomer of A or alanine, and "(dE)" refers to the D-isomer of E or glutamic acid. In some instances, the D-isomer of an amino acid is notated by "D-" followed by an amino acid designated in its three-letter code. Thus, for example, "D-Ala" refers to the D-isomer of alanine, "D-Asp" refers to the D-isomer of aspartic acid, and "D-Glu" refers to the D-siomer of glutamic acid. Such D-forms and other non-conservative amino acid substitutions previously defined are included in a definition of unnatural amino acids.

If, due to typing errors, there are deviations from the commonly used codes, the commonly used codes apply. The amino acids present in the peptides are, preferably, amino acids which can be coded for by a nucleic acid. As is apparent from the above examples, amino acid residues may be identified by their full name, their one-letter code, and/or their three-letter code. These three ways are fully equivalent.

As used herein the term "charged amino acid" or "charged residue" refers to an amino acid that comprises a side chain that is negative-charged (i.e., de-protonated) or positive-charged (i.e., protonated) in aqueous solution at physiological pH. For example, negative-charged amino acids include aspartic acid, glutamic acid, cysteic acid, homocysteic acid, and homoglutamic acid, whereas positive-charged amino acids include arginine, lysine and histidine. Charged amino acids include the charged amino acids among the 20 coded amino acids, as well as atypical or non-naturally occurring or non-coded amino acids.

As used herein the term "acidic amino acid" refers to an amino acid that comprises a second acidic moiety (other than the carboxylic acid of the amino acid), including for example, a carboxylic acid or sulfonic acid group.

As used herein, the term "acylated amino acid" refers to an amino acid comprising an acyl group which is non-native to a naturally-occurring amino acid, regardless of the means by which it is produced (e.g. acylation prior to incorporating the amino acid into a peptide, or acylation after incorporation into a peptide).

As used herein the term "alkylated amino acid" refers to an amino acid comprising an alkyl group which is non-native to a naturally-occurring amino acid, regardless of the means by which it is produced. Accordingly, the acylated amino acids and alkylated amino acids of the present disclosures are non-coded amino acids.

A skilled artisan will be able to determine active variants of peptides as set forth herein using materials and methods (such as synthesis techniques and activity assays) described herein, including, fatty acid metabolism, and other metabolic assays. See, Examples section. In certain embodiments, one skilled in the art may identify suitable areas of the molecule that may be changed without destroying activity by targeting regions not believed to be important for activity. In other embodiments, the skilled artisan can identify residues and portions of the molecules that are conserved among similar peptides (such as peptide described herein having similar modulating activities). In further embodiments, even areas that may be important for biological activity or for structure may be subject to conservative amino acid substitutions without destroying the biological activity or without adversely affecting the peptide structure.

Additionally, one skilled in the art can review structure-function studies identifying residues in similar peptides that are important for activity or structure. In view of such a comparison, the skilled artisan can predict the importance of amino acid residues in a peptide that correspond to amino acid residues important for activity or structure in similar peptides. One skilled in the art may opt for chemically similar amino acid substitutions for such predicted important amino acid residues.

One skilled in the art can also analyze the three-dimensional structure and amino acid sequence in relation to that structure in similar peptides. In view of such information, one skilled in the art may predict the alignment of amino acid residues of a peptide with respect to its three-dimensional structure. In certain embodiments, one skilled in the art may choose to not make radical changes to amino acid residues predicted to be on the surface of the peptide, since such residues may be involved in important interactions with other molecules. Moreover, one skilled in the art may generate test variants containing a single amino acid substitution at each desired amino acid residue. The variants can then be screened using activity assays known to those skilled in the art. Such variants could be used to gather information about suitable variants. For example, if one discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

The term "derivative" as used herein means a chemically modified peptide, in which one or more substituents or moieties have been covalently attached to the peptide. A derivative comprising such substituents or moieties will thus be "derivatized" peptide or "derivatized" analog. The term may also refer to peptides containing one or more chemical moieties not normally a part of the peptide molecule such as esters and amides of free carboxy groups, acyl and alkyl derivatives of free amino groups, phospho esters and ethers of free hydroxy groups. Such modifications may be introduced into the molecule by reacting targeted amino acid residues of the peptide with an organic derivatizing agent that is capable of reacting with selected side chains or terminal residues. Preferred chemical derivatives include peptides that have been phosphorylated, C-termini amidated or N-termini acetylated. The term may also refer to peptides as used herein which may be prepared from the functional groups which occur as side chains on the residues or the N- or C-terminal groups, by means known in the art, and are included herein as long as they remain pharmaceutically acceptable, i.e., they do not destroy the activity of the peptide, do not confer toxic properties on compositions containing it and do not adversely affect the antigenic properties thereof. These derivatives may, for example, include aliphatic esters of the carboxyl groups, amides of the carboxyl groups produced by reaction with ammonia or with primary or secondary amines, N-acyl derivatives of free amino groups of the amino acid residues formed by reaction with acyl moieties (e.g., alkanoyl or carbocyclic aroyl groups) or O-acyl derivatives of free hydroxyl group (for example that of seryl or threonyl residues) formed by reaction with acyl moieties.

A modified amino acid residue is an amino acid residue in which any group or bond was modified by deletion, addition, or replacement with a different group or bond, as long as the functionality of the amino acid residue is preserved or if functionality changed (for example replacement of tyrosine with substituted phenylalanine) as long as the modification did not impair the activity of the peptide containing the modified residue.

The term "substituent" as used herein means any suitable moiety bonded, in particular covalently bonded, to an amino acid residue, in particular to any available position on an amino acid residue. Typically, the suitable moiety is a chemical moiety.

The term "fatty acid" refers to aliphatic monocarboxylic acids having from 4 to 28 carbon atoms, it is preferably un-branched, and it may be saturated or unsaturated. In the present disclosure fatty acids comprising 10 to 16 amino acids are preferred.

The term "fatty diacid" refers to fatty acids as defined above but with an additional carboxylic acid group in the omega position. Thus, fatty diacids are dicarboxylic acids. In the present disclosure fatty acids comprising 14 to 20 amino acids are preferred.

The term "% sequence identity" is used interchangeably herein with the term "% identity" and refers to the level of amino acid sequence identity between two or more peptide sequences or the level of nucleotide sequence identity between two or more nucleotide sequences, when aligned using a sequence alignment program. For example, as used herein, 80% identity means the same thing as 80% sequence identity determined by a defined algorithm, and means that a given sequence is at least 80% identical to another length of another sequence.

The term "% sequence homology" is used interchangeably herein with the term "% homology" and refers to the level of amino acid sequence homology between two or more peptide sequences or the level of nucleotide sequence homology between two or more nucleotide sequences, when aligned using a sequence alignment program. For example, as used herein, 80% homology means the same thing as 80% sequence homology determined by a defined algorithm, and accordingly a homologue of a given sequence has greater than 80% sequence homology over a length of the given sequence.

Exemplary computer programs which can be used to determine degrees of identity or homology between two sequences include, but are not limited to, the suite of BLAST programs, e.g., BLASTN, BLASTX, and TBLASTX, BLASTP and TBLASTN, publicly available on the Internet at the NCBI website. See also Altschul et al., 1990, J. Mol. Biol. 215:403-10 (with special reference to the published default setting, i.e., parameters w=4, t=17) and Altschul et al., 1997, Nucleic Acids Res., 25:3389-3402. Sequence searches are typically carried out using the BLASTP program when evaluating a given amino acid sequence relative to amino acid sequences in the GenBank Protein Sequences and other public databases. The BLASTX program is preferred for searching nucleic acid sequences that have been translated in all reading frames against amino acid sequences in the GenBank Protein Sequences and other public databases. Both BLASTP and BLASTX are run using default parameters of an open gap penalty of 11.0, and an extended gap penalty of 1.0, and utilize the BLOSUM-62 matrix. (Id). In addition to calculating percent sequence identity, the BLAST algorithm also performs a statistical analysis of the similarity between two sequences (see, e.g., Karlin & Altschul, Proc. Nat'l. Acad. Sci. USA, 90:5873-5787 (1993)). One measure of similarity provided by the BLAST algorithm is the smallest sum probability (P(N)), which provides an indication of the probability by which a match between two nucleotide or amino acid sequences would occur by chance.

As used herein, a "therapeutically effective amount" of a peptide that when provided to a subject in accordance with the disclosed and claimed methods affects biological activities, such as decreasing free fatty acid levels, serum triglyceride levels, blood glucose levels, body weight, fat mass, or modulating fatty acid metabolism.

The terms "treat", "treating" and "treatment" refer refers to an approach for obtaining beneficial or desired clinical results. Further, references herein to "treatment" include references to curative, palliative and prophylactic treatment. The term "treating" refers to inhibiting, preventing or arresting the development or progression of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology.

The term "improving cell survival" refers to an increase in the number of cells that survive a given condition, as compared to a control, e.g., the number of cells that would survive the same conditions in the absence of treatment. Conditions can be in vitro, in vivo, ex vivo, or in situ. Improved cell survival can be expressed as a comparative value, e.g., twice as many cells survive if cell survival is improved two-fold. Improved cell survival can result from a reduction in apoptosis, an increase in the life-span of the cell, or an improvement of cellular function and condition.

For clarity, the term "instructing" is meant to include information on a label approved by a regulatory agency, in addition to its commonly understood definition.

As used herein and in the appended claims, the singular forms "a," "or," and "the" include plural referents unless the context clearly dictates otherwise. It is understood that aspects and variations of the disclosure described herein include "consisting" and/or "consisting essentially of" aspects and variation.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

As used herein, the term "preventing" refers to keeping a disease, disorder or condition from occurring in a subject who may be at risk for the disease, but has not yet been diagnosed as having the disease. Preventing (and doses effective to prevent) can be demonstrated in a population study. For example, an amount effective to prevent a given disease or medical condition is an amount effective to decrease the occurrence in a treated population, relative to an untreated control population.

As used herein, the term "subject" includes mammals, preferably human beings at any age which suffer from the pathology. Preferably, this term encompasses individuals who are at risk to develop the pathology.

Peptides

The present disclosure provides peptides and peptide analogs that decrease free fatty acid levels in adipocytes. Advantageously, the peptides and peptide analogs of the present disclosure demonstrate sufficient stability in plasma, as further discussed herein.

In exemplary embodiments, the peptide of the present disclosure comprises an amino acid sequence of Formula I:

(I)
(SEQ ID NO: 1)
$X^1$-Q-E-$X^2$-$X^3$-Y-I-$X^4$-Y-$X^5$-R-$X^6$ or a pharmaceutically acceptable salt thereof;
wherein $X^1$ is absent or if present is $X^7$—RW—, wherein $X^7$ is absent or if present is an amino acid with a non-polar side chain or a polar side chain; $X^2$ and $X^3$ are each independently an amino acid with a non-polar side chain or a polar side chain; $X^4$ and $X^5$ are each independently an amino acid with a non-polar side chain; $X^6$ is absent or if present is —KL-$X^8$ or —$X^9$-LR, wherein $X^8$ is absent or if present is an amino acid with a non-polar side chain and $X^9$ is an amino acid with a non-polar side chain; provided that the peptide is none of: MRWQEMGYIFYPRKLR (SEQ ID NO: 2); MRWQEMGYIFYFRKLR (SEQ ID NO: 316); MGWQEMGYIFYPRKLR (SEQ ID NO: 317); and/or MGYIFYPRKLR (SEQ ID NO: 318).

In exemplary embodiments, the peptide of the present disclosure comprises an amino acid sequence of Formula II:

(II)
(SEQ ID NO: 378)
$X^{17}$-$X^{18}$-$X^{19}$-Q-E-$X^{20}$-$X^{21}$-Y-I-$X^{22}$-Y-$X^{23}$-$X^{24}$-$X^{25}$ wherein $X^{17}$ is absent or if present is is an amino acid with a non-polar side chain or a polar side chain; $X^{18}$ is absent or if present is is an amino acid with a non-polar side chain or a polar side chain; $X^{19}$ is absent or if present is an amino acid with a non-polar side chain or a polar side chain; $X^{20}$ is an amino acid with a non-polar side chain or a polar side chain; $X^{21}$ is an amino acid with a non-polar side chain or a polar side chain; $X^{22}$ is an amino acid with a non-polar side chain or a polar side chain; $X^{23}$ is an amino acid with a non-polar side chain or a polar side chain; $X^{24}$ is an amino acid with a non-polar side chain or a polar side chain; and $X^{25}$ is absent or if present is selected from an amino acid with a non-polar side chain or a polar side chain, -LKR, —KLX$^{26}$, —X$^{27}$LR, —KX$^{28}$R, —RX$^{29}$R and —KRX$^{30}$; wherein $X^{26}$ is absent or if present is selected from an amino acid with a non-polar side chain or a polar side chain; wherein $X^{27}$ is selected from an amino acid with a non-polar side chain or a polar side chain; wherein $X^{28}$ is selected from an amino acid with a non-polar side chain or a polar side chain; wherein $X^{29}$ is selected from an amino acid with a non-polar side chain or a polar side chain; and wherein $X^{30}$ is absent or if present is selected from an amino acid with a non-polar side chain; provided that the peptide is not a peptide consisting of any one of the amino acid sequences of SEQ ID NOs: 2, 42, 77, 78, 316-318, and 328-349; further provided $X^{17}$ and $X^{18}$ are absent if $X^{19}$ is absent; and further provided $X^{17}$ is absent if $X^{18}$ is absent; and or C-terminal acids or amides, or N-acetyl derivatives thereof, or pharmaceutically acceptable salts thereof.

In exemplary embodiments, the peptide comprises an amino acid sequence of Formula II, wherein $X^{17}$ is absent or if present is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), Nle, I, (dI), F, (dF), W, (dW), P (dP), M and (dM); $X^{18}$ is absent or if present is selected from D, (dD), E, (dE), K, (dK), R, (dR), H, (dH), N, (dN), Q, (dQ), S, (dS), T, (dT), Y, (dY), C, (dC), G, A, (dA), Aib, V, (dV), L, (dL), I, (dI), F, (dF), W, (dW), P (dP), M and (dM); $X^{19}$ is absent or if present is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); $X^{20}$ is selected from D, (dD), E, (dE), K, (dK), R, (dR), H, (dH), N, (dN), Q, (dQ), S, (dS), T, (dT), Y, (dY), C, (dC), G, A, (dA), Aib, V, (dV), L, (dL), I, (dI), F, (dF), W, (dW), P (dP), M and (dM); $X^{21}$ is selected from D, (dD), E, (dE), K, (dK), R, (dR), H, (dH), N, (dN), Q, (dQ), S, (dS), T, (dT), Y, (dY), C, (dC), G, A, (dA), Aib, V, (dV), L, (dL), I, (dI), F, (dF), W, (dW), P (dP), M and (dM); $X^{22}$ is selected from D, (dD), E, (dE), K, (dK), R, (dR), H, (dH), N, (dN), Q, (dQ), S, (dS), T, (dT), Y, (dY), C, (dC), G, A, (dA), Aib, V, (dV), L, (dL), I, (dI), F, (dF), W, (dW), P (dP), M and (dM); $X^{23}$ is selected from D, (dD), E, (dE), K, (dK), R, (dR), H, (dH), N, (dN), Q, (dQ), S, (dS), T, (dT), Y, (dY), C, (dC), G, A, (dA), Aib, V, (dV), L, (dL), I, (dI), F, (dF), W, (dW), P (dP), M and (dM); $X^{24}$ is absent or if present is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); and $X^{25}$ is absent or if present is selected from selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M, (dM), -LKR, —KL$X^{26}$, —$X^{27}$LR, —K$X^{28}$R, —R$X^{29}$R and —KR$X^{30}$; wherein $X^{26}$ is absent or if present is selected from —RE, D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); wherein $X^{27}$ is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); wherein $X^{28}$ is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); wherein $X^{29}$ is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); and wherein $X^{30}$ is absent or if present is selected from G, A, (dA), V, (dV), L, (dL), I, (dI), F, (dF), W, (dW), P (dP), M and (dM); or C-terminal acids or amides, or N-acetyl derivatives thereof, or a pharmaceutically acceptable salt thereof.

In exemplary embodiments, the peptide comprises an amino acid sequence of Formula II, wherein $X^{17}$ is absent or if present is M, L, G, K, E, A, (dA) or Nle; $X^{18}$ is absent or if present is R, A, G, D, K, Aib, (dA) or E; $X^{19}$ is absent or if present is W, A, (dA), G, or E; $X^{20}$ is Nle, G, K, Ccyc, (dA), M or A; $X^{21}$ is G, N, Q, (dA) or A; $X^{22}$ is F, G, E, (dA) or A; $X^{23}$ is P, G, E, F, Ccyc, Kcyc, (dA) or A; $X^{24}$ is absent or if present is R, G, D, L, K, E, (dA) or A; and $X^{25}$ is absent or if present is selected from —K, —R, N, Q, (dA), —KL, —KR, —R(Da), —KLR, —K(Ac)LR, —K(cyc)LR, -ALR, -(dA)LR, -GLR, -ELR, -NLR, -QLR, —KAR, —K(dA)R, —KGR, —KER, —KLA, —KL(dA), —KLD, —KLE, —KLG, —KLK, —RKR, —RLR, -LKR, —KRL, and —KLRE; C-terminal acids or amides, or N-acetyl derivatives thereof; or a pharmaceutically acceptable salt thereof.

In exemplary embodiments, the peptide of the present disclosure comprises an amino acid sequence of Formula III:

(III)
(SEQ ID NO: 379)
$X^{31}$-$X^{32}$-$X^{33}$-$X^{34}$-$X^{35}$-$X^{36}$-$X^{37}$-$X^{38}$-$X^{39}$-$X^{40}$-$X^{41}$-$X^{42}$-$X^{43}$-$X^{44}$-$X^{45}$-$X^{46}$-$X^{47}$ wherein $X^{31}$ is absent or if present is M, L, G, K, E, A, (dA) or Nle; $X^{32}$ is absent or if present is R, A, G, D, K, Aib, (dA) or E; $X^{33}$ is absent or if present is W, A, (dA), G, or E; $X^{34}$ is Q, G, A, (dA), Ecyc, N or E; $X^{35}$ is E, Ecyc, D, G, (dA) or A; $X^{36}$ is Nle, G, K, Ccyc, (dA), M or A; $X^{37}$ is G, N, Q, (dA) or A; $X^{38}$ is Y, G, E, (dA) or A; $X^{39}$ is I, G, E, (dA) or A; $X^{40}$ is F, G, E, (dA) or A; $X^{41}$ is Y, G, E, (dA) or A; $X^{42}$ is absent or if present is P, G, E, F, Ccyc, Kcyc, (dA) or A; $X^{43}$ is absent or if present is R, G, D, L, K, E, (dA) or A; $X^{44}$ is absent or if present is K, K—Ac, G, R, L, Q, N, Kcyc, E, (dA) or A; $X^{45}$ is absent or if present is L, G, R, K, Deg, E, (dA) or A; $X^{46}$ is absent or if present is R, D, E, L, K, G, (dA) or A; and $X^{47}$ is absent or if present is E; provided that the peptide is wherein the peptide is not a peptide consisting of any one of the amino acid sequences of SEQ ID NOs: 2, 42, 77, 78, 316-318, and 328-349; further provided $X^{31}$ and $X^{32}$ are absent if $X^{33}$ is absent; further provided $X^{31}$ is absent if $X^{32}$ is absent; further provided $X^{47}$, $X^{46}$, $X^{45}$, $X^{44}$, and $X^{43}$ are absent if $X^{42}$ is absent; further provided $X^{47}$, $X^{46}$, $X^{45}$, and $X^{44}$, are absent if $X^{43}$ is absent; further provided $X^{47}$, $X^{46}$, and $X^{45}$, are absent if $X^{44}$ is absent; further provided $X^{47}$ and $X^{46}$, are absent if $X^{45}$ is absent; and further provided $X^{47}$ is absent if $X^{46}$ is absent; and or C-terminal acids or amides, or N-acetyl derivatives thereof; or pharmaceutically acceptable salts thereof.

In exemplary embodiments, the peptide comprises an amino acid sequence of Formula III, wherein $X^{34}$ is Q; $X^{35}$ is E; $X^{36}$ is M; $X^{37}$ is G; $X^{38}$ is Y; $X^{39}$ is I; $X^{40}$ is F; $X^{41}$ is Y; $X^{42}$ is P; $X^{43}$ is R; $X^{44}$ is absent or if present is K; $X^{45}$ is absent or if present is L; $X^{46}$ is absent or if present is R; and $X^{47}$ is absent; C-terminal acids or amides, or N-acetyl derivatives thereof; or a pharmaceutically acceptable salt thereof.

In exemplary embodiments, the peptide of Formula I-III is isolated.

In exemplary embodiments, the peptide comprises a modification of a peptide sequence selected from

MRWQEAGYIFYPRKLR; (SEQ ID NO: 11)

MRWQEMGYIFYPR(dA)LR; (SEQ ID NO: 149)

MRWQEMNYIFYPR; (SEQ ID NO: 208)

MRWQEMGYIFYPRNLR; (SEQ ID NO: 213)

MRWQEMQYIFYPRALR; (SEQ ID NO: 219)

RWQEMNYIFYPR; (SEQ ID NO: 210)

MRWQEMGYIFYPRALR; (SEQ ID NO: 19)

MRWQEMGYIFYPRKLA; (SEQ ID NO: 21)

MRWQEMGYIFYARKLR; (SEQ ID NO: 17)

RWQEMGYIFYPRQLR; (SEQ ID NO: 217)

MRWQEEGYIFYPRKLR; (SEQ ID NO: 172)

MRWQEMGYIFYPRKL; (SEQ ID NO: 45)

(SEQ ID NO: 241)

ERWQEAGYIAYPR;

RWQEMQYIFYPR; (SEQ ID NO: 211)

MRWQEMGYIFYPAKLR; (SEQ ID NO: 18)

wherein the modification comprises substituting at least one amino acid in the peptide with another amino acid selected from (i) an amino acid having a D-configuration, and (ii) a non-naturally occurring amino acid residue; or pharmaceutically acceptable salts thereof.

In exemplary embodiments, the peptide is formulated with an excipient to provide a pharmaceutical composition which composition can be used to treat a disease in a patient or another medical condition.

In exemplary embodiments, the peptide comprises an amino acid sequence of Formula I, wherein $X^1$ is absent or if present is $X^7$—RW—, wherein $X^7$ is absent or if present is selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); $X^2$ and $X^3$ are each independently selected from D, (dD), E, (dE), K, (dK), R, (dR), H, (dH), N, (dN), Q, (dQ), S, (dS), T, (dT), Y, (dY), C, (dC), G, A, (dA), V, (dV), L, (dL), I, (dI), F, (dF), W, (dW), P (dP), M and (dM); $X^4$ and $X^5$ are each independently selected from G, A, (dA), V, (dV), L, (dL), I, (dI), F, (dF), W, (dW), P (dP), M and (dM); $X^6$ is absent or if present is —KL-$X^8$ or —$X^9$-LR, wherein $X^8$ is absent or if present is selected from G, A, (dA), V, (dV), L, (dL), I, (dI), F, (dF), W, (dW), P (dP), M and (dM) and $X^9$ is selected from G, A, (dA), V, (dV), L, (dL), I, (dI), F, (dF), W, (dW), P (dP), M and (dM); or a pharmaceutically acceptable salt thereof.

In exemplary embodiments, the peptide comprises an amino acid sequence of Formula I wherein $X^1$ is absent or if present is $X^7$—RW—, wherein $X^7$ is absent or if present is M or E; $X^2$ is M, A or E; $X^3$ is G, N or Q; $X^4$ is F or A; $X^5$ is P or A; $X^6$ is absent or if present is —KL-$X^8$ or —$X^9$-LR, wherein $X^8$ is absent or if present is R or A and $X^9$ is selected from K, A, (dA), N and Q; or a pharmaceutically acceptable salt thereof.

In exemplary embodiments, the peptide comprises a sequence selected from the group consisting of: MRWQEAGYIFYPRKLR (SEQ ID NO: 11); MRWQEMGYIFYPR(dA)LR (SEQ ID NO: 149); MRWQEMNYIFYPR (SEQ ID NO: 208); MRWQEMGYI-FYPRNLR (SEQ ID NO: 213); MRWQEMQYIFYPRALR (SEQ ID NO: 219); RWQEMNYIFYPR (SEQ ID NO: 210); MRWQEMGYIFYPRALR (SEQ ID NO: 19); MRWQEMGYIFYPRKLA (SEQ ID NO: 21); MRWQEMGYIFYARKLR (SEQ ID NO: 17); RWQEMGYIFYPRQLR (SEQ ID NO: 217); MRWQE-EGYIFYPRKLR (SEQ ID NO: 172); MRWQEMGYIFY-PRKL (SEQ ID NO: 45); ERWQEAGYIAYPR (SEQ ID NO: 241); RWQEMQYIFYPR (SEQ ID NO: 211); MRWQEMGYIFYPAKLR (SEQ ID NO: 18); and a pharmaceutically acceptable salt thereof.

In exemplary embodiments, the peptide or peptide analog of the present disclosure comprises (a) RWQE (SEQ ID NO: 294), (b) YIFY (SEQ ID NO: 295), or (c) both RWQE (SEQ ID NO: 294) and YIFY (SEQ ID NO: 295), wherein the peptide or peptide analog (i) exhibits at least a 10% stability in mouse plasma for 60 minutes at 37 degrees Celsius, (ii) decreases free fatty acid levels in human primary adipocytes, (iii) or both (i) and (ii). In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog comprises Met immediately N-terminal to the Arg of SEQ ID NO: 294 or immediately C-terminal to the Glu of SEQ ID NO: 294. In exemplary embodiments, the peptide or peptide analog comprises MRWQE (SEQ ID NO: 350), RWQEM (SEQ ID NO: 351), or MRWQEM (SEQ ID NO: 352). In exemplary embodiments, the peptide or peptide analog comprises Gly immediately N-terminal to the first amino acid of SEQ ID NO: 295, Pro immediately C-terminal to the last amino acid of SEQ ID NO: 295, or comprises GYIFYP (SEQ ID NO: 353). In exemplary embodiments, the peptide or peptide analog comprises YIFYPR (SEQ ID NO: 296), YIFYPRK (SEQ ID NO: 297), YIFYPRKL (SEQ ID NO: 298), or YIFYPRKLR (SEQ ID NO: 299).

In exemplary embodiments, the peptide or peptide analog of the present disclosure comprises (A) an amino acid sequence of RWQE (SEQ ID NO: 294) and (B) an amino acid sequence of YIFY (SEQ ID NO: 295) with one amino acid substitution. In exemplary embodiments, the amino acid sequence of YIFY (SEQ ID NO: 295) with one amino acid substitution comprises XIFY (SEQ ID NO: 300), YXFY (SEQ ID NO: 301), YIXY (SEQ ID NO: 302), or YIFX (SEQ ID NO: 303), wherein X is any amino acid. In exemplary embodiments, the X of any one of SEQ ID NOs: 300-303 is a small aliphatic amino acid or an acidic amino acid. In exemplary embodiments, the X of any one of SEQ ID NOs: 300-303 is selected from the group consisting of: Ala, Gly, (dA), and Glu. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises (A) an amino acid sequence of RWQE (SEQ ID NO: 294) and (B) an amino acid sequence of YIFY (SEQ ID NO: 295) with two amino acid modifications. In exemplary embodiments, the peptide or peptide analog of the present disclosure comprises an amino acid sequence of RWQE (SEQ ID NO: 294) and (B) an amino acid sequence of YIFY (SEQ ID NO: 295) with two amino acid substitutions. In exemplary embodiments, the peptide or peptide analog of the present disclosure comprises an amino acid sequence of RWQE (SEQ ID NO: 294) and YIAE (SEQ ID NO: 308) or EIFE (SEQ ID NO: 309). In exemplary embodiments, the peptide or peptide analog of the present disclosure comprises an amino acid sequence of RWQE (SEQ ID NO: 294) and YI or YIF. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog comprises (A) an amino acid sequence of YIFY (SEQ ID NO: 295) and (B) an amino acid sequence of RWQE (SEQ ID NO: 294) with one amino acid substitution. In exemplary embodiments, the amino acid sequence of RWQE (SEQ ID NO: 294) with one amino acid substitution comprises XWQE (SEQ ID NO: 304), RXQE (SEQ ID NO: 305), RWXE (SEQ ID NO: 306), or RWQX (SEQ ID NO: 307), wherein X is any amino acid. In exemplary embodiments, X is an aliphatic amino acid or a charged amino acid. In exemplary aspects, when the peptide or peptide analog comprises XWQE (SEQ ID NO: 304), X is selected from the group consisting of: Ala, Gly, Asp, Lys, Aib, (dA), Glu. In exemplary aspects, when the peptide or peptide analog comprises RXQE (SEQ ID NO: 305), X is selected from the group consisting of: Ala, Gly, (dA), Glu. In exemplary aspects, when the peptide or peptide analog comprises RWXE (SEQ ID NO: 306), X is selected from the group consisting of: Gln, Ala, Glu, Gly, Asn, (dA). In exemplary aspects, when the peptide or peptide analog comprises RWQX (SEQ ID NO; 307), X is selected from the group consisting of: Glu, Ala, Gly, Asp, (dA). In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises an amino acid sequence of RWQEX$^1$X$^2$YIFY (SEQ ID NO: 319), wherein each of X$^1$ and X$^2$ independently is any amino acid. In exemplary aspects, X$^1$ is selected from a group consisting of: Met, Ala, Nle, Gly, (dA), Glu, Cys, and equivalents thereof. In exemplary aspects, X$^1$ is selected from a group consisting of: Met, Ala, Nle, Gly, (dA), Glu, and Cys. In exemplary aspects, X$^2$ is selected from a group consisting of: Asn, Gln, Gly, (dA), Glu, and equivalents thereof. In exemplary aspects, X$^2$ is selected from a group consisting of: Asn, Gln, Gly, (dA), and Glu. In exemplary aspects, —X$^1$X$^2$— is Met-Asn, Met-Gln, Ala-Gly, Met-Ala, Nle-Gly, Gly-Gly, Met-(dA), (dA)-Gly, Glu-Gly, Met-Glu, Cys-Gly, Glu-Asn, or Glu-Gln. In exemplary aspects, the peptide or peptide analog does not consist of the sequence SEQ ID NO: 2. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises an amino acid sequence of RWQEX$^{48}$X$^{49}$X$^{50}$IFY (SEQ ID NO: 373), wherein each of X$^{48}$, X$^{49}$ and X$^{50}$ independently is any amino acid. In exemplary aspects, X$^{48}$ is selected from a group consisting of: Met, Ala, Nle, Gly, (dA), Glu, Cys, and equivalents thereof. In exemplary aspects, X$^{48}$ is selected from a group consisting of: Met, Ala, Nle, Gly, (dA), Glu, and Cys. In exemplary aspects, X$^{49}$ is selected from a group consisting of: Asn, Gln, Gly, (dA), Glu, and equivalents thereof. In exemplary aspects, X$^{49}$ is selected from a group consisting of: Asn, Gln, Gly, (dA), and Glu. In exemplary embodiments, X$^{50}$ is selected from the group consisting of: Ala, Gly, (dA), and Glu, and equivalents thereof. In exemplary embodiments, X$^{50}$ is selected from the group consisting of: Ala, Gly, (dA), and Glu. In exemplary aspects, the peptide or peptide analog does not consist of the sequence SEQ ID NO: 2. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises an amino acid sequence an amino acid sequence of RWQEX$^1$X$^2$X$^3$IFY (SEQ ID NO: 320), RWQEX$^1$X$^2$YX$^3$FY (SEQ ID NO: 321), RWQEX$^1$X$^2$YIX$^3$Y (SEQ ID NO: 322) or RWQEX$^1$X$^2$YIFX$^3$ (SEQ ID NO: 323), wherein each X is independently any amino acid. In exemplary aspects, X$^1$ is selected from a group consisting of: Met, Ala, Nle, Gly, (dA), Glu, Cys, and equivalents thereof. In exemplary aspects, X$^1$ is selected from a group consisting of: Met, Ala, Nle, Gly, (dA), Glu, and Cys. In exemplary aspects, X$^2$ is selected from a group consisting of: Asn, Gln, Gly, (dA), Glu, and equivalents thereof. In exemplary aspects, X$^2$ is selected from a group consisting of: Asn, Gln, Gly, (dA), and Glu. In exemplary aspects, X$^1$X$^2$ is Met-Asn, Met-Gln, Ala-Gly, Met-Ala, Nle-Gly, Gly-Gly, Met-(dA), (dA)-Gly, Glu-Gly, Met-Glu, Cys-Gly, Glu-Asn, or Glu-Gln. In exemplary embodiments, X$^3$ is a small aliphatic amino acid or an acidic amino acid. In exemplary embodiments, X$^3$ is selected from the group consisting of: Ala, Gly, (dA), and Glu. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In exemplary embodiments, the peptide or peptide analog of the present disclosure comprises an amino acid sequence an amino acid sequence of RWQEX$^{48}$X$^{49}$X$^{50}$IFY (SEQ ID NO: 373), RWQEX$^{48}$X$^{49}$YX$^{51}$FY (SEQ ID NO: 374), RWQEX$^{48}$X$^{49}$YIX$^{52}$Y (SEQ ID NO: 375) or RWQEX$^{48}$X$^{49}$YIFX$^{53}$ (SEQ ID NO: 376), wherein each of X$^{48}$, X$^{49}$, X$^{50}$, X$^{51}$, X$^{52}$ and X$^{53}$ is independently any amino acid. In exemplary embodiments, the peptide or peptide analog of the present disclosure comprises an amino acid sequence of SEQ ID NOs: 1, 3-41, 43-76, and 79-293, 310-315, 319-323 and 354-377. In exemplary embodiments, the peptide or peptide analog of the present disclosure comprises a structure and/or amino acid sequence set forth in Table 1. In exemplary aspects, X$^{48}$ is selected from a group consisting of: Met, Ala, Nle, Gly, (dA), Glu, Cys, and equivalents thereof. In exemplary aspects, X$^{48}$ is selected from a group consisting of: Met, Ala, Nle, Gly, (dA), Glu, and Cys. In exemplary aspects, X$^{49}$ is selected from a group consisting of: Asn, Gln, Gly, (dA), Glu, and equivalents thereof. In exemplary aspects, X$^{49}$ is selected from a group consisting of: Asn, Gln, Gly, (dA), and Glu. In exemplary aspects, —X⁴⁸X⁴⁹— is Met-Asn, Met-Gln, Ala-Gly, Met-Ala, Nle-Gly, Gly-Gly, Met-(dA), (dA)-Gly, Glu-Gly, Met-Glu, Cys-Gly, Glu-Asn, or Glu-Gln. In exemplary embodiments, each of X⁵⁰, X⁵¹, X⁵² and X⁵³ is a small aliphatic amino acid or an acidic amino acid. In exemplary embodiments, each of X⁵⁰, X⁵¹, X⁵² and X⁵³ is selected from the group consisting of: Ala, Gly, (dA), and Glu. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

In each of the embodiments of the present disclosure, the peptide is not a peptide consisting of the amino acid sequence: MRWQEMGYIFYPRKLR (SEQ ID NO: 2); MRWQEMGYIFYFRKLR (SEQ ID NO: 316); MGWQEMGYIFYPRKLR (SEQ ID NO: 317); or MGYIFYPRKLR (SEQ ID NO: 318). In each of the embodiments of the present disclosure, the peptide also is not a peptide consisting of any one of the amino acid sequences of SEQ ID NOs: 42, 77, 78, 328-349. In exemplary embodiments, the peptide of the present disclosure additionally is not a naturally-occurring peptide. In exemplary aspects, the peptide is not a peptide consisting of any one of the amino acid sequences of SEQ ID NOs: 328-349. In other exemplary embodiments, the peptide does not comprise any of the aforementioned sequences. Peptide embodiments of the invention do not include peptides specifically described by amino acid sequence in the following documents: U.S. Patent Application Publication No. 2014/0296139, International Publication Number WO01/76532, and Lee et al., Cell Metabolism 21:443-454 (2015), each of which are incorporated by reference for their disclosures of peptides and peptide sequences.

In exemplary embodiments, the peptide or peptide analog of the present disclosure comprises an amino acid sequence of SEQ ID NOs: 1, 3-41, 43-76, and 79-293, 310-315, 319-323 and 354-377. In exemplary embodiments, the peptide or peptide analog of the present disclosure comprises an amino acid sequence set forth in Table 1. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

A peptide or peptide analog comprising, consisting essentially of, or consisting of any one of SEQ ID NOs: 1, 3-41, 43-76, and 79-293, 310-315, 319-323 and 354-377, or comprising, consisting essentially of, or consisting of a sequence which has at least or about 75%, at least or about 80%, at least or about 85%, at least or about 90%, or at least or about 95% sequence identity to one of SEQ ID NOs: 1, 3-41, 43-76, and 79-293, 310-315, 319-323 and 354-377. In exemplary embodiments, the peptide or peptide analog is 8 to 20 amino acids in length. In exemplary aspects, the peptide or peptide analog comprises, consists essentially of, or consists of a sequence of any one of SEQ ID NOs: 1, 3-41, 43-76, and 79-293, 310-315, 319-323 and 354-377 with one or two amino acid substitutions. In exemplary embodiments, the peptide or peptide analog is 8 to 20 amino acids in length. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii). In exemplary aspects, the peptide or peptide analog comprises, consists essentially of, or consists of any one of SEQ ID NOs: 11, 17-19, 21, 32, 45, 148, 172, 208, 210, 211, 213, 219, and 241, or comprising, consisting essentially of, or consisting of a sequence which has at least or about 75%, at least or about 80%, at least or about 85%, at least or about 90%, or at least or about 95% sequence identity to one of SEQ ID NOs: 11, 17-19, 21, 32, 45, 148, 172, 208, 210, 211, 213, 219, and 241. In exemplary embodiments, the peptide or peptide analog is 8 to 20 amino acids in length. In exemplary embodiments, part (A) of the peptide or peptide analog is N-terminal to part (B), with 0-10 intervening amino acids, especially, one, two three, four, or five amino acids intervening amino acids. In exemplary embodiments, the peptide or peptide analog (i) exhibits at least a 10% stability in mouse plasma for 60 minutes at 37 degrees Celsius, (ii) decreases free fatty acid levels in human primary adipocytes, (iii) or both (i) and (ii).

TABLE 1

| Peptide Structure/Sequence | SEQ ID NO: |
|---|---|
| MRWQEMGYIFYPRKLR | 2 |
| Acetyl-MRWQEMGYIFYPRKLR-Amide | 3 |
| Acetyl-MRWQEMGYIFYPRKLR | 4 |
| MRWQEMGYIFYPRKLR-Amide | 5 |
| ARWQEMGYIFYPRKLR | 6 |
| MAWQEMGYIFYPRKLR | 7 |
| MRAQEMGYIFYPRKLR | 8 |
| MRWAEMGYIFYPRKLR | 9 |
| MRWQAMGYIFYPRKLR | 10 |
| MRWQEAGYIFYPRKLR | 11 |
| MRWQEMAYIFYPRKLR | 12 |
| MRWQEMGAIFYPRKLR | 13 |
| MRWQEMGYAFYPRKLR | 14 |
| MRWQEMGYIAYPRKLR | 15 |
| MRWQEMGYIFAPRKLR | 16 |
| MRWQEMGYIFYARKLR | 17 |
| MRWQEMGYIFYPAKLR | 18 |
| MRWQEMGYIFYPRALR | 19 |
| MRWQEMGYIFYPRKAR | 20 |
| MRWQEMGYIFYPRKLA | 21 |
| Acetyl-ARWQEMGYIFYPRKLR-Amide | 22 |

TABLE 1-continued

| Peptide Structure/Sequence | SEQ ID NO: |
|---|---|
| Acetyl-MAWQEMGYIFYPRKLR-Amide | 23 |
| Acetyl-MRAQEMGYIFYPRKLR-Amide | 24 |
| Acetyl-MRWAEMGYIFYPRKLR-Amide | 25 |
| Acetyl-MRWQAMGYIFYPRKLR-Amide | 26 |
| Acetyl-MRWQEAGYIFYPRKLR-Amide | 27 |
| Acetyl-MRWQEMAYIFYPRKLR-Amide | 28 |
| Acetyl-MRWQEMGAIFYPRKLR-Amide | 29 |
| Acetyl-MRWQEMGYAFYPRKLR-Amide | 30 |
| Acetyl-MRWQEMGYIAYPRKLR-Amide | 31 |
| Acetyl-MRWQEMGYIFAPRKLR-Amide | 32 |
| Acetyl-MRWQEMGYIFYARKLR-Amide | 33 |
| Acetyl-MRWQEMGYIFYPAKLR-Amide | 34 |
| Acetyl-MRWQEMGYIFYPRALR-Amide | 35 |
| Acetyl-MRWQEMGYIFYPRKAR-Amide | 36 |
| Acetyl-MRWQEMGYIFYPRKLA-Amide | 37 |
| RWQEMGYIFYPRKLR | 38 |
| WQEMGYIFYPRKLR | 39 |
| QEMGYIFYPRKLR | 40 |
| EMGYIFYPRKLR | 41 |
| MGYIFYPRKLR | 42 |
| GYIFYPRKLR | 43 |
| YIFYPRKLR | 44 |
| MRWQEMGYIFYPRKL | 45 |
| MRWQEMGYIFYPRK | 46 |
| MRWQEMGYIFYPR | 47 |
| MRWQEMGYIFYP | 48 |
| MRWQEMGYIFY | 49 |
| MRWQEMGYIF | 50 |
| MRWQEMGYI | 51 |
| Acetyl-RWQEMGYIFYPRKLR-Amide | 52 |
| Acetyl-WQEMGYIFYPRKLR-Amide | 53 |
| Acetyl-QEMGYIFYPRKLR-Amide | 54 |
| Acetyl-EMGYIFYPRKLR-Amide | 55 |
| Acetyl-MGYIFYPRKLR-Amide | 56 |
| Acetyl-GYIFYPRKLR-Amide | 57 |
| Acetyl-YIFYPRKLR-Amide | 58 |
| Acetyl-MRWQEMGYIFYPRKL-Amide | 59 |
| Acetyl-MRWQEMGYIFYPRK-Amide | 60 |
| Acetyl-MRWQEMGYIFYPR-Amide | 61 |
| Acetyl-MRWQEMGYIFYP-Amide | 62 |
| Acetyl-MRWQEMGYIFY-Amide | 63 |
| Acetyl-MRWQEMGYIF-Amide | 64 |
| Acetyl-MRWQEMGYI-Amide | 65 |
| (Nle)RWQEMGYIFYPRKLR | 66 |
| MRWQE(Nle)GYIFYPRKLR | 67 |
| (Nle)RWQE(Nle)GYIFYPRKLR | 68 |
| MRWQEMGYIFYPR(K-Acetyl)LR | 69 |
| Acetyl-MRWQEMGYIFYPR(K-Acetyl)LR | 70 |
| MRWQEMGYIFYPR(K-Acetyl)LR-Amide | 71 |
| Acetyl-MRWQEMGYIFYPR(K-Acetyl)LR-Amide | 72 |
| MRWEEMGYIFYPRKLR | 73 |
| Acetyl-MRWEEMGYIFYPRKLR | 74 |
| MRWEEMGYIFYPRKLR-Amide | 75 |
| Acetyl-MRWEEMGYIFYPRKLR-Amide | 76 |
| MGWQEMGYIFYPRKLR | 77 |
| MGYIFYPRKLR | 78 |
| Acetyl-MDWQEMGYIFYPRKLR-Amide | 79 |
| Acetyl-MRWQEMGYIFYPDKLR-Amide | 80 |
| Acetyl-MRWQEMGYIFYPRKLD-Amide | 81 |
| Acetyl-GRWQEMGYIFYPRKLR-Amide | 82 |
| Acetyl-MGWQEMGYIFYPRKLR-Amide | 83 |
| Acetyl-MRGQEMGYIFYPRKLR-Amide | 84 |
| Acetyl-MRWGEMGYIFYPRKLR-Amide | 85 |
| Acetyl-MRWQGMGYIFYPRKLR-Amide | 86 |
| Acetyl-MRWQEGGYIFYPRKLR-Amide | 87 |
| Acetyl-MRWQEM(dA)YIFYPRKLR-Amide | 88 |
| Acetyl-MRWQEMGGIFYPRKLR-Amide | 89 |
| Acetyl-MRWQEMGYGFYPRKLR-Amide | 90 |
| Acetyl-MRWQEMGYIGYPRKLR-Amide | 91 |
| Acetyl-MRWQEMGYIFGPRKLR-Amide | 92 |
| Acetyl-MRWQEMGYIFYGRKLR-Amide | 93 |
| Acetyl-MRWQEMGYIFYPGKLR-Amide | 94 |
| Acetyl-MRWQEMGYIFYPRGLR-Amide | 95 |
| Acetyl-MRWQEMGYIFYPRKGR-Amide | 96 |
| Acetyl-MRWQEMGYIFYPRKLG-Amide | 97 |
| MRWQEMGYIFYPRKLRPRGFSCLLLLTGEIDLP | 98 |
| PRGFSCLLLLTGEIDLPMRWQEMGYTYPRKLR | 99 |

TABLE 1-continued

| Peptide Structure/Sequence | SEQ ID NO: |
|---|---|
| MRWQEMGYIFYPRGFSCLLLLTGEIDLP | 100 |
| PRGFSCLLLLTGEIDLPMRWQEMGYIFY | 101 |
| MRWQEMGYIFYMAPRGFSCLLLLTGEIDLPVKRRA | 102 |
| MRWQEMG(Y-P03H2)IFYPRKLR | 103 |
| MRWQEMGYIF(Y-P03H2)PRKLR | 104 |
| Palm-MRWQEMGYIFYPRKLR | 105 |
| MRWQEMGYIFYPRK(Palm)LR | 106 |
| MRWQEMGYIFYPRK(E-Palm)LR | 107 |
| Acetyl-LRWQEMGYIFYPLRKLR-Amide | 108 |
| Acetyl-LRWQEMGYIFYPRLKR-Amide | 109 |
| Acetyl-LRWQEMGYIFYPRLKR-Amide | 110 |
| Acetyl-LRWQEMGYIFYPRKRL-Amide | 111 |
| Acetyl-LKWQEMGYIFYPRKLR-Amide | 112 |
| Acetyl-LKWQEMGYIFYPLRKR-Amide | 113 |
| Acetyl-LKWQEMGYIFYPRLKR-Amide | 114 |
| Acetyl-LKWQEMGYIFYPRKRL-Amide | 115 |
| Acetyl-LRWQEMGYIFYPRKR-Amide | 116 |
| Acetyl-LKWQEMGYIFYPRKR-Amide | 117 |
| M(Aib)WQEMGYIFYPRKLR | 118 |
| M(Aib)WQEMGYIFYPRKLR-Amide | 119 |
| Acetyl-M(Aib)WQEMGYIFYPRKLR | 120 |
| Acetyl-M(Aib)WQEMGYIFYPRKLR-Amide | 121 |
| MKWQEMGYIFYPRKLR | 122 |
| MRWQEMGYIFYPKKLR | 123 |
| MRWQEMGYIFYPRKLK | 124 |
| MRWQEMGYIFYPRRLR | 125 |
| MRWQDMGYIFYPRRLR | 126 |
| MRWNEMGYIFYPRKLR | 127 |
| Acetyl-MKWQEMGYIFYPRKLR-Amide | 128 |
| Acetyl-MRWQEMGYIFYPKKLR-Amide | 129 |
| Acetyl-MRWQEMGYIFYPRKLK-Amide | 130 |
| Acetyl-MRWQEMGYIFYPRRLR-Amide | 131 |
| Acetyl-MRWQDMGYIFYPRRLR-Amide | 132 |
| Acetyl-MRWNEMGYIFYPRKLR-Amide | 133 |
| MRWQEMGEIFEPRKLR | 134 |
| Acetyl-MRWQEMGEIFEPRKLR-Amide | 135 |
| (dA)RWQEMGYIFYPRKLR | 136 |
| M(dA)WQEMGYIFYPRKLR | 137 |
| MR(dA)QEMGYIFYPRKLR | 138 |

TABLE 1-continued

| Peptide Structure/Sequence | SEQ ID NO: |
|---|---|
| MRW(dA)EMGYIFYPRKLR | 139 |
| MRWQ(dA)MGYIFYPRKLR | 140 |
| MRWQE(dA)GYIFYPRKLR | 141 |
| MRWQEM(dA)YIFYPRKLR | 142 |
| MRWQEMG(dA)IFYPRKLR | 143 |
| MRWQEMGY(dA)FYPRKLR | 144 |
| MRWQEMGYI(dA)YPRKLR | 145 |
| MRWQEMGYIF(dA)PRKLR | 146 |
| MRWQEMGYIFY(dA)RKLR | 147 |
| MRWQEMGYIFYP(dA)KLR | 148 |
| MRWQEMGYIFYPR(dA)LR | 149 |
| MRWQEMGYIFYPRK(dA)R | 150 |
| MRWQEMGYIFYPRKL(dA) | 151 |
| Acetyl-(dA)RWQEMGYIFYPRKLR-Amide | 152 |
| Acetyl-M(dA)WQEMGYIFYPRKLR-Amide | 153 |
| Acetyl-MR(dA)QEMGYIFYPRKLR-Amide | 154 |
| Acetyl-MRW(dA)EMGYIFYPRKLR-Amide | 155 |
| Acetyl-MRWQ(dA)MGYIFYPRKLR-Amide | 156 |
| Acetyl-MRWQE(dA)GYIFYPRKLR-Amide | 157 |
| Acetyl-MRWQEM(dA)YIFYPRKLR-Amide | 158 |
| Acetyl-MRWQEMG(dA)IFYPRKLR-Amide | 159 |
| Acetyl-MRWQEMGY(dA)FYPRKLR-Amide | 160 |
| Acetyl-MRWQEMGYI(dA)YPRKLR-Amide | 161 |
| Acetyl-MRWQEMGYIF(dA)PRKLR-Amide | 162 |
| Acetyl-MRWQEMGYIFY(dA)RKLR-Amide | 163 |
| Acetyl-MRWQEMGYIFYP(dA)KLR-Amide | 164 |
| Acetyl-MRWQEMGYIFYPR(dA)LR-Amide | 165 |
| Acetyl-MRWQEMGYIFYPRK(dA)R-Amide | 166 |
| Acetyl-MRWQEMGYIFYPRKL(dA)-Amide | 167 |
| ERWQEMGYIFYPRKLR | 168 |
| MEWQEMGYIFYPRKLR | 169 |
| MREQEMGYIFYPRKLR | 170 |
| MRWEEMGYIFYPRKLR | 171 |
| MRWQEGYIFYPRKLR | 172 |
| MRWQEMEYIFYPRKLR | 173 |
| MRWQEMGEIFYPRKLR | 174 |
| MRWQEMGYEFYPRKLR | 175 |
| MRWQEMGYIEYPRKLR | 176 |

TABLE 1-continued

| Peptide Structure/Sequence | SEQ ID NO: |
|---|---|
| MRWQEMGYIFEPRKLR | 177 |
| MRWQEMGYIFYERKLR | 178 |
| MRWQEMGYIFYPEKLR | 179 |
| MRWQEMGYIFYPRELR | 180 |
| MRWQEMGYIFYPRKER | 181 |
| MRWQEMGYIFYPRKLE | 182 |
| Acetyl-ERWQEMGYIFYPRKLR-Amide | 183 |
| Acetyl-MEWQEMGYIFYPRKLR-Amide | 184 |
| Acetyl-MREQEMGYIFYPRKLR-Amide | 185 |
| Acetyl-MRWEEMGYIFYPRKLR-Amide | 186 |
| Acetyl-MRWQEEGYIFYPRKLR-Amide | 187 |
| Acetyl-MRWQEMEYIFYPRKLR-Amide | 188 |
| Acetyl-MRWQEMGEIFYPRKLR-Amide | 189 |
| Acetyl-MRWQEMGYEFYPRKLR-Amide | 190 |
| Acetyl-MRWQEMGYIEYPRKLR-Amide | 191 |
| Acetyl-MRWQEMGYIFEPRKLR-Amide | 192 |
| Acetyl-MRWQEMGYIFYERKLR-Amide | 193 |
| Acetyl-MRWQEMGYIFYPEKLR-Amide | 194 |
| Acetyl-MRWQEMGYIFYPRELR-Amide | 195 |
| Acetyl-MRWQEMGYIFYPRKER-Amide | 196 |
| Acetyl-MRWQEMGYIFYPRKLE-Amide | 197 |
| MRWQEMGYIFYPRK(Deg)R | 198 |
| Acetyl-MRWQEMGYIFYPRK(Deg)R | 199 |
| MRWQEMGYIFYPRK(Deg)R-Amide | 200 |
| Acetyl-MRWQEMGYIFYPRK(Deg)R-Amide | 201 |
| MRWQEMGYIFYPR | 202 |
| MRWQEMGYIFYPRN | 203 |
| MRWQEMGYIFYPRQ | 204 |
| RWQEMGYIFYPR | 205 |
| RWQEMGYIFYPRN | 206 |
| RWQEMGYIFYPRQ | 207 |
| MRWQEMNYIFYPR | 208 |
| MRWQEMQYIFYPR | 209 |
| RWQEMNYIFYPR | 210 |
| RWQEMQYIFYPR | 211 |
| MRWQEMGYIFYPRALR | 212 |
| MRWQEMGYIFYPRNLR | 213 |
| MRWQEMGYIFYPRQLR | 214 |
| RWQEMGYIFYPRALR | 215 |
| RWQEMGYIFYPRNLR | 216 |
| RWQEMGYIFYPRQLR | 217 |
| MRWQEMNYIFYPRALR | 218 |
| MRWQEMQYIFYPRALR | 219 |
| MRWQE(Ccyc)GYIFY(Ccyc)RKLR | 220 |
| MRWQEEcycGYIFY(Kcyc)RKLR | 221 |
| MRWQ(Ecyc)MGYIFYPR(Kcyc)LR | 222 |
| MRW(Ecyc)EMGYIFY(Kcyc)RKLR | 223 |
| MRWQ(Ecyc)MGYIFY(Kcyc)RKLR | 224 |
| Acetyl-MRWQE(Ccyc)GYIFY(Ccyc)RKLR-Amide | 225 |
| Acetyl-MRWQE(Ecyc)GYIFY(Kcyc)RKLR-Amide | 226 |
| Acetyl-MRWQ(Ecyc)MGYIFYPR(Kcyc)LR-Amide | 227 |
| Acetyl-MRW(Ecyc)EMGYIFY(Kcyc)RKLR-Amide | 228 |
| Acetyl-MRWQ(Ecyc)MGYIFY(Kcyc)RKLR-Amide | 229 |
| (dA)RWQEEGYIFYPRKLA | 230 |
| (dA)RWQEEGYIFYPRKL(dA) | 231 |
| (dA)RWQEEGYIFYPR | 232 |
| ERWQEAGYIFYPRKLA | 233 |
| ERWQEAGYIFYPRKL(dA) | 234 |
| ERWQEAGYIFYPR | 235 |
| (dA)RWQEEGYIAYPRKLA | 236 |
| (dA)RWQEEGYIAYPRKL(dA) | 237 |
| (dA)RWQEEGYIAYPR | 238 |
| ERWQEAGYIAYPRKLA | 239 |
| ERWQEAGYIAYPRKL(dA) | 240 |
| ERWQEAGYIAYPR | 241 |
| (dA)RWQEAGYIFEPRKLA | 242 |
| (dA)RWQEAGYIFEPRKL(dA) | 243 |
| (dA)RWQEAGYIFEPR | 244 |
| (dA)RWQEAGYIAEPRKLA | 245 |
| (dA)RWQEAGYIAEPRKL(dA) | 246 |
| (dA)RWQEAGYIAEPR | 247 |
| RWQEMNYIFYPR | 248 |
| RWQEMNYIFEPR | 249 |
| RWQEMNYIAYPR | 250 |
| RWQEMNYIAEPR | 251 |
| RWQEMNYIFYPAR | 252 |
| RWQEMQYIFYPR | 253 |

TABLE 1-continued

| Peptide Structure/Sequence | SEQ ID NO: |
|---|---|
| RWQEMQYIFEPR | 254 |
| RWQEMQYIAYPR | 255 |
| RWQEMQYIAEPR | 256 |
| RWQEMQYIFYPAR | 257 |
| RWQEENYIFYPR | 258 |
| RWQEENYIFEPR | 259 |
| RWQEENYIAYPR | 260 |
| RWQEENYIAEPR | 261 |
| RWQEENYIFYPAR | 262 |
| RWQEEQYIFYPR | 263 |
| RWQEEQYIFEPR | 264 |
| RWQEEQYIAYPR | 265 |
| RWQEEQYIAEPR | 266 |
| RWQEEQYIFYPAR | 267 |
| RWQEMGYIFYPRKL | 268 |
| WQEMGYIFYPRKL | 269 |
| QEMGYIFYPRKL | 270 |
| MRWQEMNYIFYPR | 271 |
| RWQEMNYIFYPR | 272 |
| RWQEMNYIFEPR | 273 |
| RWQEMNYIAYPR | 274 |
| RWQEMNYIAEPR | 275 |
| RWQEMNYIFYPAR | 276 |
| RWQEENYIFYPR | 277 |
| RWQEENYIFEPR | 278 |
| RWQEENYIAYPR | 279 |
| RWQEENYIAEPR | 280 |
| RWQEENYIFYPAR | 281 |
| MRWQEMNYIFYP | 282 |
| RWQEMNYIFYP | 283 |
| WQEMNYIFYPR | 284 |
| WQEMNYIFYP | 285 |
| Acetyl-MRWQEMNYIFYPR | 286 |
| MRWQEMNYIFYP-Amide | 287 |
| (dA)RWQEMNYIFYPR | 288 |
| Palm-MRWQEMNYIFYPR | 289 |
| RWQEMNYIFYPRK-PEG600 | 290 |
| WQEMNYIFYPR | 291 |
| WQEMNYIFYPRK-Palm | 292 |
| WQEMNYIFYPR-Amide | 293 |
| RWQE | 294 |
| YIFY | 295 |
| YIFYPR | 296 |
| YIFYPRK | 297 |
| YIFYPRKL | 298 |
| YIFYPRKLR | 299 |
| XIFY | 300 |
| YXFY | 301 |
| YIXY | 302 |
| YIFX | 303 |
| XWQE | 304 |
| RXQE | 305 |
| RWXE | 306 |
| RWQX | 307 |
| YIAE | 308 |
| EIFE | 309 |
| MRWQEMGYIFYPRKLR-C7-C20 | 310 |
| MRWQEMGYIFYPRKLR-C7-C20 | 311 |
| MRWQEMGYIFYPRKLRE-C7-C20 | 312 |
| MRWQEMNYIFYPR-C7-C20 | 313 |
| WQEMNYIFYPRK-C7-C20 | 314 |
| RWQEMNYIFYPRK-PEG600 | 315 |
| MRWQEMGYIFYFRKLR | 316 |
| MGWQEMGYIFYPRKLR | 317 |
| MGYIFYPRKLR | 318 |
| MRWQEMGYIFYPRKFYD | 328 |
| MRWQEMGYIFYPRKFYN | 329 |
| MRWQEMGYIFYFRKLR | 330 |
| MRWQEMGYIFYTQKILL | 331 |
| MRWQEMGYIFYIRQISQ | 332 |
| MRWQEMGYIFYTQKISR | 333 |
| MRWQEMGYIFYVQKLS | 334 |
| MRWQEMGYIFYTQKISRVRNTVDSRVPPKPSFGSRLTNQLIPVLRTCVAGSGRSL | 335 |
| MRWQEMGYIFYPRKLR | 336 |
| MRWQEMGYIFYPRKLR | 337 |
| MRRQEMGYIFYPRKLR | 338 |
| MEWQEMGYIFYFRKLR | 339 |

TABLE 1-continued

| Peptide Structure/Sequence | SEQ ID NO: |
|---|---|
| MKWEEMGYIFL | 340 |
| MKRKEMGYIFFSQRTLRNPL | 341 |
| MKWEEMGYIFLYKNINDSYHEI | 342 |
| MRWEEMGYIFYPRTFHECFYEIKN | 343 |
| MKWEEMGYILYTKRIKHESYYETNNQRRI | 344 |
| MKWEEMGYTFYPRIYENVT | 345 |
| MRWEAMGYIFYN | 346 |
| MGWEEMGYIFYSRTTYESFYETKN | 347 |
| MGWREMGYIFYPKNKNFNPDESLHETGD | 348 |
| MDWEEMGYIFYNKNTP | 349 |
| MRWQE | 350 |
| RWQEM | 351 |
| MRWQEM | 352 |
| GYIFYP | 353 |
| RWQEMNYIFYPRamide | 354 |
| RWQEMNYIFYPR(dA) | 355 |
| RWQEMNYIFYPRR(dA) | 356 |
| (PEG600)-KRWQEMNYIFYPR | 357 |
| (Biotin)-RWQEMNYIFYPR | 358 |
| RWQEMNYIFYPRK-(Biotin) | 359 |
| IFYPR | 360 |
| NYIFYPR | 361 |
| EMNYIFYP | 362 |
| QEMNYIFYP | 363 |
| EMNYIFYPR | 364 |
| WQEMNYIFY | 365 |
| QEMNYIFYPR | 366 |
| (Biotin)-KRWQEMNYIFYPR | 367 |
| (PEG600)-KNYIFYPR | 368 |
| (PEG600)-KEMNYIFYPR | 369 |
| (PEG600)-KWQEMNYIFYPR | 370 |
| (PEG600)-KRWQEMNYIFYP | 371 |
| (PEG600)-KWQEMNYIFYP | 372 |
| RWQEMNYIFYPRK-PEG600 | 377 |

Biological Activity

In exemplary aspects, the peptide or peptide analog of the present disclosure decreases free fatty acid levels in adipocytes, e.g., human primary adipocytes. In exemplary aspects, the free fatty acids level is decreased by at least or about 5%, relative to a control. In exemplary aspects, the free fatty acids level is decreased by at least or about 10%, at least or about 20%, at least or about 30%, at least or about 40%, at least or about 50%, at least or about 60%, at least or about 70%, at least or about 80%, at least or about 90%, relative to a control. In exemplary aspects, the free fatty acids level is decreased by greater than 90%, relative to a control. In exemplary aspects, the peptide or peptide analog of the present disclosure decreases free fatty acid levels in adipocytes, e.g., human primary adipocytes, to a better extent relative to that achieved by or associated with a MOTS-c peptide (e.g., the peptide consisting of SEQ ID NO: 2). In exemplary aspects, the peptide or peptide analog of the present disclosure decreases free fatty acid levels in adipocytes, e.g., human primary adipocytes, to an extent which is at least or about 10%, at least or about 20%, at least or about 30%, at least or about 40%, at least or about 50%, at least or about 60%, at least or about 70%, at least or about 80%, at least or about 90%, lower than the decrease caused by or associated with a MOTS-c peptide (e.g., the peptide consisting of SEQ ID NO: 2). Suitable methods of assaying free fatty acid levels in adipocytes are known, a few exemplary methods of which are described here in Examples 2-5 and 17. In exemplary aspects, the peptide or peptide analog of the present disclosure decreases free fatty acid levels in adipocytes, e.g., human primary adipocytes, as assayed by a method described in one of Examples 2-5 and 17. In exemplary aspects, the peptide or peptide analog of the present disclosure decreases free fatty acid levels in adipocytes, e.g., human primary adipocytes, as assayed by a single dose assay described in one of Examples 2-5 and 17.

In exemplary aspects, the peptide or peptide analog of the present disclosure decreases body weight, blood glucose levels, and/or fat mass in mammals, e.g., DIO mice, humans. In exemplary aspects, body weight, blood glucose levels, and/or fat mass is decreased by at least or about 5%, relative to a control, in a mammal. In exemplary aspects, body weight, blood glucose levels, and/or fat mass is decreased by at least or about 10%, at least or about 20%, at least or about 30%, at least or about 40%, at least or about 50%, at least or about 60%, at least or about 70%, at least or about 80%, relative to a control, in a mammal. In exemplary aspects, the peptide or peptide analog of the present disclosure decreases body weight, blood glucose levels, and/or fat mass in mammals, e.g., DIO mice, humans, to a better extent relative to that achieved by or associated with a MOTS-c peptide (e.g., the peptide consisting of SEQ ID NO: 2). In exemplary aspects, the peptide or peptide analog of the present disclosure decreases body weight, blood glucose levels, and/or fat mass in mammals, e.g., DIO mice, humans, to an extent which is at least or about 10%, at least or about 20%, at least or about 30%, at least or about 40%, at least or about 50%, at least or about 60%, at least or about 70%, at least or about 80%, at least or about 90%, lower than the decrease caused by or associated with a MOTS-c peptide (e.g., the peptide consisting of SEQ ID NO: 2). In exemplary aspects, the peptide or peptide analog of the present disclosure decreases serum triglyceride levels and/or serum levels of enzyme markers of liver damage (e.g., AST, ALT). In exemplary aspects, serum triglyceride levels and/or serum levels of enzyme markers of liver damage (e.g., AST, ALT) are decreased by at least or about 5%, relative to a control, in a mammal. In exemplary aspects, serum triglyceride levels and/or serum levels of enzyme markers of liver damage (e.g., AST, ALT) are decreased by at least or about 10%, at least or about 20%, at least or about 30%, at least or about 40%, at least or about 50%, at least or about 60%, at least or about 70%, at least or about 80%, at least or about 90%, relative to a control, in a mammal. In exemplary aspects, serum triglyceride levels and/or serum levels of enzyme markers of liver damage (e.g., AST, ALT) are decreased by greater than 90%, relative to a control, in a mammal. In exemplary aspects, the peptide or peptide analog of the present disclosure decreases serum triglyceride levels and/or serum levels of enzyme markers of liver damage (e.g., AST, ALT) to a better extent relative to that achieved by or associated with a MOTS-c peptide (e.g., the peptide consisting of SEQ ID NO: 2). In exemplary aspects, the peptide or peptide analog of the present disclosure decreases serum triglyceride levels and/or serum levels of enzyme markers of liver damage (e.g., AST, ALT), to an extent which is at least or about 10%, at least or about 20%, at least or about 30%, at least or about 40%, at least or about 50%, at least or about 60%, at least or about 70%, at least or about 80%, at least or about 90%, lower than the decrease caused by or associated with a MOTS-c peptide (e.g., the peptide consisting of SEQ ID NO: 2). Suitable methods of assaying body weight, blood glucose levels, fat mass, serum triglyceride levels, and serum levels of enzyme markers of liver damage in a mammal are known in the art, a few exemplary methods of which are described here in Examples 6-9 and 18-20. In exemplary aspects, the peptide or peptide analog of the present disclosure decreases body weight, blood glucose levels, and/or fat mass in mammals, e.g., DIO mice, humans, as assayed by a method described in one of Examples 6-9 and 18-20, e.g., once or twice daily by subcutaneous or intraperitoneal injection at a dose of 15 mg/kg/dose for 10 days (Example 6), twice daily by appropriate routes at a dose of 15 mg/kg/dose for 21 days (Example 7), once daily by appropriate routes at a dose of 5 mg/kg/dose for 21 days (Example 8), twice daily by appropriate routes at a dose of 15 mg/kg/dose for 21 days (Example 9).

In exemplary aspects, the peptide or peptide analog of the present disclosure exhibits at least a 10% stability in mouse plasma for 60 minutes at 37 degrees Celsius. In other words, at least 10% of the starting assay amount of the peptide or peptide analog is present in an intact state (e.g., not degraded, cleaved, etc.) after being incubated in mouse plasma for 60 minutes at 37 degrees Celsius. In exemplary aspects, the peptide or peptide analog exhibits at least a 20% stability, at least or about a 30% stability, at least or about a 40% stability, at least or about a 50% stability, at least or about a 60% stability, at least or about a 70% stability, at least or about a 80% stability, or at least or about a 90% stability, in plasma for 60 minutes at 37 degrees Celsius. Suitable methods of assaying the stability of peptides in plasma (included mouse plasma) are known in the art, a few exemplary methods of which are described here in Examples 14-16. In exemplary aspects, the peptide or peptide analog of the present disclosure exhibits at least a 10% stability in mouse plasma for 60 minutes at 37 degrees Celsius, as assayed by a method described in one of Examples 14-16. In exemplary aspects, the peptide or peptide analog of the present disclosure exhibits at least a 10% stability in mouse plasma for 60 minutes at 37 degrees Celsius, as assayed by a single peptide dose/concentration assay described in Example 14.

Peptide Length

In exemplary embodiments, the peptide or peptide analog of the present disclosure is a peptide or peptide analog comprising at least four amino acids connected via peptide bonds or other covalent linkages, as described herein. In exemplary aspects, the peptide or peptide analog is about 4 to about 50 amino acids in length. All integer subranges of 4 to 50 amino acids are specifically contemplated for peptides herein. In exemplary aspects, the peptide or peptide analog is about 5 to about 35 amino acids in length, about 5 to about 30 amino acids in length, about 5 to about 25 amino acids in length, or about 5 to about 20 amino acids in length. In exemplary aspects, the peptide or peptide analog is about 6 to about 35 amino acids in length, about 7 to about 30 amino acids in length, about 6 to about 25 amino acids in length, or about 6 to about 20 amino acids in length. In exemplary aspects, the peptide or peptide analog is about 7 to about 35 amino acids in length, about 7 to about 30 amino acids in length, about 7 to about 25 amino acids in length, or about 7 to about 20 amino acids in length. In exemplary aspects, the peptide or peptide analog is about 8 to about 35 amino acids in length, about 8 to about 30 amino acids in length, about 8 to about 25 amino acids in length, or about 8 to about 20 amino acids in length. In exemplary aspects, the peptide is about 8 to about 17 or 18 or about 9 to about 16 or 17 amino acids in length. In exemplary aspects, the peptide is about 10 to about 17 or about 12 to about 16 or 17 or about 14 to about 16 amino acids in length. In some embodiments, the peptide is a 5-mer, 6-mer, 7-mer, 8-mer, 9-mer-10-mer, 11-mer, 12-mer, 13-mer, 14-mer, 15-mer, 16-mer, 17-mer, 18-mer, 19-mer, or 20-mer.

Peptide Modifications

Peptides of the disclosure include peptides that have been modified in any way and for any reason, for example, to: (1) reduce susceptibility to proteolysis, (2) alter binding affinities, and (3) confer or modify other physicochemical or functional properties. For example, single or multiple amino acid substitutions (e.g., equivalent, conservative or non-conservative substitutions, deletions or additions) may be made in a sequence. In exemplary aspects, the peptide or peptide analog of the present disclosure comprises a sequence listed in Table 1, or a modified sequence thereof. In exemplary embodiments of the present disclosure, the peptide or peptide analog is lipidated (e.g., myritoylated, palmitoylated, linked to a $C_7$-$C_{20}$ lipid moiety), glycosylated, amidated, carboxylated, phosphorylated, esterified, acylated, acetylated, cyclized, pegylated (e.g., linked to a 5-20 kDa PEG, linked to a 5 kDa PEG, 12 kDa PEG, 20 kDa PEG) to or converted into an acid addition salt and/or optionally dimerized or polymerized, or conjugated, as further described herein. PEG in sizes of 200-4600 mol wt also would be of use for modifying the peptides of the current invention. PEG that are linear, branched and star geometries also would be of use for modifying the peptides of the current invention. PEG600 is also known as PEG12. In exemplary embodiments of the present disclosure, the peptide or peptide analog is acetylated at the N-terminus, amidated at the C-terminus, and/or phosphorylated on a Tyr residue. In exemplary aspects, the peptide or peptide analog is linked to a lipid moiety at the N-terminus or side chain of an internal residue. In exemplary aspects, the peptide or peptide analog is directly linked to a lipid moiety. In exemplary aspects, the peptide or peptide analog is indirectly linked to a lipid moiety. For example, the lipid moiety may be attached to the peptide via a linker. The linker may be an amino acid. In exemplary aspects, the lipid moiety is attached to a Lys residue of the peptide or peptide analog via a Glu residue optionally attached via the epsilon amine. Examples of modified peptides of the invention are found in Table 1.

The peptides of some embodiments are preferably in a linear form, though it will be appreciated that in cases where cyclization does not severely interfere with peptide characteristics, cyclic forms of the peptide can also be utilized and are contemplated as embodiments of the present disclosure.

In exemplary aspects, the peptide or peptide analog is cyclized. For example, the peptide or peptide analog comprises two Cys residues, the sulfur atoms of which participate in the formation of a disulfide bridge. In exemplary aspects, the peptide or peptide analog comprises a Cys residue as the terminal residues. Suitable methods of modifying peptides with disulfide bridges or sulfur-based cyclization are described in, for example, Jackson et al., *J. Am. Chem. Soc.* 113: 9391-9392 (1991) and Rudinger and Jost, *Experientia* 20: 570-571 (1964).

The peptide or peptide analog can alternatively be stabilized through other means of peptide cyclizing, which means are reviewed in Davies, J. Peptide. Sci. 9: 471-501 (2003). The peptide or peptide analog can be stabilized via the formation of an amide bridge, thioether bridge, thioester bridge, urea bridge, carbamate bridge, sulfonamide bridge, lactam bridge, lactone bridge, and the like. For example, a thioester bridge can be formed between the C-terminus and the side chain of a Cys residue. Alternatively, a thioester can be formed via side chains of amino acids having a thiol (Cys) and a carboxylic acid (e.g., Asp, Glu). In another method, a cross-linking agent, such as a dicarboxylic acid, e.g., suberic acid (octanedioic acid), etc. can introduce a link between two functional groups of an amino acid side chain, such as a free amino, hydroxyl, thiol group, and combinations thereof. In exemplary embodiments, the peptide or peptide analog can cyclized via a lactam bridge. Examples of amino acid pairs that can form a lactam bridge include, but are not limited to, ornithine (Orn) and Glu, Lys and Asp, Lys and Glu, homolysine and Asp, Orn and homoglutamic acid, 4-aminoPhe and Asp, homolysine and Glu, Lys and homoglutamic acid, and 4-aminoPhe and Glu. In exemplary embodiments, the peptide or peptide analog can cyclized via a lactone bridge. Examples of amino acid pairs that can form a lactone bridge include, but are not limited to, Homoser-Homoglu, Tyr and Glu, and Tyr and Asp.

In exemplary embodiments, the peptide or peptide analog comprises, consists essentially of, or consists of a sequence set forth in Table 1. In alternative embodiments of the present disclosure, the peptide or peptide analog comprises, consists essentially of, or consists of a modified sequence relative to the sequence set forth in Table 1. In exemplary embodiments, the peptide or peptide analog of the present disclosure comprises an amino acid sequence which has at least 50% sequence identity to any one of the amino acid sequences in Table 1. In exemplary embodiments, the peptide or peptide analog of the present disclosure comprises an amino acid sequence which has at least at least 60%, at least 70%, at least 80%, at least 85%, at least 90% or has greater than 90% sequence identity to any one of the amino acid sequences in Table 1. In exemplary aspects, the peptide or peptide analog comprises, consists essentially of, or consists of a modified sequence relative to the sequence set forth in Table 1, wherein the peptide or peptide analog comprises, consists essentially of, or consists of a sequence set forth in Table 1 with one or more (e.g., 2, 3, or 4) amino acid substitutions. In exemplary aspects, the amino acid substitution is a conservative amino acid substitution or an equivalent amino acid substitution.

A conservative amino acid substitution refers to the substitution in a peptide of an amino acid with a functionally similar amino acid having similar properties, e.g., size, charge, hydrophobicity, hydrophilicity, and/or aromaticity. The following six groups each contain amino acids that are conservative substitutions for one another are found in Table 2.

TABLE 2

| | |
|---|---|
| Group I | Alanine (A), Serine (S), and Threonine (T) |
| Group II | Aspartic acid (D) and Glutamic acid (E) |
| Group III | Asparagine (N) and Glutamine (Q) |
| Group IV | Arginine (R) and Lysine (K) |
| Group V | Isoleucine (I), Leucine (L), Methionine (M), and Valine (V) |
| Group VI | Phenylalanine (F), Tyrosine (Y), and Tryptophan (W) |

Additionally, within the meaning of the term "equivalent amino acid substitution" as applied herein, one amino acid may be substituted for another, in one embodiment, within the groups of amino acids indicated herein below:

Amino acids with polar side chains Asp, Glu, Lys, Arg, His, Asn, Gln, Ser, Thr, Tyr, and Cys Amino acids with small nonpolar or slightly polar residues Ala, Ser, Thr, Pro, Gly Amino acids with non-polar side chains Gly, Ala, Val, Leu, Ile, Phe, Trp, Pro, and Met Amino acids with large, aliphatic, nonpolar residues Met, Leu, Ile, Val, Cys, Norleucine (Nle), homocysteine Amino acids with aliphatic side chains Gly, Ala Val, Leu, Ile Amino acids with cyclic side chains Phe, Tyr, Trp, His, Pro Amino acids with aromatic side chains Phe, Tyr, Trp Amino acids with acidic side chains Asp, Glu Amino acids with basic side chains Lys, Arg, His Amino acids with amide side chains Asn, Gln Amino acids with hydroxy side chains Ser, Thr Amino acids with sulphur-containing side chains Cys, Met Neutral, weakly hydrophobic amino acids Pro, Ala, Gly, Ser, Thr Hydrophilic, acidic amino acids Gln, Asn, Glu, Asp Hydrophobic amino acids Leu, Ile, Val Other amino acid substitutions are set forth in Table 3.

TABLE 3

| Original Residues | Substitutions | Preferred Substitutions |
|---|---|---|
| Ala | Val, Leu, Ile | Val |
| Arg | Lys, Gln, Asn | Lys |
| Asn | Gln | |
| Asp | Glu | |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn, 1,4 Diamino-butyric Acid | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

In exemplary embodiments, the amino acid substitution is not a conservative amino acid substitution, e.g., is a non-conservative amino acid substitution. This class generally includes corresponding D-amino acids, homo-amino acids, N-alkyl amino acids, beta amino acids and other unnatural amino acids. The non-conservative amino acid substitutions still fall within the descriptions identified for the equivalent amino acid substitutions above [e.g. polar, nonpolar, etc.]. A "non-conservative amino acid substitution" also refers to the substitution of a member of one of these classes for a member from another class. In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is understood in the art (see, for example, Kyte et al., 1982, J. Mol. Biol. 157:105-131). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included. It is also understood in the art that the substitution of like amino acids can be made effectively on the basis of hydrophilicity, particularly where the biologically functional protein or peptide thereby created is intended for use in immunological embodiments, as disclosed herein. In certain embodiments, the greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0.+−.1); glutamate (+3.0.+−. 1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within +1 are included, and in certain embodiments, those within ±0.5 are included.

Examples of non-conservative amino acids are provided below.

Non limiting examples for alanine non-conservative amino acids are: D-alanine [Dala, (dA), a], N-Acetyl-3-(3, 4-dimethoxyphenyl)-D-alanine, N-Me-D-Ala-OH, N-Me-Ala-OH, H-β-Ala-β-naphthalene, L-(−)-2-Amino-3-ureidopropionic acid, (R)-(+)-α-Allylalanine, (S)-(−)-α-Allylalanine, D-2-Aminobutyric acid, L-2-Aminobutyric acid, DL-2-Aminobutyric acid, 2-Aminoisobutyric acid, α-Aminoisobutyric acid, (S)-(+)-2-Amino-4-phenylbutyric acid ethyl ester, Benzyl α-aminoisobutyrate, Abu-OH, Aib-OH, β-(9-anthryl)-Ala-OH, β-(3-benzothienyl)-Ala-OH, β-(3-benzothienyl)-D-Ala-OH, Cha-OH, Cha-OMe, β-(2-furyl)-Ala-OH, β-(2-furyl)-D-Ala-OH, β-iodo-Ala-OBzl, β-iodo-D-Ala-OBzl, 3-iodo-D-Ala-OMe, β-iodo-Ala-OMe, 1-Nal-OH, D-1-Nal-OH, 2-Nal-OH, D-2-Nal-OH, (R)-3-(2-naphthyl)-β-Ala-OH, (S)-3-(2-naphthyl)-β-Ala-OH, β-phenyl-Phe-OH, 3-(2-pyridyl)-Ala-OH, 3-(3-pyridyl)-Ala-OH, 3-(3-pyridyl)-D-Ala-OH, (S)-3-(3-pyridyl)-β-Ala-OH, 3-(4-pyridyl)-Ala-OH, 3-(4-pyridyl)-D-Ala-OH, β-(2-quinolyl)-Ala-OH, 3-(2-quinolyl)-DL-Ala-OH, 3-(3-quinolyl)-DL-Ala-OH, 3-(2-quinoxalyl)-DL-Ala-OH, β-(4-thiazolyl)-Ala-OH, β-(2-thienyl)-Ala-OH, β-(2-thienyl)-D-Ala-OH, β-(3-thienyl)-Ala-OH, β-(3-thienyl)-D-Ala-OH, 3-Chloro-D-alanine methyl ester, N-[(4-Chlorophenyl)sulfonyl]-β-alanine, 3-Cyclohexyl-D-alanine, 3-Cyclopentyl-DL-alanine, (−)-3-(3,4-Dihydroxyphenyl)-2-methyl-L-alanine, 3,3-Diphenyl-D-alanine, 3,3-Diphenyl-L-alanine, N—[(S)-(+)-1-(Ethoxycarbonyl)-3-phenylpropyl]-L-alanine, N-[1-(S)-(+)-Ethoxycarbonyl-3-phenylpropyl]-L-alanyl carboxyanhydride, N-(3-fluorobenzyl)alanine, N-(3-Indolylacetyl)-L-alanine, Methyl (RS)-2-(aminomethyl)-3-phenylpropionate, 3-(2-Oxo-1,2-dihydro-4-quinolinyl) alanine, 3-(1-Pyrazolyl)-L-alanine, 3-(2-Pyridyl)-D-alanine, 3-(2-Pyridyl)-L-alanine, 3-(3-Pyridyl)-L-alanine, 3-(4-Pyridyl)-D-alanine, 3-(4-Pyridyl)-L-alanine, 3-(2-Quinolyl)-DL-alanine, 3-(4-Quinolyl)-DL-alanine, D-styrylalanine, L-styrylalanine, 3-(2-Thienyl)-L-alanine, 3-(2-Thienyl)-DL-alanine, 3-(2-Thienyl)-DL-alanine, 3,3,3-Trifluoro-DL-alanine, N-Methyl-L-alanine, 3-Ureidopropionic acid, Aib-OH, Cha-OH, Dehydro-Ala-OMe, dehydro-Ala-OH, D-2-Nal-OH, β-Ala-ONp, β-Homoala-OH, β-D-Homoala-OH, β-Alanine, β-Alanine ethyl ester, β-Alanine methyl ester, (S)-diphenyl-β-Homoala-OH, (R)-4-(4-pyridyl)-β-Homoala-OH, (S)-4-(4-pyridyl)-β-Homoala-OH, β-Ala-OH, (S)-diphenyl-β-Homoala-OH, L-β-Homoalanine, (R)-4-(3-pyridyl)-β-Homoala-OH, α-methyl-α-naphthylalanine [Manap], N-methyl-cyclohexylalanine [Nmchexa], cyclohexylalanine [Chexa], N-methyl-cyclopentylalanine [Nmcpen], cyclopentylalanine [Cpen], N-methyl-α-naphthylalanine [Nmanap], α-naphthylalanine [Anap], L-N-methylalanine [Nmala], D-N-methylalanine [Dnmala], α-methyl-cyclohexylalanine [Mchexa], α-methyl-cyclopentylalanine [Mcpen]. Each possibility represents a separate embodiment.

Non limiting examples for arginine non-conservative amino acids are: homoarginine (hArg), N-methyl arginine (NMeArg), citruline, 2-amino-3-guanidinopropionic acid, N-iminoethyl-L-ornithine, Nω-monomethyl-L-arginine, Nω-nitro-L-arginine, D-arginine, 2-amino-3-ureidopropionic acid, Nω,ω-dimethyl-L-arginine, Nω-Nitro-D-arginine, L-α-methylarginine [Marg], D-α-methylarginine [Dmarg], L-N-methylarginine [Nmarg], D-N-methylarginine [Dnmarg], β-Homoarg-OH, L-Homoarginine, N-(3-guanidinopropyl)glycine [Narg], and D-arginine [Darg, (dR), r]. Each possibility represents a separate embodiment.

Non limiting examples for asparagine non-conservative amino acids are: L-α-methylasparagine [Masn], D-α-methylasparagine [Dmasn], L-N-methylasparagine [Nmasn], D-N-methylasparagine [Dnmasn], N-(carbamylmethyl)glycine [Nasn] and D-asparagine [Dasn, (dN), n]. Each possibility represents a separate embodiment.

Non limiting examples for aspartic acid non-conservative amino acids are: L-α-methylaspartate [Masp], D-α-methylaspartate [Dmasp], L-N-methylaspartic acid [Nmasp], D-N-methylasparatate [Dnmasp], N-(carboxymethyl)glycine [Nasp] and D-aspartic acid [Dasp, (dD), d]. Each possibility represents a separate embodiment.

Non limiting examples for cysteine non-conservative amino acids are: L-Cysteic acid, L-Cysteinesulfinic acid, D-Ethionine, S-(2-Thiazolyl)-L-cysteine, DL-Homocysteine, L-Homocysteine, L-Homocystine, L-α-methylcysteine [Mcys], D-α-methylcysteine [Dmcys], L-N-methylcysteine [Nmcys], D-N-methylcysteine [Dnmcys], N-(thiomethyl) glycine [Ncys] and D-cysteine [Dcys, (dC), c]. Each possibility represents a separate embodiment.

Non limiting examples for glutamic acid non-conservative amino acids are: γ-Carboxy-DL-glutamic acid, 4-Fluoro-DL-glutamic acid, P3-Glutamic acid, L-3-Homoglutamic acid, L-α-methylglutamate [Mglu], D-α-methyl glutamic acid [Dmglu], L-N-methylglutamic acid [Nmglu], D-N-methylglutamate [Dnmglu], N-(2-carboxyethyl)glycine [Nglu], and D-glutamic acid [Dglu, (dE), e]. Each possibility represents a separate embodiment.

Non limiting examples for glutamine non-conservative amino acids are: Cit-OH, D-Citrulline, Thio-L-citrulline, β-Gln-OH, L-β-Homoglutamine, L-α-methylglutamine [Mgln], D-α-methylglutamine [Dmgln], L-N-methylglutamine [Nmgln], D-N-methylglutamine [Dnmgln], N-(2-carbamylethyl)glycine [Ngln], and D-glutamine [Dgln, (dQ), q]. Each possibility represents a separate embodiment.

Non limiting examples for glycine non-conservative amino acids are: tBu-Gly-OH,D-Allylglycine, N-[Bis(methylthio)methylene]glycine methyl ester, Chg-OH, D-Chg-OH, D-cyclopropylglycine, L-cyclopropylglycine, (R)-4-fluorophenylglycine, (S)-4-fluorophenylglycine, iminodiacetic acid, (2-indanyl)-Gly-OH, (±)-α-phosphonoglycine trimethyl ester, D-propargylglycine, propargyl-Gly-OH, (R)-2-thienylglycine, (S)-2-thienylglycine, (R)-3-thienylglycine, (S)-3-thienylglycine, 2-(4-trifluoromethylphenyl)-DL-glycine, (2S,3R,4S)-α-(Carboxycyclopropyl) glycine, N-(Chloroacetyl)glycine ethyl ester, (S)-(+)-2-chlorophenylglycine methyl ester, N-(2-chlorophenyl)-N-(methylsulfonyl)glycine, D-α-Cyclohexylglycine, L-α-Cyclopropylglycine, Di-tert-butyl-iminodicarboxylate, Ethyl acetamidocyanoacetate, N-(2-fluorophenyl)-N-(methylsulfonyl) glycine, N-(4-fluorophenyl)-N-(methylsulfonyl) glycine, N-(2-Furfurylideneacetyl)glycine methyl ester, N-(2-Furoyl)glycine, N-(2-Hydroxyethyl)iminodiacetic acid, N-(4-Hydroxyphenyl)glycine, Iminodiacetic acid, N-Lauroylsarcosine sodium salt, L-α-Neopentylglycine, N-(Phosphonomethyl)glycine, D-Propargylglycine, L-C-Propargylglycine, Sarcosine, N,N-Dimethylglycine, N,N-Dimethylglycine ethyl ester, D-Chg-OH, α-Phosphonoglycine trimethyl ester, N-cyclobutylglycine [Ncbut], L-α-methylethylglycine [Metg], N-cycloheptylglycine [Nchep], L-α-methyl-i-butylglycine [Mtbug], N-methylglycine [Nmgly], L-N-methyl-ethylglycine [Nmetg], L-ethylglycine [Etg], α,α-diethylglycine [Deg], L-N-methyl-t-butylglycine [Nmtbug], L-t-butylglycine [Tbug], N-cyclohexylglycine [Nchex], N-cyclodecylglycine [Ncdec], N-cyclododecylglycine [Ncdod], N-cyclooctylglycine [Ncoct], N-cyclopropylglycine [Ncpro], N-cycloundecylglycine [Ncund], N-(2-aminoethyl)glycine [Naeg], N—(N-(2,2-diphenylethyl) diphenylethyl)glycine [Nnbhm], N-(2,2-carbamylmethyl-glycine [Nbhm], N—(N-(3,3-diphenylpropyl) diphenylpropyl)glycine [Nnbhe] and N-(3,3-carbamylmethyl-glycine [Nbhe]. Each possibility represents a separate embodiment.

Non limiting examples for histidine non-conservative amino acids are: L-α-methylhistidine [Mhis], D-α-methyl-histidine [Dmhis], L-N-methylhistidine [Nmhis], D-N-methylhistidine [Dnmhis], N-(imidazolylethyl)glycine [Nhis], and D-histidine [Dhis, (dH), h]. Each possibility represents a separate embodiment.

Non limiting examples for isoleucine non-conservative amino acids are: N-Methyl-L-isoleucine [Nmile], N-(3-Indolylacetyl)-L-isoleucine, allo-Isoleucine, D-allo-Isoleucine, L-3-Homoisoleucine, L-α-methylisoleucine [Mile], D-α-methylisoleucine [Dmile], D-N-methylisoleucine [Dnmile], N-(1-methylpropyl)glycine [Nile], and D-isoleucine [Dile, (dD), i]. Each possibility represents a separate embodiment.

Non limiting examples for leucine non-conservative amino acids are: D-leuine [Dleu, (dL), l]. Cycloleucine, DL-leucine, N-Formyl-Leu-OH, D-tert-Leucine, L-tert-Leucine, DL-tert-Leucine, L-tert-Leucine methyl ester, 5,5,5-Trifluoro-DL-leucine, D-β-Leu-OH, L-β-Leucine, DL-β-Leucine, L-β-Homoleucine, DL-β-Homoleucine, L-N-methyl-leucine [Nmleu], D-N-methyl-leucine [Dnmleu], L-α-methyl-leucine [Mleu], D-α-methyl-leucine [Dmleu], N-(2-methylpropyl)glycine [Nleu], D-leucine [Dleu, l], D-Norleucine, L-Norleucine, DL-Norleucine, L-N-methyl-norleucine [Nmnle] and L-norleucine [Nle]. Each possibility represents a separate embodiment.

Non limiting examples for lysine non-conservative amino acids are: DL-5-Hydroxylysine, (5R)-5-Hydroxy-L-lysine, β-Lys-OH, L-β-Homolysine, L-α-methyl-lysine [Mlys], D-α-methyl-lysine [Dmlys], L-N-methyl-lysine [Nmlys], D-N-methyl-lysine [Dnmlys], N-(4-aminobutyl)glycine [Nlys], and D-lysine [Dlys, (dK), k]. Each possibility represents a separate embodiment.

Non limiting examples for methionine non-conservative amino acids are: L-β-Homomethionine, DL-β-Homomethionine, L-α-methylmethionine [Mmet], D-α-methylmethionine [Dmmet], L-N-methylmethionine [Nmmet], D-N-methylmethionine [Dnmmet], N-(2-methylthioethyl)glycine [Nmet], and D-methionine [Dmet, (dM), m]. Each possibility represents a separate embodiment.

Non limiting examples for phenylalanine non-conservative amino acids are: N-Acetyl-2-fluoro-DL-phenylalanine, N-Acetyl-4-fluoro-DL-phenylalanine, 4-Amino-L-phenylalanine, 3-[3,4-bis(trifluoromethyl)phenyl]-L-alanine, Bpa-OH, D-Bpa-OH, 4-tert-butyl-Phe-OH, 4-tert-butyl-D-Phe-OH, 4-(amino)-L-phenylalanine, rac-(β²-homophenylalanine, 2-methoxy-L-phenylalanine, (S)-4-methoxy-β-Phe-OH, 2-nitro-L-phenylalanine, pentafluoro-D-phenylalanine, pentafluoro-L-phenylalanine, Phe(4-Br)—OH, D-Phe(4-Br)—OH, Phe(2-CF$_3$)—OH, D-Phe(2-CF$_3$)—OH, Phe(3-CF$_3$)—OH, D-Phe(3-CF$_3$)—OH, Phe(4-CF$_3$)—OH, D-Phe(4-CF$_3$)—OH, Phe(2-Cl)—OH, D-Phe(2-Cl)—OH, Phe(2,4-Cl$_2$)—OH, D-Phe(2,4-Cl$_2$)—OH, D-Phe (3-Cl)—OH, Phe(3,4-Cl$_2$)—OH, Phe(4-Cl)—OH, D-Phe(4-Cl)—OH, Phe(2-CN)—OH, D-Phe(2-CN)—OH, D-Phe(3-CN)—OH, Phe(4-CN)—OH, D-Phe(4-CN)—OH, Phe(2-Me)-OH, D-Phe(2-Me)-OH, Phe(3-Me)-OH, D-Phe(3-Me)-OH, Phe(4-Me)-OH, Phe(4-NH$_2$)—OH, Phe(4-NO$_2$)—OH, Phe(2-F)—OH, D-Phe(2-F)—OH, Phe(3-F)—OH, D-Phe (3-F)—OH, Phe(3,4-F$_2$)—OH, D-Phe(3,4-F$_2$)—OH, Phe(3, 5-F$_2$)—OH, Phe(4-F)—OH, D-Phe(4-F)—OH, Phe(4-I)—OH, D-3,4,5-trifluorophenylalanine, p-Bromo-DL-phenylalanine, 4-Bromo-L-phenylalanine, β-phenyl-D-phenylalanine, 4-Chloro-L-phenylalanine, DL-2,3-Difluorophenylalanine, DL-3,5-Difluorophenylalanine, 3,4-Dihydroxy-L-phenylalanine, 3-(3,4-Dimethoxyphenyl)-L-alanine, N-[(9H-Fluoren-9-ylmethoxy)carbonyl]-2-methoxy-L-phenylalanine, o-Fluoro-DL-phenylalanine, m-Fluoro-L-phenylalanine, m-Fluoro-DL-phenylalanine, p-Fluoro-L-phenylalanine, p-Fluoro-DL-phenylalanine, 4-Fluoro-D-phenylalanine, 2-fluoro-L-phenylalanine methyl ester, p-fluoro-DL-Phe-OMe, D-3-bromophenylalanine, D-4-bromophenylalanine, L-3-(6-chloro-4-pyridinyl) alanine, D-3,5-difluorophenylalanine, L-3-fluorophenylalanine, L-4-fluorophenylalanine, L-β-(1H-5-indolyl)alanine, 2-nitro-L-phenylalanine, pentafluoro-L-phenylalanine, phe (3-br)-oh, Phe(4-Br)—OH, Phe(2-CF$_3$)—OH, D-Phe(2-CF$_3$)—OH, Phe(3-CF$_3$)—OH, D-Phe(3-CF$_3$)—OH, Phe(4-CF$_3$)—OH, D-Phe(4-CF$_3$)—OH, Phe(2-Cl)—OH, D-Phe(2-Cl)—OH, Phe(2,4-Cl$_2$)—OH, D-Phe(2,4-Cl$_2$)—OH, Phe(3, 4-Cl$_2$)—OH, D-Phe(3,4-Cl$_2$)—OH, Phe(4-Cl)—OH, D-Phe (4-Cl)—OH, Phe(2-CN)—OH, D-Phe(2-CN)—OH, D-Phe(3-CN)—OH, Phe(4-CN)—OH, Phe(2-Me)-OH, Phe(3-Me)-OH, D-Phe(3-Me)-OH, Phe(4-NO$_2$)—OH, D-Phe(4-NO$_2$)—OH, D-Phe(2-F)—OH, Phe(3-F)—OH, D-Phe(3-F)—OH, Phe(3,4-F$_2$)—OH, Phe(3,5-F$_2$)—OH, D-Phe(4-F)—OH, Phe(4-I)—OH, D-Phe(4-I)—OH, 4-(phosphonomethyl)-Phe-OH, L-4-trifluoromethylphenylalanine, 3,4,5-trifluoro-D-phenylalanine, L-3,4,5-trifluorophenylalanine, 6-Hydroxy-DL-DOPA, 4-(Hydroxymethyl)-D-phenylalanine, N-(3-Indolylacetyl)-L-phenylalanine, p-Iodo-D-phenylalanine, 4-Iodo-L-phenylalanine, α-Methyl-D-phenylalanine, α-Methyl-L-phenylalanine, α-Methyl-DL-phenylalanine, α-Methyl-DL-phenylalanine methyl ester, 4-Nitro-D-phenylalanine, 4-Nitro-L-phenylalanine, 4-Nitro-DL-phenylalanine, (S)-(+)-4-Nitrophenylalanine methyl ester, 2-(Trifluoromethyl)-D-phenylalanine, 2-(Trifluoromethyl)-L-phenylalanine, 3-(Trifluoromethyl)-D-phenylalanine, 3-(Trifluoromethyl)-L-phenylalanine, 4-(Trifluoromethyl)-D-phenylalanine, 3,3',5-Triiodo-L-thyronine, (R)-4-bromo-β-Phe-OH N-Acetyl-DL-β-phenylalanine, (S)-4-bromo-β-Phe-OH, (R)-4-chloro-β-Homophe-OH, (S)-4-chloro-β-Homophe-OH, (R)-4-chloro-β-Phe-OH, (S)-4-chloro-β-Phe-OH, (S)-2-cyano-β-Homophe-OH, (R)-4-cyano-β-Homophe-OH, (S)-4-cyano-β-Homophe-OH, (R)-3-cyano-β-Phe-OH, (S)-4-cyano-β-Phe-OH, (S)-4-cyano-β-Phe-OH, (R)-3,4-dimethoxy-β-Phe-OH, (S)-3,4-dimethoxy-β-Phe-OH, (R)-4-fluoro-β-Phe-OH, (S)-4-fluoro-β-Phe-OH, (S)-4-iodo-β-Homophe-OH, (S)-3-cyano-β-Homophe-OH, (S)-3,4-difluoro-β-Homophe-OH, (R)-4-fluoro-β-Homophe-OH, (S)-β2-homophenylalanine, (R)-3-methoxy-β-Phe-OH, (S)-3-methoxy-β-Phe-OH, (R)-4-methoxy-β-Phe-OH, (S)-4-methyl-β-Homophe-OH, (R)-2-methyl-β-Phe-OH, (S)-2-methyl-β-Phe-OH, (R)-3-methyl-β-Phe-OH, (S)-3-methyl-β-Phe-OH, (R)-4-methyl-β-Phe-OH, (S)-4-methyl-β-Phe-OH, β-Phe-OH, D-β-Phe-OH, (S)-2-(trifluoromethyl)-β-Homophe-OH, (S)-2-(trifluoromethyl)-β-Homophe-OH, (S)-3-(trifluoromethyl)-β-Homophe-OH, (R)-4-(trifluoromethyl)-β-Homophe-OH, (S)-2-(trifluoromethyl)-β-Phe-OH, (R)-3-(trifluoromethyl)-β-Phe-OH, (S)-3-(trifluoromethyl)-β-Phe-OH, (R)-4-(trifluoromethyl)-β-Phe-OH, (S)-4-(trifluoromethyl)-β-Phe-OH, β-Homophe-OH, D-β-Homophe-OH, (S)-2-methyl-β-Homophe-OH, (S)-3-methyl-β-Homophe-OH, β-Phe-OH, β-D-Phe-OH, (S)-3-(trifluoromethyl)-β-Homophe-OH, L-β-Homophenylalanine, DL-β-Homophenylalanine, DL-β-Phenylalanine, DL-homophenylalanine methyl ester, D-Homophenylalanine, L-Homophenylalanine, DL-Homophenylalanine, D-Homophenylalanine ethyl ester, (R)-β$^2$-homophenylalanine, L-α-methyl-homophenylalanine [Mhphe], L-α-methylphenylalanine [Mphe], D-α-methylphenylalanine [Dmphe], L-N-methyl-homophenylalanine [Nm phe], L-homophenylalanine [Hphe], L-N-methylphenylalanine [Nmphe], D-N-methylphenylalanine [Dnmphe], N-benzylglycine [Nphe] and D-phenylalanine [Dphe, (dF), f]. Each possibility represents a separate embodiment.

Non limiting examples for proline non-conservative amino acids are: homoproline (hPro), (4-hydroxy)Pro (4HyP), (3-hydroxy)Pro (3HyP), gamma-benzyl-proline, gamma-(2-fluoro-benzyl)-proline, gamma-(3-fluoro-benzyl)-proline, gamma-(4-fluoro-benzyl)-proline, gamma-(2-chloro-benzyl)-proline, gamma-(3-chloro-benzyl)-proline, gamma-(4-chloro-benzyl)-proline, gamma-(2-bromo-benzyl)-proline, gamma-(3-bromo-benzyl)-proline, gamma-(4-bromo-benzyl)-proline, gamma-(2-methyl-benzyl)-proline, gamma-(3-methyl-benzyl)-proline, gamma-(4-methyl-benzyl)-proline, gamma-(2-nitro-benzyl)-proline, gamma-(3-nitro-benzyl)-proline, gamma-(4-nitro-benzyl)-proline, gamma-(1-naphthalenylmethyl)-proline, gamma-(2-naphthalenylmethyl)-proline, gamma-(2,4-dichloro-benzyl)-proline, gamma-(3,4-dichloro-benzyl)-proline, gamma-(3,4-difluoro-benzyl)-proline, gamma-(2-trifluoro-methyl-benzyl)-proline, gamma-(3-trifluoro-methyl-benzyl)-proline, gamma-(4-trifluoro-methyl-benzyl)-proline, gamma-(2-cyano-benzyl)-proline, gamma-(3-cyano-benzyl)-proline, gamma-(4-cyano-benzyl)-proline, gamma-(2-iodo-benzyl)-proline, gamma-(3-iodo-benzyl)-proline, gamma-(4-iodo-benzyl)-proline, gamma-(3-phenyl-allyl-benzyl)-proline, gamma-(3-phenyl-propyl-benzyl)-proline, gamma-(4-tert-butyl-benzyl)-proline, gamma-benzhydryl-proline, gamma-(4-biphenyl-methyl)-proline, gamma-(4-thiazolyl-methyl)-proline, gamma-(3-benzothienyl-methyl)-proline, gamma-(2-thienyl-methyl)-proline, gamma-(3-thienyl-methyl)-proline, gamma-(2-furanyl-methyl)-proline, gamma-(2-pyridinyl-methyl)-proline, gamma-(3-pyridinyl-methyl)-proline, gamma-(4-pyridinyl-methyl)-proline, gamma-allyl-proline, gamma-propynyl-proline, alpha-modified-proline residues, pipecolic acid, azetidine-3-carboxylicacid, L-β-Homoproline, L-β$^3$-homoproline, L-β-Homohydroxyproline, hydroxyproline [Hyp], L-☐-methylproline [Mpro], D-☐-methylproline [Dmpro], L-N-methylproline [Nmpro], D-N-methylproline [Dnmpro], and D-proline [Dpro, (dP), p]. Each possibility represents a separate embodiment.

Non limiting examples for serine non-conservative amino acids are: (2R,3S)-3-phenylisoserine, D-cycloserine, L-Isoserine, DL-Isoserine, DL-3-Phenylserine, L-β-Homoserine, D-Homoserine, D-Homoserine, L-3-Homoserine, L-homoserine, L-α-methylserine [Mser], D-α-methylserine [Dmser], L-N-methylserine [Nmser], D-N-methylserine [Dnmser], D-serine [Dser, (dS), s], N-(hydroxymethyl)glycine [Nser] and phosphoserine [pSer]. Each possibility represents a separate embodiment.

Non limiting examples for threonine non-conservative amino acids are: L-allo-Threonine, D-Thyroxine, L-β-Homothreonine, L-α-methylthreonine [Mthr], D-α-methylthreonine [Dmthr], L-N-methylthreonine [Nmthr], D-N-methylthreonine [Dnmthr], D-threonine [Dthr, (dT), t], N-(1-hydroxyethyl)glycine [Nthr] and phosphothreonine [pThr]. Each possibility represents a separate embodiment.

Non limiting examples for tryptophan non-conservative amino acids are: 5-Fluoro-L-tryptophan, 5-Fluoro-DL-tryptophan, 5-Hydroxy-L-tryptophan, 5-Methoxy-DL-tryptophan, L-abrine, 5-Methyl-DL-tryptophan, H-Tpi-OMe. β-Homotrp-OMe, L-β-Homotryptophan, L-α-methyltryptophan [Mtrp], D-α-methyltryptophan [Dmtrp], L-N-methyltryptophan [Nmtrp], D-N-methyltryptophan [Dnmtrp], N-(3-indolylethyl)glycine [Nhtrp], D-tryptophan [Dtrp, (dW), w]. Each possibility represents a separate embodiment.

Non limiting examples for tyrosine non-conservative amino acids are: 3,5 diiodotyrosine (3,5-dITyr), 3,5 diBromotyrosine (3,5-dBTyr), homotyrosine, D-tyrosine, 3-amino-L-tyrosine, 3-amino-D-tyrosine, 3-iodo-L-tyrosine, 3-iodo-D-tyrosine, 3-methoxy-L-tyrosine, 3-methoxy-D-tyrosine, L-thyroxine, D-thyroxine, L-thyronine, D-thyronine, O-methyl-L-tyrosine, O-methyl-D-tyrosine, D-thyronine, O-ethyl-L-tyrosine, O-ethyl-D-tyrosine, 3,5,3'-triiodo-L-thyronine, 3,5,3'-triiodo-D-thyronine, 3,5-diiodo-L-thyronine, 3,5-diiodo-D-thyronine, D-meta-tyrosine, L-meta-tyrosine, D-ortho-tyrosine, L-ortho-tyrosine, phenylalanine, substituted phaenylalanine, N-nitro phenylalanine, p-nitro phenylalanine, 3-chloro-Dtyr-oh, Tyr(3,5-diI), 3-Chloro-L-tyrosine, Tyr(3-NO$_2$)—OH, Tyr(3,5-diI)—OH, N-Me-Tyr-OH, α-Methyl-DL-tyrosine, 3-Nitro-L-tyrosine, DL-o-Tyrosine, β-Homotyr-OH, (R)-β-Tyr-OH, (S)-β-Tyr-OH, L-oa-methyltyrosine [Mtyr], D-α-methyltyrosine [Dmtyr], L-N-methyltyrosine [Nmtyr], D-N-methyltyrosine [Dnmtyr], D-tyrosine [Dtyr, (dY), y], O-methyl-tyrosine, and phosphotyrosine [pTyr]. Each possibility represents a separate embodiment.

Non limiting examples for valine non-conservative amino acids are: 3-Fluoro-DL-valine, 4,4,4,4',4',4'-Hexafluoro-DL-valine, D-valine [Dval, (dV), v], N-Me-Val-OH [Nmval], N-Me-Val-OH, L-α-methylvaline [Mval], D-α-methylvaline [Dmval], (R)-(+)-α-Methylvaline, (S)-(−)-α-Methylvaline and D-N-methylvaline [Dnmval]. Each possibility represents a separate embodiment.

Other non-natural amino acids that may be substituted as non-conservative replacements include: Ornithine and its modifications: D-Ornithine [Dorn], L-Ornithine [Orn], DL-Ornithine, L-α-methylornithine [Morn], D-α-methylornithine [Dmorn], L-N-methylornithine [Nmorn], D-N-methylornithine [Dnmorn] and N-(3-aminopropyl)glycine [Norn]. Each possibility represents a separate embodiment.

Alicyclic amino acids: L-2,4-Diaminobutyric acid, L-2,3-Diaminopropionic Acid, N-Me-Aib-OH, (R)-2-(amino)-5-hexynoic acid, piperidine-2-carboxylic acid, aminonorbornyl-carboxylate [Norb], alpha-aminobutyric acid [Abu], aminocyclopropane-carboxylate [Cpro], (cis)-3-Aminobicyclo[2.2.1]heptane-2-carboxylic acid, exo-cis-3-Aminobicyclo[2.2.1]hept-5-ene-2-carboxylic acid, 1-Amino-1-cyclobutanecarboxylic acid, cis-2-Aminocycloheptanecarboxylic acid, 1-Aminocyclohexanecarboxylic acid, cis-2-Aminocyclohexanecarboxylic acid, trans-2-Aminocyclohexanecarboxylic acid, cis-6-Amino-3-cyclohexene-1-carboxylic acid, 2-(1-Aminocyclohexyl)acetic acid, cis-2-Amino-1-cyclooctanecarboxylic acid, cis-2-Amino-3-cyclooctene-1-carboxylic acid, (1R,2S)-(−)-2-Amino-1-cyclopentanecarboxylic acid, (1S,2R)-(+)-2-Amino-1-cyclopentanecarboxylic acid, cis-2-Amino-1-cyclopentanecarboxylic acid, 2-(1-Aminocyclopentyl)acetic acid, cis-2-Amino-2-methylcyclohexanecarboxylic acid, cis-2-Amino-2-methylcyclopentanecarboxylic acid, 3-Amino-3-(4-nitrophenyl)propionic acid, 3-Azetidinecarboxylic acid, amchc-oh, 1-aminocyclobutane carboxylic acid, 1-(amino)cyclohexanecarboxylic acid, cis-2-(amino)-cyclohexanecarboxylic acid, trans-2-(amino)-cyclohexanecarboxylic acid, cis-4-(amino)cyclohexanecarboxylic acid, trans-4-(amino)cyclohexanecarboxylic acid, (±)-cis-2-(amino)-3-cyclohexene-1-carboxylic acid, (±)-cis-6-(amino)-3-cyclohexene-1-carboxylic acid, 2-(1-aminocyclohexyl)acetic acid, cis-[4-(amino)cyclohexyl]acetic acid, 1-(amino)cyclopentanecarboxylic acid, (±)-cis-2-(amino) cyclopentanecarboxylic acid, (1R,4S)-(+)-4-(amino)-2-cyclopentene-1-carboxylic acid, (±)-cis-2-(amino)-3-cyclopentene-1-carboxylic acid, 2-(1-aminocyclopentyl)acetic acid, 1-(amino)cyclopropanecarboxylic acid, Ethyl 1-aminocyclopropanecarboxylate, 1,2-trans-achec-oh, 1-(amino) cyclobutanecarboxylic acid, 1-(amino)cyclohexanecarboxylic acid, cis-2-(amino)-cyclohexanecarboxylic acid, trans-2-(amino)cyclohexanecarboxylic acid, cis-4-(amino) cyclohexanecarboxylic acid, trans-4-(amino) cyclohexanecarboxylic acid, cis-[4-(amino)cyclohexyl] acetic acid, 1-(amino)cyclopentanecarboxylic acid, (1R,4S)-(+)-4-(amino)-2-cyclopentene-1-carboxylic acid, (1 S,4R)-(−)-4-(amino)-2-cyclopentene-1-carboxylic acid, 1-(amino) cyclopropanecarboxylic acid, trans-4-(aminomethyl) cyclohexanecarboxylic acid, β-Dab-OH, 3-Amino-3-(3-bromophenyl)propionic acid, 3-Aminobutanoic acid, cis-3-Amino-3-cyclopentene-1-carboxylic acid, DL-3-Aminoisobutyric acid, (R)-3-Amino-2-phenylpropionic acid, (±)-3-(amino)-4-(4-biphenylyl)butyric acid, cis-3-(amino)cyclohexanecarboxylic acid, (1S,3R)-(+)-3-(amino) cyclopentanecarboxylic acid, (2R,3R)-3-(amino)-2-hydroxy-4-phenylbutyric acid, (2S,3R)-3-(amino)-2-hydroxy-4-phenylbutyric acid, 2-(aminomethyl)phenylacetic acid, (R)-3-(amino)-2-methylpropionic acid, (S)-3-(amino)-2-methylpropionic acid, (R)-3-(amino)-4-(2-naphthyl)butyric acid, (S)-3-(amino)-4-(2-naphthyl)butyric acid, (R)-3-(amino)-5-phenylpentanoic acid, (R)-3-(amino)-2-phenyl-propionic acid, Ethyl 3-(benzylamino)propionate, cis-3-(amino)cyclohexanecarboxylic acid, (S)-3-(amino)-5-hexenoic acid, (R)-3-(amino)-2-methylpropionic acid, (S)-3-(amino)-2-methylpropionic acid, (R)-3-(amino)-4-(2-naphthyl)butyric acid, (S)-3-(amino)-4-(2-naphthyl)butyric acid, (R)-(−)-Pyrrolidine-3-carboxylic acid, (S)-(+)-Pyrrolidine-3-carboxylic acid, N-methyl-γ-aminobutyrate [Nmgabu], γ-aminobutyric acid [Gabu], N-methyl-α-amino-α-methylbutyrate [Nmaabu], α-amino-α-methylbutyrate [Aabu], N-methyl-α-aminoisobutyrate [Nmaib], α-aminoisobutyric acid [Aib], α-methyl-γ-aminobutyrate [Mgabu]. Each possibility represents a separate embodiment.

Phenyl glycine and its modifications: Phg-OH, D-Phg-OH, 2-(piperazino)-2-(3,4-dimethoxyphenyl)acetic acid, 2-(piperazino)-2-(2-fluorophenyl)acetic acid, 2-(4-piperazino)-2-(3-fluorophenyl)acetic acid, 2-(4-piperazino)-2-(4-methoxyphenyl)acetic acid, 2-(4-piperazino)-2-(3-pyridyl) acetic acid, 2-(4-piperazino)-2-[4-(trifluoromethyl)phenyl] acetic acid, L-(+)-2-Chlorophenylglycine, (±)-2-Chlorophenylglycine, (±)-4-Chlorophenylglycine, (R)-(−)-2-(2,5-Dihydrophenyl)glycine, (R)-(−)-N-(3,5-Dinitrobenzoyl)-α-phenylglycine, (S)-(+)-N-(3,5-Dinitrobenzoyl)-α-phenylglycine, 2,2-Diphenylglycine, 2-Fluoro-DL-α-phenylglycine, 4-Fluoro-D-α-phenylglycine, 4-Hydroxy-D-phenylglycine, 4-Hydroxy-L-phenylglycine, 2-Phenylglycine, D-(−)-α-Phenylglycine, D-(−)-α-Phenylglycine, DL-α-Phenylglycine, L-(+)-α-Phenylglycine, N-Phenylglycine, (R)-(−)-2-Phenylglycine methyl ester, (S)-(+)-2-Phenylglycine methyl ester, 2-Phenylglycinonitrile hydrochloride, α-Phenylglycinonitrile, 3-(Trifluoromethyl)-DL-phenylglycine, and 4-(Trifluoromethyl)-L-phenylglycine. Each possibility represents a separate embodiment.

Penicillamine and its modifications: N-Acetyl-D-penicillamine, D-Penicillamine, L-Penicillamine [Pen], DL-Penicillamine. α-methylpenicillamine [Mpen], N-methylpenicillamine [Nmpen]. Each possibility represents a separate embodiment.

β-Homopyrrolidine. Each possibility represents a separate embodiment.

Aromatic amino acids: 3-Acetamidobenzoic acid, 4-Acetamidobenzoic acid, 4-Acetamido-2-methylbenzoic acid, N-Acetylanthranilic acid, 3-Aminobenzoic acid, 3-Aminobenzoic acid hydrochloride, 4-Aminobenzoic acid, 4-Aminobenzoic acid, 4-Aminobenzoic acid, 4-Aminobenzoic acid, 4-Aminobenzoic acid, 4-Aminobenzoic acid, 2-Aminobenzophenone-2'-carboxylic acid, 2-Amino-4-bromobenzoic acid, 2-Amino-5-bromobenzoic acid, 3-Amino-2-bromobenzoic acid, 3-Amino-4-bromobenzoic acid, 3-Amino-5-bromobenzoic acid, 4-Amino-3-bromobenzoic acid, 5-Amino-2-bromobenzoic acid, 2-Amino-3-bromo-5-methylbenzoic acid, 2-Amino-3-chlorobenzoic acid, 2-Amino-4-chlorobenzoic acid, 2-Amino-5-chlorobenzoic acid, 2-Amino-5-chlorobenzoic acid, 2-Amino-6-chlorobenzoic acid, 3-Amino-2-chlorobenzoic acid, 3-Amino-4-chlorobenzoic acid, 4-Amino-2-chlorobenzoic acid, 4-Amino-3-chlorobenzoic acid, 5-Amino-2-chlorobenzoic acid, 5-Amino-2- chlorobenzoic acid, 4-Amino-5-chloro-2-methoxybenzoic acid, 2-Amino-5-chloro-3-methylbenzoic acid, 3-Amino-2,5-dichlorobenzoic acid, 4-Amino-3,5-dichlorobenzoic acid, 2-Amino-4,5-dimethoxybenzoic acid, 4-(2-Aminoethyl) benzoic acid hydrochloride, 2-Amino-4-fluorobenzoic acid, 2-Amino-5-fluorobenzoic acid, 2-Amino-6-fluorobenzoic acid, 4-Amino-2-fluorobenzoic acid, 2-Amino-5-hydroxybenzoic acid, 3-Amino-4-hydroxybenzoic acid, 4-Amino-3-hydroxybenzoic acid, 2-Amino-5-iodobenzoic acid, 5-Aminoisophthalic acid, 2-Amino-3-methoxybenzoic acid, 2-Amino-4-methoxybenzoic acid, 2-Amino-5-methoxybenzoic acid, 3-Amino-2-methoxybenzoic acid, 3-Amino-4-methoxybenzoic acid, 3-Amino-5-methoxybenzoic acid, 4-Amino-2-methoxybenzoic acid, 4-Amino-3-methoxybenzoic acid, 5-Amino-2-methoxybenzoic acid, 2-Amino-3-methylbenzoic acid, 2-Amino-5-methylbenzoic acid, 2-Amino-6-methylbenzoic acid, 3-(Aminomethyl)benzoic acid, 3-Amino-2-methylbenzoic acid, 3-Amino-4-methylbenzoic acid, 4-(Aminomethyl)benzoic acid, 4-Amino-2-methylbenzoic acid, 4-Amino-3-methylbenzoic acid, 5-Amino-2-methylbenzoic acid, 3-Amino-2-naphthoic acid, 6-Amino-2-naphthoic acid, 2-Amino-3-nitrobenzoic acid, 2-Amino-5-nitrobenzoic acid, 2-Amino-5-nitrobenzoic acid, 4-Amino-3-nitrobenzoic acid, 5-Amino-2-nitrobenzoic acid, 3-(4-Aminophenyl)propionic acid, 3-Aminophthalic acid, 4-Aminophthalic acid, 3-Aminosalicylic acid, 4-Aminosalicylic acid, 5-Aminosalicylic acid, 5-Aminosalicylic acid, 2-Aminoterephthalic acid, 2-Amino-3,4,5,6-tetrafluorobenzoic acid, 4-Amino-2,3,5,6-tetrafluorobenzoic acid, (R)-2-Amino-1,2,3,4-tetrahydronaphthalene-2-carboxylic acid, (S)-2-Amino-1,2,3,4-tetrahydro-2-naphthalenecarboxylic acid, 2-Amino-3-(trifluoromethyl)benzoic acid, 2-Amino-3-(trifluoromethyl)benzoic acid, 3-Amino-5-(trifluoromethyl) benzoic acid, 5-Amino-2,4,6-triiodoisophthalic acid, 2-Amino-3,4,5-trimethoxybenzoic acid, 2-Anilinophenylacetic acid, 2-Abz-OH, 3-Abz-OH, 4-Abz-OH, 2-(aminomethyl)benzoic acid, 3-(aminomethyl)benzoic acid, 4-(aminomethyl)benzoic acid, tert-Butyl 2-aminobenzoate, tert-Butyl 3-aminobenzoate, tert-Butyl 4-aminobenzoate, 4-(Butylamino)benzoic acid, 2,3-Diaminobenzoic acid, 3,4-Diaminobenzoic acid, 3,5-Diaminobenzoic acid, 3,5-Diaminobenzoic acid, 3,5-Dichloroanthranilic acid, 4-(Diethylamino)benzoic acid, 4,5-Difluoroanthranilic acid, 4-(Dimethylamino)benzoic acid, 4-(Dimethylamino)benzoic acid, 3,5-Dimethylanthranilic acid, 5-Fluoro-2-methoxybenzoic acid, 2-Abz-OH, 3-Abz-OH, 4-Abz-OH, 3-(aminomethyl)benzoic acid, 4-(aminomethyl)benzoic acid, 4-(2-hydrazino)benzoic acid, 3-Hydroxyanthranilic acid, 3-Hydroxyanthranilic acid, Methyl 3-aminobenzoate, 3-(Methylamino)benzoic acid, 4-(Methylamino)benzoic acid, Methyl 2-amino-4-chlorobenzoate, Methyl 2-amino-4,5-dimethoxybenzoate, 4-Nitroanthranilic acid, N-Phenylanthranilic acid, N-Phenylanthranilic acid, and Sodium 4-aminosalicylate. Each possibility represents a separate embodiment.

Other amino acids: (S)-α-Amino-γ-butyrolactone, DL-2-Aminocaprylic acid, 7-Aminocephalosporanic acid, 4-Aminocinnamic acid, (S)-(+)-α-Aminocyclohexanepropionic acid, (R)-Amino-(4-hydroxyphenyl)acetic acid methyl ester, 5-Aminolevulinic acid, 4-Amino-nicotinic acid, 3-Aminophenylacetic acid, 4-Aminophenylacetic acid, 2-Amino-2-phenylbutyric acid, 4-(4-Aminophenyl)butyric acid, 2-(4-Aminophenylthio)acetic acid, DL-α-Amino-2-thiopheneacetic acid, 5-Aminovaleric acid, 8-Benzyl (S)-2-aminooctanedioate, 4-(amino)-1-methylpyrrole-2-carboxylic acid, 4-(amino)tetrahydrothiopyran-4-carboxylic acid, (1R,3S,4S)-2-azabicyclo[2.2.1]heptane-3-carboxylic acid, L-azetidine-2-carboxylic acid, azetidine-3-carboxylic acid, 4-(amino)piperidine-4-carboxylic acid, diaminoacetic acid, Inp-OH, (R)-Nip-OH, (S)-4-oxopiperidine-2-carboxylic acid, 2-(4-piperazino)-2-(4-fluorophenyl)acetic acid, 2-(4-piperazino)-2-phenylacetic acid, 4-piperidineacetaldehyde, 4-piperidylacetic acid, (−)-L-thioproline, Tle-OH, 3-piperidinecarboxylic acid, L-(+)-Canavanine, (±)-Carnitine, Chlorambucil, 2,6-Diaminopimelic acid, meso-2,3-Diaminosuccinic acid, 4-(Dimethylamino)cinnamic acid, 4-(Dimethylamino)phenylacetic acid, Ethyl (S)—N-Boc-piperidine-3-carboxylate, ethyl-piperazinoacetate, 4-[2-(amino)ethyl]piperazin-1-ylacetic acid, (R)-4-(amino)-5-phenylpentanoic acid, (S)-azetidine-2-carboxylic acid, azetidine-3-carboxylic acid, guvacine, Inp-OH, (R)-Nip-OH, DL-Nip-OH, 4-phenyl-piperidine-4-carboxylic acid, 1-piperazineacetic acid, 4-piperidineacetic acid, (R)-piperidine-2-carboxylic acid, (S)-piperidine-2-carboxylic acid, (S)-1,2,3,4-tetrahydronorharmane-3-carboxylic acid, Tic-OH, D-Tic-OH, Iminodiacetic acid, Indoline-2-carboxylic acid, DL-Kynurenine, L-aziridine-2-carboxylate, Methyl 4-aminobutyrate, (S)-2-Piperazinecarboxylic acid, 2-(1-Piperazinyl)acetic acid, (R)-(−)-3-Piperidinecarboxylic acid, 2-Pyrrolidone-5-carboxylic acid, (R)-(+)-2-Pyrrolidone-5-carboxylic acid, (R)-1,2,3,4-Tetrahydro-3-isoquinolinecarboxylic acid, (S)-1,2,3,4-Tetrahydro-3-isoquinolinecarboxylic acid, L-4-Thiazolidinecarboxylic acid, (4R)-(−)-2-Thioxo-4-thiazolidinecarboxylic acid, hydrazinoacetic acid, and 3,3′,5-Triiodo-L-thyronine. Each possibility represents a separate embodiment.

In some embodiments, the peptide or peptide analog comprises at position 1 or 2, or at both positions 1 and 2, an amino acid which achieves resistance of the peptides to peptidase cleavage. In some embodiments, the peptide or peptide analog comprises at position 1 an amino acid selected from the group consisting of: D-histidine, desaminohistidine, hydroxyl-histidine, acetyl-histidine, homo-histidine, N-methyl histidine, alpha-methyl histidine, imidazole acetic acid, or alpha, alpha-dimethyl imidazole acetic acid (DMIA). In some embodiments, the peptide or peptide analog comprises at position 2 an amino acid selected from the group consisting of: D-serine, D-alanine, valine, glycine, N-methyl serine, N-methyl alanine, or alpha, aminoisobutyric acid. In some embodiments, the peptide or peptide analog comprises at position 2 an amino acid which achieves resistance of the peptide or peptide analog to peptidases and the amino acid which achieves resistance of the peptide or peptide analog to peptidases is not D-serine. In some embodiments, this covalent bond is an intramolecular bridge other than a lactam bridge. For example, suitable covalent bonding methods include any one or more of olefin metathesis, lanthionine-based cyclization, disulfide bridge or modified sulfur-containing bridge formation, the use of α,ω-diaminoalkane tethers, the formation of metal-atom bridges, and other means of peptide cyclization.

In some embodiments, the peptide or peptide analog is modified by amino acid substitutions and/or additions that introduce a charged amino acid into the C-terminal portion of the analog. In some embodiments, such modifications enhance stability and solubility. As used herein the term "charged amino acid" or "charged residue" refers to an amino acid that comprises a side chain that is negative-charged (i.e., de-protonated) or positive-charged (i.e., protonated) in aqueous solution at physiological pH. In some aspects, these amino acid substitutions and/or additions that introduce a charged amino acid modifications may be at a C-terminal position. In some embodiments, one, two or three (and in some instances, more than three) charged amino acids may be introduced at the C-terminal position. In exemplary embodiments, one, two or all of the charged amino acids may be negative-charged. The negative-charged amino acid in some embodiments is aspartic acid, glutamic acid, cysteic acid, homocysteic acid, or homoglutamic acid. In some aspects, these modifications increase solubility.

In accordance with some embodiments, the peptides or peptide analogs disclosed herein may be modified by truncation of the C-terminus by one or two amino acid residues. In this regard, the peptides or peptide analogs in exemplary aspects comprise a sequence of any one of SEQ ID NOs: 1, 3-41, 43-76, and 79-293, 310-315, 319-323 and 354-377 truncated at the C-terminus by one or two amino acid residues, optionally with any of the additional modifications described herein.

In some embodiments, the peptide comprises a modified sequence of any one of SEQ ID NOs: 1, 3-41, 43-76, and 79-293, 310-315, 319-323 and 354-377 in which the carboxylic acid of the C-terminal amino acid is replaced with a charge-neutral group, such as an amide or ester. Accordingly, in some embodiments, the peptide is an amidated peptide, such that the C-terminal residue comprises an amide in place of the alpha carboxylate of an amino acid. As used herein a general reference to a peptide or analog is intended to encompass peptides that have a modified amino terminus, a modified carboxy terminus, or modifications of both amino and carboxy termini. For example, an amino acid chain composing an amide group in place of the terminal carboxylic acid is intended to be encompassed by an amino acid sequence designating the standard amino acids.

In accordance with some embodiments, the peptides disclosed herein may be modified by conjugation on at least one amino acid residue. In this regard, the peptides in exemplary aspects comprise a sequence of any one of SEQ ID NOs: 1, 3-41, 43-76, and 79-293, 310-315, 319-323 and 354-377 conjugated to a heterologous moiety, as described herein.

Peptide Analogs

The present disclosure provides peptide analogs, such as, but not limited to, peptidomimetic compounds, which may have improved stability and cell permeability properties. In exemplary embodiments, the peptidomimetic compound comprises a sequence according to any one of SEQ ID NO: 1, 3-41, 43-76, and 79-293, 310-315, 319-323 and 354-377, wherein one of more peptide bonds (—CO—NH—) within the peptide are substituted, for example, by N-methylated amide bonds (—N(CH3)-CO—), ester bonds (—C(=O)—O—), ketomethylene bonds (—CO—CH$_2$—), sulfinylmethylene bonds (—S(=O)—CH$_2$—), α-aza bonds (—NH—N(R)—CO—), wherein R is any alkyl (e.g., methyl), amine bonds (—CH$_2$—NH—), sulfide bonds (—CH$_2$—S—), ethylene bonds (—CH$_2$—CH$_2$—), hydroxyethylene bonds (—CH(OH)—CH$_2$—), thioamide bonds (—CS—NH—), olefinic double bonds (—CH=CH—), fluorinated olefinic double bonds (—CF=CH—), or retro amide bonds (—NH—CO—), peptide derivatives (—N(R$^x$)—CH$_2$—CO—), wherein R$^x$ is the "normal" side chain, naturally present on the carbon atom. These modifications can occur at any of the bonds along the peptide chain and even at several (2-3) bonds at the same time.

In exemplary aspects, the peptide analog is a peptidomimetic. Peptidomimetics as well as methods of making the same are known in the art. See, for example, *Advances in Amino Acid Mimetics and Peptidomimetics*, Volumes 1 and 2, ed., Abell, A., JAI Press Inc., Greenwich, C T, 2006. In exemplary aspects, the peptidomimetic is a D-peptide peptidomimetic comprising D-isomer amino acids. In exemplary aspects, the peptidomimetic is a peptoid in which the side chain of an amino acid is connected to the alpha nitrogen atom of the peptide backbone. Methods of making peptoids are known in the art. See, e.g., Zuckermann et al., *JACS* 114(26): 10646-10647 (1992) and *Design, Synthesis, and Evaluation of Novel Peptoids*, Fowler, Sarah, University of Wisconsin-Madison, 2008. In some aspects, the peptidomimetic is a β-peptide comprising β amino acids which have their amino group bonded to the β-carbon rather than the alpha carbon. Methods of making β-peptides are known in the art. See, for example, Seebach et al., *Helvetica Chimica Acta* 79(4): 913-941 (1996).

Conjugates

The present disclosure further provides the peptides or peptide analogs described herein conjugated, linked, bridged, adjoined, or bonded to a heterologous moiety. Accordingly, the present disclosure provides conjugates comprising one or more of the peptides or peptide analogs described herein and a heterologous moiety. As used herein, the term "heterologous moiety" is synonymous with the term "conjugate moiety" and refers to any molecule (chemical or biochemical, naturally-occurring or non-coded) which is different from the peptides described herein. Exemplary conjugate moieties that can be linked to any of the peptides or peptide analogs described herein include but are not limited to a heterologous peptide or polypeptide (including for example, a plasma protein), a targeting agent, an immunoglobulin or portion thereof (e.g., variable region, CDR, or Fc region), a diagnostic label such as a radioisotope, fluorophore or enzymatic label, a polymer including water soluble polymers, or other therapeutic or diagnostic agents. In some embodiments, a conjugate is provided comprising a peptide and a plasma protein, wherein the plasma protein is selected from the group consisting of albumin, transferin, fibrinogen and globulins. In some embodiments, the plasma protein moiety of the conjugate is albumin or transferin.

The conjugate in some embodiments comprises one or more of the peptides or peptide analogs described herein and one or more of: a different peptide (which is distinct from the peptides described herein), a polypeptide, a nucleic acid molecule, an antibody or fragment thereof, a polymer, a quantum dot, a small molecule, a toxin, a diagnostic agent, a carbohydrate, or an amino acid.

In some embodiments, the heterologous moiety is a polymer. In some embodiments, the polymer is selected from the group consisting of: polyamides, polycarbonates, polyalkylenes and derivatives thereof including, polyalkylene glycols, polyalkylene oxides, polyalkylene terephtalates, polymers of acrylic and methacrylic esters, including poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene. In some aspects, the polymer is a biodegradable polymer, including a synthetic biodegradable polymer (e.g., polymers of lactic acid and glycolic acid, polyanhydrides, poly(ortho)esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion. In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In some embodiments, the polymer is a water-soluble polymer or a hydrophilic polymer. Hydrophilic polymers are further described herein under "Hydrophilic Moieties." Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In specific embodiments, the polymer is a polyalkylene glycol, including, for example, polyethylene glycol (PEG).

In some embodiments, the heterologous moiety is a carbohydrate. In some embodiments, the carbohydrate is a monosaccharide (e.g., glucose, galactose, fructose), a disaccharide (e.g., sucrose, lactose, maltose), an oligosaccharide (e.g., raffinose, stachyose), a polysaccharide (a starch, amylase, amylopectin, cellulose, chitin, callose, laminarin, xylan, mannan, fucoidan, or galactomannan.

In some embodiments, the heterologous moiety is a lipid. The lipid, in some embodiments, is a fatty acid, eicosanoid, prostaglandin, leukotriene, thromboxane, N-acyl ethanolamine), glycerolipid (e.g., mono-, di-, tri-substituted glycerols), glycerophospholipid (e.g., phosphatidylcholine, phosphatidylinositol, phosphatidylethanolamine, phosphatidylserine), sphingolipid (e.g., sphingosine, ceramide), sterol lipid (e.g., steroid, cholesterol), prenol lipid, saccharolipid, or a polyketide, oil, wax, cholesterol, sterol, fat-soluble vitamin, monoglyceride, diglyceride, triglyceride, or a phospholipid.

In some embodiments, the heterologous moiety is attached via non-covalent or covalent bonding to the peptide or peptide analog of the present disclosure. In certain aspects, the heterologous moiety is attached to the peptide or peptide analog of the present disclosure via a linker. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other. The peptide or peptide analog in some embodiments is linked to conjugate moieties via direct covalent linkage by reacting targeted amino acid residues of the analog with an organic derivatizing agent that is capable of reacting with selected side chains or the N- or C-terminal residues of these targeted amino acids. Reactive groups on the analog or conjugate moiety include, e.g., an aldehyde, amino, ester, thiol, $\alpha$-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the analog indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier. Cysteinyl residues are most commonly reacted with $\alpha$-haloacetates (and corresponding amines), such as chloroacetic acid, chloroacetamide to give carboxymethyl or carboxyamidomethyl derivatives. Cysteinyl residues also may be derivatized by reaction with bromotrifluoroacetone, alpha-bromo-3-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues may be derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino-terminal residues may be reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Carboxyl side groups (aspartyl or glutamyl) may be selectively modified by reaction with carbodiimides (R—N=C=N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues may be converted to asparaginyl and glutaminyl residues by reaction with ammonium ions. Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group. Another type of covalent modification involves chemically or enzymatically coupling glycosides to the peptide or peptide analog. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981). In some embodiments, the peptide or peptide analog is conjugated to a heterologous moiety via covalent linkage between a side chain of an amino acid of the peptides and the heterologous moiety. In some aspects, the amino acid covalently linked to a heterologous moiety (e.g., the amino acid comprising a heterologous moiety) is a Cys, Lys, Orn, homo-Cys, or Ac-Phe, and the side chain of the amino acid is covalently bonded to a heterologous moiety. In some embodiments, the conjugate comprises a linker that joins the peptide or peptide analog to the heterologous moiety. In some aspects, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms may be all carbon atoms. In some embodiments, the chain atoms in the backbone of the linker may be selected from the group consisting of C, O, N, and S. Chain atoms and linkers may be selected according to their expected solubility (hydrophilicity) so as to provide a more soluble conjugate. In some embodiments, the linker provides a functional group that is subject to cleavage by an enzyme or other catalyst or hydrolytic conditions found in the target tissue or organ or cell. In some embodiments, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers may be from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

In exemplary embodiments, the peptide or peptide analog is conjugated to a non-naturally occurring analog of humanin. In exemplary aspects, the peptide or peptide analog is conjugated at the N- or C-terminus to a humanin analog, HNG17, which is a 17-mer truncated analog of humanin with a S→G substitution. In exemplary aspects, the peptide or peptide analog is conjugated at the N- or C-terminus to a humanin analog, HNG, which is a 24-mer truncated analog of humanin with a S→G substitution. Conjugates comprising the peptide or peptide analog linked to a humanin analog are provided by the present disclosure as SEQ ID NOs: 98-102.

In some embodiments, the peptides or peptide analogs may be conjugated, e.g., fused to an immunoglobulin or portion thereof (e.g., variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC). For example, according to some definitions the human IgG heavy chain Fc region stretches from Cys226 to the C-terminus of the heavy chain. The "hinge region" generally extends from Glu216 to Pro230 of human IgG1 (hinge regions of other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In related embodiments, the Fc region may comprise one or more native or modified constant regions from an immunoglobulin heavy chain, other than CH1, for example, the CH2 and CH3 regions of IgG and IgA, or the CH3 and CH4 regions of IgE. Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain. Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J Immunol. 175:6694-701, 2005). Amino acid residues involved in IgE receptor binding are described in Sayers et al. (J Biol Chem. 279(34):35320-5, 2004). Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety. In certain embodiments, a peptide or peptide analog described herein is inserted into a loop region within the immunoglobulin molecule. In other embodiments, a peptide or peptide analog described herein replaces one or more amino acids of a loop region within the immunoglobulin molecule.

The peptides or peptide analogs described herein can be further modified to improve its solubility and stability in aqueous solutions at physiological pH, while retaining the biological activity. Hydrophilic moieties such as PEG groups can be attached to the analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water-soluble polymer to one or more proteins include without limitation sulfone, maleimide, sulfhydryl, thiol, triflate, tresylate, azidirine, oxirane, 5-pyridyl, and alpha-halogenated acyl group (e.g., alpha-iodo acetic acid, alpha-bromoacetic acid, alpha-chloroacetic acid). If attached to the analog by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995). In specific aspects, an amino acid residue of the peptides or peptide analogs having a thiol is modified with a hydrophilic moiety such as PEG. In some embodiments, the thiol is modified with maleimide-activated PEG in a Michael addition reaction to result in a PEGylated analog comprising a thioether linkage. In some embodiments, the thiol is modified with a haloacetyl-activated PEG in a nucleophilic substitution reaction to result in a PEGylated analog comprising a thioether linkage. Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly (.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by al-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. Resulting preparations of conjugates may be essentially monodisperse or polydisperse, and may have about 0.5, 0.7, 1, 1.2, 1.5 or 2 polymer moieties per analog.

In some embodiments, the peptide or peptide analog is conjugated to a hydrophilic moiety via covalent linkage between a side chain of an amino acid of the peptide or peptide analog and the hydrophilic moiety. In some embodiments, the peptide or peptide analog is conjugated to a hydrophilic moiety via the side chain of an amino acid, a position within a C-terminal extension, or the C-terminal amino acid, or a combination of these positions. In some aspects, the amino acid covalently linked to a hydrophilic moiety (e.g., the amino acid comprising a hydrophilic moiety) is a Cys, Lys, Orn, homo-Cys, or Ac-Phe, and the side chain of the amino acid is covalently bonded to a hydrophilic moiety (e.g., PEG). In some embodiments, the conjugate of the present disclosure comprises the peptide or peptide analog fused to an accessory analog which is capable of forming an extended conformation similar to chemical PEG (e.g., a recombinant PEG (rPEG) molecule), such as those described in International Patent Application Publication No. WO2009/023270 and U.S. Patent Application Publication No. US20080286808. The rPEG molecule in some aspects is a polypeptide comprising one or more of glycine, serine, glutamic acid, aspartic acid, alanine, or proline. In some aspects, the rPEG is a homopolymer, e.g., polyglycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the peptide or peptide analog. In some aspects, the rPEG comprises a net positive or net negative charge. The rPEG in some aspects lacks secondary structure. In some embodiments, the rPEG is greater than or equal to 10 amino acids in length and in some embodiments is about 40 to about 50 amino acids in length. The accessory peptide in some aspects is fused to the N- or C-terminus of the peptide or peptide analog of the present disclosure through a peptide bond or a proteinase cleavage site, or is inserted into the loops of the peptide or peptide analog of the present disclosure. The rPEG in some aspects comprises an affinity tag or is linked to a PEG that is greater than 5 kDa. In some embodiments, the rPEG confers the peptide or peptide analog of the present disclosure with an increased hydrodynamic radius, serum half-life, protease resistance, or solubility and in some aspects confers the analog with decreased immunogenicity.

The peptides or peptide analogs comprising a sequence as set forth in Table 1 (SEQ ID NO: 3-293 and 354-377), optionally with any of the conjugations described herein are contemplated as an embodiment.

The present disclosure further provides multimers or dimers of the peptides or peptide analogs disclosed herein, including homo- or hetero-multimers or homo- or heterodimers. Two or more of the peptides or peptide analogs can be linked together using standard linking agents and procedures known to those skilled in the art. For example, dimers can be formed between two peptides or peptide analogs through the use of bifunctional thiol crosslinkers and bifunctional amine crosslinkers, particularly for the analogs that have been substituted with cysteine, lysine ornithine, homocysteine or acetyl phenylalanine residues. The dimer can be a homodimer or alternatively can be a heterodimer. In certain embodiments, the linker connecting the two (or more) peptides or peptide analogs is PEG, e.g., a 5 kDa PEG, 20 kDa PEG. In some embodiments, the linker is a disulfide bond. For example, each monomer of the dimer may comprise a Cys residue (e.g., a terminal or internally positioned Cys) and the sulfur atom of each Cys residue participates in the formation of the disulfide bond. In some aspects, the monomers may be connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer may be attached together in a "tail-to-tail" orientation in which the C-terminal amino acids of each monomer may be attached together.

According to some embodiments, conjugates comprising any of the peptides or peptide analogs described herein are conjugated to a heterologous moiety for extending half-life or increasing cell penetration. For example, the half-life extending moiety may be a peptide or protein and the conjugate is a fusion protein or chimeric polypeptide. Alternatively, the half-life extending moiety may be a polymer, e.g., a polyethylene glycol. The present disclosures furthermore provide dimers and multimers comprising any of the peptides and analogs described herein.

Any heterologous moiety known in the art to facilitate actively or passively or enhance permeability of the peptides into cells may be used for conjugation with the peptide core. Non-limitative examples include: hydrophobic moieties such as fatty acids, steroids and bulky aromatic or aliphatic compounds; moieties which may have cell-membrane receptors or carriers, such as steroids, vitamins and sugars, natural and non-natural amino acids and transporter peptides. According to a preferred embodiment, the hydrophobic moiety is a lipid moiety or an amino acid moiety. The permeability-enhancing moiety may be connected to any position in the peptide moiety, directly or through a spacer or linker, preferably to the amino terminus of the peptide moiety. The hydrophobic moiety may preferably comprise a lipid moiety or an amino acid moiety. According to a specific embodiment the hydrophobic moiety is selected from the group consisting of: phospholipids, steroids, sphingosines, ceramides, octyl-glycine, 2-cyclohexylalanine, benzolylphenylalanine, propionoyl ($C_3$); butanoyl ($C_4$); pentanoyl ($C_5$); caproyl ($C_6$); heptanoyl ($C_7$); capryloyl ($C_8$); nonanoyl ($C_9$); capryl ($C_{10}$); undecanoyl (Cn); lauroyl ($C_{12}$); tridecanoyl ($C_{13}$); myristoyl ($C_{14}$); pentadecanoyl ($C_{15}$); palmitoyl ($C_{16}$); phtanoyl (($CH_3)_4$); heptadecanoyl ($C_{16}$); stearoyl ($C_{18}$); nonadecanoyl ($C_{19}$); arachidoyl ($C_{20}$); heniecosanoyl ($C_{21}$); behenoyl ($C_{22}$); trucisanoyl ($C_{23}$); and lignoceroyl ($C_{24}$); wherein said hydrophobic moiety is attached to said chimeric polypeptide with amide bonds, sulfhydryls, amines, alcohols, phenolic groups, or carbon-carbon bonds. Other examples of lipidic moieties which may be used include: Lipofectamine, Transfectace, Transfectam, Cytofectin, DMRIE, DLRIE, GAP-DLRIE, DOTAP, DOPE, DMEAP, DODMP, DOPC, DDAB, DOSPA, EDLPC, EDMPC, DPH, TMADPH, CTAB, lysyl-PE, DC-Cho, -alanyl cholesterol; DCGS, DPPES, DCPE, DMAP, DMPE, DOGS, DOHME, DPEPC, Pluronic, Tween, BRIJ, plasmalogen, phosphatidylethanolamine, phosphatidylcholine, glycerol-3-ethylphosphatidylcholine, dimethyl ammonium propane, trimethyl ammonium propane, diethylammonium propane, triethylammonium propane, dimethyldioctadecylammonium bromide, a sphingolipid, sphingomyelin, a lysolipid, a glycolipid, a sulfatide, a glycosphingolipid, cholesterol, cholesterol ester, cholesterol salt, oil, N-succinyldioleoylphosphatidylethanolamine, 1,2-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine, palmitoylhomocystiene, N,N'-Bis (dodecyaminocarbonylmethylene)-N,N'-bis((—N,N,N-trimethylammoniumethylami nocarbonylmethylene)ethylenediamine tetraiodide; N,N''-Bis(hexadecylaminocarbonylmethylene)-N,N',N''-tris ((—N,N,N-trimethylammonium-ethylaminocarbonylmethylenediethylenetri amine hexaiodide; N,N'-Bis(dodecylaminocarbonylmethylene)-N,N''-bis((—N,N,N-trimethylammonium ethylaminocarbonylmethylene) cyclohexylene-1,4-diamine tetraiodide; 1,7,7-tetra-((—N,N, N,N-tetramethylammoniumethylaminocarbonylmethylene)-3-hexadecylarninocarbonyl-methylene-1,3,7-triaazaheptane heptaiodide; N,N,N',N'-tetra((—N,N,N-trimethylammonium-ethylaminocarbonylmethylene)-N'-(1,2-dioleoylglycero-3-phosphoethanolamino carbonylmethylene) diethylenetriamine tetraiodide; dioleoylphosphatidylethanolamine, a fatty acid, a lysolipid, phosphatidylcholine, phosphatidylethanolamine, phosphatidylserine, phosphatidylglycerol, phosphatidylinositol, a sphingolipid, a glycolipid, a glucolipid, a sulfatide, a glycosphingolipid, phosphatidic acid, palmitic acid, stearic acid, arachidonic acid, oleic acid, a lipid bearing a polymer, a lipid bearing a sulfonated saccharide, cholesterol, tocopherol hemisuccinate, a lipid with an ether-linked fatty acid, a lipid with an ester-linked fatty acid, a polymerized lipid, diacetyl phosphate, stearylamine, cardiolipin, a phospholipid with a fatty acid of 6-8 carbons in length, a phospholipid with asymmetric acyl chains, 6-(5-cholesten-3b-yloxy)-1-thio-b-D-galactopyranoside, digalactosyldiglyceride, 6-(5-cholesten-3b-yloxy)hexyl-6-amino-6-deoxy-1-thio-b-D-galactopyranoside, 6-(5-cholesten-3b-yloxy)hexyl-6-amino-6-deoxyl-1-thio-a-D-mannopyranoside, 12-(((7'-diethylamino-coumarin-3-yl)carbonyl) methylamino)-octadecanoic acid; N-[12-(((7'-diethylaminocoumarin-3-yl)carbonyl)methyl-amino) octadecanoyl]-2-aminopalmitic acid; cholesteryl)4'-trimethyl-ammonio)butanoate; N-succinyldioleoyl-phosphatidylethanolamine; 1,2-dioleoyl-sn-glycerol; 1,2-dipalmitoyl-3-succinyl-glycerol; 1,3-dipalmitoyl-2-succinylglycerol, 1-hexadecyl-2-palmitoylglycero-phosphoethanolamine, and palmitoylhomocysteine.

The peptides or peptide analogs disclosed herein may be conjugated to one or more heterologous moieties that cause the conjugate to function as a prodrug. For example, the N-amino acid related moieties described in U.S. Pat. No. 8,969,288 and US Patent Publication 2016/0058881 can be conjugated to the peptides or peptide analogs disclosed herein and such conjugates are included in this disclosure.

According to some embodiments the peptides or peptide analogs may be attached (either covalently or non-covalently) to a penetrating agent. As used herein the phrase "penetrating agent" refers to an agent which enhances translocation of any of the attached peptide across a cell membrane. Typically, peptide based penetrating agents have an amino acid composition containing either a high relative abundance of positively charged amino acids such as lysine or arginine, or have sequences that contain an alternating pattern of polar/charged amino acids and non-polar, hydrophobic amino acids. By way of a non-limiting example, cell penetrating peptide (CPP) sequences may be used in order to enhance intracellular penetration. CPPs may include short and long versions of the protein transduction domain (PTD) of HIV TAT protein, such as for example, YARAAARQARA (SEQ ID NO: 324), YGRKKRR (SEQ ID NO: 325), YGRKKRRQRRR (SEQ ID NO: 326), or RRQRR (SEQ ID NO: 327). However, the disclosure is not so limited, and any suitable penetrating agent may be used, as known by those of skill in the art. Another method of enhancing cell penetration is via N-terminal myristoilation. In this protein modification, a myristoyl group (derived from myristic acid) is covalently attached via an amide bond to the alpha-amino group of an N-terminal amino acid of the peptide or peptide analog.

According to some embodiments the peptide or peptide analog is modified to include a duration enhancing moiety. The duration enhancing moiety can be a water soluble polymer, or a long chain aliphatic group. In some embodiments, a plurality of duration enhancing moieties may be attached to the peptide or peptide analog, in which case each linker to each duration enhancing moiety is independently selected from the linkers described herein.

According to some embodiments the amino terminus of the peptide or peptide analog is modified, e.g. acylated. According to additional embodiments the carboxy terminus is modified, e.g., it may be acylated, amidated, reduced or esterified. In accordance with some embodiments, the peptide or peptide analog comprises an acylated amino acid (e.g., a non-coded acylated amino acid (e.g., an amino acid comprising an acyl group which is non-native to a naturally-occurring amino acid)). In accordance with one embodiment, the peptide or peptide analog comprises an acyl group which is attached to the peptide or peptide analog via an ester, thioester, or amide linkage for purposes of prolonging half-life in circulation and/or delaying the onset of and/or extending the duration of action and/or improving resistance to proteases. Acylation can be carried out at any position within the peptide or peptide analog, (e.g., the amino acid at the C-terminus), provided that activity is retained, if not enhanced. The peptide in some embodiments can be acylated at the same amino acid position where a hydrophilic moiety is linked, or at a different amino acid position. The acyl group can be covalently linked directly to an amino acid of the peptide or peptide analog, or indirectly to an amino acid of the peptide via a spacer, wherein the spacer is positioned between the amino acid of the peptide and the acyl group.

In specific aspects, the peptide or peptide analog is modified to comprise an acyl group by direct acylation of an amine, hydroxyl, or thiol of a side chain of an amino acid of the peptide. In this regard, the acylated peptide can comprise the amino acid sequence of any of SEQ ID NOs: 1, 3-41, 43-76, 79-293, 310-315, 319-323 and 354-377, modified to comprise an acyl group.

In some embodiments, the peptide or peptide analog comprises a spacer between the analog and the acyl group. In some embodiments, the peptide or peptide analog is covalently bound to the spacer, which is covalently bound to the acyl group. In some embodiments, the spacer is an amino acid comprising a side chain amine, hydroxyl, or thiol, or a dipeptide or tripeptide comprising an amino acid comprising a side chain amine, hydroxyl, or thiol. The amino acid to which the spacer is attached can be any amino acid (e.g., a singly or doubly α-substituted amino acid) comprising a moiety which permits linkage to the spacer. For example, an amino acid comprising a side chain $NH_2$, —OH, or —COOH (e.g., Lys, Orn, Ser, Asp, or Glu) is suitable. In some embodiments, the spacer is an amino acid comprising a side chain amine, hydroxyl, or thiol, or a dipeptide or tripeptide comprising an amino acid comprising a side chain amine, hydroxyl, or thiol. When acylation occurs through an amine group of a spacer, the acylation can occur through the alpha amine of the amino acid or a side chain amine. In the instance in which the alpha amine is acylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp, Glu, homoglutamic acid, homocysteic acid, cysteic acid, gamma-glutamic acid. In the instance in which the side chain amine of the amino acid of the spacer is acylated, the amino acid of the spacer is an amino acid comprising a side chain amine. In this instance, it is possible for both the alpha amine and the side chain amine of the amino acid of the spacer to be acylated, such that the peptide or peptide analog is diacylated. Embodiments include such diacylated molecules. When acylation occurs through a hydroxyl group of a spacer, the amino acid or one of the amino acids of the dipeptide or tripeptide can be Ser. When acylation occurs through a thiol group of a spacer, the amino acid or one of the amino acids of the dipeptide or tripeptide can be Cys. In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate.

In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). In some embodiments, the spacer is a hydrophobic bifunctional spacer. Hydrophobic bifunctional spacers are known in the art. See, e.g., *Bioconjugate Techniques*, G. T. Hermanson (Academic Press, San Diego, Calif., 1996), which is incorporated by reference in its entirety. In certain embodiments, the hydrophobic bifunctional spacer comprises two or more reactive groups, e.g., an amine, a hydroxyl, a thiol, and a carboxyl group or any combinations thereof. In certain embodiments, the hydrophobic bifunctional spacer comprises a hydroxyl group and a carboxylate. In other embodiments, the hydrophobic bifunctional spacer comprises an amine group and a carboxylate. In other embodiments, the hydrophobic bifunctional spacer comprises a thiol group and a carboxylate. Suitable hydrophobic bifunctional spacers comprising a carboxylate and a hydroxyl group or a thiol group are known in the art and include, for example, 8-hydroxyoctanoic acid and 8-mercaptooctanoic acid. In some embodiments, the bifunctional spacer is not a dicarboxylic acid comprising an unbranched, methylene of 1-7 carbon atoms between the carboxylate groups. In some embodiments, the bifunctional spacer is a dicarboxylic acid comprising an unbranched, methylene of 1-7 carbon atoms between the carboxylate groups. The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms) in length. In more specific embodiments, the spacer is about 3 to 10 atoms (e.g., 6 to 10 atoms) in length and the acyl group is a $C_{12}$ to $C_{18}$ fatty acyl group, e.g., $C_{14}$ fatty acyl group, $C_{16}$ fatty acyl group, such that the total length of the spacer and acyl group is 14 to 28 atoms, e.g., about 14, 15, 16, 17, 18, 19, 20, 21, 22, 23, 24, 25, 26, 27, or 28 atoms. In some embodiments, the length of the spacer and acyl group is 17 to 28 (e.g., 19 to 26, 19 to 21) atoms. In accordance with certain foregoing embodiments, the bifunctional spacer can be a synthetic or naturally occurring amino acid (including, but not limited to, any of those described herein) comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. Each amino acid of the dipeptide or tripeptide spacer can be the same as or different from the other amino acid(s) of the dipeptide or tripeptide and can be independently selected from the group consisting of: naturally-occurring or coded and/or non-coded or non-naturally occurring amino acids, including, for example, any of the D or L isomers of the naturally-occurring amino acids (Ala, Cys, Asp, Glu, Phe, Gly, His, Ile, Lys, Leu, Met, Asn, Pro, Arg, Ser, Thr, Val, Trp, Tyr), or any D or L isomers of the non-naturally occurring or non-coded amino acids selected from the group consisting of: β-alanine (β-Ala), N-α-methyl-alanine (Me-Ala), aminobutyric acid (Abu), γ-aminobutyric acid (7-Abu), aminohexanoic acid (ε-Ahx), aminoisobutyric acid (Aib), aminomethylpyrrole carboxylic acid, aminopiperidinecarboxylic acid, aminoserine (Ams), aminotetrahydropyran-4-carboxylic acid, arginine N-methoxy-N-methyl amide, β-aspartic acid (β-Asp), azetidine carboxylic acid, 3-(2-benzothiazolyl)alanine, α-tert-butylglycine, 2-amino-5-ureido-n-valeric acid (citrulline, Cit), β-Cyclohexylalanine (Cha), acetamidomethyl-cysteine, diaminobutanoic acid (Dab), diaminopropionic acid (Dpr), dihydroxyphenylalanine (DOPA), dimethylthiazolidine (DMTA), γ-Glutamic acid (γ-Glu), homoserine (Hse), hydroxyproline (Hyp), isoleucine N-methoxy-N-methyl amide, methyl-isoleucine (MeIle), isonipecotic acid (Isn), methyl-leucine (MeLeu), methyl-lysine, dimethyl-lysine, trimethyl-lysine, methanoproline, methionine-sulfoxide (Met(O)), methionine-sulfone (Met(O$_2$)), norleucine (Nle), methyl-norleucine (Me-Nle), norvaline (Nva), ornithine (Orn), para-aminobenzoic acid (PABA), penicillamine (Pen), methylphenylalanine (MePhe), 4-Chlorophenylalanine (Phe (4-Cl)), 4-fluorophenylalanine (Phe(4-F)), 4-nitrophenylalanine (Phe(4-NO$_2$)), 4-cyanophenylalanine ((Phe(4-CN)), phenylglycine (Phg), piperidinylalanine, piperidinylglycine, 3,4-dehydroproline, pyrrolidinylalanine, sarcosine (Sar), selenocysteine (Sec), O-Benzyl-phosphoserine, 4-amino-3-hydroxy-6-methylheptanoic acid (Sta), 4-amino-5-cyclohexyl-3-hydroxypentanoic acid (ACHPA), 4-amino-3-hydroxy-5-phenylpentanoic acid (AHPPA), 1,2,3,4,-tetrahydro-isoquinoline-3-carboxylic acid (Tic), tetrahydropyranglycine, thienylalanine (Thi), O-benzyl-phosphotyrosine, O-Phosphotyrosine, methoxytyrosine, ethoxytyrosine, O-(bis-dimethylamino-phosphono)-tyrosine, tyrosine sulfate tetrabutylamine, methyl-valine (Me-Val), and alkylated 3-mercaptopropionic acid. In some embodiments, the spacer comprises an overall negative charge, e.g., comprises one or two negative-charged amino acids. In some embodiments, the dipeptide is not any of the dipeptides of general structure A-B, wherein A is selected from the group consisting of Gly, Gln, Ala, Arg, Asp, Asn, Ile, Leu, Val, Phe, and Pro, wherein B is selected from the group consisting of Lys, His, Trp. In some embodiments, the dipeptide spacer is selected from the group consisting of: Ala-Ala, β-Ala-β-Ala, Leu-Leu, Pro-Pro, γ-aminobutyric acid-γ-aminobutyric acid, Glu-Glu, and γ-Glu-γ-Glu.

Suitable methods of peptide acylation via amines, hydroxyls, and thiols are known in the art. See, for example, Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); Bioconjugate Chem. "Chemical Modifications of Proteins: History and Applications" pages 1, 2-12 (1990); Hashimoto et al., Pharmaceutical Res. "Synthesis of Palmitoyl Derivatives of Insulin and their Biological Activity" Vol. 6, No: 2 pp. 171-176 (1989). The acyl group of the acylated amino acid can be of any size, e.g., any length carbon chain, and can be linear or branched. In some specific embodiments, the acyl group is a $C_4$ to $C_{30}$ fatty acid. For example, the acyl group can be any of a $C_4$ fatty acid, $C_6$ fatty acid, $C_8$ fatty acid, $C_{10}$ fatty acid, $C_{12}$ fatty acid, $C_{14}$ fatty acid, $C_{16}$ fatty acid, $C_{18}$ fatty acid, $C_{20}$ fatty acid, $C_{22}$ fatty acid, $C_{24}$ fatty acid, $C_{26}$ fatty acid, $C_{28}$ fatty acid, or a $C_{30}$ fatty acid. In some embodiments, the acyl group is a $C_8$ to $C_{20}$ fatty acid, e.g., a $C_{14}$ fatty acid or a $C_{16}$ fatty acid. In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid. In some embodiments, the peptide or peptide analog comprises an acylated amino acid by acylation of a long chain alkane on the peptide or peptide analog. In specific aspects, the long chain alkane comprises an amine, hydroxyl, or thiol group (e.g., octadecylamine, tetradecanol, and hexadecanethiol) which reacts with a carboxyl group, or activated form thereof, of the peptide or peptide analog. The carboxyl group, or activated form thereof, of the peptide or peptide analog can be part of a side chain of an amino acid (e.g., glutamic acid, aspartic acid) of the peptide or can be part of the analog backbone. In certain embodiments, the peptide or peptide analog is modified to comprise an acyl group by acylation of the long chain alkane by a spacer which is attached to the peptide or peptide analog. In specific aspects, the long chain alkane comprises an amine, hydroxyl, or thiol group which reacts with a carboxyl group, or activated form thereof, of the spacer. Suitable spacers comprising a carboxyl group, or activated form thereof, are described herein and include, for example, bifunctional spacers, e.g., amino acids, dipeptides, tripeptides, hydrophilic bifunctional spacers and hydrophobic bifunctional spacers.

As used herein, the term "activated form" of a carboxyl group refers to a carboxyl group with the general formula $R(C=O)X^a$, wherein $X^a$ is a leaving group and R is the peptide or the spacer. For example, activated forms of a carboxyl groups may include, but are not limited to, acyl chlorides, anhydrides, and esters. In some embodiments, the activated carboxyl group is an ester with a N-hydroxysuccinimide ester (NHS) leaving group.

With regard to these aspects, in which a long chain alkane is acylated by the peptide or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane.

Also, in some embodiments, an amine, hydroxyl, or thiol group of the peptide or peptide analog is acylated with a cholesterol acid. In a specific embodiment, the peptide or peptide analog is linked to the cholesterol acid through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety.

The peptides or peptide analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. In this regard, the acylated peptide can of any of SEQ ID NOs: 1, 3-41, 43-76, and 79-293, 310-315, 319-323 and 354-377, including any of the modifications described herein, in which at least one of the amino acids comprises an acyl group and at least one of the amino acids is covalently bonded to a hydrophilic moiety (e.g., PEG). In some embodiments, the acyl group is attached via a spacer comprising Cys, Lys, Orn, homo-Cys, or Ac-Phe, and the hydrophilic moiety is incorporated at a Cys residue.

Alternatively, the peptides or peptide analogs can comprise a spacer, wherein the spacer is both acylated and modified to comprise the hydrophilic moiety. Nonlimiting examples of suitable spacers include a spacer comprising one or more amino acids selected from the group consisting of Cys, Lys, Orn, homo-Cys, and Ac-Phe.

In accordance with some embodiments, the peptide or peptide analog comprises an alkylated amino acid (e.g., a non-coded alkylated amino acid (e.g., an amino acid comprising an alkyl group which is non-native to a naturally-occurring amino acid)). Alkylation can be carried out at any positions within the peptides or peptide analogs, including any of the positions described herein as a site for acylation, including but not limited to, any of amino acid positions, at a position within a C-terminal extension, or at the C-terminus, provided that the biological activity is retained. The alkyl group can be covalently linked directly to an amino acid of the peptides or peptide analogs, or indirectly to an amino acid of the peptides or peptide analogs via a spacer, wherein the spacer is positioned between the amino acid of the peptides and the alkyl group. The peptides or peptide analogs may be alkylated at the same amino acid position where a hydrophilic moiety is linked, or at a different amino acid position. In specific aspects, the peptides or peptide analogs may be modified to comprise an alkyl group by direct alkylation of an amine, hydroxyl, or thiol of a side chain of an amino acid of the peptides. In this regard, the alkylated peptides can comprise an amino acid sequence with at least one of the amino acids modified to any amino acid comprising a side chain amine, hydroxyl, or thiol. In yet other embodiments, the amino acid comprising a side chain amine, hydroxyl, or thiol is a disubstituted amino acid. In some embodiments, the alkylated peptide comprises a spacer between the peptide and the alkyl group. In some embodiments, the peptide or peptide analog is covalently bound to the spacer, which is covalently bound to the alkyl group. In some exemplary embodiments, the peptide is modified to comprise an alkyl group by alkylation of an amine, hydroxyl, or thiol of a spacer, which spacer is attached to a side chain of an amino acid. The amino acid to which the spacer is attached can be any amino acid comprising a moiety which permits linkage to the spacer. For example, an amino acid comprising a side chain $NH_2$, —OH, or —COOH (e.g., Lys, Orn, Ser, Asp, or Glu) is suitable. In some embodiments, the spacer is an amino acid comprising a side chain amine, hydroxyl, or thiol or a dipeptide or tripeptide comprising an amino acid comprising a side chain amine, hydroxyl, or thiol. When alkylation occurs through an amine group of a spacer, the alkylation can occur through the alpha amine of an amino acid or a side chain amine. In the instance in which the alpha amine is alkylated, the amino acid of the spacer can be any amino acid. For example, the amino acid of the spacer can be a hydrophobic amino acid, e.g., Gly, Ala, Val, Leu, Ile, Trp, Met, Phe, Tyr, 6-amino hexanoic acid, 5-aminovaleric acid, 7-aminoheptanoic acid, and 8-aminooctanoic acid. Alternatively, the amino acid of the spacer can be an acidic residue, e.g., Asp and Glu, provided that the alkylation occurs on the alpha amine of the acidic residue. In the instance in which the side chain amine of the amino acid of the spacer is alkylated, the amino acid of the spacer is an amino acid comprising a side chain amine, e.g., an amino acid of Formula I (e.g., Lys or Orn). In this instance, it is possible for both the alpha amine and the side chain amine of the amino acid of the spacer to be alkylated, such that the peptide or peptide analog is dialkylated. Embodiments include such dialkylated molecules. When alkylation occurs through a hydroxyl group of a spacer, the amino acid can be Ser. When alkylation occurs through a thiol group of spacer, the amino acid can be Cys. In some embodiments, the spacer is a hydrophilic bifunctional spacer. In certain embodiments, the hydrophilic bifunctional spacer comprises two or more reactive groups, e.g., an amine, a hydroxyl, a thiol, and a carboxyl group or any combinations thereof. In certain embodiments, the hydrophilic bifunctional spacer comprises a hydroxyl group and a carboxylate. In other embodiments, the hydrophilic bifunctional spacer comprises an amine group and a carboxylate. In other embodiments, the hydrophilic bifunctional spacer comprises a thiol group and a carboxylate. In a specific embodiment, the spacer comprises an amino poly(alkyloxy)carboxylate. In this regard, the spacer can comprise, for example, $NH_2(CH_2CH_2O)_n(CH_2)_mCOOH$, wherein m is any integer from 1 to 6 and n is any integer from 2 to 12, such as, e.g., 8-amino-3,6-dioxaoctanoic acid, which is commercially available from Peptides International, Inc. (Louisville, Ky.). Suitable hydrophobic bifunctional spacers comprising a carboxylate and a hydroxyl group or a thiol group are known in the art and include, for example, 8-hydroxyoctanoic acid and 8-mercaptooctanoic acid. The spacer (e.g., amino acid, dipeptide, tripeptide, hydrophilic bifunctional spacer, or hydrophobic bifunctional spacer) in specific embodiments is 3 to 10 atoms (e.g., 6 to 10 atoms, (e.g., 6, 7, 8, 9, or 10 atoms)) in length. In more specific embodiments, the spacer is about 3 to 10 atoms (e.g., 6 to 10 atoms) in length and the alkyl is a $C_{12}$ to $C_{18}$ alkyl group, e.g., $C_{14}$ alkyl group, $C_{16}$ alkyl group, such that the total length of the spacer and alkyl group is 14 to 28 atoms, e.g., about 14, 15, 16, 17, 18, 19, 20, 21, 22, 23, 24, 25, 26, 27, or 28 atoms. In some embodiments, the length of the spacer and alkyl is 17 to 28 (e.g., 19 to 26, 19 to 21) atoms. In accordance with certain foregoing embodiments, the bifunctional spacer can be a synthetic or non-naturally occurring or non-coded amino acid comprising an amino acid backbone that is 3 to 10 atoms in length (e.g., 6-amino hexanoic acid, 5-aminovaleric acid, 7-aminoheptanoic acid, and 8-aminooctanoic acid). Alternatively, the spacer can be a dipeptide or tripeptide spacer having a peptide backbone that is 3 to 10 atoms (e.g., 6 to 10 atoms) in length. The dipeptide or tripeptide spacer can be composed of naturally-occurring or coded and/or non-coded or non-naturally occurring amino acids, including, for example, any of the amino acids taught herein. In some embodiments, the spacer comprises an overall negative charge, e.g., comprises one or two negative-charged amino acids. In some embodiments, the dipeptide spacer is selected from the group consisting of: Ala-Ala, 3-Ala-β-Ala, Leu-Leu, Pro-Pro, γ-aminobutyric acid-γ-aminobutyric acid, and γ-Glu-γ-Glu. Suitable methods of peptide alkylation via amines, hydroxyls, and thiols are known in the art. For example, a Williamson ether synthesis can be used to form an ether linkage between a hydroxyl group of the peptides and the alkyl group. Also, a nucleophilic substitution reaction of the peptide or peptide analog with an alkyl halide can result in any of an ether, thioether, or amino linkage. The alkyl group of the alkylated peptides or peptide analogs can be of any size, e.g., any length carbon chain, and can be linear or branched. In some embodiments, the alkyl group is a $C_4$ to $C_{30}$ alkyl. For example, the alkyl group can be any of a $C_4$ alkyl, $C_6$ alkyl, $C_8$ alkyl, $C_{10}$ alkyl, $C_{12}$ alkyl, $C_{14}$ alkyl, $C_{16}$ alkyl, $C_{18}$ alkyl, $C_{20}$ alkyl, $C_{22}$ alkyl, $C_{24}$ alkyl, $C_{26}$ alkyl, $C_{28}$ alkyl, or a $C_{30}$ alkyl. In some embodiments, the alkyl group is a $C_8$ to $C_{20}$ alkyl, e.g., a $C_{14}$ alkyl or a $C_{16}$ alkyl. In some embodiments of the disclosure, the peptide or peptide analog comprises an alkylated amino acid by reacting a nucleophilic, long chain alkane with the peptide or peptide analog, wherein the peptide or peptide analog comprises a leaving group suitable for nucleophilic substitution. In specific aspects, the nucleophilic group of the long chain alkane comprises an amine, hydroxyl, or thiol group (e.g., octadecylamine, tetradecanol, and hexadecanethiol). The leaving group of the peptide or peptide analog can be part of a side chain of an amino acid or can be part of the peptide backbone. Suitable leaving groups include, for example, N-hydroxysuccinimide, halogens, and sulfonate esters. In certain embodiments, the peptide or peptide analog is modified to comprise an alkyl group by reacting the nucleophilic, long chain alkane with a spacer which is attached to the peptide or peptide analog, wherein the spacer comprises the leaving group. In specific aspects, the long chain alkane comprises an amine, hydroxyl, or thiol group. In certain embodiments, the spacer comprising the leaving group can be any spacer discussed herein, e.g., amino acids, dipeptides, tripeptides, hydrophilic bifunctional spacers and hydrophobic bifunctional spacers further comprising a suitable leaving group. With regard to these aspects of the disclosure, in which a long chain alkane is alkylated by the peptides or the spacer, the long chain alkane may be of any size and can comprise any length of carbon chain. The long chain alkane can be linear or branched. In certain aspects, the long chain alkane is a $C_4$ to $C_{30}$ alkane. For example, the long chain alkane can be any of a $C_4$ alkane, $C_6$ alkane, $C_8$ alkane, $C_{10}$ alkane, $C_{12}$ alkane, $C_{14}$ alkane, $C_{16}$ alkane, $C_{18}$ alkane, $C_{20}$ alkane, $C_{22}$ alkane, $C_{24}$ alkane, $C_{26}$ alkane, $C_{28}$ alkane, or a $C_{30}$ alkane. In some embodiments, the long chain alkane comprises a $C_8$ to $C_{20}$ alkane, e.g., a $C_{14}$ alkane, $C_{16}$ alkane, or a $C_{18}$ alkane. Also, in some embodiments, alkylation can occur between the peptides and a cholesterol moiety. For example, the hydroxyl group of cholesterol can displace a leaving group on the long chain alkane to form a cholesterol-peptides product. The alkylated peptides described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein. Alternatively, the alkylated peptides can comprise a spacer, wherein the spacer is both alkylated and modified to comprise the hydrophilic moiety. Nonlimiting examples of suitable spacers include a spacer comprising one or more amino acids selected from the group consisting of Cys, Lys, Orn, homo-Cys, and Ac-Phe.

Methods of Making Peptides and Peptide Analogs

The peptides and peptide analogs disclosed herein are made in a variety of ways, including, but not limited to any of those described in Example 1. Suitable methods of de novo synthesizing peptides are described in, for example, N. Leo Benoiton, *Chemistry of Peptide Synthesis* CRC Press, Boca Raton, Fla., 2006; Merrifield, J. Am. Chem. Soc, 85, 2149 (1963); Davis et al., Biochem. Intl., 10, 394-414 (1985); Larsen et al., J. Am. Chem. Soc, 115, 6247 (1993); Smith et al., J. Peptide Protein Res., 44, 183 (1994); O'Donnell et al., J. Am. Chem. Soc, 118, 6070 (1996); Stewart and Young, Solid Phase Peptide Synthesis, Freeman (1969); Finn et al., The Proteins, 3 ed., vol. 2, pp. 105-253 (1976); Erickson et al., The Proteins, $3^{rd}$ ed., vol. 2, pp. 257-527 (1976); and Chan et al., Fmoc Solid Phase Peptide Synthesis, Oxford University Press, Oxford, United Kingdom, 2005. The disclosure contemplates synthetic peptides. Methods of making the peptides are themselves embodiments of the invention. Accordingly, the present disclosure provides a method of producing the peptides or peptide analogs. In exemplary embodiments, the method comprises (i) reacting a first amino acid with a second amino acid to form a covalent linkage between the first amino acid and the second amino acid, wherein the first amino acid or the second amino acid optionally is attached to another amino acid, and (ii) repeating the reacting step of (i), whereupon the peptide or peptide analog is produced. In exemplary aspects, the method comprises one or more steps of solid-phase synthesis. In exemplary aspects, the method comprises one or more steps described in Example 1.

Alternatively, the peptide can be expressed recombinantly by introducing a nucleic acid encoding a peptide into host cells, which may be cultured to express the peptide using standard recombinant methods. See, for instance, Sambrook et al., Molecular Cloning: A Laboratory Manual. 3rd ed., Cold Spring Harbor Press, Cold Spring Harbor, N.Y. 2001; and Ausubel et al., Current Protocols in Molecular Biology, Greene Publishing Associates and John Wiley & Sons, N.Y., 1994. Such peptides may be purified from the culture media or cell pellets.

In some embodiments, the peptides of the disclosure can be isolated. In some embodiments, the peptides of the disclosure may be purified. It is recognized that "purity" is a relative term, and not to be necessarily construed as absolute purity or absolute enrichment or absolute selection. In some aspects, the purity is at least or about 50%, is at least or about 60%, at least or about 70%, at least or about 80%, or at least or about 90% (e.g., at least or about 91%, at least or about 92%, at least or about 93%, at least or about 94%, at least or about 95%, at least or about 96%, at least or about 97%, at least or about 98%, at least or about 99% or is approximately 100%.

In some embodiments, the peptides described herein can be commercially synthesized by companies, such as Genscript (Piscataway, N.J.), New England Peptide (Gardner, Mass.), and CPC Scientific (Sunnyvale, Calif.), Peptide Technologies Corp. (Gaithersburg, Md.), and Multiple Peptide Systems (San Diego, Calif.). In this respect, the peptides can be synthetic, recombinant, isolated, and/or purified.

Nucleic Acids

Provided herein are nucleic acids comprising a nucleotide sequence encoding any of the peptides or conjugates described herein (including peptide analogs thereof). The nucleic acid can comprise any nucleotide sequence which encodes any of the peptides, or analogs thereof, or conjugates.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. In other embodiments, the nucleic acid comprises one or more insertions, deletions, inversions, and/or substitutions.

In some aspects, the nucleic acids of the present disclosure are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids in some aspects are constructed based on chemical synthesis and/or enzymatic ligation reactions using procedures known in the art. See, for example, Sambrook et al., supra; and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridme, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, N-substituted adenine, 7-methylguanine, 5-methylammomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouratil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

Expression Vector

The nucleic acids of the present disclosure in some aspects are incorporated into an expression vector. In this regard, the present disclosure provides expression vectors comprising any of the presently disclosed nucleic acids. For purposes herein, the term "expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the present disclosure are not naturally-occurring as a whole. However, parts of the vectors can be naturally-occurring. The presently disclosed expression vectors may comprise any type of nucleotides, including, but not limited to DNA and RNA, which may be single-stranded or double-stranded, synthesized or obtained in part from natural sources, and which can contain natural, non-natural or altered nucleotides. The expression vectors may comprise naturally-occurring or non-naturally-occuring internucleotide linkages, or both types of linkages. In some aspects, the altered nucleotides or non-naturally occurring internucleotide linkages do not hinder the transcription or replication of the vector.

The expression vector of the present disclosure can be any suitable expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT1O, λGT1 1, XZapII (Stratagene), λEMBL4, and λNM1 149, also can be used. Examples of plant expression vectors include pBIO1, pBI101.2, pBI101.3, pBI121 and pBIN19 (Clontech). Examples of animal expression vectors include pEUK-Cl, pMAM and pMAMneo (Clontech). In some aspects, the recombinant expression vector is a viral vector, e.g., a retroviral vector.

The expression vectors of the present disclosure can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2μ plasmid, λ, SV40, bovine papilloma virus, and the like.

In some aspects, the expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The expression vector may include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the presently disclosed expression vectors include, for instance, neomycin/G418 resistance genes, hygromycin resistance genes, histidinol resistance genes, tetracycline resistance genes, and ampicillin resistance genes.

The expression vector can comprise a native or normative promoter operably linked to the nucleotide sequence encoding the peptide, or to the nucleotide sequence which is complementary to or which hybridizes to the nucleotide sequence encoding the peptide. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The presently disclosed expression vectors may be designed for either transient expression, for stable expression, or for both. Also, the expression vectors may be made for constitutive expression or for inducible expression. Further, the expression vectors may be made to include a suicide gene. As used herein, the term "suicide gene" refers to a gene that causes the cell expressing the suicide gene to die. The suicide gene in some aspects is a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews. Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Host Cells

The present disclosure provides host cells comprising a nucleic acid or expression vector described herein. As used herein, the term "host cell" refers to any type of cell that can contain the presently disclosed expression vector. The host cell in some aspects is a eukaryotic cell, e.g., plant, animal, fungi, or algae, or can be a prokaryotic cell, e.g., bacteria or protozoa. The host cell in some aspects is a cultured cell or a primary cell, i.e., isolated directly from an organism, e.g., a human. The host cell in some aspects is an adherent cell or a suspended cell, i.e., a cell that grows in suspension. Suitable host cells are known in the art and include, for instance, DH5α E. coli cells, Chinese hamster ovarian cells, monkey VERO cells, COS cells, HEK293 cells, and the like. For purposes of amplifying or replicating the expression vector, the host cell is in some aspects is a prokaryotic cell, e.g., a DH5α cell. For purposes of producing a peptide, the host cell is in some aspects a mammalian cell, e.g., a human cell. The host cell may be of any cell type, can originate from any type of tissue, and can be of any developmental stage.

Also provided by the invention is a population of cells comprising at least one host cell described herein. The population of cells in some aspects is a heterogeneous population comprising the host cell comprising any of the nucleic acids or expression vectors described herein, in addition to at least one other cell, which does not comprise any of the nucleic acids or expression vectors. Alternatively, in some aspects, the population of cells is a substantially homogeneous population, in which the population comprises mainly of host cells (e.g., consisting essentially of) comprising the expression vector. The population in some aspects is a clonal population of cells, in which all cells of the population are clones of a single host cell comprising a expression vector, such that all cells of the population comprise the expression vector. In one embodiment of the invention, the population of cells is a clonal population comprising host cells comprising a nucleic acid or expression vector as described herein.

Pharmaceutical Compositions and Formulations

Provided herein are compositions comprising the peptide, peptide analog, conjugate, nucleic acid, expression vector, host cell or a combination thereof, and a carrier, excipient, or diluent. In exemplary aspects, the composition is a pharmaceutical composition. A "pharmaceutical composition" refers to a composition suitable for pharmaceutical use in an animal or human. A pharmaceutical composition comprises a pharmacologically and/or therapeutically effective amount of an active agent and a pharmaceutically acceptable excipient or carrier. Pharmaceutical compositions and methods for their preparation will be readily apparent to those skilled in the art. Such compositions and methods for their preparation may be found, for example, in Remington's Pharmaceutical Sciences, 19th Edition (Mack Publishing Company, 1995). The pharmaceutical compositions are generally formulated as sterile, substantially isotonic and in full compliance with all GMP regulations of the U.S. Food and Drug Administration. The term also encompasses any of the agents listed in the US Pharmacopeia for use in animals, including humans. Suitable pharmaceutical carriers and formulations are described in Remington's Pharmaceutical Sciences, 21st Ed. 2005, Mack Publishing Co, Easton. "Pharmaceutically acceptable carrier" or "pharmaceutically acceptable excipient" refers to compositions that do not produce adverse, allergic, or other untoward reactions when administered to an animal or a human. As used herein, "pharmaceutically acceptable carrier" or "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, the excipients will include isotonic agents, for example, sugars, polyalcohols such as mannitol, sorbitol, or sodium chloride in the composition. Additional examples of pharmaceutically acceptable excipients are wetting agents or minor amounts of auxiliary substances such as wetting or emulsifying agents, preservatives or buffers, which enhance the shelf life or effectiveness of the peptide.

The pharmaceutical composition in exemplary aspects comprise any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents.

In some embodiments, the foregoing component(s) may be present in the pharmaceutical composition at any concentration, such as, for example, at least A, wherein A is 0.0001% w/v, 0.001% w/v, 0.01% w/v, 0.1% w/v, 1% w/v, 2% w/v, 5% w/v, 10% w/v, 20% w/v, 30% w/v, 40% w/v, 50% w/v, 60% w/v, 70% w/v, 80% w/v, or 90% w/v. In some embodiments, the foregoing component(s) may be present in the pharmaceutical composition at any concentration, such as, for example, at most B, wherein B is 90% w/v, 80% w/v, 70% w/v, 60% w/v, 50% w/v, 40% w/v, 30% w/v, 20% w/v, 10% w/v, 5% w/v, 2% w/v, 1% w/v, 0.1% w/v, 0.001% w/v, or 0.0001%. In other embodiments, the foregoing component(s) may be present in the pharmaceutical composition at any concentration range, such as, for example from about A to about B. In some embodiments, A is 0.0001% and B is 90%.

In some embodiments, the pharmaceutical composition comprises any of the peptides or peptide analogs disclosed herein at a purity level suitable for administration to a patient. In some embodiments, the analog has a purity level of at least about 90%, preferably above about 95%, more preferably above about 99%, and a pharmaceutically acceptable diluent, carrier or excipient. In exemplary aspects, the pharmaceutical composition is sterile.

The pharmaceutical compositions may be formulated to achieve a physiologically compatible pH. In some embodiments, the pH of the pharmaceutical composition may be at least 2 or at least 3 or at least 4 or at least 5, or at least 6, or at least 7, or at least 8, depending on the formulation and route of administration. In some embodiments the pH of the pharmaceutical composition may be from 3 to 9.

In an embodiment, the peptides may be administered as their nucleotide equivalents via gene therapy methods. In one embodiment, the peptide-related polynucleotide is encoded in a plasmid or vector, which may be derived from an adeno-associated virus (AAV). The AAV may be a recombinant AAV virus and may comprise a capsid serotype such as, but not limited to, of AAV1, AAV2, AAV3, AAV4, AAV5, AAV6, AAV7, AAV8, AAV9, AAV9.47, AAV9 (hu14), AAV10, AAV11, AAV12, AAVrh8, AAVrh10, AAV-DJ, and AAV-DJ8. As a non-limiting example, the capsid of the recombinant AAV virus is AAV2. As a non-limiting example, the capsid of the recombinant AAV virus is AAVrh10. As a non-limiting example, the capsid of the recombinant AAV virus is AAV9(hu14). As a non-limiting example, the capsid of the recombinant AAV virus is AAV-DJ. As a non-limiting example, the capsid of the recombinant AAV virus is AAV9.47. As a non-limiting example, the capsid of the recombinant AAV virus is AAV-DJ8. An embodiment comprises the nucleotide equivalents of the peptide sequences of SEQ ID No: 1, 3-41, 43-76, 79-293, 310-315, 319-323 and 354-377.

A person skilled in the art may recognize that a target cell may require a specific promoter including but not limited to a promoter that is species specific, inducible, tissue-specific, or cell cycle-specific Parr et al, Nat. Med. 3:1145-9 (1997); the contents of which are herein incorporated by reference in its entirety).

As used herein, a "vector" is any molecule or moiety which transports, transduces or otherwise acts as a carrier of a heterologous molecule such as the polynucleotides of the invention. A "viral vector" is a vector which comprises one or more polynucleotide regions encoding or comprising payload molecule of interest, e.g., a transgene, a polynucleotide encoding a polypeptide or multi-polypeptide. Viral vectors of the present invention may be produced recombinantly and may be based on adeno-associated virus (AAV) parent or reference sequence. Serotypes which may be useful in the present invention include any of those arising from AAV1, AAV2, AAV3, AAV4, AAV5, AAV6, AAV7, AAV8, AAV9, AAV9.47, AAV9(hu14), AAV10, AAV11, AAV12, AAVrh8, AAVrh10, AAV-DJ, and AAV-DJ8.

In one embodiment, the serotype which may be useful in the present invention may be AAV-DJ8. The amino acid sequence of AAV-DJ8 may comprise two or more mutations in order to remove the heparin binding domain (HBD). As a non-limiting example, the AAV-DJ sequence described as SEQ ID NO: 1 in U.S. Pat. No. 7,588,772, the contents of which are herein incorporated by reference in its entirety, may comprise two mutations: (1) R587Q where arginine (R; arg) at amino acid 587 is changed to glutamine (Q; gln) and (2) R590T where arginine (R; arg) at amino acid 590 is changed to threonine (T; thr). As another non-limiting example, may comprise three mutations: (1) K406R where lysine (K; lys) at amino acid 406 is changed to arginine (R; arg), (2) R587Q where arginine (R; arg) at amino acid 587 is changed to glutamine (Q; gln) and (3) R590T where arginine (R; arg) at amino acid 590 is changed to threonine (T; thr).

AAV vectors may also comprise self-complementary AAV vectors (scAAVs). scAAV vectors contain both DNA strands which anneal together to form double stranded DNA. By skipping second strand synthesis, scAAVs allow for rapid expression in the cell.

In one embodiment, the pharmaceutical composition comprises a recombinant adeno-associated virus (AAV) vector comprising an AAV capsid and an AAV vector genome. The AAV vector genome may comprise at least one peptide related polynucleotide described herein, such as, but not limited to, SEQ ID NO 1, 3-41, 43-76, 79-293, 310-315, 319-323 and 354-377 or variants having at least 95% identity thereto. The recombinant AAV vectors in the pharmaceutical composition may have at least 70% which contain an AAV vector genome.

In one embodiment, the pharmaceutical composition comprises a recombinant adeno-associated virus (AAV) vector comprising an AAV capsid and an AAV vector genome. The AAV vector genome may comprise at least one peptide related polynucleotide described herein, such as, but not limited to, SEQ ID NO 1, 3-41, 43-76, 79-293, 310-315, 319-323 and 354-377 or variants having at least 95% identity thereto, plus an additional N-terminal proline. The recombinant AAV vectors in the pharmaceutical composition may have at least 70% which contain an AAV vector genome.

In one embodiment, the viral vector comprising a peptide-related polynucleotide may be administered or delivered using the methods for the delivery of AAV virions described in European Patent Application No. EP1857552, the contents of which are herein incorporated by reference in its entirety.

In one embodiment, the viral vector comprising a peptide-related polynucleotide may be administered or delivered using the methods for delivering proteins using AAV vectors described in European Patent Application No. EP2678433, the contents of which are herein incorporated by reference in its entirety.

In one embodiment, the viral vector comprising a peptide-related polynucleotide may be administered or delivered using the methods for delivering DNA molecules using AAV vectors described in U.S. Pat. No. 5,858,351, the contents of which are herein incorporated by reference in its entirety.

In one embodiment, the viral vector comprising a peptide-related polynucleotide may be administered or delivered using the methods for delivering DNA to the bloodstream described in U.S. Pat. No. 6,211,163, the contents of which are herein incorporated by reference in its entirety.

In one embodiment, the viral vector comprising a peptide-related polynucleotide may be administered or delivered using the methods for delivering AAV virions described in U.S. Pat. No. 6,325,998, the contents of which are herein incorporated by reference in its entirety.

In one embodiment, the viral vector comprising a peptide-related polynucleotide may be administered or delivered using the methods for delivering a payload to the central nervous system described in U.S. Pat. No. 7,588,757, the contents of which are herein incorporated by reference in its entirety.

In one embodiment, the viral vector comprising a peptide-related polynucleotide may be administered or delivered using the methods for delivering a payload described in U.S. Pat. No. 8,283,151, the contents of which are herein incorporated by reference in its entirety.

In one embodiment, the viral vector comprising a peptide-related polynucleotide may be administered or delivered using the methods for delivering a payload using a glutamic acid decarboxylase (GAD) delivery vector described in International Patent Publication No. WO2001089583, the contents of which are herein incorporated by reference in its entirety.

In one embodiment, the viral vector comprising a peptide-related polynucleotide may be administered or delivered using the methods for delivering a payload to neural cells described in International Patent Publication No. WO2012057363, the contents of which are herein incorporated by reference in its entirety.

In one embodiment, the viral vector comprising a peptide-related polynucleotide may be administered or delivered using the methods for delivering a payload to cells described in U.S. Pat. No. 9,585,971, the contents of which are herein incorporated by reference in its entirety.

In one embodiment, the viral vector comprising a peptide-related polynucleotide may be administered or delivered using the methods for delivering a payload to cells described in Deverman et al. Nature Biotechnology, 34, 204-09 (2016).

In one embodiment, the viral vector comprising a peptide-related polynucleotide may be administered or delivered using the methods for the delivery of AAV virions described in U.S. Pat. No. 7,198,951 [adeno-associated virus (AAV) serotype 9 sequences, vectors containing same, and uses therefor], U.S. Pat. No. 9,217,155 [isolation of novel AAV's and uses thereof], WO2011126808 [pharmacologically induced transgene ablation system], U.S. Pat. No. 6,015,709 [transcriptional activators, and compositions and uses related thereto], U.S. Pat. No. 7,094,604 [Production of pseudotyped recombinant AAV virions], WO2016126993 [anti-tau constructs], U.S. Pat. No. 7,094,604 [recombinant AAV capsid protein], U.S. Pat. No. 8,292,769 [Avian adeno-associated virus (aaav) and uses thereof], U.S. Pat. No. 9,102,949 [CNS targeting aav vectors and methods of use thereof], US20160120960 [adeno-associated virus mediated gene transfer to the central nervous system], WO2016073693 [AADC polynucleotides for the treatment of parkinson's disease], WO2015168666 [AAV VECTORS FOR RETINAL AND CNS GENE Therapy], US20090117156 [Gene Therapy for Niemann-Pick Disease type A] or WO2005120581 [gene therapy for neurometabolic disorders].

The pharmaceutical compositions of viral vectors described herein may be characterized by one or more of bioavailability, therapeutic window and/or volume of distribution.

In some embodiments, peptide-related nucleotides and/or peptide-related nucleotide compositions of the present invention may be combined with, coated onto or embedded in a device. Devices may include, but are not limited to stents, pumps, and/or other implantable therapeutic device. Additionally, peptide-related nucleotides and/or peptide-related nucleotide compositions may be delivered to a subject while the subject is using a compression device such as, but not limited to, a compression device to reduce the chances of deep vein thrombosis (DVT) in a subject. The present invention provides for devices which may incorporate viral vectors that encode one or more peptide-related polynucleotide payload molecules. These devices contain in a stable formulation the viral vectors which may be immediately delivered to a subject in need thereof, such as a human patient.

Devices for administration may be employed to deliver the viral vectors comprising a peptide-related nucleotides of the present invention according to single, multi- or split-dosing regimens taught herein.

Brain Administration

Delivery of peptides or compositions of this invention to the CNS may, in some embodiments of this invention, be by systemic administration, injection into CSF pathways, or direct injection into the brain, and in some embodiments, the compositions of this invention are formulated for any of these routes. In one embodiment, the compositions of the present invention are administered by systemic or direct administration into the CNS for targeted action in the CNS, and in some embodiments, the compositions of this invention are formulated for any of these routes. In one embodiment, the composition as set forth herein is formulated for brain-specific delivery, and in some embodiments, the compositions of this invention are formulated for any of these routes. In one embodiment, strategies for drug delivery to the brain include osmotic and chemical opening of the blood-brain barrier (BBB), as well as the use of transport or carrier systems, enzymes, and receptors that control the penetration of molecules in the blood-brain barrier endothelium, and in some embodiments, the compositions of this invention are formulated for any of these routes. In another embodiment, receptor-mediated transcytosis can transport peptides and proteins across the BBB, and in some embodiments, the compositions of this invention are formulated for any of these routes. In other embodiments, strategies for drug delivery to the brain involve bypassing the BBB, and in some embodiments, the compositions of this invention are formulated for any of these routes. In some embodiments, various pharmacological agents are used to open the BBB, and in some embodiments, the compositions of this invention are formulated for any of these routes. In another embodiment, the route of administration may be directed to a different organ or system than the one that is affected by neurodegenerative conditions. For example, compounds may be administered parenterally to treat neurodegenerative conditions. Thus, the present invention provides for the use of various dosage forms suitable for administration using any of the routes listed herein, and any routes which avail the CNS of such materials, as will be appreciated by one skilled in the art.

Pharmaceutically Acceptable Salts

The present disclosure further provides a pharmaceutically acceptable salt of the peptide or peptide analog described herein. As used herein the term "pharmaceutically acceptable salt" refers to salts of peptides that retain the biological activity of the parent peptide, and which are not biologically or otherwise undesirable. Many of the peptides disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Representative acid addition salts include, but are not limited to acetate, adipate, alginate, citrate, aspartate, benzoate, benzenesulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate, and undecanoate. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Examples of acids which can be employed to form pharmaceutically acceptable acid addition salts include, for example, an inorganic acid, e.g., hydrochloric acid, hydrobromic acid, sulphuric acid, and phosphoric acid, and an organic acid, e.g., oxalic acid, maleic acid, succinic acid, and citric acid.

Basic addition salts also can be prepared in situ during the final isolation and purification of the source of salicylic acid, or by reacting a carboxylic acid-containing moiety with a suitable base such as the hydroxide, carbonate, or bicarbonate of a pharmaceutically acceptable metal cation or with ammonia or an organic primary, secondary, or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, and ethylammonium, amongst others. Other representative organic amines useful for the formation of base addition salts include, for example, ethylenediamine, ethanolamine, diethanolamine, piperidine, piperazine, and the like. Salts derived from organic bases include, but are not limited to, salts of primary, secondary and tertiary amines.

Further, basic nitrogen-containing groups can be quaternized with the analog of the present disclosure as lower alkyl halides such as methyl, ethyl, propyl, and butyl chlorides, bromides, and iodides; long chain halides such as decyl, lauryl, myristyl, and stearyl chlorides, bromides, and iodides; arylalkyl halides like benzyl and phenethyl bromides and others. Water or oil-soluble or dispersible products are thereby obtained.

It may be convenient or desirable to prepare, purify, and/or handle a corresponding solvate of the peptide. The term "solvate" is used herein in the conventional sense to refer to a complex of solute (e.g., peptide, salt of peptide) and solvent. If the solvent is water, the solvate may be conveniently referred to as a hydrate, for example, a monohydrate, a di-hydrate, a tri-hydrate, etc. Unless otherwise specified, a reference to a particular peptide also includes solvate and hydrate forms thereof.

The "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to a per se known co-crystallization method. The terms co-crystal (or cocrystal) or co-crystal salt also refer to a multicomponent system in which there exists a host API (active pharmaceutical ingredient) molecule or molecules, such as a peptide of Formula I, and a guest (or co-former) molecule or molecules.

Routes of Administration, Dose, and Dosing Regimen

The pharmaceutical compositions are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous injection, intraperitoneal injection, intramuscular injection, intrasternal injection, intravenous injection, intraarterial injection, intrathecal injection, intraventricular injection, intraurethral injection, intracranial injection, intrasynovial injection or infusions; or kidney dialytic infusion techniques.

In various embodiments, the peptide is admixed with a pharmaceutically acceptable excipients to form a pharmaceutical composition that can be systemically administered to the subject orally or via intravenous injection, intramuscular injection, subcutaneous injection, intraperitoneal injection, transdermal injection, intra-arterial injection, intrasternal injection, intrathecal injection, intraventricular injection, intraurethral injection, intracranial injection, intrasynovial injection or via infusions. The pharmaceutical composition preferably contains at least one component that is not found in nature.

Formulations of a pharmaceutical composition suitable for parenteral administration typically generally comprise the active ingredient combined with a pharmaceutically acceptable excipient, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition. Parenteral formulations also include aqueous solutions which may contain carriers such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation. Formulations for parenteral administration may be formulated to be immediate and/or modified release. Modified release formulations include delayed-, sustained-, pulsed-, controlled-, targeted and programmed release.

The present disclosure includes compositions and methods for transdermal or topical delivery, to act locally at the point of application, or to act systemically once entering the body's blood circulation. In these systems, delivery may be achieved by techniques such as direct topical application of a substance or drug in the form of an ointment or the like, or by adhesion of a patch with a reservoir or the like that holds the drug (or other substance) and releases it to the skin in a time-controlled fashion. For topical administration, the compositions can be in the form of emulsions, lotions, gels, creams, jellies, solutions, suspensions, ointments, and transdermal patches. Some topical delivery compositions may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid. Such topical formulations may comprise one or more emulsifiers, one or more surfactants, one or more polyglycols, one or more lecithins, one or more fatty acid esters, or one or more transdermal penetration enhancers. Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, *arachis* oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like.

For example, in one aspect, sterile injectable solutions can be prepared by incorporating a peptide in the required amount in an appropriate solvent with one or a combination of ingredients enumerated above, as required, followed by filtered sterilization. Generally, dispersions are prepared by incorporating the active peptide into a sterile vehicle that contains a basic dispersion medium and the required other ingredients from those enumerated above. In the case of sterile powders for the preparation of sterile injectable solutions, methods of preparation such as vacuum drying and freeze-drying yield a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin. In various embodiments, the injectable compositions will be administered using commercially available disposable injectable devices.

The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind known in the art. Injectable formulations are in accordance with the disclosure. The requirements for effective pharmaceutical excipients for injectable compositions are well-known to those of ordinary skill in the art (see, e.g., Pharmaceutics and Pharmacy Practice, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Additionally, the peptides of the present disclosures can be made into suppositories for rectal administration by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

It will be appreciated by one of skill in the art that, in addition to the above-described pharmaceutical compositions, the peptides of the disclosure can be formulated as inclusion complexes, such as cyclodextrin inclusion complexes, or liposomes.

The peptide can be administered intranasally or by inhalation, typically in the form of a dry powder (either alone, as a mixture, or as a mixed component particle, for example, mixed with a suitable pharmaceutically acceptable carrier) from a dry powder inhaler, as an aerosol spray from a pressurized container, pump, spray, atomiser (preferably an atomiser using electrohydrodynamics to produce a fine mist), or nebulizer, with or without the use of a suitable propellant, or as nasal drops. The pressurized container, pump, spray, atomizer, or nebulizer generally contains a solution or suspension of a peptide comprising, for example, a suitable agent for dispersing, solubilizing, or extending release of the active, a propellant(s) as solvent. Prior to use in a dry powder or suspension formulation, the drug product is generally micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying. Capsules, blisters and cartridges for use in an inhaler or insufflator may be formulated to contain a powder mix of the peptide, a suitable powder base and a performance modifier. Suitable flavors, such as menthol and levomenthol, or sweeteners, such as saccharin or saccharin sodium, may be added to those formulations intended for inhaled/intranasal administration. Formulations for inhaled/intranasal administration may be formulated to be immediate and/or modified release. Modified release formulations include delayed-, sustained-, pulsed-, controlled-, targeted and programmed release. In the case of dry powder inhalers and aerosols, the dosage unit is determined by means of a valve which delivers a metered amount. Units are typically arranged to administer a metered dose or "puff" of a peptide. The overall daily dose will typically be administered in a single dose or, more usually, as divided doses throughout the day.

Dosages

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the present disclosure.

It is to be noted that dosage values may vary with the type and severity of the condition to be ameliorated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. Further, the dosage regimen with the compositions of this disclosure may be based on a variety of factors, including the type of disease, the age, weight, sex, medical condition of the subject, the severity of the condition, the route of administration, and the particular peptide employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-subject dose-escalation as determined by the skilled artisan. Determining appropriate dosages and regimens are well-known in the relevant art and would be understood to be encompassed by the skilled artisan once provided the teachings disclosed herein.

The dose of the peptide of the present disclosure also will be determined by the existence, nature and extent of any adverse side effects that might accompany the administration of a particular peptide of the present disclosure. Typically, the attending physician will decide the dosage of the peptide of the present disclosure with which to treat each individual patient, taking into consideration a variety of factors, such as age, body weight, general health, diet, sex, peptide of the present disclosure to be administered, route of administration, and the severity of the condition being treated. By way of example and not intending to be limiting, the dose of the peptide of the present disclosure can be about 0.0001 to about 100 mg/kg body weight of the subject being treated/day, from about 0.001 to about 10 mg/kg body weight/day, or about 0.01 mg to about 1 mg/kg body weight/day. The peptide can be administered in one or more doses, such as from 1 to 3 doses.

In various embodiments, single or multiple administrations of the pharmaceutical compositions are administered depending on the dosage and frequency as required and tolerated by the subject. In any event, the composition should provide a sufficient quantity of at least one of the peptide disclosed herein to effectively treat the subject. The dosage can be administered once but may be applied periodically until either a therapeutic result is achieved or until side effects warrant discontinuation of therapy.

The dosing frequency of the administration of the peptide pharmaceutical composition depends on the nature of the therapy and the particular disease being treated. The administration may be once, twice, three times or four times daily, for the peptide. Treatment of a subject with a therapeutically effective amount of a peptide, can include a single treatment or, preferably, can include a series of treatments. In a preferred example, a subject is treated with peptide daily, one time per week or biweekly.

Combination Therapy

According to another embodiment, the peptides are co-administered or co-formulated with other known therapeutic agents. According to a further aspect of the present disclosure, provided herein is a combination treatment comprising the administration of a pharmacologically effective amount of a peptide or peptide analog according to the present disclosure, or a pharmaceutically acceptable salt thereof, optionally together with a pharmaceutically acceptable diluent or carrier, with the simultaneous, sequential or separate administration of one or more of the following agents selected from: (1) insulin and insulin analogues; (2) insulin secretagogues, including sulphonylureas (e.g. glipizide) and prandial glucose regulators (sometimes called "short-acting secretagogues"), such as meglitinides (e.g. repaglinide and nateglinide); (3) agents that improve incretin action, for example dipeptidyl peptidase IV (DPP-4) inhibitors (e.g. vildagliptin, saxagliptin, and sitagliptin), and glucagon-like peptide-1 (GLP-1) agonists (e.g. exenatide); (4) insulin sensitising agents including peroxisome proliferator activated receptor gamma (PPARγ) agonists, such as thiazolidinediones (e.g. pioglitazone and rosiglitazone), and agents with any combination of PPAR alpha, gamma and delta activity; (5) agents that modulate hepatic glucose balance, for example biguanides (e.g. metformin), fructose 1,6-bisphosphatase inhibitors, glycogen phopsphorylase inhibitors, glycogen synthase kinase inhibitors, and glucokinase activators; (6) agents designed to reduce/slow the absorption of glucose from the intestine, such as alpha-glucosidase inhibitors (e.g. miglitol and acarbose); and (7) agents which antagonise the actions of or reduce secretion of glucagon, such as amylin analogues (e.g. pramlintide); (7) agents that prevent the reabsorption of glucose by the kidney, such as sodium-dependent glucose transporter 2 (SGLT-2) inhibitors (e.g. dapagliflozin); (8) agents designed to treat the complications of prolonged hyperglycaemia, such as aldose reductase inhibitors (e.g. epalrestat and ranirestat); and agents used to treat complications related to micro-angiopathies; (9) anti-dyslipidemia agents, such as HMG-CoA reductase inhibitors (statins, e.g. rosuvastatin) and other cholesterol-lowering agents; PPARα agonists (fibrates, e.g. gemfibrozil and fenofibrate); bile acid sequestrants (e.g. cholestyramine); (10) cholesterol absorption inhibitors (e.g. plant sterols (i.e. phytosterols), synthetic inhibitors); cholesteryl ester transfer protein (CETP) inhibitors; inhibitors of the ileal bile acid transport system (I BAT inhibitors); bile acid binding resins; nicotinic acid (niacin) and analogues thereof; anti-oxidants, such as probucol; and omega-3 fatty acids; (11) antihypertensive agents, including adrenergic receptor antagonists, such as beta blockers (e.g. atenolol), alpha blockers (e.g. doxazosin), and mixed alpha/beta blockers (e.g. labetalol); adrenergic receptor agonists, including alpha-2 agonists (e.g. clonidine); angiotensin converting enzyme (ACE) inhibitors (e.g. lisinopril), calcium channel blockers, such as dihydropyridines (e.g. nifedipine), phenylalkylamines (e.g. verapamil), and benzothiazepines (e.g. diltiazem); angiotensin II receptor antagonists (e.g. candesartan); aldosterone receptor antagonists (e.g. eplerenone); centrally acting adrenergic drugs, such as central alpha agonists (e.g. clonidine); and diuretic agents (e.g. furosemide); (12) haemostasis modulators, including anti-thrombotics, such as activators of fibrinolysis; thrombin antagonists; factor VIIa inhibitors; anticoagulants, such as vitamin K antagonists (e.g. warfarin), heparin and low molecular weight analogues thereof, factor Xa inhibitors, and direct thrombin inhibitors (e.g. argatroban); antiplatelet agents, such as cyclooxygenase inhibitors (e.g. aspirin), adenosine diphosphate (ADP) receptor inhibitors (e.g. clopidogrel), phosphodiesterase inhibitors (e.g. cilostazol), glycoprotein I IB/I I A inhibitors (e.g. tirofiban), and adenosine reuptake inhibitors (e.g. dipyridamole); (14) anti-obesity agents, such as appetite suppressant (e.g. ephedrine), including noradrenergic agents (e.g. phentermine) and serotonergic agents (e.g. sibutramine), pancreatic lipase inhibitors (e.g. orlistat), microsomal transfer protein (MTP) modulators, diacyl glycerolacyltransferase (DGAT) inhibitors, and cannabinoid (CB1) receptor antagonists (e.g. rimonabant); (15) feeding behavior modifying agents, such as orexin receptor modulators and melanin-concentrating hormone (MCH) modulators; (16) glucagon like peptide-1 (GLP-1) receptor modulators; (17) neuropeptideY (NPY)/NPY receptor modulators; (18) pyruvate dehydrogenase kinase (PDK) modulators; (19) serotonin receptor modulators; (20) leptin/leptin receptor modulators; (21) ghrelin/ghrelin receptor modulators; or (22) monoamine transmission-modulating agents, such as selective serotonin reuptake inhibitors (SSRI) (e.g. fluoxetine), noradrenaline reuptake inhibitors (NARI), noradrenaline-serotonin reuptake inhibitors (SNRI), triple monoamine reuptake blockers (e.g. tesofensine), and monoamine oxidase inhibitors (MAOI) (e.g. toloxatone and amiflamine), or a pharmaceutically acceptable salt, solvate, solvate of such a salt or a prodrug thereof, optionally together with a pharmaceutically acceptable carrier to a mammal, such as man, in need of such therapeutic treatment.

According to another embodiment, the peptides are co-administered or co-formulated with other known therapeutic agents for treating NASH. According to a further aspect of the present disclosure, provided herein is a combination treatment comprising the administration of a pharmacologically effective amount of a peptide or peptide analog according to the present disclosure, or a pharmaceutically acceptable salt thereof, optionally together with a pharmaceutically acceptable diluent or carrier, with the simultaneous, sequential or separate administration of one or more of the following agents selected from: (miR-103/107 antagonists, FXR agonists, Galectin-1/3 agonists, ACC inhibitors, CB-1 inhibitors, Ketohexakinase inhibitors, PDE4 inhbitors, PPARγ agonists, A3AR agonists, PDE inhibitors, fluoroketolide, mTOT insulin sensitizers, Caspase inhibitors, Leptin analogs, Galectin-1/3 agonists, SCD1 inhibitors, PPARαδ agonists, LOXL2 antibodies, ASK1 inhibitors, 11β-HSD1 inhibitors, PPARαδγ agonists, THR-β agonists, Aldosterone inhibitors, FGF-19 analogs, SBAT inhibitors, CCR2/CCR5 inhbitors, GLP-1 agonists, and PPARay agonists). Combinations together with the following compounds are also contemplated as embodiments of the current invention: Astra ZenecA AZD4076, Enanta EDP-305, Galectin Therapeutics GR-MD-02, gemcabene, Gilead GS-0976, Gilead GS-9674, Merck MK-4074, pioglitazone, Pfizer PF-06835919, Pfizer CP-945598, Astellas ASP9831, Boehringer Ingelheim BI 1467335, Bristol Myers Squibb BMS-986036, avandia, metformin, losartan, Can-Fite CF102, pentoxifylline, solithromycin, Cirius MSDC-0602K, emricasan, Conatus IDN-6556, metreleptin, aramchol, Genfit GFT505, simtuzumab, Gilead GS-4997, Gilead GS-9450, Roche TRO19622, Roche RO05093151, Immuron IMM-124E, obeticholic acid, Inventiva IVA337, Madrigal MGL-3196, MN-001, Mitsubishi Tanabe MT-3995, Mochida EPA-E, NGM Biopharma NGM282, Novartis LMB763, Novartis LJN452, Shire SHP626, cenicriviroc, liraglutide, and saroglitazar.

Comorbidities Linked to Obesity—Monotherapy or Combination

For example, in addition to being overweight or obese, a subject or patient can further have overweight- or obesity-related comorbidities, i.e., diseases and other adverse health conditions associated with, exacerbated by, or precipitated by being overweight or obese. Contemplated herein are disclosed peptides of the current invention administered alone in combination with at least one other agent that has previously been shown to treat these overweight- or obesity-related conditions.

For example, Type II diabetes has been associated with obesity. Certain complications of Type II diabetes, e.g., disability and premature death, can be prevented, ameliorated, or eliminated by sustained weight loss (Astrup, A. Pub Health Nutr (2001) 4:499-515). Agents administered to treat Type II diabetes include sulfonylureas (e.g., Chlorpropamide, Glipizide, Glyburide, Glimepiride); meglitinides (e.g., Repaglinide and Nateglinide); biguanides (e.g., Metformin); thiazolidinediones (Rosiglitazone, Troglitazone, and Pioglitazone); dipeptidylpeptidase-4 inhibitors (e.g., Sitagliptin, Vildagliptin, and Saxagliptin); glucagon-like peptide-1 mimetics (e.g., Exenatide and Liraglutide); and alpha-glucosidase inhibitors (e.g., Acarbose and Miglitol.

Cardiac disorders and conditions, for example hypertension, dyslipidemia, ischemic heart disease, cardiomyopathy, cardiac infarction, stroke, venous thromboembolic disease and pulmonary hypertension, have been linked to overweight or obesity. For example, hypertension has been linked to obesity because excess adipose tissue secretes substances that are acted on by the kidneys, resulting in hypertension. Additionally, with obesity there are generally higher amounts of insulin produced (because of the excess adipose tissue) and this excess insulin also elevates blood pressure. A major treatment option of hypertension is weight loss. Agents administered to treat hypertension include Chlorthalidone; Hydrochlorothiazide; Indapamide, Metolazone; loop diuretics (e.g., Bumetanide, Ethacrynic acid, Furosemide, Lasix, Torsemide); potassium-sparing agents (e.g., Amiloride hydrochloride, benzamil, Spironolactone, and Triamterene); peripheral agents (e.g., Reserpine); central alpha-agonists (e.g., Clonidine hydrochloride, Guanabenz acetate, Guanfacine hydrochloride, and Methyldopa); alpha-blockers (e.g., Doxazosin mesylate, Prazosin hydrochloride, and Terazosin hydrochloride); beta-blockers (e.g., Acebutolol, Atenolol, Betaxolol, Bisoprolol fumarate, Carteolol hydrochloride, Metoprolol tartrate, Metoprolol succinate, Nadolol, Penbutolol sulfate, Pindolol, Propranolol hydrochloride, and Timolol maleate); combined alpha- and beta-blockers (e.g., Carvedilol and Labetalol hydrochloride); direct vasodilators (e.g., Hydralazine hydrochloride and Minoxidil); calcium antagonists (e.g., Diltiazem hydrochloride and Verapamil hydrochloride); dihydropyridines (e.g., Amlodipine besylate, Felodipine, Isradipine, Nicardipine, Nifedipine, and Nisoldipine); ACE inhibitors (benazepril hydrochloride, Captopril, Enalapril maleate, Fosinopril sodium, Lisinopril, Moexipril, Quinapril hydrochloride, Ramipril, Trandolapril); Angiotensin II receptor blockers (e.g., Losartan potassium, Valsartan, and Irbesartan); Renin inhibitors (e.g., Aliskiren); and combinations thereof. These compounds are administered in regimens and at dosages known in the art.

Carr et al. (The Journal of Clinical Endocrinology & Metabolism (2004) Vol. 89, No. 6 2601-2607) discusses a link between being overweight or obese and dyslipidemia. Dyslipidemia is typically treated with statins. Statins, HMG-CoA reductase inhibitors, slow down production of cholesterol in a subject and/or remove cholesterol buildup from arteries. Statins include mevastatin, lovastatin, pravastatin, simvastatin, velostatin, dihydrocompactin, fluvastatin, atorvastatin, dalvastatin, carvastatin, crilvastatin, bevastatin, cefvastatin, rosuvastatin, pitavastatin, and glenvastatin. These compounds are administered in regimens and at dosages known in the art. Eckel (Circulation (1997) 96:3248-3250) discusses a link between being overweight or obese and ischemic heart disease. Agents administered to treat ischemic heart disease include statins, nitrates (e.g., Isosorbide Dinitrate and Isosorbide Mononitrate), beta-blockers, and calcium channel antagonists. These compounds are administered in regimens and at dosages known in the art.

Wong et al. (Nature Clinical Practice Cardiovascular Medicine (2007) 4:436-443) discusses a link between being overweight or obese and cardiomyopathy. Agents administered to treat cardiomyopathy include inotropic agents (e.g., Digoxin), diuretics (e.g., Furosemide), ACE inhibitors, calcium antagonists, anti-arrhythmic agents (e.g., Sotolol, Amiodarone and Disopyramide), and beta-blockers. These compounds are administered in regimens and at dosages known in the art. Yusef et al. (Lancet (2005) 366(9497): 1640-1649) discusses a link between being overweight or obese and cardiac infarction. Agents administered to treat cardiac infarction include ACE inhibitors, Angiotensin II receptor blockers, direct vasodilators, beta blockers, anti-arrhythmic agents and thrombolytic agents (e.g., Alteplase, Retaplase, Tenecteplase, Anistreplase, and Urokinase). These compounds are administered in regimens and at dosages known in the art.

Suk et al. (Stroke (2003) 34: 1586-1592) discusses a link between being overweight or obese and strokes. Agents administered to treat strokes include anti-platelet agents (e.g., Aspirin, Clopidogrel, Dipyridamole, and Ticlopidine), anticoagulant agents (e.g., Heparin), and thrombolytic agents. Stein et al. (The American Journal of Medicine (2005) 18(9):978-980) discusses a link between being overweight or obese and venous thromboembolic disease. Agents administered to treat venous thromboembolic disease include anti-platelet agents, anticoagulant agents, and thrombolytic agents. Sztrymf et al. (Rev Pneumol Clin (2002) 58(2): 104-10) discusses a link between being overweight or obese and pulmonary hypertension. Agents administered to treat pulmonary hypertension include inotropic agents, anticoagulant agents, diuretics, potassium (e.g., K-dur), vasodilators (e.g., Nifedipine and Diltiazem), Bosentan, Epoprostenol, and Sildenafil. Respiratory disorders and conditions such as obesity-hypoventilation syndrome, asthma, and obstructive sleep apnea, have been linked to being overweight or obese. Elamin (Chest (2004) 125: 1972-1974) discusses a link between being overweight or obese and asthma. Agents administered to treat asthma include bronchodilators, anti-inflammatory agents, leukotriene blockers, and anti-Ige agents. Particular asthma agents include Zafirlukast, Flunisolide, Triamcinolone, Beclomethasone, Terbutaline, Fluticasone, Formoterol, Beclomethasone, Salmeterol, Theophylline, and Xopenex.

Kessler et al. (Eur Respir J (1996) 9:787-794) discusses a link between being overweight or obese and obstructive sleep apnea. Agents administered to treat sleep apnea include Modafinil and amphetamines.

Hepatic disorders and conditions, such as nonalcoholic fatty liver disease, have been linked to being overweight or obese. Tolman et al. (Ther Clin Risk Manag (2007) 6: 1153-1163) discusses a link between being overweight or obese and nonalcoholic fatty liver disease. Agents administered to treat nonalcoholic fatty liver disease include antioxidants (e.g., Vitamins E and C), insulin sensitizers (Metformin, Pioglitazone, Rosiglitazone, and Betaine), hepatoprotectants, and lipid-lowering agents.

Skeletal disorders and conditions, such as, back pain and osteoarthritis of weight-bearing joints, have been linked to being overweight or obese, van Saase (J Rheumatol (1988) 15(7): 1152-1158) discusses a link between being overweight or obese and osteoarthritis of weight-bearing joints. Agents administered to treat osteoarthritis of weight-bearing joints include Acetaminophen, non-steroidal anti-inflammatory agents (e.g., Ibuprofen, Etodolac, Oxaprozin, Naproxen, Diclofenac, and Nabumetone), COX-2 inhibitors (e.g., Celecoxib), steroids, supplements (e.g. glucosamine and chondroitin sulfate), and artificial joint fluid.

Metabolic disorders and conditions, for example, Prader-Willi Syndrome and polycystic ovary syndrome, have been linked to being overweight or obese. Cassidy (Journal of Medical Genetics (1997) 34:917-923) discusses a link between being overweight or obese and Prader-Willi Syndrome. Agents administered to treat Prader-Willi Syndrome include human growth hormone (HGH), somatropin, and weight loss agents (e.g., Orlistat, Sibutramine, Methamphetamine, Ionamin, Phentermine, Bupropion, Diethylpropion, Phendimetrazine, Benzphetermine, and Topamax).

Hoeger (Obstetrics and Gynecology Clinics of North America (2001) 28(1):85-97) discusses a link between being overweight or obese and polycystic ovary syndrome. Agents administered to treat polycystic ovary syndrome include insulin-sensitizers, combinations of synthetic estrogen and progesterone, Spironolactone, Eflornithine, and Clomiphene. Reproductive disorders and conditions such as sexual dysfunction, erectile dysfunction, infertility, obstetric complications, and fetal abnormalities, have been linked to being overweight or obese. Larsen et al. (Int J Obes (Lond) (2007) 8: 1189-1198) discusses a link between being overweight or obese and sexual dysfunction. Chung et al. (Eur Urol (1999) 36(1):68-70) discusses a link between being overweight or obese and erectile dysfunction. Agents administered to treat erectile dysfunction include phosphodiesterase inhibitors (e.g., Tadalafil, Sildenafil citrate, and Vardenafil), prostaglandin E analogs (e.g., Alprostadil), alkaloids (e.g., Yohimbine), and testosterone. Pasquali et al. (Hum Reprod (1997) 1:82-87) discusses a link between being overweight or obese and infertility. Agents administered to treat infertility include Clomiphene, Clomiphene citrate, Bromocriptine, Gonadotropin-releasing Hormone (GnRH), GnRH agonist, GnRH antagonist, Tamoxifen/nolvadex, gonadotropins, Human Chorionic Gonadotropin (HCG), Human Menopausal Gonadotropin (HmG), progesterone, recombinant follicle stimulating hormone (FSH), UrofoUitropin, Heparin, Follitropin alfa, and Follitropin beta.

Weiss et al. (American Journal of Obstetrics and Gynecology (2004) 190(4): 1091-1097) discusses a link between being overweight or obese and obstetric complications. Agents administered to treat obstetric complications include Bupivacaine hydrochloride, Dinoprostone PGE2, Meperidine HCl, Ferro-folic-500/iberet-folic-500, Meperidine, Methylergonovine maleate, Ropivacaine HCl, Nalbuphine HCl, Oxymorphone HCl, Oxytocin, Dinoprostone, Ritodrine, Scopolamine hydrobromide, Sufentanil citrate, and Oxytocic.

Psychiatric disorders and conditions, for example, weight-associated depression and anxiety, have been linked to being overweight or obese. Dixson et al. (Arch Intern Med (2003) 163:2058-2065) discusses a link between being overweight or obese and depression. Agents administered to treat depression include serotonin reuptake inhibitors (e.g., Fluoxetine, Escitalopram, Citalopram, Paroxetine, Sertraline, and Venlafaxine); tricyclic antidepressants (e.g., Amitriptyline, Amoxapine, Clomipramine, Desipramine, Dosulepin hydrochloride, Doxepin, Imipramine, Iprindole, Lofepramine, Nortriptyline, Opipramol, Protriptyline, and Trimipramine); monoamine oxidase inhibitors (e.g., Isocarboxazid, Moclobemide, Phenelzine, Tranylcypromine, Selegiline, Rasagiline, Nialamide, Iproniazid, Iproclozide, Toloxatone, Linezolid, Dienolide kavapyrone desmethoxyyangonin, and Dextroamphetamine); psychostimulants (e.g., Amphetamine, Methamphetamine, Methylphenidate, and Arecoline); antipsychotics (e.g., Butyrophenones, Phenothiazines, Thioxanthenes, Clozapine, Olanzapine, Risperidone, Quetiapine, Ziprasidone, Amisulpride, Paliperidone, Symbyax, Tetrabenazine, and Cannabidiol); and mood stabilizers (e.g., Lithium carbonate, Valproic acid, Divalproex sodium, Sodium valproate, Lamotrigine, Carbamazepine, Gabapentin, Oxcarbazepine, and Topiramate).

Simon et al. (Archives of General Psychiatry (2006) 63(7):824-830) discusses a link between being overweight or obese and anxiety. Agents administered to treat anxiety include serotonin reuptake inhibitors, mood stabilizers, benzodiazepines (e.g., Alprazolam, Clonazepam, Diazepam, and Lorazepam), tricyclic antidepressants, monoamine oxidase inhibitors, and beta-blockers.

Another aspect of the invention provides methods for facilitating and maintaining weight loss in a subject involving administering to the subject an amount of a disclosed compound effective to result in weight loss in the subject; and administering a therapeutically effective amount of a different weight loss agent to maintain a reduced weight in the subject. Weight loss agents include serotonin and noradrenergic re-uptake inhibitors; noradrenergic re-uptake inhibitors; selective serotonin re-uptake inhibitors; and intestinal lipase inhibitors. Particular weight loss agents include liraglutide, orlistat, sibutramine, methamphetamine, ionamin, phentermine, bupropion, diethylpropion, phendimetrazine, benzphetermine, bromocriptine, lorcaserin, topiramate, or agents acting to modulate food intake by blocking ghrelin action, inhibiting diacylglycerol acyltransferase 1 (DGAT1) activity, inhibiting stearoyl Co A desaturase 1 (SCD1) activity, inhibiting neuropeptide Y receptor 1 function, activating neuropeptide Y receptor 2 or 4 function, or inhibiting activity of sodium-glucose cotransporters 1 or 2. These compounds are administered in regimens and at dosages known in the art.

Methods of Treatment

The data presented herein demonstrate the ability of the presently disclosed peptides to decrease free fatty acid levels in adipocytes and support the use of such peptides for decreasing body weight, blood glucose levels, and/or fat mass in mammals in need thereof. The data presented herein also demonstrate the stability of such peptides in plasma and support their use as therapeutic peptides suitable for administration to mammals. Accordingly, the present disclosure provides methods of treating diseases relating to body weight, blood glucose levels, and fat mass, e.g., metabolic diseases, including obesity, fatty liver disease, and diabetes.

Without being bound by a specific theory, free fatty acids (FFA) in cell culture media after treatment of adipocytes with the peptides indicates a modulation of pathways involved in cellular regulation of lipid or fatty acid levels. Decreases in fatty acid levels in the media may result from a number of processes, including but not limited to inhibition of signaling pathways, reduction in cellular lipogenesis, reduction in lipolysis, or increase in fatty acid oxidation. Peptides that have an effect on the net concentration of free fatty acids have potential utility for treatment of metabolic disorders. The present disclosure accordingly provides a method of modulating fatty acid metabolism in a subject in need thereof, comprising administering to the subject a peptide or peptide analog, a conjugate, a nucleic acid, a recombinant expression vector, or a host cell of the present disclosure in an amount effective to modulate fatty acid metabolism. In exemplary aspects, the method is a method of increasing fatty acid metabolism in a subject in need thereof. The present disclosure also provides a method of modulating fatty acid metabolism in a cell, comprising contacting the cell with a peptide or peptide analog, a conjugate, a nucleic acid, a recombinant expression vector, or a host cell of the present disclosure in an amount effective to modulate fatty acid metabolism. In exemplary aspects, the method is a method of increasing fatty acid metabolism in a cell.

Lipodystrophy is a common name for disorders characterized by selective loss of adipose tissue (body fat) from various body regions and/or accumulation of excess fat in other areas. Localized fat loss from one area, such as the face, is called lipoatrophy. The extent of fat loss can range from very small areas on one part of the body to near total absence of adipose tissue from the entire body. In addition, patients may have either severe metabolic complications or mere cosmetic problems. Lipodystrophy associated with severe fat loss may contribute to metabolic complications related to insulin resistance, such as diabetes mellitus, high levels of serum triglycerides and fatty liver (hepatic steatosis). Lipodystrophy may be either congenital (such as familial partial lipodystrophy or Beradinelli-Seip syndrome) or acquired (e.g. associated with various types of illnesses or drugs). Acquired lipodystrophies are caused by medications, autoimmune mechanisms or may be idiopathic. Acquired lipodystrophies include lipodystrophy in HIV-infected patients (LD-HIV) which may be induced by highly active antiretroviral therapy (HAART), acquired generalized lipodystrophy (AGL), acquired partial lipodystrophy (APL) and localized lipodystrophy. Acquired lipodystrophies do not have a direct genetic basis. According to some embodiments, the present invention provides a method for reducing, ameliorating or preventing lipodystrophy.

The peptides are useful in the treatment of conditions associated with an unbalanced metabolic state manifested by abnormal blood levels of glucose, reactive oxygen species (ROS) and/or free fatty acids (FFA). A favorable metabolic status is defined as a balanced energy homeostasis, characterized by blood levels of glucose, ROS and FFA that are equivalent to those of healthy subjects (within the range of average levels for the healthy population). Accordingly, an unfavorable metabolic status as used herein refers to blood levels of glucose, ROS and/or FFA that are abnormal, i.e. significantly altered compared to their respective levels in healthy control subjects (e.g. as evaluated by a physician or skilled artisan). The term unfavorable metabolic status refers in some embodiments to blood levels of glucose, ROS and/or FFA that are significantly enhanced compared to their respective levels in healthy control subjects (e.g. as evaluated by a physician or skilled artisan). An unfavorable metabolic status may result from abnormal metabolism which may involve glucose (carbohydrate) and/or fatty acid oxidation pathways. When aberrations in fatty acid oxidation pathways are involved, the unfavorable metabolic status is typically manifested by ROS blood levels that are significantly enhanced compared to healthy control subjects and/or by abnormal FFA blood levels. These aberrations may also be manifested by elevated blood levels of oxidized low density lipoproteins (LDL). When aberrations in glucose metabolism are involved, glucose blood levels are typically significantly enhanced compared to healthy control subjects. As used herein, a patient with significantly enhanced blood glucose levels that do not exceed the threshold for unbalanced glycemic control will be defined as having an unfavorable metabolic status if said enhancement is accompanied by abnormal blood ROS and/or FFA values, as described herein. An unbalanced metabolic state may also be evaluated by said physician or skilled artisan by considering the energy intake and various energy consumption and utilization parameters, as known in the art. For example, without limitation, parameters at the cellular level such as cellular (e.g. platelet) ATP production and cellular oxidation, and parameters at the whole body level such as respiratory quotient (RQ) may be evaluated to determine the metabolic status of the subject. For example, by comparing the relative ratio of such parameters between healthy and sick patients the skilled artisan may evaluate the metabolic status of the subject compared to healthy controls. An unfavorable metabolic status may be found in patients afflicted with chronic metabolic and/or inflammatory disorders that are not adequately treated or balanced by a suitable therapeutic regimen.

The present disclosure accordingly provides a method of treating a metabolic disease in a subject in need thereof, comprising administering to the subject a peptide or peptide analog, a conjugate, a nucleic acid, a recombinant expression vector, or a host cell of the present disclosure in an amount effective to treat the metabolic disease.

The term "metabolic disease" or "metabolic disorder" refers to a group of identified disorders in which errors of metabolism, imbalances in metabolism, or sub-optimal metabolism occur, which may involve glucose (carbohydrate), fatty acid and/or protein oxidation pathways. Accordingly, when unbalanced, these disorders are typically manifested by an unfavorable metabolic status characterized by abnormal blood levels of glucose, ROS and/or FFA compared to their respective levels in healthy control subjects, as described herein. Such disorders include without limitation diabetes and disorders associated with nutritional or endocrine imbalance.

An unfavorable metabolic status may also occur as a result of chronic inflammatory disorders, in which a non-resolving, unbalanced inflammatory process is accompanied by secondary metabolic complications manifested by abnormal blood levels of glucose, ROS and/or FFA compared to their respective levels in healthy control subjects. Non-limitative examples of such disorders are sepsis and autoimmune diseases.

Syndrome X (or metabolic syndrome) denotes a set of signs and symptoms associated with the accumulation of fat in the abdomen. This form of fat distribution is common in middle-aged men and is often visible as a pot belly or paunch. Syndrome X is characterized by a number of disorders including gout, impaired glucose metabolism (increasing susceptibility to diabetes), raised blood pressure, and elevated blood cholesterol levels. People with Syndrome X have a high risk of heart disease. Syndrome X is defined as a constellation of metabolic abnormalities in serum or plasma insulin/glucose level ratios, lipids, uric acid levels, vascular physiology, and coagulation factor imbalances by the American Association of Clinical Endocrinologists. The term "syndrome X" as used herein thus refers to a condition characterized by positive diagnosis of at least two of the following: Non-insulin-dependent diabetes, blood pressure above a level considered normal, insulin level above a level considered normal, dyslipidemia, and obesity.

A peptide may be useful in the following metabolic diseases (a) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(b) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(c) improving β-cell function, such as decreasing β-cell apoptosis, increasing β-cell function and/or β-cell mass, and/or for restoring glucose sensitivity to β-cells;

(d) prevention and/or treatment of cognitive disorders and/or neurodegenerative disorders, such as Alzheimer's disease, Parkinson's disease, and/or multiple sclerosis;

(e) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(f) prevention and/or treatment of diabetic complications, such as angiopathy; neuropathy, including peripheral neuropathy; nephropathy; and/or retinopathy;

(g) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo (a)) in vitro and/or in vivo;

(h) prevention and/or treatment of cardiovascular diseases, such as syndrome X, atherosclerosis, myocardial infarction, coronary heart disease, reperfusion injury, stroke, hypoxia, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atherosclerosis obliterans), diastolic dysfunction, and/or systolic dysfunction; and/or reduction of blood pressure, such as reduction of systolic blood pressure;

(i) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriatic arthritis, rheumatoid arthritis, and/or systemic lupus erythematosus;

(j) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteremia, septicemia, and/or septic shock during hospitalization; and/or stabilizing blood glucose, insulin balance and optionally metabolism in intensive care unit patients with acute illness;

(k) prevention and/or treatment of polycystic ovary syndrome (PCOS);

(l) prevention and/or treatment of cerebral disease, such as cerebral ischemia, cerebral hemorrhage, and/or traumatic brain injury;

(m) prevention and/or treatment of sleep apnea;

(n) prevention and/or treatment of abuse, such as alcohol abuse and/or drug abuse;

(o) prevention or treatment of fatty liver conditions, including but not limited to Fatty Liver Disease (FLD), nonalcoholic fatty liver disease (NAFLD), and nonalcoholic steatohepatitis (NASH); and/or (p) treatment of intracellular production of reactive oxygen species (ROS).

In further aspects, methods are provided herein for treating diabetes and/or diabetes related complications by administering an effective amount, of the peptides to a patient in need of treatment. Advantageously, the peptides used for treating diabetes and/or related complications according to methods provided herein have anti-apoptotic activity against and/or stimulate proliferation of pancreatic β cells, such that administering the peptides increases the number of insulin producing β cells and the level of insulin produced by the patient.

Liver Diseases

The present disclosure also provides a method of treating a liver disease in a subject in need thereof, comprising administering to the subject a peptide or peptide analog, a conjugate, a nucleic acid, a recombinant expression vector, or a host cell of the present disclosure in an amount effective to treat the liver disease.

In some embodiments, the disease or medical condition is Nonalcoholic fatty liver disease (NAFLD). NAFLD refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes). Simple fatty liver is the abnormal accumulation of a certain type of fat, triglyceride, in the liver cells with no inflammation or scarring. In NASH, the fat accumulation is associated with varying degrees of inflammation (hepatitis) and scarring (fibrosis) of the liver. The inflammatory cells can destroy the liver cells (hepatocellular necrosis). In the terms "steatohepatitis" and "steatonecrosis", steato refers to fatty infiltration, hepatitis refers to inflammation in the liver, and necrosis refers to destroyed liver cells. NASH can ultimately lead to scarring of the liver (fibrosis) and then irreversible, advanced scarring (cirrhosis). Cirrhosis that is caused by NASH is the last and most severe stage in the NAFLD spectrum. (Mendler, Michel, "Fatty Liver: Nonalcoholic Fatty Liver Disease (NAFLD) and Nonalcoholic Steatohepatitis (NASH)," ed. Schoenfield, Leslie J., MedicineNet-.com, Aug. 29, 2005).

Alcoholic Liver Disease, or Alcohol-Induced Liver Disease, encompasses three pathologically distinct liver diseases related to or caused by the excessive consumption of alcohol: fatty liver (steatosis), chronic or acute hepatitis, and cirrhosis. Alcoholic hepatitis can range from a mild hepatitis, with abnormal laboratory tests being the only indication of disease, to severe liver dysfunction with complications such as jaundice (yellow skin caused by bilirubin retention), hepatic encephalopathy (neurological dysfunction caused by liver failure), ascites (fluid accumulation in the abdomen), bleeding esophageal varices (varicose veins in the esophagus), abnormal blood clotting and coma. Histologically, alcoholic hepatitis has a characteristic appearance with ballooning degeneration of hepatocytes, inflammation with neutrophils and sometimes Mallory bodies (abnormal aggregations of cellular intermediate filament proteins). Cirrhosis is characterized anatomically by widespread nodules in the liver combined with fibrosis. (Worman, Howard J., "Alcoholic Liver Disease", Columbia University Medical Center website).

Without being bound to any particular theory, the peptides and peptide analogs described herein are useful for the treatment of Alcoholic Liver Disease, NAFLD, or any stage thereof, including, for example, steatosis, steatohepatitis, hepatitis, hepatic inflammation, NASH, cirrhosis, or complications thereof. Accordingly, the present disclosures provides a method of preventing or treating Alcoholic Liver Disease, NAFLD, or any stage thereof, in a subject comprising providing to a subject a peptide or peptide analog described herein in an amount effective to prevent or treat Alcoholic Liver Disease, NAFLD, or the stage thereof. Such treatment methods include reduction in one, two, three or more of the following: liver fat content, incidence or progression of cirrhosis, incidence of hepatocellular carcinoma, signs of inflammation, e.g., abnormal hepatic enzyme levels (e.g., aspartate aminotransferase AST and/or alanine aminotransferase ALT, or LDH), elevated serum ferritin, elevated serum bilirubin, and/or signs of fibrosis, e.g., elevated TGF-beta levels. In exemplary embodiments, the peptide or peptide analog is used to treat patients who have progressed beyond simple fatty liver (steatosis) and exhibit signs of inflammation or hepatitis. Such methods may result, for example, in reduction of AST and/or ALT levels.

Cancer Treatment

In some embodiments, the peptides have anticancer activity. For example, in some aspects, the peptides have pro-apoptotic activity against cancer cells, such as but not limited to, prostate cancer cells and/or breast cancer cells. In further aspects, the peptides have anti-proliferative activity against cancer cells, such as but not limited to, prostate cancer cells and/or breast cancer cells.

The present disclosure also provides a method of treating cancer in a subject in need thereof, comprising administering to the subject a peptide or peptide analog, a conjugate, a nucleic acid, a recombinant expression vector, or a host cell of the present disclosure in an amount effective to treat the cancer. The present disclosure also includes methods of treating cancer comprising administering an effective amount of a peptide or a variant thereof to a subject in need of treatment. The peptides provided herein exert a variety of anticancer effects and can be used to treat a wide range of cancers and other proliferative disorders. Peptides provided herein can have a variety of anticancer activities, such as but not limited to, inducing apoptosis in cancerous cells, inhibiting tumor angiogenesis, inhibiting tumor metastasis, modulating the cell cycle, inhibiting cancer cell proliferation, promoting cancer cell differentiation, inhibiting production of and/or protecting against reactive oxygen species, and enhancing stress resistance. A "cancer" refers generally to a disease characterized by uncontrolled, abnormal cell growth and proliferation. A "tumor" or "neoplasm" is an abnormal mass of tissue that results from excessive, un controlled, and progressive cell division. Methods described herein are useful for treating cancers and proliferative disorders of any type, including but not limited to, carcinomas, sarcomas, soft tissue sarcomas, lymphomas, hematological cancers, leukemias, germ cell tumors, and cancers without solid tumors (e.g., hematopoietic cancers). In various aspects, the peptides can be used to treat cancers and/or tumors originating from and/or effecting any tissue, including but not limited to, lung, breast, epithelium, large bowel, rectum, testicle, bladder, thyroid, gallbladder, bile duct, biliary tract, prostate, colon, stomach, esophagus, pancreas, liver, kidney, uterus, cervix, ovary, and brain tissues. Non-limiting examples of specific cancers treatable with the peptides include, but are not limited to, acute lymphoblastic leukemia, acute myeloid leukemia, chronic lymphocytic leukemia, chronic myelogenous leukemia, adrenocortical carcinoma, AIDS-related lymphoma, anal cancer, astrocytoma, cerebral basal cell carcinoma, bile duct cancer, extrahepatic bladder cancer, bladder cancer, bone cancer, osteosarcoma/malignant fibrous histiocytoma, brain stem glioma, brain tumor, brain stem glioma, cerebral astrocytoma/malignant glioma, ependymoma, medulloblastoma, supratentorial primitive neuroectodermal tumor, visual pathway and hypothalamic glioma, breast cancer, male bronchial adenomas/carcinoids, Burkitt's lymphoma, carcinoid tumor, gastrointestinal carcinoma of unknown primary central nervous system lymphoma, cervical cancer, chronic lymphocytic leukemia, chronic myelogenous leukemia, chronic myeloproliferative disorders, colon cancer, colorectal cancer, cutaneous t-cell lymphoma, mycosis fungoides and sezary syndrome, endometrial cancer, ependymoma, esophageal cancer, Ewing's family tumors, germ cell tumors, extrahepatic bile duct cancer, eye cancer, intraocular melanoma, retinoblastoma, gallbladder cancer, gastric (stomach) cancer, gastrointestinal carcinoid tumors, ovarian gestational, trophoblastic tumors, glioma, hypothalamic skin cancer (melanoma), skin cancer (non-melanoma), skin carcinoma, small cell lung cancer, small intestine cancer, soft tissue sarcoma, squamous cell carcinoma, squamous neck cancer with occult primary, metastatic stomach (gastric) cancer, stomach (gastric) cancer, t-cell lymphoma, testicular cancer, thymoma, thymic carcinoma, thyroid cancer, transitional cell cancer of the renal pelvis, ureter trophoblastic tumors, transitional cell cancer, urethral cancer, uterine cancer, uterine sarcoma, vaginal cancer, hypothalamic glioma, vulvar cancer, Waldenstrom's macroglobulinemia, Wilms' tumor, hairy cell leukemia, head and neck cancer, hepatocellular (liver) cancer, Hodgkin's lymphoma, hypopharyngeal cancer, islet cell carcinoma (endocrine pancreas), Kaposi's sarcoma, kidney (renal cell) cancer, kidney cancer, laryngeal cancer, hairy cell lip and oral cavity cancer, liver cancer, lung cancer, non-small cell lung cancer, small cell lymphoma, Burkitt's lymphoma, cutaneous t-cell, Hodgkin's lymphoma, non-Hodgkin's lymphoma, Waldenstrom's malignant fibrous histiocytoma of bone/osteosarcoma medulloblastoma, intraocular (eye) merkel cell carcinoma, mesothelioma, malignant mesothelioma, metastatic squamous neck cancer with occult primary multiple endocrine neoplasia syndrome, multiple myeloma/plasma cell neoplasm, mycosis fungoides myelodysplastic syndromes, myelodysplastic/myeloproliferative diseases, myelogenous leukemia, multiple myeloproliferative disorders, chronic nasal cavity and paranasal sinus cancer, nasopharyngeal cancer, pleoropulmonary blastoma, osteosarcoma/malignant fibrous histiocytoma of bone, pheochromocytoma, pineoblastoma, and supratentorial primitive neuroectodermal tumors. In some preferred aspects, the cancer is breast cancer. In some preferred aspects, the cancer is prostate cancer.

In some aspects, administering a peptide according to a method provided herein enhances efficacy of an established cancer therapy. In further aspects, administering a peptide according to a method provided herein enhances the anti-cancer activity of another cancer therapy, such as radiation or chemotherapy. In some aspects, methods are provided herein for inducing cell death in cancer cells and/or tumor cells, the methods comprising administering a peptide described herein in an amount sufficient to induce cancer cell death and/or tumor cell death.

In some embodiments, the peptides have one or more cell protective or cytoprotective activities. For example, in some aspects, the peptides are capable of preventing cell damage, improving cell survival, and/or enhancing resistance to environmental stress, such as but not limited to, heat shock, serum withdrawal, chemotherapy, and/or radiation.

In some aspects, administering a peptide according to a method provided herein decreases adverse effects of an established cancer therapy.

Further preferred medical uses include treatment or prevention of degenerative disorders, particularly neurodegenerative disorders such as Alzheimer's disease, Parkinson's disease, Huntington's disease, ataxia, e.g. spinocerebellar ataxia, Kennedy disease, myotonic dystrophy, Lewy body dementia, multi-systemic atrophy, amyotrophic lateral sclerosis, primary lateral sclerosis, spinal muscular atrophy, prion-associated diseases, e.g. Creutzfeldt-Jacob disease, multiple sclerosis, telangiectasia, Batten disease, corticobasal degeneration, corticobasal degeneration, subacute combined degeneration of spinal cord, Tabes *dorsalis*, Tay-Sachs disease, toxic encephalopathy, infantile Refsum disease, Refsum disease, neuroacanthocytosis, Niemann-Pick disease, Lyme disease, Machado-Joseph disease, Sandhoff disease, Shy-Drager syndrome, wobbly hedgehog syndrome, proteopathy, cerebral β-amyloid angiopathy, retinal ganglion cell degeneration in glaucoma, synucleinopathies, tauopathies, frontotemporal lobar degeneration (FTLD), dementia, cadasil syndrome, hereditary cerebral hemorrhage with amyloidosis, Alexander disease, seipinopathies, familial amyloidotic neuropathy, senile systemic amyloidosis, serpinopathies, AL (light chain) amyloidosis (primary systemic amyloidosis), AH (heavy chain) amyloidosis, AA (secondary) amyloidosis, aortic medial amyloidosis, ApoAI amyloidosis, ApoAII amyloidosis, ApoAIV amyloidosis, familial amyloidosis of the Finnish type (FAF), Lysozyme amyloidosis, Fibrinogen amyloidosis, Dialysis amyloidosis, Inclusion body myositis/myopathy, Cataracts, Retinitis pigmentosa with rhodopsin mutations, medullary thyroid carcinoma, cardiac atrial amyloidosis, pituitary prolactinoma, Hereditary lattice corneal dystrophy, Cutaneous lichen amyloidosis, Mallory bodies, corneal lactoferrin amyloidosis, pulmonary alveolar proteinosis, odontogenic (Pindborg) tumor amyloid, cystic fibrosis, sickle cell disease or critical illness myopathy (CIM). Without being limited by a particular theory, it is believed that the peptides provided herein have one or more activities capable of repairing and/or preventing neurodegenerative damage of neural cells and/or other cell types. "Neurodegenerative diseases" treatable according to methods provided herein are progressive diseases resulting in the degeneration and/or loss of neurons, for example due to neuronal cell death (apoptosis). Examples of neurodegenerative diseases include, but are not limited to, cerebral degenerative diseases (e.g., Alzheimer's disease (AD), Parkinson's disease, progressive supranuclear palsy, and Huntington's disease (HDI))), and spinal degenerative disease/motor neuron degenerative diseases (e.g., amyotrophic lateral sclerosis (ALS), (SMA: Werdnig-Hoffmann disease or Kugelberg-Welander syndrome), spinocerebellar ataxia, bulbospinal muscular atrophy (BSMA; Kennedy-Alter-Sung syndrome)). A "motor neuron degenerative disease" is a neurodegenerative disease characterized by a progressive, retrograde disorder of upper and lower motor neurons that control motion in the body. In further aspects, the peptides and compositions thereof are also effective in ameliorating conditions resulting from motor neuron degenerative disease, such as muscular atrophy, muscular weakness, bulbar palsy (muscular atrophy or weakness in the face, pharynx, and tongue, and aphasia or dysphagia caused thereby), muscular fasciculation, and respiratory disorder.

Further uses include the prevention and treatment of diseases or conditions associated with mitochondrial dysfunction. Mitochondria, central to metabolic processes, are involved with energy production, programmed cell death, and reactive oxygen species (ROS) generation. Traditionally, mitochondria have been considered as "end-function" organelles, receiving and processing vast amounts of cellular signals to regulate energy production and cell death. The peptides and peptide analogs and pharmaceutical formulations thereof can be used to treat various age-related diseases associated with mitochondrial dysfunction. Also they have been shown in various ways in vitro and in vivo to affect metabolic processes such as mitochondrial respiration, glucose transport, glucose utilization, glycolysis, insulin regulation and cellular proliferation/survival. Mitochondrial dysfunction is associated with but not limited to metabolic disorders, neurodegenerative diseases, chronic inflammatory diseases, and diseases of aging. Some mitochondrial diseases are due to mutations or deletions in the mitochondrial genome. Mitochondria divide and proliferate with a faster turnover rate than their host cells, and their replication is under control of the nuclear genome. If a threshold proportion of mitochondria in a cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved. In addition to congenital disorders involving inherited defective mitochondria, acquired mitochondrial dysfunction contributes to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxic neuronal injury, such as that associated with seizures or ischemia. Other disorders associated with mitochondrial dysfunction include chronic inflammatory disorders and metabolic disorders.

Peptides that are cytoprotective have potential utility to extend the viability of cells in culture. The peptides are useful for manufacture of biological products, including proteins, antibodies and the like. The present disclosure relates generally to peptides and processes for modulating one or more properties of a cell culture, including mammalian cell cultures such as CHO cell cultures, or E. coli cell cultures. In one embodiment, there is provided a method of increasing specific productivity in a mammalian cell culture expressing a recombinant protein comprising establishing a mammalian cell culture in a culture medium; increasing cell growth viability by contacting the cell culture with a culture medium comprising a peptide; and maintaining the cell culture by contacting the culture with a culture medium comprising a peptide.

Kits

The peptides or peptide analogs of the present disclosure can be provided in accordance with one embodiment as part of a kit. Accordingly, in some embodiments, a kit for administering a peptide or peptide analog, to a patient in need thereof is provided wherein the kit comprises a peptide as described herein.

In one embodiment the kit is provided with a device for administering the composition to a patient, e.g., syringe needle, pen device, jet injector or another needle-free injector. The kit may alternatively or in addition include one or more containers, e.g., vials, tubes, bottles, single or multi-chambered pre-filled syringes, cartridges, infusion pumps (external or implantable), jet injectors, pre-filled pen devices and the like, optionally containing the peptide in a lyophilized form or in an aqueous solution. The kits in some embodiments comprise instructions for use. In accordance with one embodiment the device of the kit is an aerosol dispensing device, wherein the composition is prepackaged within the aerosol device. In another embodiment the kit comprises a syringe and a needle, and in one embodiment the sterile composition is prepackaged within the syringe.

The following examples are given merely to illustrate the present invention and not in any way to limit its scope.

EXAMPLES

In the following examples, a test peptide is referenced by a unique SEQ ID NO: which corresponds to that listed in Table 1 (see Appendix) and the sequence listing submitted herewith.

Example 1

This example demonstrates exemplary methods of synthesizing the peptides or peptide analogs of the present disclosure.

The peptides are prepared via solid phase synthesis on a suitable resin using t-Boc or Fmoc chemistry or other well established techniques, (see for example: Stewart and Young, Solid Phase Peptide Synthesis, Pierce Chemical Co., Rockford, Ill., 1984; E. Atherton and R. C. Sheppard, Solid Phase Peptide Synthesis. A Practical Approach, Oxford-IRL Press, New York, 1989; Greene and Wuts, "Protective Groups in Organic Synthesis", John Wiley & Sons, 1999; Florencio Zaragoza Dorwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000) by a method similar to that described below, unless specified otherwise.

Solid phase synthesis is initiated by attaching an N-terminally protected amino acid with its carboxy terminus to an inert solid support carrying a cleavable linker. This solid support can be any polymer that allows coupling of the initial amino acid, e.g. a Pam resin, trityl resin, a chlorotrityl resin, a Wang resin or a Rink resin in which the linkage of the carboxy group (or carboxamide for Rink resin) to the resin is sensitive to acid (when Fmoc strategy is used). The polymer support is stable under the conditions used to deprotect the α-amino group during the peptide synthesis. After the first amino acid has been coupled to the solid support, the α-amino protecting group of this amino acid is removed. The remaining protected amino acids are then coupled one after the other in the order represented by the peptide sequence using appropriate amide coupling reagents, for example BOP (benzotriazol-1-yl-oxy-tris-(dimethylamino)-phosphonium), HBTU (2-(1H-benzotriazol-1-yl)-1,1,3,3-tetramethyl-uronium), HATU (O-(7-azabenztriazol-1-yl-oxy-tris-(dimethylamino)-phosphonium) or DIC (N,N'-diisopropylcarbodiimide)/HOBt (1-hydroxybenzotriazol), wherein BOP, HBTU and HATU are used with tertiary amine bases. Alternatively, the liberated N-terminus can be functionalized with groups other than amino acids, for example carboxylic acids, etc. Usually, reactive side-chain groups of the amino acids are protected with suitable blocking groups. These protecting groups are removed after the desired peptides have been assembled. They are removed concomitantly with the cleavage of the desired product from the resin under the same conditions. Protecting groups and the procedures to introduce protecting groups can be found in Protective Groups in Organic Synthesis, 3d ed., Greene, T. W. and Wuts, P. G. M., Wiley & Sons (New York: 1999). In some cases, it might be desirable to have side-chain protecting groups that can selectively be removed while other side-chain protecting groups remain intact. In this case the liberated functionality can be selectively functionalized. For example, a lysine may be protected with an ivDde protecting group (S. R. Chhabra et al., Tetrahedron Lett. 39, (1998), 1603) which is labile to a very nucleophilic base, for example 4% hydrazine in DMF (dimethyl formamide). Thus, if the N-terminal amino group and all side-chain functionalities are protected with acid labile protecting groups, the ivDde ([1-(4,4-dimethyl-2,6-dioxocyclohex-1-ylidene)-3-methylbutyl] group can be selectively removed using 4% hydrazine in DMF and the corresponding free amino group can then be further modified, e.g. by acylation. The lysine can alternatively be coupled to a protected amino acid and the amino group of this amino acid can then be deprotected resulting in another free amino group which can be acylated or attached to further amino acids. Finally, the peptide is cleaved from the resin. This can be achieved by using HF or King's cocktail (D. S. King, C. G. Fields, G. B. Fields, Int. J. Peptide Protein Res. 36, 1990, 255-266). The raw material can then be purified by chromatography, e.g. preparative RP-HPLC, if necessary.

Those peptides, analogs or derivatives which include non-natural amino acids and/or a covalently attached N-terminal mono- or dipeptide mimetic may be produced as described in the experimental part, or see e.g., Hodgson et al: "The synthesis of peptides and proteins containing non-natural amino acids", and Chemical Society Reviews, vol. 33, no. 7 (2004), p. 422-430.

The peptides are prepared according to the below-mentioned peptide synthesis and the sequences as presented in the Table 1 can be prepared similar to the below-mentioned synthesis, unless specified otherwise.

One method of peptide synthesis is by Fmoc chemistry on a microwave-based Liberty peptide synthesizer (CEM Corp., North Carolina). The resin is Tentagel S RAM with a loading of about 0.25 mmol/g or PAL-ChemMatrix with a loading of about 0.43 mmol/g or PAL AM matrix with a loading of 0.5-0.75 mmol/g. The coupling chemistry is DIC/HOAt or DIC/Oxyma in NMP or DMF using amino acid solutions of 0.3 M and a molar excess of 6-8 fold. Coupling conditions are 5 minutes at up to 70° C. Deprotection is with 10% piperidine in NMP at up to 70° C. The protected amino acids used are standard Fmoc-amino acids (supplied from e.g. Anaspec or Novabiochem or Protein Technologies).

Another method of peptide synthesis is by Fmoc chemistry on a Prelude peptide synthesizer (Protein Technologies, Arizona). The resin is Tentagel S RAM with a loading of about 0.25 mmol/g or PAL-ChemMatrix with a loading of about 0.43 mmol/g or PAL AM with a loading of 0.5-0.75 mmol/g. The coupling chemistry is DIC/HOAt or DIC/Oxyma in NMP or DMF using amino acid solutions of 0.3 M and a molar excess of 6-8 fold. Coupling conditions are single or double couplings for 1 or 2 hours at room temperature. Deprotection is with 20% piperidine in NMP. The protected amino acids used are standard Fmoc-amino acids (supplied from e.g. Anaspec or Novabiochem or Protein Technologies). The crude peptides are purified such as by semipreparative HPLC on a 20 mm×250 mm column packed with either 5 um or 7 um C-18 silica. Peptide solutions are pumped onto the HPLC column and precipitated peptides are dissolved in 5 ml 50% acetic acid $H_2O$ and diluted to 20 ml with $H_2O$ and injected on the column which then is eluted with a gradient of 40-60% $CH_3CN$ in 0.1% TFA 10 ml/min during 50 min at 40° C. The peptide containing fractions are collected. The purified peptide is lyophilized after dilution of the eluate with water.

All peptides with C terminal amides described herein are prepared by a method similar to that described below unless specified otherwise. MBHA resin (4-methylbenzhydrylamine polystyrene resin is used during peptide synthesis. MBHA resin, 100-180 mesh, 1% DVB cross-linked polystyrene; loading of 0.7-1.0 mmol/g), Boc-protected and Fmoc protected amino acids can be purchased from Midwest Biotech. The solid phase peptide syntheses using Boc-protected amino acids are performed on an Applied Biosystem 430A Peptide Synthesizer. Fmoc protected amino acid synthesis is performed using the Applied Biosystems Model 433 Peptide Synthesizer.

Synthesis of the peptides is performed on the Applied Biosystem Model 430A Peptide Synthesizer. Synthetic peptides are constructed by sequential addition of amino acids to a cartridge containing 2 mmol of Boc protected amino acid. Specifically, the synthesis is carried out using Boc DEPBT-activated single couplings. At the end of the coupling step, the peptidyl-resin is treated with TFA to remove the N-terminal Boc protecting group. It is washed repeatedly with DMF and this repetitive cycle is repeated for the desired number of coupling steps. After the assembly, the sidechain protection, Fmoc, is removed by 20% piperidine treatment and acylation was conducted using DIC. The peptidyl-resin at the end of the entire synthesis is dried by using DCM, and the peptide is cleaved from the resin with anhydrous HF. The peptidyl-resin is treated with anhydrous HF, and this typically yielded approximately 350 mg (~50% yield) of a crude deprotected-peptide. Specifically, the peptidyl-resin (30 mg to 200 mg) is placed in the hydrogen fluoride (HF) reaction vessel for cleavage. 500 μL of p-cresol was added to the vessel as a carbonium ion scavenger. The vessel is attached to the HF system and submerged in the methanol/dry ice mixture. The vessel is evacuated with a vacuum pump and 10 ml of HF is distilled to the reaction vessel. This reaction mixture of the peptidyl-resin and the HF is stirred for one hour at 0° C., after which a vacuum is established and the HF is quickly evacuated (10-15 min). The vessel is removed carefully and filled with approximately 35 ml of ether to precipitate the peptide and to extract the p-cresol and small molecule organic protecting groups resulting from HF treatment. This mixture is filtered utilizing a Teflon filter and repeated twice to remove all excess cresol. This filtrate is discarded. The precipitated peptide dissolves in approximately 20 ml of 10% acetic acid (aq). This filtrate, which contained the desired peptide, is collected and lyophilized.

Example 2

This example demonstrates the effect of the exemplary peptides on free fatty acid levels in cultured mouse adipocytes.

Mouse 3T3-L1 cells were seeded at a density between 1,000-20,000 cells per well on 96-well, 48-well, or 24-well plates in Pre-adipocyte Medium (Zen-Bio, Durham, N.C.) and grown to confluence at 37° C. in a humidified atmosphere of 5% CO2/95% air. Two days after confluence, cells were placed in Adipocyte Differentiation Medium (Zen-Bio, Durham, N.C.) and cultured for three additional days at 37° C. in a humidified atmosphere of 5% CO2/95% air. The culture media was then replaced with Adipocyte Maintenance Medium (Zen-Bio) and the cells were maintained for an additional 9-14 days at 37° C. in a humidified atmosphere of 5% CO2/95% air with partial medium replacement every other day. Following 12-17 days of differentiation, test peptides were added at a final concentration of 25 μM and incubated for 18-20 hours in Adipocyte Maintenance Medium at 37° C. in a humidified atmosphere of 5% CO2/95%. After 18-20 hours, the media was exchanged with fresh Adipocyte Maintenance Medium containing test peptides and incubated for 1 h at 37° C. in a humidified atmosphere of 5% CO2/95%. After 1 h media was exchanged with Assay Buffer (Zen-Bio) containing isoproterenol (1 nM) (added to all samples except untreated controls) and the test peptides. Cells were incubated for a further 3 hours at 37° C. in a humidified atmosphere of 5% CO2/95%. Free fatty acid concentrations in the media were determined using a Free Fatty Acid Assay Kit (Zen-Bio) according to the manufacturer's instructions using a plate reader (540 nm).

Absorbance values were corrected for untreated background and expressed relative to isoproterenol treated cells. Treatment with isoproterenol (1 nM) alone was used as the free fatty acid level stimulatory control. The relative standard deviation of the isoproterenol control was <10%. Insulin was used as a highly potent positive control for decreasing free fatty acid levels. Free fatty acid levels for insulin (100 nM) treatment were <5% of the isoproterenol control value. The results are reported in Table 4.

TABLE 4

Free Fatty Acid Levels in 3T3-L1 Adipocytes Expressed as a Percent of Isoproterenol Control

| SEQ ID NO: | Percent of Control Value |
|---|---|
| 22 | 78.7 |
| 23 | 74.7 |
| 25 | 27.8 |
| 28 | 35.5 |
| 34 | 70.7 |
| 35 | 31.3 |
| 6 | 58.6 |
| 11 | 78.8 |
| 15 | 67.9 |
| 19 | 66.0 |
| 21 | 45.1 |
| 39 | 84.3 |
| 40 | 83.1 |
| 45 | 37.9 |
| 46 | 43.1 |
| 47 | 24.5 |
| 48 | 57.1 |
| 49 | 103.3 |
| 50 | 97.4 |
| 52 | 85.6 |
| 58 | 97.3 |
| 59 | 92.2 |
| 60 | 89.3 |
| 61 | 92.9 |
| 52 | 99.5 |
| 63 | 70.5 |
| 64 | 90.6 |
| 69 | 61.3 |
| 108 | 101.3 |
| 109 | 76.6 |
| 110 | 82.6 |
| 111 | 106.0 |
| 112 | 90.5 |
| 113 | 82.8 |
| 114 | 78.4 |
| 115 | 83.4 |
| 116 | 101.8 |
| 117 | 97.7 |
| 118 | 84.6 |
| 119 | 89.2 |
| 120 | 86.0 |
| 121 | 89.8 |
| 122 | 52.1 |
| 123 | 58.8 |
| 124 | 68.9 |
| 125 | 50.2 |
| 126 | 55.6 |
| 127 | 55.6 |
| 128 | 90.0 |
| 129 | 82.5 |
| 130 | 85.4 |
| 131 | 78.1 |
| 132 | 102.6 |
| 133 | 87.5 |
| 134 | 56.2 |
| 135 | 79.0 |
| 136 | 44.2 |
| 137 | 91.4 |
| 138 | 71.5 |
| 139 | 58.1 |
| 140 | 60.8 |
| 141 | 56.9 |
| 142 | 31.9 |
| 143 | 64.5 |
| 144 | 57.0 |
| 145 | 50.2 |
| 146 | 55.9 |
| 147 | 60.9 |
| 148 | 25.0 |
| 149 | 38.6 |
| 150 | 53.9 |
| 151 | 47.9 |
| 152 | 81.9 |
| 153 | 93.1 |

TABLE 4-continued

Free Fatty Acid Levels in 3T3-L1 Adipocytes Expressed as a Percent of Isoproterenol Control

| SEQ ID NO: | Percent of Control Value |
|---|---|
| 154 | 95.7 |
| 155 | 90.1 |
| 156 | 94.7 |
| 157 | 85.0 |
| 88 | 75.1 |
| 159 | 87.4 |
| 160 | 87.1 |
| 161 | 83.7 |
| 162 | 82.4 |
| 163 | 91.8 |
| 164 | 77.2 |
| 165 | 82.0 |
| 166 | 78.0 |
| 167 | 70.9 |
| 168 | 52.2 |
| 169 | 49.2 |
| 170 | 48.0 |
| 171 | 45.9 |
| 172 | 54.2 |
| 173 | 43.9 |
| 174 | 38.8 |
| 175 | 50.6 |
| 176 | 57.0 |
| 177 | 61.4 |
| 178 | 67.6 |
| 179 | 47.2 |
| 180 | 47.0 |
| 181 | 58.9 |
| 182 | 36.6 |
| 183 | 81.6 |
| 184 | 97.1 |
| 185 | 77.0 |
| 186 | 102.1 |
| 187 | 98.9 |
| 188 | 86.5 |
| 189 | 87.6 |
| 190 | 95.0 |
| 191 | 81.7 |
| 192 | 66.8 |
| 193 | 71.2 |
| 194 | 107.2 |
| 195 | 58.9 |
| 196 | 80.5 |
| 197 | 84.6 |
| 198 | 69.2 |
| 199 | 48.0 |
| 200 | 80.2 |
| 201 | 92.8 |
| 203 | 52.9 |
| 204 | 38.8 |
| 205 | 71.5 |
| 206 | 53.8 |
| 207 | 44.6 |
| 208 | 57.9 |
| 209 | 30.1 |
| 210 | 44.6 |
| 211 | 29.9 |
| 213 | 48.1 |
| 214 | 52.3 |
| 215 | 27.2 |
| 216 | 36.3 |
| 217 | 27.3 |
| 218 | 41.0 |
| 219 | 38.9 |
| 220 | 70.5 |
| 221 | 25.5 |
| 223 | 64.6 |
| 224 | 56.2 |
| 225 | 97.0 |
| 226 | 79.8 |
| 227 | 24.5 |
| 228 | 69.9 |
| 230 | 94.5 |
| 231 | 61.6 |
| 232 | 46.5 |
| 233 | 69.7 |
| 234 | 73.8 |
| 235 | 71.8 |
| 236 | 74.8 |
| 237 | 85.6 |
| 238 | 52.9 |
| 239 | 66.6 |
| 240 | 48.6 |
| 241 | 50.9 |
| 242 | 64.9 |
| 243 | 82.3 |
| 244 | 90.3 |
| 245 | 78.1 |
| 246 | 73.9 |
| 248 | 50.4 |
| 249 | 81.3 |
| 250 | 83.0 |
| 251 | 83.7 |
| 260 | 75.9 |
| 264 | 63.2 |
| 265 | 66.7 |
| 266 | 72.7 |
| 268 | 41.9 |
| 269 | 59.2 |
| 270 | 66.9 |
| 282 | 71.8 |
| 283 | 90.8 |
| 284 | 97.1 |
| 285 | 96.0 |
| 286 | 94.8 |
| 287 | 78.1 |
| 288 | 93.0 |
| 289 | 94.5 |
| 290 | 90.6 |
| 290 | 77.8 |
| 77 | 112.5 |
| 42 | 115.2 |
| 2 | 63.3 |

Example 3

This example demonstrates the effect of the exemplary peptides on free fatty acid levels in cultured mouse adipocytes.

Mouse 3T3-L1 cells wre seeded at 1,000-20,000 cells per well on 96-well, 48-well, or 24-well plates in Pre-adipocyte Medium (Zen-Bio, Durham, N.C.) and grown to confluence at 37° C. in a humidified atmosphere of 5% CO2/95% air. Two days after confluence, cells were placed in Adipocyte Differentiation Medium (Zen-Bio, Durham, N.C.) and cultured for three additional days at 37° C. in a humidified atmosphere of 5% CO2/95% air. The culture media was then replaced with Adipocyte Maintenance Medium (Zen-Bio) and the cells were maintained for an additional 9-14 days at 37° C. in a humidified atmosphere of 5% CO2/95% air with partial medium replacement every other day. Following 12-17 days of differentiation, test peptides were added at a final concentration of 25 µM and incubated for 18-20 hours in Adipocyte Maintenance Medium at 37° C. in a humidified atmosphere of 5% CO2/95%. After 18-20 hours, the media was exchanged with fresh Adipocyte Maintenance Medium containing test peptides and incubated for 1 h at 37° C. in a humidified atmosphere of 5% CO2/95%. After 1 h media was exchanged with Assay Buffer (Zen-Bio) containing forskolin (1 µM) (added to all samples except untreated controls) and test peptides. Cells were incubated for a further 3 hours at 37° C. in a humidified atmosphere of 5% CO2/95%. Free fatty acid concentrations in the media were determined using a Free Fatty Acid Assay Kit (Zen-Bio) according to the manufacturer's instructions using a plate reader (540 nm). Absorbance values were corrected for untreated background and expressed relative to forskolin treated cells. Treatment with forskolin (1 μM) alone was used as the free fatty acid level stimulatory control. The relative standard deviation of the forskolin control was <10%. Insulin was used as a highly potent positive control for decreasing free fatty acid levels. Free fatty acid levels for insulin (100 nM) treatment were <9% of the forskolin control value. The results are reported in Table 5.

TABLE 5

Free Fatty Acid Levels in 3T3-L1 Adipocytes Expressed as a Percent of Forskolin Control

| SEQ ID NO: | Percent of Control Value |
|---|---|
| 21 | 56.0 |
| 39 | 114 |
| 40 | 96.1 |
| 46 | 66.8 |
| 47 | 45.3 |
| 52 | 88.0 |
| 203 | 54.5 |
| 204 | 57.3 |
| 205 | 64.5 |
| 206 | 50.6 |
| 207 | 51.6 |
| 208 | 62.4 |
| 209 | 33.3 |
| 210 | 29.2 |
| 211 | 33.7 |
| 213 | 36.0 |
| 214 | 50.2 |
| 215 | 37.4 |
| 216 | 50.1 |
| 217 | 40.3 |
| 218 | 43.6 |
| 219 | 41.5 |
| 2 | 59.2 |

Example 4

This example demonstrates the effect of the exemplary peptides on free fatty acid levels in cultured human primary adipocytes. Human primary adipocytes were seeded at 5,000-100,000 cells per well on 96-well, 48-well, or 24-well plates in Pre-adipocyte Medium (Zen-Bio, Durham, N.C.) and grown to confluence at 37° C. in a humidified atmosphere of 5% CO2/95% air. Two days after confluence, cells were placed in Adipocyte Differentiation Medium (Zen-Bio, Durham, N.C.) and cultured for three additional days at 37° C. in a humidified atmosphere of 5% CO2/95% air. The culture media was then replaced with Adipocyte Maintenance Medium (Zen-Bio) and the cells were maintained for an additional 11-21 days at 37° C. in a humidified atmosphere of 5% CO2/95% air with partial medium replacement every other day. Following 14-24 days of differentiation, test peptides were added at a final concentration of 25 μM and incubated for 18-20 hours in Adipocyte Maintenance Medium at 37° C. in a humidified atmosphere of 5% CO2/95%. After 18-20 hours, the media was exchanged with fresh Adipocyte Maintenance Medium containing test peptides and incubated for 1 h at 37° C. in a humidified atmosphere of 5% CO2/95%. After 1 h media was exchanged with Assay Buffer (Zen-Bio) containing isoproterenol (1 nM) (added to all samples except untreated controls) and test peptides. Cells were incubated for a further 3 hours at 37° C. in a humidified atmosphere of 5% CO2/95%. Free fatty acid concentrations in the media were determined using a Free Fatty Acid Assay Kit (Zen-Bio) according to the manufacturer's instructions using a plate reader (540 nm). Absorbance values were corrected for untreated background and expressed relative to isoproterenol treated cells. Treatment with isoproterenol (1 nM) alone was used as the free fatty acid level stimulatory control. The relative standard deviation of the isoproterenol control was <14%. Insulin was used as a highly potent positive control for decreasing free fatty acid levels. Free fatty acid levels for insulin (100 nM) treatment were <5% of the isoproterenol control value. The results are reported in Table 6.

TABLE 6

Free Fatty Acid Levels in Human Primary Adipocytes Expressed as a Percent of Isoproterenol Control

| SEQ ID NO: | Percent of Control Value |
|---|---|
| 8 | 22.2 |
| 21 | 88.9 |
| 39 | 22.2 |
| 40 | 122 |
| 45 | 22.2 |
| 46 | 71.6 |
| 47 | 60.5 |
| 52 | 126 |
| 58 | 164 |
| 69 | 53.0 |
| 208 | 70.9 |
| 209 | 66.8 |
| 210 | 75.5 |
| 211 | 79.9 |
| 213 | 103 |
| 219 | 69.4 |
| 2 | 107 |

Example 5

This example demonstrates the effect of the exemplary peptides on free fatty acid levels in cultured human primary adipocytes. Human primary adipocytes were seeded at 5,000-100,000 cells per well on 96-well, 48-well, or 24-well plate in Pre-adipocyte Medium (Zen-Bio, Durham, N.C.) and grown to confluence at 37° C. in a humidified atmosphere of 5% CO2/95% air. Two days after confluence, cells were placed in Adipocyte Differentiation Medium (Zen-Bio, Durham, N.C.) and cultured for three additional days at 37° C. in a humidified atmosphere of 5% CO2/95% air. The culture media was then replaced with Adipocyte Maintenance Medium (Zen-Bio) and the cells were maintained for an additional 11-21 days at 37° C. in a humidified atmosphere of 5% CO2/95% air with partial medium replacement every other day. Following 14-24 days of differentiation, test peptides were added at a final concentration of 25 μM and incubated for 18-20 hours in Adipocyte Maintenance Medium at 37° C. in a humidified atmosphere of 5% CO2/95%. After 18-20 hours, the media was exchanged with fresh Adipocyte Maintenance Medium containing test peptides and incubated for 1 h at 37° C. in a humidified atmosphere of 5% CO2/95%. After 1 h media was exchanged with Assay Buffer (Zen-Bio) containing forskolin (1 μM) (added to all samples except untreated controls) and test peptides. Cells were incubated for a further 3 hours at 37° C. in a humidified atmosphere of 5% CO2/95%. Free fatty acid concentrations in the media were determined using a Free Fatty Acid Assay Kit (Zen-Bio) according to the manufacturer's instructions using a plate reader (540 nm). Absorbance values were corrected for untreated background and expressed relative to forskolin treated cells. Treatment with forskolin (1 μM) alone was used as the free fatty acid level stimulatory control. The relative standard deviation of the forskolin control was <20%. Insulin was used as a highly potent positive control for decreasing free fatty acid levels. Free fatty acid levels for insulin (100 nM) treatment were <8% of the forskolin control value. The results are reported in Table 7.

TABLE 7

Free Fatty Acid Levels in Human Primary Adipocytes Expressed as a Percent of Forskolin Control

| SEQ ID NO: | Percent of Control Value |
|---|---|
| 8 | 107 |
| 18 | 101 |
| 19 | 113 |
| 21 | 113 |
| 39 | 80.8 |
| 40 | 107 |
| 45 | 125 |
| 46 | 73.9 |
| 47 | 89.9 |
| 52 | 107 |
| 58 | 134 |
| 69 | 119 |
| 203 | 75.2 |
| 204 | 94.3 |
| 205 | 94.5 |
| 206 | 100 |
| 207 | 108 |
| 208 | 90.2 |
| 209 | 90.1 |
| 210 | 95.2 |
| 211 | 90.1 |
| 213 | 90.8 |
| 214 | 89.9 |
| 215 | 102 |
| 216 | 110 |
| 217 | 108 |
| 218 | 75.4 |
| 219 | 84.0 |
| 2 | 111 |

Example 6

This example demonstrates the effect of the exemplary peptides on body weight, blood glucose levels, and fat mass in Diet Induced Obese (DIO) mice. Male C57BL/6 mice were maintained on a high fat diet for 18 weeks to develop diet induced obesity. Animals were randomized to treatment groups based on blood glucose levels and body weight. The peptides of the invention were administered to two groups of male DIO mice once or twice daily by subcutaneous or intraperitoneal injection at a dose of 15 mg/kg/dose for 10 days (N=8 animals per treatment group). An additional group of male DIO mice (n=8) received vehicle (water or saline) alone. Body weight, blood glucose levels and food intake were monitored. Body mass distribution (fat vs lean) was determined by quantitative whole body NMR prior to dosing and at the end of dosing. Administration of the peptides of the invention produced greater body weight loss, greater reduction in blood glucose, and greater decrease in fat mass from baseline values when compared to animals treated with vehicle alone (Table 8).

TABLE 8

Mean Difference from Vehicle Control for the Decrease from Baseline in Metabolic Parameters in Male DIO Mice Following 10 Days of Twice Daily Intraperitoneal Treatment at 15 mg/kg (N = 8)

| Treatment (SEQ ID NO) | Dose (mg/kg/dose) | Difference from Vehicle Control: Decrease from Baseline in Body Weight (%) | Difference from Vehicle Control: Decrease from Baseline in Blood Glucose (mg/dL) | Difference from Vehicle Control: Decrease from Baseline in Fat Mass (g) |
|---|---|---|---|---|
| 8 | 15 | −0.24 | −20.0 | −0.20 |
| 11 | 15 | −8.81 | −27.6 | −5.85 |
| 17 | 15 | −2.87 | −2.63 | −0.65 |
| 18 | 15 | −0.80 | 1.52 | −0.65 |
| 19 | 15 | −3.27 | −14.5 | −2.34 |
| 21 | 15 | −3.00 | −4.21 | −2.03 |
| 45 | 15 | −2.01 | 6.00 | −0.69 |
| 149 | 15 | −5.22 | −11.4 | −2.13 |
| 172 | 15 | −2.48 | −31.5 | −0.77 |
| 208 | 15 | −5.05 | −11.5 | −1.87 |
| 210 | 15 | −3.70 | 8.25 | −1.45 |
| 211 | 15 | −1.04 | −2.25 | −0.43 |
| 213 | 15 | −4.21 | −20.1 | −1.16 |
| 215 | 15 | 2.31 | 16.4 | 0.67 |
| 217 | 15 | −2.54 | −9.75 | −0.89 |
| 219 | 15 | −4.09 | −17.3 | −1.37 |
| 241 | 15 | −1.49 | −7.00 | −0.34 |
| 251 | 15 | −0.55 | −34.3 | 0.02 |
| 2 | 15 | −0.58 | −4.88 | −0.24 |

Example 7

This example demonstrates a 21-day study purposed to determine the effect of the exemplary peptides on body weight and fat mass in Diet Induced Obese (DIO) mice. Male C57BL/6 mice were maintained on a high fat diet for 12 to 22 weeks to develop diet induced obesity. Animals were randomized to treatment groups based on blood glucose levels and body weight. The peptides (SEQ ID No: 208 and SEQ ID NO: 210) were each administered to a group of male DIO mice twice daily by appropriate routes at a dose of 15 mg/kg/dose for 21 days (N=8 to 12 animals per treatment group). Additional groups of male DIO mice (n=8/group) received control test articles (liraglutide or pioglitazone) or vehicle (water or saline) alone. Metabolic parameters including body weight, blood glucose levels and food intake were monitored. Body mass distribution (fat vs lean) was determined where appropriate by quantitative whole body NMR prior to dosing and at the end of dosing. Administration of the peptides produced greater body weight loss, greater reduction in blood glucose, and/or greater decrease in fat mass from baseline values when compared to animals treated with the peptide of SEQ ID NO: 2, control test articles (pioglitazone or liraglutide) or with vehicle alone (Table 9).

TABLE 9

Mean (SD) Decrease from Baseline in Metabolic Parameters in Male DIO Mice Following 21 Days of Twice Daily Treatment at 15 mg/kg (N = 8-12)

| Treatment | Route | Dose (mg/kg/dose) | Decrease from Baseline in Body Weight (%) | Decrease from Baseline in Fat Mass (g) |
|---|---|---|---|---|
| Vehicle | IP | N/A | −5.7 (6.7) | −0.4 (1.2) |
| SEQ ID NO: 208 | IP | 15 | −17.2 (3.0) | −6.4 (0.5) |
| SEQ ID NO: 210 | IP | 15 | −14.1 (4.8) | ND |
| SEQ ID NO: 2 | IP | 15 | −9.3 (5.0) | ND |
| Liraglutide* | IP | 10 nmol/kg | −9.3 (2.9) | −2.1 (1.5) |
| Pioglitazone | PO | 15 | 1.0 (3.1) | ND |

*Once daily treatment.
IP—intraperitoneal.
PO—oral.
ND—not determined.

Example 8

This example demonstrates a 21-day study purposed to determine the effect of a combination therapy comprising the exemplary peptides of the present disclosure and a commercially-available anti-diabetes therapeutic on body weight and fat mass in Diet Induced Obese (DIO) mice.

Male C57BL/6 mice were maintained on a high fat diet for 12 to 22 weeks to develop diet induced obesity. Animals were randomized to treatment groups based on blood glucose levels and body weight. The peptides (SEQ ID No: 208 and SEQ ID NO: 210) were each administered to a group of male DIO mice once daily by appropriate routes at a dose of 5 mg/kg/dose for 21 days (N=8 animals per treatment group) in conjunction with intraperitoneal administration of liraglutide (10 nmol/kg per day). Additional groups of male DIO mice (n=8/group) received control test articles (liraglutide alone) or vehicle (water or saline) alone. Metabolic parameters including body weight, blood glucose levels and food intake were monitored. Body mass distribution (fat vs lean) was determined where appropriate by quantitative whole body NMR prior to dosing and at the end of dosing. Administration of the peptides in conjunction with liraglutide produced greater body weight loss, greater reduction in blood glucose, and/or greater decrease in fat mass from baseline values when compared to animals treated with liraglutide alone or with vehicle alone (Table 10).

TABLE 10

Mean (SD) Decrease from Baseline in Metabolic Parameters in Male DIO Mice Following 21 Days of Once Daily Treatment at 5 mg/kg (N = 8)

| Treatment | Route | Dose (mg/kg/dose) | Decrease from Baseline in Body Weight (%) | Decrease from Baseline in Fat Mass (g) |
|---|---|---|---|---|
| Vehicle* | IP | N/A | −5.7 | −0.4 |
| SEQ ID NO: 208 + liraglutide | SC IP | 5 10 nmol/kg | −11.3 | −3.5 |
| SEQ ID NO: 210 + liraglutide | SC IP | 5 10 nmol/kg | −11.8 | −3.9 |
| Liraglutide | IP | 10 nmol/kg | −9.3 | −2.1 |

*Twice daily treatment.

Example 9

This example demonstrates the effect of the exemplary peptides on triglyceride levels and markers of liver damage.

Male C57BL/6 mice were maintained on a high fat diet for 12 to 22 weeks to develop diet induced obesity. Animals were randomized to treatment groups based on blood glucose levels and body weight. The peptides (SEQ ID No: 208, and SEQ ID NO: 210) were each administered to a group of male DIO mice twice daily by appropriate routes at a dose of 15 mg/kg/dose for 21 days (N=8 to 12 animals per treatment group). Additional groups of male DIO mice (n=8/group) received control test articles (liraglutide) or vehicle (water or saline) alone. Serum samples were obtained at termination 2 hours after the first dose on Day 21. Samples were analyzed for standard clinical chemistry parameters by methods well known in the art. Administration of the peptides of SEQ ID NO: 208 and SEQ ID NO: 210 produced a greater reduction in serum triglycerides, ALT and AST when compared to animals treated with the control test article (liraglutide), or with vehicle alone (Table 11).

TABLE 11

Mean Concentrations of Triglycerides and Enzyme Markers of Liver Damage in Serum of Male DIO Mice Following 21 Days of Twice Daily Treatment (N = 8 – 12)

| Treatment | Route | Dose (mg/kg/dose) | Triglycerides (mg/dL) | ALT (U/L) | AST (U/L) |
|---|---|---|---|---|---|
| Vehicle | IP | N/A | 122 | 97.0 | 136 |
| SEQ ID NO: 208 | IP | 15 | 76.0 | 40.4 | 70.0 |
| SEQ ID NO: 210 | IP | 15 | 93.0 | 45.0 | 125 |
| Liraglutide* | IP | 10 nmol/kg | 109 | 70.8 | 119 |

*Once daily treatment.
IP—intraperitonea.

Example 10

This example demonstrates the pharmacokinetics of the exemplary peptides of the present disclosure in cynomolgus monkeys.

Male cynomolgus monkeys (2 to 6 kg) are fasted for 8 hours prior to dosing. Animals are injected with a single intravenous or subcutaneous bolus dose of the test peptide (0.1 to 15 mg/kg). Intravenous injections are administered via the saphenous or another suitable vein. Subcutaneous injections are administered in the scapular region. Blood samples are withdrawn at intervals over 24 hours and processed for plasma. Food is returned at four hours post-injection. Concentrations of peptides and/or metabolites in plasma samples are determined by suitable analytical methods (e.g., LCMS) and pharmacokinetic parameters are calculated by non-compartmental methods. The peptides of the invention show increased exposure (e.g., increased $C_{max}$, AUC, and/or half-life) relative to SEQ ID No: 2.

Example 11

This example demonstrates the efficacy of the exemplary peptides of the present disclosure in a non-human primate model of obesity.

Spontaneously obese male cynomolgus monkeys are acclimated to dosing and handling for at least 3 weeks. Baseline animal characteristics are determined and animals are randomized into treatment groups based upon body weight and baseline metabolic parameters such as triglyceride levels. Following randomization, groups of monkeys receive daily or twice daily doses of the peptides of the present invention administered by a suitable route for 4 or more weeks. Control groups of monkeys receive daily doses of vehicle or positive control. Food consumption and body weight are measured at intervals during the study. Effects of the administered peptides on body weight, food intake, BMI and/or metabolic parameters are compared to control animals treated with vehicle.

Example 12

This example demonstrates the efficacy of the exemplary peptides of the present disclosure in STAM® Mouse Model of Non-alcoholic Steatohepatitis (NASH).

In the STAM model of NASH, C57/bl6 are injected with a single subcutaneous dose of streptotoxin, three days after birth to destroy pancreatic β-cells. At the age of 4 weeks, animals are put on a high fat diet. This combined treatment results in the development of steatosis, fibrosis, cirrhosis and finally hepatocellular carcinoma (HCC) along with hyperglycemia and moderate hyperlipidemia thus closely resembling human NASH. Beginning at 5 weeks of age, groups of STAM animals (8 animals per group) are treated with the peptides of the present invention administered daily or twice daily by an appropriate route, until study termination. A control group of animals receive daily administration of a suitable positive control compound (e.g. telmisartan). At approximately 10 weeks of age, metabolic parameters are determined and animals are sacrificed. Liver samples are obtained and fixed, embedded in paraffin, stained with hematoxylin and eosin or Masson's trichrome, and examined by light microscopy. The extent of steatosis and the non-alcoholic fatty liver disease (NAFLD) activity score (NAS) are determined histopathologically according to methods known in the art.

Example 13

This example demonstrates the efficacy of the exemplary peptides of the present disclosure on tumor growth in mouse xenograft models bearing tumors.

Mouse xenograft models are prepared by methods well known in the art. For example, SCID mice are injected with human tumor cells (for example, MCF-7, MDA-MB-231, PC-3, or the like) and tumor growth is monitored. When tumors are of sufficient size, animals are randomized to treatment groups and dosed daily, every other day, or weekly with the peptides of the invention, vehicle control, positive control (e.g., gemcitabine or paclitaxel) or the combination of the peptides of the invention+positive control. Tumor growth, body weight, and survival are monitored over 14 to 28 days. Administration of the peptides of the invention alone and/or in combination with positive control is examined for decreased tumor growth and/or extension of survival when compared to animals treated with vehicle control.

Example 14

This example demonstrates the stability of exemplary peptides of the present disclosure in mouse plasma.

Peptides (100 uM) were incubated in pooled mouse plasma at 37° C. and samples were removed and immediately analyzed for the concentration of intact peptide by LC/MS/MS over the course of 3 hours. The percent of peptide remaining in plasma at each time point was calculated relative to the initial peak area (Table 12).

TABLE 12

Stability in Mouse Plasma

| SEQ ID NO: | % Remaining at Each Time Point | | | | | |
|---|---|---|---|---|---|---|
| | 0 min | 15 min | 30 min | 60 min | 120 min | 180 min |
| 8 | 100 | 13.2 | 11.2 | 10.1 | 11.7 | 9.81 |
| 18 | 100 | 30.8 | 24.0 | 19.4 | 9.02 | 4.53 |
| 19 | 100 | 18.8 | 18.2 | 8.52 | 1.82 | 0.22 |
| 21 | 100 | 29.9 | 31.0 | 21.5 | 6.41 | 2.13 |
| 61 | 100 | 69.1 | 65.8 | 59.1 | 43.3 | 29.1 |
| 6 | 100 | 17.5 | 19.3 | 21.4 | 10.9 | 6.89 |
| 11 | 100 | 18.3 | 17.5 | 11.5 | 5.25 | 2.38 |
| 15 | 100 | 19.5 | 18.8 | 21.8 | 6.63 | 0.00 |
| 39 | 100 | 39.5 | 38.8 | 54.9 | 24.0 | 16.3 |
| 46 | 100 | 28.1 | 26.4 | 31.4 | 12.4 | 12.6 |
| 47 | 100 | 56.7 | 49.0 | 38.9 | 23.8 | 18.3 |
| 69 | 100 | 33.1 | 37.7 | 19.3 | 5.96 | 2.11 |
| 208 | 100 | 63.3 | 53.1 | 48.9 | 45.3 | 47.7 |
| 209 | 100 | 47.5 | 38.9 | 38.0 | 36.3 | 38.3 |

TABLE 12-continued

Stability in Mouse Plasma

| SEQ ID NO: | % Remaining at Each Time Point | | | | | |
|---|---|---|---|---|---|---|
| | 0 min | 15 min | 30 min | 60 min | 120 min | 180 min |
| 210 | 100 | 56.2 | 44.8 | 39.6 | 34.4 | 41.4 |
| 213 | 100 | 41.0 | 29.4 | 20.5 | 10.0 | 7.45 |
| 215 | 100 | 71.2 | 37.1 | 42.1 | 15.4 | 6.98 |
| 217 | 100 | 71.0 | 33.2 | 53.6 | 22.8 | 14.1 |
| 219 | 100 | 44.5 | 40.9 | 41.3 | 19.8 | 12.2 |
| 2 | 100 | 32.0 | 14.8 | 7.58 | 4.78 | 1.21 |

Example 15

This example demonstrates the stability of exemplary peptides of the present disclosure in mouse plasma.

Peptides (10 uM) were incubated in pooled mouse plasma at 37° C. and samples were removed and immediately analyzed for the concentration of intact peptide by LC/MS/MS over the course of 3 hours. The percent of peptide remaining in plasma at each time point was calculated relative to the initial peak area (Table 13).

TABLE 13

Stability in Mouse Plasma

| SEQ ID NO: | % Remaining at Each Time Point | | | | | |
|---|---|---|---|---|---|---|
| | 0 min | 15 min | 30 min | 60 min | 120 min | 180 min |
| 17 | 100 | 46.0 | 26.8 | 11.9 | 11.3 | 7.35 |
| 45 | 100 | 66.5 | 33.0 | 7.31 | 0.00 | 0.00 |
| 149 | 100 | 59.3 | 36.1 | 11.1 | 0.98 | 0.28 |
| 172 | 100 | 59.4 | 33.6 | 6.43 | 0.44 | 0.00 |
| 208 | 100 | 77.0 | 51.8 | 21.0 | 3.94 | 1.09 |
| 210 | 100 | 85.7 | 79.5 | 61.9 | 35.4 | 23.0 |
| 211 | 100 | 85.2 | 72.8 | 52.3 | 30.3 | 17.9 |
| 241 | 100 | 98.8 | 96.8 | 89.5 | 84.3 | 80.7 |
| 249 | 100 | 46.7 | 40.5 | 28.3 | 15.8 | 11.1 |
| 250 | 100 | 63.2 | 54.1 | 35.9 | 20.0 | 11.7 |
| 251 | 100 | 70.6 | 47.5 | 44.4 | 38.1 | 30.2 |
| 254 | 100 | 52.4 | 33.3 | 30.3 | 24.0 | 18.1 |
| 255 | 100 | 78.3 | 62.6 | 40.9 | 28.7 | 19.6 |
| 258 | 100 | 63.2 | 53.5 | 36.3 | 30.3 | 21.7 |
| 259 | 100 | 82.2 | 65.2 | 42.2 | 32.8 | 34.8 |
| 260 | 100 | 79.4 | 68.8 | 53.1 | 35.7 | 35.9 |
| 261 | 100 | 85.0 | 73.4 | 69.3 | 68.1 | 73.7 |
| 263 | 100 | 80.7 | 68.6 | 46.9 | 40.5 | 30.8 |
| 264 | 100 | 76.7 | 68.2 | 54.5 | 59.4 | 56.1 |
| 265 | 100 | 83.3 | 74.5 | 54.9 | 56.0 | 51.7 |
| 266 | 100 | 70.7 | 72.3 | 38.3 | 74.8 | 51.1 |
| 268 | 100 | 76.1 | 49.5 | 20.3 | 0.48 | 0.00 |
| 269 | 100 | 70.0 | 45.8 | 17.2 | 2.64 | 0.43 |
| 270 | 100 | 13.8 | 3.22 | 0.59 | 0.36 | 0.21 |
| 282 | 100 | 34.9 | 25.7 | 1.92 | 0.41 | 0.29 |
| 283 | 100 | 54.3 | 25.8 | 2.05 | 0.35 | 0.14 |
| 284 | 100 | 75.3 | 60.1 | 41.1 | 22.1 | 13.7 |
| 285 | 100 | 38.5 | 16.7 | 9.17 | 1.76 | 0.87 |
| 286 | 100 | 88.4 | 74.7 | 57.1 | 36.4 | 25.9 |
| 287 | 100 | 64.0 | 45.2 | 26.8 | 8.76 | 2.93 |
| 288 | 100 | 90.0 | 81.9 | 77.4 | 69.2 | 67.0 |
| 289 | 100 | 82.9 | 74.6 | 78.4 | 77.2 | 75.6 |
| 290 | 100 | 89.5 | 81.5 | 79.4 | 70.8 | 68.0 |
| 2 | 100 | 78.3 | 38.9 | 9.6 | 0.8 | 0.4 |

Example 16

This example demonstrates the stability of the exemplary peptides of the present disclosure in monkey and human plasma. Peptides (10 uM) were incubated in pooled mouse or human plasma at 37° C. and samples were removed and immediately analyzed for the concentration of intact peptide by LC/MS/MS over the course of 3 hours. The percent of peptide remaining in plasma at each time point was calculated relative to the initial peak area (Table 14).

TABLE 14

Stability in Monkey and Human Plasma

| SPECIES | SEQ ID NO: | % Remaining at Each Time Point | | | |
|---|---|---|---|---|---|
| | | 0 min | 60 min | 120 min | 180 min |
| Monkey | 208 | 100 | 106 | 89.0 | 68.0 |
| | 210 | 100 | 105 | 87.9 | 77.9 |
| | 2 | 100 | 72.8 | 39.8 | 23.4 |
| Human | 208 | 100 | 105 | 86.6 | 85.4 |
| | 210 | 100 | 106 | 90.8 | 95.8 |
| | 2 | 100 | 56.3 | 44.7 | 38.4 |

Example 17

This example demonstrates the effect of the exemplary peptides on free fatty acid levels in cultured mouse adipocytes. Mouse 3T3-L1 cells were seeded at a density between 1,000-20,000 cells per well on 96-well, 48-well, or 24-well plates in Pre-adipocyte Medium (Zen-Bio, Durham, N.C.) and grown to confluence at 37° C. in a humidified atmosphere of 5% CO2/95% air. Two days after confluence, cells were placed in Adipocyte Differentiation Medium (Zen-Bio, Durham, N.C.) and cultured for three additional days at 37° C. in a humidified atmosphere of 5% CO2/95% air. The culture media was then replaced with Adipocyte Maintenance Medium (Zen-Bio) and the cells were maintained for an additional 9-14 days at 37° C. in a humidified atmosphere of 5% CO2/95% air with partial medium replacement every other day. Following 12-17 days of differentiation, test peptides were added at a final concentration of 25-50 μM and incubated for 18-20 hours in Adipocyte Maintenance Medium at 37° C. in a humidified atmosphere of 5% CO2/95%. After the media incubation, media was removed and exchanged with Assay Buffer (Zen-Bio) containing isoproterenol (1 nM) (added to all samples except untreated controls) and the test peptides. Cells were incubated for a further 3 hours at 37° C. in a humidified atmosphere of 5% CO2/95%. Free fatty acid concentrations in the media were determined using a Free Fatty Acid Assay Kit (Zen-Bio) according to the manufacturer's instructions using a plate reader (540 nm).

Absorbance values were corrected for untreated background and expressed relative to isoproterenol treated cells. Treatment with isoproterenol (1 nM) alone was used as the free fatty acid level stimulatory control. The relative standard deviation of the isoproterenol control was <10%. Insulin was used as a highly potent positive control for decreasing free fatty acid levels. Free fatty acid levels for insulin (100 nM) treatment were <5% of the isoproterenol control value. The results are reported in Table 15.

TABLE 15

Free Fatty Acid Levels in 3T3-L1 Adipocytes Expressed as a Percent of Isoproterenol Control

| SEQ ID NO: | Peptide Concentration (μM) | Percent of Control Value |
|---|---|---|
| 354 | 25 | 92.3 |
| 355 | 25 | 97.8 |
| 356 | 25 | 100.6 |

TABLE 15-continued

Free Fatty Acid Levels in 3T3-L1 Adipocytes Expressed as a Percent of Isoproterenol Control

| SEQ ID NO: | Peptide Concentration (µM) | Percent of Control Value |
|---|---|---|
| 357 | 25 | 30.8 |
| 358 | 25 | 60.8 |
| 359 | 25 | 34.8 |
| 360 | 25 | 94.6 |
| 351 | 25 | 100.1 |
| 296 | 25 | 85.0 |
| 361 | 25 | 76.3 |
| 362 | 25 | 92.5 |
| 363 | 25 | 131.5 |
| 364 | 25 | 87.2 |
| 365 | 25 | 85.6 |
| 366 | 25 | 82.0 |
| 367 | 50 | 59.0 |
| 368 | 50 | 70.0 |
| 369 | 50 | 87.5 |
| 370 | 50 | 129.0 |
| 371 | 50 | 118.0 |
| 372 | 50 | 168.0 |

Example 18

This example demonstrates the efficacy of the exemplary peptides of the present disclosure in STAM® Mouse Model of Non-alcoholic Steatohepatitis (NASH). In the STAM® model of NASH, C57/BL6 mice were injected with a single subcutaneous dose of 200 µg streptotoxin, two days after birth to destroy pancreatic β-cells. At the age of 4 weeks, animals were put on a high fat diet (57% kcal from fat) and maintained on the same diet throughout the study. This combined treatment resulted in the development of steatosis, fibrosis, cirrhosis and finally hepatocellular carcinoma (HCC) along with hyperglycemia and moderate hyperlipidemia thus closely resembling human NASH. Beginning at 6 weeks of age, groups of STAM animals (8 animals per group) were treated with the peptides of the present invention administered twice daily by intraperitoneal injection, until study termination. A control group of STAM animals (n=8) received daily doses of telmisartan control compound (10 mg/kg). An additional group of normal mice (n=8) received no treatment. After 21 days of dosing, at 9 weeks of age, metabolic parameters were determined and animals were sacrificed. Liver samples were obtained and fixed, embedded in paraffin, stained with hematoxylin and eosin, and examined by light microscopy. The extent of steatosis and the non-alcoholic fatty liver disease (NAFLD) activity score (NAS) were determined histopathologically according to methods known in the art. The resulting NAS scores are shown in Table 16.

TABLE 16

Mean (SD) NAFLD Activity Score (NAS) in Male STAM® Mice Following 21 Days of Treatment Beginning at 6 Weeks of Age (N = 8)

| Mice | Treatment | Route | Frequency | Dose (mg/kg/dose) | NAFLD Activity Score (NAS) |
|---|---|---|---|---|---|
| Normal | None | N/A | N/A | N/A | 0.0 (0.0) |
| STAM | Vehicle* | IP | BID | N/A | 4.9 (0.6) |
| STAM | SEQ ID NO: 208 | IP | BID | 15 | 3.7 (0.5)* |
| STAM | SEQ ID NO: 210 | IP | BID | 15 | 3.3 (1.1)* |
| STAM | Telmisartan | PO | QD | 10 | 2.6 (0.5)* |

*Significant reduction in NAS score compared to Vehicle control (P < 0.01 by Students t-test and Mann-Whitney test)

Example 19

This example demonstrates the efficacy of the exemplary peptides of the present disclosure in reducing liver triglyceride levels and plasma ALT levels in the STAM® Mouse Model of Non-alcoholic Steatohepatitis (NASH). In the STAM® model of NASH, C57/BL6 mice were injected with a single subcutaneous dose of 200 µg streptotoxin, two days after birth to destroy pancreatic β-cells. At the age of 4 weeks, animals were put on a high fat diet (57% kcal from fat) and maintained on the same diet throughout the study. This combined treatment resulted in the development of steatosis, fibrosis, cirrhosis and finally hepatocellular carcinoma (HCC) along with hyperglycemia and moderate hyperlipidemia thus closely resembling human NASH. Beginning at 6 weeks of age, groups of STAM animals (8 animals per group) were treated with the peptides of the present invention administered twice daily by intraperitoneal injection, until study termination. A control group of STAM animals (n=8) received daily doses of telmisartan control compound (10 mg/kg). An additional group of normal mice (n=8) received no treatment. After 21 days of dosing, at 9 weeks of age, metabolic parameters were determined and animals were sacrificed. Liver triglyceride levels were determined by homogenization in chloroform-methanol and incubation overnight at room temperature. After washing with chloroform-methanol-water, the extracts were evaporated to dryness and dissolved in isopropanol. Liver triglyceride content was then measured by Triglyceride E-test (Wako, Japan). Plasma ALT levels were determined by using Fuji Dri-Chem 7000 (Fujifilm, Japan). The results are shown in Table 17.

TABLE 17

Mean (SD) Liver Triglyceride Levels and Plasma ALT Levels in Male STAM® Mice Following 21 Days of Treatment Beginning at 6 Weeks of Age (N = 8)

| Mice | Treatment | Route | Frequency | Dose (mg/kg/dose) | Liver Triglyceride Levels (mg/g liver) | Plasma ALT (U/L) |
|---|---|---|---|---|---|---|
| Normal | None | N/A | N/A | N/A | 8.2 (2.4) | 41 (21) |
| STAM | Vehicle | IP | BID | N/A | 63.0 (20.6) | 61 (13) |
| STAM | SEQ ID NO: 208 | IP | BID | 15 | 35.3 (15.1)* | 43 (16)* |

TABLE 17-continued

Mean (SD) Liver Triglyceride Levels and Plasma ALT Levels in Male STAM ® Mice
Following 21 Days of Treatment Beginning at 6 Weeks of Age (N = 8)

| Mice | Treatment | Route | Frequency | Dose (mg/kg/dose) | Liver Triglyceride Levels (mg/g liver) | Plasma ALT (U/L) |
|---|---|---|---|---|---|---|
| STAM | SEQ ID NO: 210 | IP | BID | 15 | 43.6 (9.3)* | 37 (13)* |
| STAM | Telmisartan | PO | BID | 10 mg/kg | 18.8 (5.8)* | 39 (6)* |

*Significant difference compared to Vehicle control (P < 0.05 by Student's t-test)

Example 20

This example demonstrates the effect of the exemplary peptides on body weight, blood glucose levels, and fat mass in Diet Induced Obese (DIO) mice.

Male C57BL/6 mice were maintained on a high fat diet for 18 weeks to develop diet induced obesity. Animals were randomized to treatment groups based on blood glucose levels and body weight. The peptides of the invention were administered to two groups of male DIO mice once or twice daily by intraperitoneal or subcutaneous injection at a doses of 5 to 15 mg/kg/dose for 10 days (N=8 animals per treatment group). An additional group of male DIO mice (n=8) received vehicle (water or saline) alone. Body weight, blood glucose levels and food intake were monitored. Body mass distribution (fat vs lean) was determined by quantitative whole body NMR prior to dosing and at the end of dosing. Administration of the peptides of the invention produced body weight loss and/or decrease in fat mass from baseline values (Table 18).

TABLE 18

Mean (SEM) Decrease from Baseline in Metabolic Parameters
in Male DIO Mice Following 10 Days of Twice Daily
Intraperitoneal Treatment at 15 mg/kg (N = 8)

| Treatment (SEQ ID NO) | Dose (mg/kg/dose) | Decrease from Baseline in Body Weight (%) | Decrease from Baseline in Fat Mass (g) |
|---|---|---|---|
| 283 | 15 | −5.5 (0.4) | −3.0 (0.2) |
| 361 | 15 | −5.8 (0.8) | −3.8 (0.5) |
| 364 | 15 | −6.6 (1.6) | −3.7 (1.2) |
| 357 | 15 | −3.4 (1.0) | −1.0 (0.4) |
| 357 | 15* | −1.2 (0.6) | −0.2 (0.2) |

*Once daily administration.

Example 21.—Glucose Utilization

The effect of the peptides on glucose metabolism can be assessed using an assay of glucose utilization in cultured cultured cells such as mouse myoblasts. Peptides are initially prepared as 10 mM stock in DMSO and used at a final concentration of 10 μM (0.1% DMSO). C2C12 mouse myoblast cell line is purchased from American Type Culture Collection (Manassas, Va.). C2C12 cultures are maintained at 37° C. in a humidified atmosphere of 5% CO2/95% air with medium changes every second day. C2C12 cells are grown in DMEM (1 g/L glucose) supplemented with 10% FBS with 100 IU/ml penicillin and 100 μg/ml streptomycin. C2C12 cells are seeded at 7,000 cells per well on 96-well plates and cultured to confluence. Once the cell reached confluence the media is changed to DMEM (1 g/L glucose) supplemented with 2% HS with 100 IU/ml penicillin and 100 μg/ml streptomycin and maintained at 37° C. in a humidified atmosphere of 5% CO2/95% air. 5 days post-induction of differentiation fresh DMEM (1 g/L glucose) supplemented with 2% HS with 100 IU/ml penicillin and 100 μg/ml streptomycin is added to cultures. Cells are maintained at 37° C. in a humidified atmosphere of 5% $CO_2$ and 95% air for 5 hours. After 5 hours test peptides at 10 μM or controls (0.5 mM or 1 mM metformin in 1% DMSO) prepared in fresh differentiation medium are added to cells and the cultures are maintained at 37° C. in a humidified atmosphere of 5% CO2/95% air for 18-22 hours. At the end of the incubation culture media is removed from the cells and the remaining glucose concentration is measured using a Glucose Assay kit (Abcam) according to the manufacturer's instructions, using a Cytation 3 plate reader at 570 nm (BioTek, Winooski, Vt.). Glucose concentrations in the medium are calculated relative to 0.1% DMSO treated control cells. Metformin is used as a positive control for reduction of glucose levels. Administration of the peptides of the invention alone and/or in combination with positive control results in increased or decreased glucose utilization in C2C12 mouse myoblasts than those treated with vehicle control.

Example 22—ATP Levels in Cells Exposed to Staurosporine

The potential cytoprotective effects or potential synergistic effects on cell viability of the peptides can be assessed using an assay of ATP levels in cultured cells such as human neuroblastoma cells exposed to a suitable stress such as staurosporine exposure. Peptides are initially prepared as 10 mM stock in DMSO and tested at a final concentration of 10 μM (0.1% DMSO). Staurosporine is used as a highly potent inducer of apoptosis/cell death that reduces cellular ATP levels. Staurosporin is used at concentrations ranging from 10 nM to 1 μM. CellTiter-Glo® Assay kit is purchased from Promega. SH-SY5Y human neuroblastoma cell line is purchased from American Type Culture Collection (Manassas, Va.) and licensed from Memorial Sloan-Kettering Cancer Center (New York, N.Y.). SH-SY5Y cells are grown in DMEM/F12 medium supplemented with 10% FBS with 100 IU/ml penicillin and 100 μg/ml streptomycin. Cultures are maintained at 37° C. in a humidified atmosphere of 5% CO2/95% air. SH-SY5Y cells are seeded at 30,000 cells per well on 96-well plates. The next day cells are incubated with test peptides at 10 μM in 0.1% DMSO and staurosporine (40 μM) and maintained at 37° C. in a humidified atmosphere of 5% CO2/95% air for 18-20 hours. ATP levels are determined using a CellTiter-Glo Assay kit (Promega) according to the manufacturer's instructions. Luminescence for each sample well on the plate is measured using a Cytation 3 plate reader (BioTek, Winooski, Vt.). Activity is calculated relative to the reduction in ATP by treatment with 40 µM staurosporine. A value less than 100% is indicative of a cytoprotective effect, while a value greater than 100% is indicative of a synergistic effect on viability. The relative standard deviation of the result for the 40 µM staurosporine treated control cells is <5%. Administration of the peptides of the invention alone and/or in combination with positive control results in increased or decreased ATP levels in cultured SH-SY5Y nuroblastoma cells exposed to staurosporine than those treated with vehicle control.

All of the articles and methods disclosed and claimed herein can be made and executed without undue experimentation in light of the present disclosure. While the articles and methods of this disclosure have been described in terms of preferred embodiments, it will be apparent to those of skill in the art that variations may be applied to the articles and methods without departing from the spirit and scope of the disclosure. All such variations and equivalents apparent to those skilled in the art, whether now existing or later developed, are deemed to be within the spirit and scope of the disclosure as defined by the appended claims. For example, all aspects and/or embodiments described herein as methods of using are also contemplated as a composition for use as described, or a composition for use in a medicament for the specified use. All patents, patent applications, and publications mentioned in the specification are indicative of the levels of those of ordinary skill in the art to which the disclosure pertains. The disclosure illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended claims.

All references, including publications, patent applications, and patents, cited herein are hereby incorporated by reference in their entirety and to the same extent as if each reference were individually and specifically indicated to be incorporated by reference and were set forth in its entirety herein (to the maximum extent permitted by law). All headings and sub-headings are used herein for convenience only and should not be construed as being limiting in any way. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure. The citation and incorporation of patent documents herein is done for convenience only and does not reflect any view of the validity, patentability, and/or enforceability of such patent documents.

This disclosure includes all modifications and equivalents of the subject matter recited in the aspects appended hereto as permitted by applicable law.

What is claimed is:

1. A peptide comprising the amino acid sequence of formula I:

$$X^1\text{-QE-}X^2\text{-}X^3\text{-YI-}X^4\text{-Y-}X^5\text{-R-}X^6 \quad \text{(I) (SEQ ID NO: 1)}$$

wherein $X^1$ is absent or if present is $X^7$—RW, wherein $X^7$ is absent or if present is M or E;

$X^2$ is M, A or E;

$X^3$ is G, N or Q;

$X^4$ is F or A;

$X^5$ is P or A;

$X^6$ is absent or if present is KL-$X^8$ or $X^9$-LR, wherein $X^8$ is absent or if present is R or A and $X^9$ is selected from K, A, (dA), N and Q;

wherein the amino acid sequence of formula I is selected from the group consisting of:

MRWQEAGYIFYPRKLR; (SEQ ID NO: 11)

MRWQEMGYIFYPR(dA)LR; (SEQ ID NO: 149)

MRWQEMNYIFYPR; (SEQ ID NO: 208)

MRWQEMGYIFYPRNLR; (SEQ ID NO: 213)

MRWQEMQYIFYPRALR; (SEQ ID NO: 219)

RWQEMNYIFYPR; (SEQ ID NO: 248)

MRWQEMGYIFYPRALR; (SEQ ID NO: 19)

MRWQEMGYIFYPRKLA; (SEQ ID NO: 21)

MRWQEMGYIFYARKLR; (SEQ ID NO: 17)

RWQEMGYIFYPRQLR; (SEQ ID NO: 217)

MRWQEEGYIFYPRKLR; (SEQ ID NO: 172)

ERWQEAGYIAYPR; and (SEQ ID NO: 241)

RWQEMQYIFYPR; (SEQ ID NO: 211)

or C-terminal acids or amides, or N-acetyl derivatives thereof; or pharmaceutically acceptable salts thereof.

2. The peptide or C-terminal acids or amides, or N-acetyl derivatives thereof according to claim 1 that is isolated; or pharmaceutically acceptable salts thereof.

3. A peptide or C-terminal acids or amides, or N-acetyl derivatives thereof of claim 1, further comprising a duration enhancing moiety.

4. The peptide of claim 1 consisting of MRWQEMNYIFYPR (SEQ ID NO: 208); or C-terminal acids or amides, or N-acetyl derivatives thereof; or pharmaceutically acceptable salts thereof.

5. The peptide of claim 1 consisting of RWQEMNYIFYPR (SEQ ID NO: 248); or C-terminal acids or amides, or N-acetyl derivatives thereof; or pharmaceutically acceptable salts thereof.

6. The peptide of claim 1 consisting of RWQEMQYIFYPR (SEQ ID NO: 211); or C-terminal acids or amides, or N-acetyl derivatives thereof; or pharmaceutically acceptable salts thereof.

7. A peptide comprising the amino acid sequence of formula I:

$$X^1\text{-QE-}X^2\text{—}X^3\text{—YI—}X^4\text{—Y—}X^5\text{—R—}X^6 \quad \text{(I) (SEQ ID NO: 1)}$$

wherein

X¹ is absent or if present is X⁷—RW, wherein X⁷ is absent or if present is M or E;

X² is M, A or E;

X³ is N or Q;

X⁴ is F or A;

X⁵ is P or A; and

X⁶ is absent or if present is KL-X⁸ or X⁹-LR, wherein X⁸ is absent or if present is R or A and X⁹ is selected from K, A, (dA), N and Q; or pharmaceutically acceptable salts thereof, or C-terminal acids or amides, or N-acetyl derivatives thereof; or pharmaceutically acceptable salts thereof.

8. The peptide according to claim 1 or claim 7 that is 10-35 amino acids in length; or C-terminal acids or amides, or N-acetyl derivatives thereof; or pharmaceutically acceptable salts thereof.

9. The peptide of claim 4 or claim 7 wherein the peptide is derivatized.

10. The peptide of claim 9 wherein the derivatization is acetylation, pegylation, biotinylation or acylation.

11. The peptide of claim 10 wherein the derivative is PEG600, acetyl, biotin or palmityl.

12. A conjugate comprising the peptide of claim 1 or claim 7 and a heterologous moiety; or C-terminal acids or amides, or N-acetyl derivatives thereof; or pharmaceutically acceptable salts thereof.

13. A nucleic acid comprising a nucleotide sequence encoding the peptide of claim 1 or claim 7, wherein the peptide has an amino acid sequence that can be coded for by a nucleic acid.

14. An expression vector comprising the nucleic acid of claim 13.

15. A host cell comprising the nucleic acid of claim 13 or comprising an expression vector that comprises said nucleic acid.

16. A composition comprising the peptide of claim 1 or claim 7, and a carrier, excipient, or diluent.

17. The composition of claim 16, wherein the peptide comprises MRWQEMNYIFYPR (SEQ ID NO: 208); or C-terminal acids or amides, or N-acetyl derivatives thereof; or pharmaceutically acceptable salts thereof.

18. The composition of claim 16, wherein the peptide comprises RWQEMNYIFYPR (SEQ ID NO: 248); or C-terminal acids or amides, or N-acetyl derivatives thereof; or pharmaceutically acceptable salts thereof.

19. The composition of claim 16, wherein the peptide comprises RWQEMQYIFYPR (SEQ ID NO: 211); or C-terminal acids or amides, or N-acetyl derivatives thereof; or pharmaceutically acceptable salts thereof.

20. A kit comprising the peptide of claim 1 or claim 7, or C-terminal acids or amides, or N-acetyl derivatives thereof; or pharmaceutically acceptable salts thereof, in a container or a package.

21. A method of producing the peptide or peptide analog according to claim 1 or claim 7, said method comprising:

(i) reacting a first amino acid with a second amino acid to form a covalent linkage between the first amino acid and the second amino acid, wherein the first amino acid or the second amino acid optionally is attached to another amino acid, and (ii) repeating the reacting step of (i), whereupon the peptide or peptide analog of claim 1 or claim 7 is produced.

22. A method of treating a subject having a liver disease, comprising administering to the subject the peptide of claim 1 or claim 7 in an amount effective to treat the liver disease.

23. The method of claim 22, wherein the liver disease is a fatty liver disease.

24. The method of claim 23, wherein the fatty liver disease is NAFLD or NASH.

25. The method of claim 24, wherein the peptide comprises MRWQEMNYIFYPR (SEQ ID NO: 208); or C-terminal acids or amides, or N-acetyl derivatives thereof; or pharmaceutically acceptable salts thereof.

26. The method of claim 24, wherein the peptide comprises RWQEMNYIFYPR (SEQ ID NO: 248); or C-terminal acids or amides, or N-acetyl derivatives thereof; or pharmaceutically acceptable salts thereof.

27. The method of claim 24, wherein the peptide comprises RWQEMQYIFYPR (SEQ ID NO: 211); or C-terminal acids or amides, or N-acetyl derivatives thereof; or pharmaceutically acceptable salts thereof.

28. The method according to claim 27, wherein the peptide or C-terminal acids or amides, or N-acetyl derivatives thereof decreases free fatty acid levels in human primary adipocytes.

29. A method of reduction, remission or regression of liver disease in a subject with the liver disease, comprising administering to the subject the peptide of claim 1 or claim 7, in an amount effective to arrest the progression the liver disease.

30. A peptide or peptide analog comprising both RWQE (SEQ ID NO: 294) and YIFY (SEQ ID NO: 295), wherein the peptide or peptide analog is 8 to 20 amino acids in length, and wherein the peptide or peptide analog:

(i) exhibits at least a 20% stability in mouse plasma for 60 minutes at 37 degrees Celsius, (ii) decreases free fatty acid levels in human primary adipocytes, or (iii) or both (i) and (ii).

31. The peptide or peptide analog of claim 30 comprising the amino acid sequence of RWQEX¹X²YIFY (SEQ ID NO: 319), wherein each of X¹ and X² independently is any amino acid.

32. The peptide or peptide analog of claim 31, wherein X¹X² is Met-Asn, Met-Gln, Ala-Gly, Met-Ala, Nle-Gly, Gly-Gly, Met-(dA), (dA)-Gly, Glu-Gly, Met-Glu, Cys-Gly, Glu-Asn, or Glu-Gln.

33. The peptide or peptide analog of claim 30, or C-terminal acids or amides, or N-acetyl derivatives thereof, that decreases free fatty acid levels in human primary adipocytes.

* * * * *

UNITED STATES PATENT AND TRADEMARK OFFICE
CERTIFICATE OF CORRECTION

PATENT NO. : 11,111,271 B2
APPLICATION NO. : 16/336089
DATED : September 7, 2021
INVENTOR(S) : Kenneth C. Cundy et al.

It is certified that error appears in the above-identified patent and that said Letters Patent is hereby corrected as shown below:

In the Specification
At Column 10, Line 11, "D-siomer" should be -- D-isomer --.
At Column 39, Line 3, "P3" should be -- β -- and "L-3" should be -- L-β --.
At Column 39, Line 63, "L-3" should be -- L-β --.
At Column 40, Line 59, "L-3" should be -- L-β --.
At Column 43, Line 2, "L-oa" should be -- L-α --.
At Column 50, Line 44, "3" should be -- β --.
At Column 54, Line 9, "a1" should be -- α1 --.
At Column 63, Line 19, "3" should be -- β --.
At Column 66, Line 41, "xZapII" should be -- λZAPII --.
At Column 78, Line 46, "PPARy" should be -- PPARγ --.
At Column 78, Line 66, "PPARa" should be -- PPARα --.
At Column 80, Line 6, "PPARay" should be -- PPAR αγ --.
At Column 91, Line 25, "(HDI)))" should be -- (HD)) --.

In the Claims
At Column 285, Line 19, "claim 4" should be -- claim 1 --.
At Column 286, Line 34, "progression" should be -- progression of --.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*